(12) United States Patent
Ha et al.

(10) Patent No.: US 12,173,334 B2
(45) Date of Patent: *Dec. 24, 2024

(54) BIO-ENGINEERED HYPER-FUNCTIONAL "SUPER" HELICASES

(71) Applicant: THE BOARD OF TRUSTEES OF THE UNIVERSITY OF ILLINOIS, Urbana, IL (US)

(72) Inventors: Taekjip Ha, Baltimore, MD (US); Sinan Arslan, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/537,419

(22) Filed: Nov. 29, 2021

(65) Prior Publication Data

US 2022/0259576 A1 Aug. 18, 2022

Related U.S. Application Data

(63) Continuation of application No. 15/526,905, filed as application No. PCT/US2015/060693 on Nov. 13, 2015, now Pat. No. 11,198,855.

(60) Provisional application No. 62/079,183, filed on Nov. 13, 2014.

(51) Int. Cl.
*C12N 9/14* (2006.01)
*C12N 9/90* (2006.01)
*C12P 19/34* (2006.01)

(52) U.S. Cl.
CPC ............. *C12N 9/14* (2013.01); *C12N 9/90* (2013.01); *C12Y 306/04012* (2013.01); *C12P 19/34* (2013.01)

(58) Field of Classification Search
CPC ...................................................... C12N 9/14
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,168,038 A | 12/1992 | Tecott et al. | |
| 5,210,015 A | 5/1993 | Gelfand et al. | |
| 5,612,199 A | 3/1997 | Western et al. | |
| 5,925,517 A | 7/1999 | Tyagi et al. | |

(Continued)

FOREIGN PATENT DOCUMENTS

| | | |
|---|---|---|
| WO | WO 2005/082098 A2 | 9/2005 |
| WO | WO 2006/073504 A2 | 7/2006 |

(Continued)

OTHER PUBLICATIONS

Fransceus. J Ind Microbiol Biotechnol. May 2017;44(4-5):687-695.*

(Continued)

*Primary Examiner* — Yong D Pak
(74) *Attorney, Agent, or Firm* — Lathrop GPM LLP; James H. Velema, Esq.; Laura A. Labeots

(57) ABSTRACT

Conformationally-constrained helicases having improved activity and strength are provided. Methods of making conformationally-constrained helicases having improved activity and strength are provided. Methods of using conformationally-constrained helicases having improved activity and strength are provided.

8 Claims, 39 Drawing Sheets

Specification includes a Sequence Listing.

(56) References Cited

U.S. PATENT DOCUMENTS

| | | | |
|---|---|---|---|
| 6,124,090 | A | 9/2000 | Rose et al. |
| 6,174,670 | B1 | 1/2001 | Wittwer et al. |
| 6,261,797 | B1 | 7/2001 | Sorge et al. |
| 6,294,323 | B1 | 9/2001 | Ullman et al. |
| 6,365,375 | B1 | 4/2002 | Dietmaier et al. |
| 6,391,544 | B1 | 5/2002 | Salituro et al. |
| 6,432,360 | B1 | 8/2002 | Church et al. |
| 6,485,944 | B1 | 11/2002 | Church et al. |
| 6,511,803 | B1 | 1/2003 | Church et al. |
| 6,569,627 | B2 | 5/2003 | Wittwer et al. |
| 7,282,328 | B2 | 10/2007 | Kong et al. |
| 7,425,431 | B2 | 9/2008 | Church et al. |
| 7,662,594 | B2 | 2/2010 | Kong et al. |
| 2008/0269068 | A1 | 10/2008 | Church et al. |
| 2009/0018024 | A1 | 1/2009 | Church et al. |
| 2010/0075384 | A1 | 3/2010 | Kong et al. |
| 2010/0273164 | A1 | 10/2010 | Church et al. |
| 2013/0210019 | A1 | 8/2013 | Korfhage et al. |
| 2015/0191709 | A1* | 7/2015 | Heron .................. C12Q 1/6827 435/375 |

FOREIGN PATENT DOCUMENTS

| | | | | |
|---|---|---|---|---|
| WO | WO-2014013260 | A1 * | 1/2014 | ............... C12N 9/14 |
| WO | WO 2014/158665 | A1 | 10/2014 | |

OTHER PUBLICATIONS

Sanavia. Computational and Structural Biotechnology Journal, vol. 18, 2020, pp. 1968-1979.*

Studer. Residue mutations and their impact on protein structure and function: detecting beneficial and pathogenic changes. Biochem. J. (2013) 449, 581-594.*

Ali et al. (1997) "Kinetic measurement of the step size of DNA unwinding by *Escherichia coli* UvrD helicase," Science. 275:377-380.

Arslan et al. (Apr. 17, 2015) "Engineering of a superhelicase through conformational control," Science. 348(6232):344-347.

Arslan et al., (Aug. 2011) "Tuning helicase activity of *E.coli* Rep by 2B domain", Poster. In; FASEB Helicase, Aug. 2, 2011. Steamboat, Colorado.

Arslan et al. (Aug. 2011) "Tuning helicase activity of *E. coli* Rep by 2B domain," Presentation Slides. In; FASEB Helicase Conference, Aug. 2, 2011. Steamboat, Colorado.

Baldari et al. (1987) "A novel leader peptide which allows efficient secretion of a fragment of human interleukin 1 beta in *Saccharomyces cerevisiae*," EMBO J. 6:229-234.

Barranco-Medina et al. (2010) "DNA Binding Induces Dimerization of *Saccharomyces cerevisiae* Pif1," Biochemistry. 49:8445-8454.

Becker-Andre et al. (1989) "Absolute mRNA quantification using the polymerase chain reaction (PCR). A novel approach by a PCR aided transcript titration assay (PATTY)," Nucleic Acids Research. 17:9437-9446.

Berg-Sorensen et al. (2004) "Power spectrum analysis for optical tweezers," Review of Scientific Instruments. 75:594-612.

Bernard et al. (1999) "Color Multiplexing Hybridization Probes Using the Apolipoprotein E Locus as a Model System for Genotyping," Anal. Biochem. 273:221-228.

Branton et al. (2008) "The potential and challenges of nanopore sequencing," Nature Biotechnology. 26:1146-1153.

Brendza et al. (2005) "Autoinhibition of *Escherichia coli* Rep monomer helicase activity by its 2B subdomain," Proc. Natl. Acad. Sci. USA. 10:10076-10081.

Brewer et al. (2008) "Laminar flow cells for single-molecule studies of DNA-protein interactions," Nature Methods. 5:517-525.

Bustamante et al. (2009) "High-resolution dual-trap optical tweezers with differential detection: an introduction," Cold Spring Harb. Protoc. 2009(10):pdb.top60.

Bustamante et al. (2009) "High-resolution dual-trap optical tweezers with differential detection: instrument design," Cold Spring Harb. Protoc. 2009(10):pdb.ip73.

Cheng et al. (2001) "*E. coli* Rep oligomers are required to initiate DNA unwinding in vitro," J. Mol. Biol. 310:327-350.

Cheng et al. (2002) "The 2B domain of the Escherichia coli Rep protein is not required for DNA helicase activity," Proc. Natl. Acad. Sci. USA. 99:16006-16011.

Choi et al. (2005) "Allosteric control through mechanical tension," Phys. Rev. Lett. 95:078102.

Cleary et al. (2004) "Production of complex nucleic acid libraries using highly parallel in situ oligonucleotide synthesis," Nature Methods. 1:241-248.

Clopper et al. (1934) "The use of confidence or fiducial limits illustrated in the case of the binomial," Biometrika. 26:404-413.

Comstock et al. (Apr. 16, 2015) "Direct observation of structure-function relationship in a nucleic acid processing enzyme," Science. 348: 352-354.

Dayhoff (1978) "Matrices for detecting distant relationships," In; Atlas of Protein Sequence and Structure. 5(Suppl 3):353-358.

Dayhoff (1978) "Survey of new data and computer methods of analysis," In; Atlas of Protein Sequence and Structure. 5(Suppl 3):1-8.

Dessinges et al. (2004) "Single-molecule assay reveals strand switching and enhanced processivity of UvrD," Proc. Natl. Acad. Sci. USA. 101(17):6439-6444.

Dillingham (2011) "Superfamily I helicases as modular components of DNA-processing machines," Biochemical Society Transactions. 39(2):413-423.

Diviacco et al. (1992) "A novel procedure for quantitative polymerase chain reaction by coamplification of competitive templates," Gene. 122(2):313-320.

Freeman et al. (1999) "Quantitative RT-PCR: pitfalls and potential," Biotechniques. 26(1):112-122, 124-125.

Gal et al. (1999) "Directional cloning of native PCR products with preformed sticky ends (autosticky PCR)," Mol. Gen. Genet. 260:569-573.

Gribskov (1986) "Sigma factors from *E. coli*, B. subtilis, phage SP01, and phage T4 are homologous proteins," Nucl. Acids Res. 14(16):6745-6763.

Guatelli et al. (1990) "Isothermal, in vitro amplification of nucleic acids by a multienzyme reaction modeled after retroviral replication," Proc. Natl. Acad. Sci. USA. 87(5):1874-1878.

Ha et al. (2002) "Initiation and re-initiation of DNA unwinding by the *Escherichia coli* Rep helicase," Nature. 419:638-641.

Harada et al. (1990) "Mechanochemical coupling in actomyosin energy transduction studied by in vitro movement assay," J. Mol. Biol. 216:49-68.

Huang et al. (2006) "Interdomain conformational changes in Akt activation revealed by chemical cross-linking and tandem mass spectrometry," Mol. Cell Proteomics. 5:1045-1053.

International Search Report with Written Opinion corresponding International Patent Application No. PCT/US02015/060693, mailed Mar. 4, 2016.

Jaffe et al. (2000) "An artificial gene for human porphobilinogen synthase allows comparison of an allelic variation implicated in susceptibility to lead poisoning," J. Biol. Chem. 275(4):2619-2626.

Jia et al. (2011) "Rotations of the 2B sub-domain of *E. coli* UvrD helicase/translocase coupled to nucleotide and DNA Binding," J. Mol. Biol. 411:633-648.

Joo et al. (Oct. 2012) "Preparing sample chambers for single-molecule FRET," Cold Spring Harb Protoc. 2012, (10):1104-1108.

Kaufman et al. (1987) "Translational efficiency of polycistronic mRNAs and their utilization to express heterologous genes in mammalian cells," EMBO J. 6(1):187-193.

Khafizov (Sep. 18, 2012) "Single molecule force spectroscopy of single stranded DNA binding protein and rep helicase," Ph.D. Dissertation. University of Illinois at Urbana-Champaign. pp. 1-96.

Korolev et al. (1997) "Major domain swiveling revealed by the crystal structures of complexes of *E. coli* Rep helicase bound to single-stranded DNA and ADP," Cell. 90(4):635-647.

(56) References Cited

OTHER PUBLICATIONS

Kurjan et al. (1982) "Structure of a yeast pheromone gene (MF alpha): a putative alpha-factor precursor contains our tandem copies of mature alpha-factor," Cell. 30:933-943.
Kwoh et al. (1989) "Transcription-based amplification system and detection of amplified human immunodeficiency virus type 1 with a bead-based sandwich hybridization format", Proc. Natl. Acad. Sci. USA. 86(4): 1173-1177.
Kwok (2000) "High-throughput genotyping assay approaches," Pharmocogenomics 1:95-100.
Landegren et al. (1988) "A ligase-mediated gene detection technique," Science. 241:1077-1080.
Landegren et al. (1998) "Reading bits of genetic information: methods for single-nucleotide polymorphism analysis," Genome Res. 8:769-776.
Landry et al. (2009) "Characterization of photoactivated singlet oxygen damage in single-molecule optical trap experiments," Biophysical Journal. 97:2128-2136.
Laszlo et al. (Jun. 25, 2014) "Decoding long nanopore sequencing reads of natural DNA," Nat. Biotechnol. 32(8):829-833.
Lee et al. (2006) "UvrD helicase unwinds DNA one base pair at a time by a two-part power stroke," Cell. 127(7):1349-1360.
Lee et al. (Jun. 2012) "Elastic coupling Between RNA Degradation and Unwinding by an Exoribonuclease," Science. 336(6089):1726-1729.
Lizardi et al. (1988) "Exponential Amplification of Recombinant-RNA Hybridization Probes," BioTechnology 3:1197-1202.
Lohman et al. (2008) "Non-hexameric DNA helicases and translocases: mechanisms and regulation", Nat. Rev. Mol. Cell Biol., 9: 391-401.
Lucklow et al. (1989) "High level expression of nonfused foreign genes with Autographa califomica nuclear polyhedrosis virus expression vectors," Virology. 170:31-39.
Machon et al. (2010) "RepD-mediated recruitment of PcrA helicase at the *Staphylococcus aureus* pC221 plasmid replication origin, oriD," Nucleic Acids Research. 38(6):1874-1888.
Mackay et al. (2002) "Real-time PCR in virology," Nucleic Acids Research. 30:1292-1305.
Maluf et al. (2003) "A Dimer of *Escherichia coli* UvrD is the active form of the helicase in vitro," Journal of Molecular Biology. 325:913-935.
Manthei et al. (Mar. 23, 2015) "Structural mechanisms of DNA binding and unwinding in bacterial RecQ helicases," Proc. Natl. Acad. Sci. USA. 112(14):4292-4297.
Mechanic et al. (2000) "*Escherichia coli* MutL loads DNA helicase II onto DNA," J. Biol. Chem. 275:38337-38346.
Moffitt et al. (2009) "Intersubunit coordination in a homomeric ring ATPase," Nature. 457(7228):446-450.
Mullis et al. (1986) "Specific enzymatic amplification of DNA in vitro: the polymerase chain reaction," Cold Spring Harb. Symp. Quant. Biol. 51(Pt 1):263-273.
Murphy et al. (2004) "Probing single-stranded DNA conformational flexibility using fluorescence spectroscopy," Biophysical Journal 86:2530-2537.
Myong et al. (2005) "Repetitive shuttling of a motor protein on DNA," Nature. 437:1321-1325.
Nakazawa et al. (1994) "UV and skin cancer: specific p53 gene mutation in normal skin as a biologically relevant exposure measurement," Proc. Natl. Acad. Sci. USA. 91:360-364.
Niedziela-Majka et al. (2007) "Bacillus stearothermophilus PcrA monomer is a single-stranded DNA translocase but not a processive helicase in vitro," Journal of Biological Chemistry. 282(37):27076-27085.
Park et al. (2010) "PcrA helicase dismantles RecA filaments by reeling in DNA in uniform steps," Cell. 142:544-555.
Perkins et al. (2004) "Forward and reverse motion of single RecBCD molecules on DNA," Biophysical Journal. 36:1640-1648.
Porreca et al.(2007) "Multiplex amplification of large sets of human exons," Nat. Methods 4:931-936.
Qi et al. (May 28, 2013) "Sequence-dependent base pair stepping dynamics in XPD helicase unwinding," Elife. 2: 300334.

Raney et al. (2013) "Structure and Mechanisms of SF1 DNA Helicases," Adv. Exp. Med. Biol. 767:17-46.
Rasnik et al. (2004) "DNA-binding orientation and domain conformation of the *E. coli* rep helicase monomer bound to a partial duplex junction: single-molecule studies of fluorescently labeled enzymes," Journal of Molecular Biology. 336:395-408.
Rasnik et al. (2006) "Nonblinking and long-lasting single-molecule fluorescence imaging," Nat. Methods. 3:891-893.
Roy et al. (2008) "A practical guide to single-molecule FRET," Nat. Methods. 5:507-516.
Schierling et al. (2010) "Controlling the enzymatic activity of a restriction enzyme by light," Proc. Natl. Acad. Sci. USA. 107:1361-1366.
Schultz et al. (1987) "Expression and secretion in yeast of a 400-kDa envelope glycoprotein derived from Epstein-Barr virus," Gene 54:113-123.
Seed (1987) "An LFA-3 cDNA encodes a phospholipid-linked membrane protein homologous to its receptor CD2," Nature. 329(6142):840-842.
Shi (2001) "Enabling large-scale pharmacogenetic studies by high-throughput mutation detection and genotyping technologies," Clin. Chem. 47:164-172.
Slatter et al. (2009) "PcrA helicase tightly couples ATP hydrolysis to unwinding double-stranded DNA, modulated by the initiator protein for plasmid replication, RepD," Biochemistry. 48:6326-6334.
Smith et al. (1981) "Comparison of biosequences," Advances in Applied Mathematics. 2:482-489.
Smith et al. (1983) "Production of human beta interferon in insect cells infected with a baculovirus expression vector," Mol. Cell. Biol. 3:2156-2165.
Smith et al. (1988) "Single-step purification of polypeptides expressed in *Escherichia coli* as fusions with glutathione S-transferase," Gene. 67:31-40.
Soultanas et al. (1998) "*Escherichia coli* ribosomal protein L3 stimulates the helicase activity of the Bacillus stearothermophilus PcrA helicase," Nucleic Acids Research. 26:2374-2379.
Soultanas et al. (1999) "Plasmid replication initiator protein RepD increases the processivity of PcrA DNA helicase," Nucleic Acids Res. 27:1421-1428.
Subramanya et al. (1996) "Crystal structure of a DExx box DNA helicase," Nature. 384:379-383.
Sun et al. (2008) "Impediment of E. con UvrD by DNA-destabilizing force reveals a strained-inchworm mechanism of DNA unwinding," EMBO J. 27:3279-3287.
Tomishige et al. (2000) "Controlling kinesin by reversible disulfide cross-linking. Identifying the motility-producing conformational change," J. Cell Biol. 151:1081-1092.
Urbatsch et al. (2001) "Cysteines 431 and 1074 are responsible for inhibitory disulfide cross-linking between the WO nucleotide-binding sites in human P-glycoprotein," J. Biol. Chem. 276:26980-26987.
Veine et al. (1998) "Thioredoxin reductase from *Escherichia coli*: evidence of restriction to a single conformation upon formation of a crosslink between engineered cysteines," Protein Science. 7:369-375.
Velankar et al. (1999) "Crystal structures of complexes of PcrA DNA helicase with a DNA substrate indicate an inchworm mechanism," Cell. 97(1):75-84.
Vincent et al. (2004) "Helicase-dependent isothermal DNA amplification," EMBO Reports. 5:795-800.
Volgraf et al. (2006) "Allosteric control of an ionotropic glutamate receptor with an optical switch," Nature Chemical Biology. 2(1):47-52.
Williams et al. (2002) "In vivo protein cyclization promoted by a circularly permuted *Synechocystis* sp. PCC6803 DnaB mini-intein," J. Biol. Chem. 277:7790-7798.
Yamaguchi et al. (1998) "MutS and MutL activate DNA helicase II in a mismatch-dependent manner," J. Biol. Chem. 273:9197-9201.
Yanagida et al. (1984) "Direct observation of motion of single F-actin filaments in the presence of myosin," Nature. 307:58-60.

(56) References Cited

OTHER PUBLICATIONS

Yancey et al. (1991) "The DNA unwinding reaction catalyzed by Rep protein is facilitated by an RHSP-DNA interaction," Nucleic Acids Research. 19:3943-3951.

Yodh et al. "BLM helicase measures DNA unwound before switching strands and hRPA promotes unwinding reinitiation", The EMBO Journal, 28: 405-416.

Yodh et al. (2010) "Insight into helicase mechanism and function revealed through single-molecule approaches," Duarterly Reviews of Biophysics. 43(2):185-217.

Zhang et al., "Directional loading and stimulation of PcrA helicase by the replication initiator protein RepD", Journal of Molecular Biology, 2007, 371(2): 336-348.

Zimmerman et al., "Technical aspects of quantitative competitive PCR", Biotechniques, 1996, 21: 268-279.

* cited by examiner

Supplementary Table S2. Conserved Cys247 in Motif III of PcrA

| | | Motif Ia | | TxGx Motif | |
|---|---|---|---|---|---|
| Rep | Escherichia coli | RIAHLIRGCGYQARHIAAVTFTNKAAREMKERVGQTLGRK--EARGLMIS | TFHTLGLDIIK | 93 |
| UvrD | Escherichia coli | RIAWLMSVENCSPYSIMAVTFTNKAAAEMRHRIGQLMST--SQGGMMVG | TFHGLAHRLLR | 99 |
| UvrD | Mycobacterium tuberculosis | RIAYLMAARGVGVGQILAITFTNKAAAEMRERVVGLVGE--KARYMWVS | TFHSTQVRILR | 112 |
| UvrD | Mycoplasma capricolum | KIAYLIEKQNIDFSRILAITFTNKAAKEMKERVLQITNN--SFKSPFIS | TFHSWQSK

Fig. 4B

| | | Motif II (Walker) | | Motif III | |
|---|---|---|---|---|---|
| Rep | Escherichia coli | WQNKIRYLLLVDEYQDTNTSQYELVKLLVGSRA------ | ----- | ---RFTVVGDDQSIYSWRGARPQ | 256 |
| UvrD | Escherichia coli | YRERFTNILVDEFQDTNNIQYAWIRLLAGDTG------- | ----- | ---KVMIVGDDDQSIYGWRGAQVE | 262 |
| UvrD | Mycobacterium tuberculosis | YRRRFRHVLVDEYQDTNHAQYVLVRELVGRDSNDGIPPGEL | ----- | VVGDADQSIYAFRGATIR | 287 |
| UvrD | Mycoplasma capricolum | WRNAYDYVLVDEFQDTNELQFSLIKFLITINTN------- | ----- | ---HLTVVGDPDQTIYSWRGAKLD | 267 |
| UvrD | Deinococcus radiodurans | VQNKAKFIHVDEYQDTNRAQYELTRLLASRDR------- | ----- | ---NLIVVGDPDQSIYKFRGADIQ | 269 |
| PcrA | Geobacillus sterothermophilus | YQYKFQYIHIDEYQDTNRAQYTLVKKLAERFQ------- | ----- | ---NICAVGDADQSIYRWRGADIQ | 265 |
| PcrA | Bacillus subtilis | YQRKFQYIHVDEYQDTNRAQYMLVKQLAERFQ------- | ----- | ---NLQVVGDSDQSIYRWRGADIQ | 265 |
| PcrA | Staphylococcus aureus | YQNKFQYIHVDEYQDTNKAQYTLVKLLASKFK------- | ----- | ---NLQVVGDSDQSIYGWRGADIQ | 261 |
| PcrA | Leuconostoc citreum | YQQFEYLHVDEYQDTNDAQYTIVNLLAQRSK------- | ----- | ---NLAVVGDADQSIYGWRGANMN | 264 |
| PcrA | Fructobacillus fructosus | YQDQFRYLHVDEYQDTNDAQYLIVNMLAQGSK------- | ----- | ---NLAVVGDADQSIYGWRGANMQ | 264 |
| PcrA | Staphylococcus epidermis | YQNKFQYIHVDEYQDTNKAQYTLVKLLANKFK------- | ----- | ---NLQVVGDSDQSIYGWRGADIQ | 261 |
| PcrA | Carnobacterium maltaromaticum | YQAKFQYIHVDEYQDTNQAQYOLVQLLAQRFK------- | ----- | ---NLQVVGDADQSIYGWRGANME | 264 |
| PcrA | Alloiococcus otitis | YQGRFRYILVDEYQDTNGAQYQLTKILAARHH------- | ----- | ---NVQVVGDADQSIYGWRGADMG | 264 |
| PcrA | Mitsuokella multacida | YQEKFKYILVDEYQDTNMAQYTLVSLLAKKHH------- | ----- | ---NLQVVGDDDQSIYGWRGADIR | 261 |
| PcrA | Alkaliphilus metalliredigens | YQNKFKYILVDEYQDTNHTQYVLVNMLAESHR------- | ----- | ---NVQVVGDPNQSIYKWRGADIN | 259 |
| PcrA | Desulfotomaculum reducens | YQNKFQYIHVDEYQDTNRAQYLLVKLFAAKLR------- | ----- | ---NLQVVGDSDQSIYGWRGADIS | 265 |
| PcrA | Listeria fleischmannii | YQNKFHYIHVDEYQDTNFSQYRLVQMLASKFR------- | ----- | ---NVQVVGDSDQSIYRWRGADIQ | 268 |
| PcrA | Sporosarcina newyorkensis | YQNKFQYIHVDEYQDTNKSQYLLVKLLASKFR------- | ----- | ---NLQVVGDSDQSIYRWRGADIG | 268 |
| PcrA | Kurthia massiliensis | YQNKFHYIHVDEYQDTNRAQYMLVNMLAAKRH------- | ----- | ---NIQVVGDSDQSIYRWRGADIT | 266 |
| PcrA | Marinococcus halotolerans | YQRKFQYIHVDEYQDTNKAQYLLLVKLLADKFK------- | ----- | ---NIQVVGDSDQSIYRWRGADIG | 268 |
| PcrA | Planococcus antarcticus | YQNKFQYIHVDEYQDTNRAQYELVRLLSASRFQ------- | ----- | ---NIQVVGDSDQSIYRWRGADIG | 268 |
| PcrA | Lysinibacillus fusiformus | YQNKFQYIHVDEYQDTNKSQYLLLVQLLAKKFK------- | ----- | ---NLQVVGDSDQSIYRWRGADIG | 265 |
| PcrA | Oceanobacillus iheyensis | YQRRFQYIHVDEYQDTNHAQYQLVQLVQLASRYK------- | ----- | ---NIQVVGDSDQSIYRWRGADIS | 265 |
| PcrA | Virgibacillus sp. | YQRRFQYIHVDEYQDTNRAQYQLVQLVQLASRYQ------- | ----- | ---NIQVVGDSDQSIYRWRGADIT | 268 |
| PcrA | Caldibacillus debilus | YQRRFQYIHVDEYQDTNHAQYQLVQLVKQLASRYK------- | ----- | ---NIQVVGDSDQSIYRWRGADIS | 283 |
| PcrA | Halobacillus halophilus | YQRKFQYIHVDEYQDTNKAQYLLLVKHLAARFK------- | ----- | ---NIQVVGDSDQSIYRWRGADIG | 265 |
| PcrA | Gracilibacillus halophilus | YQRKFQYIHVDEYQDTNRAQYLLLVKMLADKFK------- | ----- | ---NIQVVGDSDQSIYRWRGADIS | 265 |
| PcrA | Bacillus cereus | YQSKFQYIHVDEYQDTNRAQYLLLVKMLADKFK------- | ----- | ---NIQVVGDSDQSIYRWRGADIT | 266 |
| PcrA | Macrococcus caseolyticus | YQRKFQYIHVDEYQDTNHVQYILTKMLAEKHQ------- | ----- | ---NIQVVGDSDQSIYRWRGADIY | 261 |
| PcrA | Laceyella sacchari | YQRKFQYIHVDEYQDTNRAQYLLISMLADMHK------- | ----- | ---NIQVVGDSDQSIYRWRGADIS | 265 |
| PcrA | Brevibacillus laterosporus | YQNKFRYIHVDEYQDTNRAQYMLCRMLADKHH------- | ----- | ---RIQVVGDSDQSIYRWRGADIS | 266 |
| PcrA | Paenibacillus sp. | YQRRFQYIHVDEYQDTNYAQYLLCRMLADKHH------- | ----- | ---NIQVVGDSDQSIYRWRGADIS | 273 |
| PcrA | Thermobacillus composti | YQRRFQYIHVDEYQDTNYAQYDLVKKLAEKYQ------- | ----- | ---NIQVVGDSDQSIYRWRGADIT | 267 |
| PcrA | Amphibacillus xylanus | YQRRFQYIHVDEYQDTNYAQYDLVKKLAEKYQ------- | ----- | ---NLQVVGDSDQSIYRWRGADIK | 266 |

Target Residues

```
P56255 PCRA_GEOSE   1 MNFLSEQLLAHLNKEQQEAVRTTEGPLLIMAGAGSGKTRVLTHRIAYLMAEKHVAPWNIL  60  ⎫
P09980 REP_ECOLI    1 ------------MRLNPGQQQAVEFVTGPCLVLAGAGSGKTRVITNKIAHLIRGCGYQARHIA  51  ⎬ Domain 1A
P03018 UVRD_ECOLI   1 ---MDVSYLLDSLNDKQREAVAAPRSNLLVLAGAGSGKTRVLVHRIAWLMSVENCSPYSIM  58  ⎭
                        **  *:**     *:*:******** :  :**  *:         *

P56255 PCRA_GEOSE  61 AITFTNKAAREMRERVQSLLGGA-AEDVWISTFHSMCVRTLRKDIDRTGNRNPSILDPT 119 ⎫
P09980 REP_ECOLI   52 AVTFTNKAAREMKERVGQTLGRKEARGLMISTFHTLGLDIIKREYAALGMKANPSLFDDT 111 ⎬ Domain 1A
P03018 UVRD_ECOLI  59 AVTFTNKAAAEMRHRIGQLMGTS-QGGWMVGTPHGLAHRLRAHMDANLPQDPQTLDSE   117 ⎭
                      *:*******  **:.*: .*    : :.*** :   :::   :  :*.:*

P56255 PCRA_GEOSE 120 DQLSVMKTILKEKNIDPKKFEPRTILGTISAAKNELLPPEQFAKRASTYYEKVVSDVVQF 179 ⎫
P09980 REP_ECOLI  112 DQLALLKELTEGLIEDD-KVLLQQLISTISNWKNDLKTPSQAAASAIGERDRIFAHCVGL 170 ⎬ Domain 1B
P03018 UVRD_ECOLI 118 DQLRLLKRLIKAMNLDEKQWPPRQAMWYINSQKDEGLRPHHIQSYG-NPVEQTWQKVVQA 176 ⎭
                     ***  ::* :   *         :    *. *:   *     :    *

P56255 PCRA_GEOSE 180 YQGRILRNIDLDFDDIMTTIQLFDRVPDVLHYYQYKFQYIHIDEYQDTNRAQYTLVKKL   239 ⎫
P09980 REP_ECOLI  171 YDAHLEACNVLDFDDLLPTLLLQRNEEVRKRWQNKIRYLLVDEYQDTNSQYELVKLL    230 ⎬
P03018 UVRD_ECOLI 177 YQEACDRAGLIDFAELLLRAHELWLNKPHILQHYRERFTNILVDEFQDTNNIQYAWIRLL 236 ⎭
                      *:    :**  :       :     *   *      :**:****  **  :: *

P56255 PCRA_GEOSE 240 AERFQNICAVGDADQSIYRWRGADIQNTLSFERDYPNAKVILLEQNYRSTKRILQAANEV 299
P09980 REP_ECOLI  231 VGSRARFTVVGDDDQSIYSWRGARPQNLVLLSQDFPALKVIKLEQNYRSSGRILKAANIL 290
P03018 UVRD_ECOLI 237 AGDTGKVMIVGDDDQSIYGWRGAQVENIQRFLNDFPGAETIRLEQNYRSTSNILSAANAL 296
                     .    ..  *** ***** ****   :  . *:*  ::  :******:  **.*** :

P56255 PCRA_GEOSE 300 IEHNVNRKPKRIWTENPEGKPILYYEAMNEADEAQFVAGRIREAVERGERRYRDFAVLYR 359
P09980 REP_ECOLI  291 IANNPHVFEKRLFSELGYGAELKVLSANNEEHEAERVTGELIAHHPVNKTQYKDYAILYR 350
P03018 UVRD_ECOLI 297 IENNGRLGKKLWTDGADGEPISLYCAPNELDEARFVNRIKTWQDNGG--ALAECAILYR  355
                     * .*   *::::.   *   ** .**  .**, *.:       :  :****

P56255 PCRA_GEOSE 360 TNAQSRVMEEMLLKANIPYQIVGGLKFYDRKEIKDIIAYLRVLANPDDDLSLLRIINVPK 419 ⎫
P09980 REP_ECOLI  351 GNHQSRVFEKFLMQNRIPYKISGGTSFFSRPEIKDLIAYLRVLTNPDDDSAIRIVNTPK   410 ⎬
P03018 UVRD_ECOLI 356 SNAQSRVLEEALLQASMPYRIYGGMRFFERQEIKDAISYLRLIANRIDDAAFRVVNTPT   415 ⎭
                     * ***.*: *: **:*. **  *: * **  *::  ***:: *:: **. *.*.

P56255 PCRA_GEOSE 420 RGIGASTIDKEVRYADHETLRIFKLGELEM-IGLGAKAAGALAAPRSQLEQWTQLQEYV  478 ⎫
P09980 REP_ECOLI  411 REIGPATLKKKEKRANTREKSMIASFDMGLSQTLSGRGYEALTRFTHWLAEIQRAERE   470 ⎬ Domain 2B
P03018 UVRD_ECOLI 416 RGIGDRTLDVVRQTSRDRQIILWQACRELLQEKALAGRAASALQRFMELIDALAQETADM 475 ⎭
                     * **  *::       :.:   ::   ::         ** :*.  *.:  ** *

P56255 PCRA_GEOSE 479 SVTELVEEVLDKSGYREM-LKAE-RTIEAQSRLENLDEFLSVTKHPENVSDKSLIAF-    534 ⎫
P09980 REP_ECOLI  471 PIAAVRDL-IHGMDYESWLYETSPSPKAAEMRMKNVQLFSWMTEMLEGSELDEPWTLTS 529 ⎬
P03018 UVRD_ECOLI 476 PLHVQTDRVIKDSGLRTM-YEQE-KGEKGQTRIENLEELVTATRQFSYMEEDRLMTLQK   533 ⎭
                         :*    :   :  :     .   *    *:*::::  *  :*

P56255 PCRA_ECOLI 535 -LTDLAISDLDELDGTEQAAEGDAVMLMTLHAAKGLEFPVVFLIGMEEGIFPHNRSLED   593 ⎫
P09980 REP_ECOLI  530 VVTRFTL-----RDMMERGESEEELDQVQLMTLHASKGLEFPYVYMVGMEEGFLPHQSSIDE 586 ⎬
P03018 UVRD_ECOLI 534 KLSHAAKEA-------GEGQADTWQDAVQLMTLHSAKGLEFPQVFIVGMEEGMFPSQMSLDE 588 ⎭
                     ::    :*      :          * * ****:******:**:***:*:.. *:::

P56255 PCRA_GEOSE 594 DDEMEEERRLAYVGITRAEEELVLTSAQMRTLFGNIQMDPPSRFLNEIPAHLLETASRRQ 653
P09980 REP_ECOLI  587 D-NIDEERRLAYVGITRAQKELTFLCKERRQYGELVRPEPSRFLLELPQDDLIWEQERK  645
P03018 UVRD_ECOLI 589 GGRLEEERRLAYVGVTRAMQKLTLTYAETRRLYGKEVYHRPSRFIGELPEECVEEVRLEA 648
                      . ::*******.*:**  *: :   *:*: *::            ****:  :*

P56255 PCRA_GEOSE 654 AGASRPAVSRP------QASGAVGSWKVGDRANHRKWGTGTVVSVRGGGDDQELDIAFPSPIG 710
P09980 REP_ECOLI  646 VVSAEERM---QKGQSHLANLKAMMAA----------KRGK---------------------  673
P03018 UVRD_ECOLI 649 -TVSRPVSHQRMGTPMVENDSGYKLGQRVRHAKFGEGTIVNMEGSGEHSRLQVAFQG--QG   706
                                                      :     .       . *  * .

P56255 PCRS_GEOSE 711 IKRLLAKFAPIEKV          724
P09980 REP_ECOLI  674 --------------           673
P03018 UVRD_ECOLI 707 IKWLVAAYARLESV           720
```

*Fig. 9A*

Domain 1A
Target Residues

| Accession | Name | Start | Sequence | End |
|---|---|---|---|---|
| P09980 | REP_ECOLI | 60 | AREMKERVGQTLGRKEARGLMISTFHTLGLDIIKREYAALGMKANFSLFDTDQLALLKE | 119 |
| O51889 | REP_BUCAP | 60 | AHEIKVRLAKHLNLLQIKKMIISTFHSLGLEIIKKEINTLKPNSNPSLFDERDQMMLLKK | 119 |
| P57654 | REP_BUCAI | 60 | AYEMRIRLSKYLNIPEIKKIIISTFHSLGLEIIKKEIDALELNNNPTLLDEKDQILLLKK | 119 |
| P44804 | REP_HAEIN | 60 | AREMKERVAHSIGKEQSKGLLVSTFHTLGFDILKREYKALGFKSNMTLFDEHDQFALLKE | 119 |
| Q9L6S1 | REP_SALTY | 60 | AREMKERVGQTLGRKEARGLMISTFHTLGLDIIKREYAALGMKSNFSLFDDTDQVALLKE | 119 |
| A0A077ZIR6 | A0A077ZIR6_TRITR | 77 | AREMKERVGQTLGRKEARGLMISTFHTLGLDIIKREYAALGMKANFSLFDDTDQLALLKE | 136 |
| S3IEG5 | S3IEG5_9ENTR | 60 | AREMKERVSQTLGRKEARGLMISTFHTLGLEIIKREYAALGMKSNFSLFDDTDQTALLKE | 119 |
| J1R585 | J1R585_9ENTR | 60 | AREMKERVAQTLGRKEARGLMISTFHTLGLTIIKREFAALGMKSNFSLFDDTDQVALLKE | 119 |
| K8ABZ8 | K8ABZ8_9ENTR | 41 | AREMKERVAQTLGRKEARGLMISTFHTLGLEIIKREYAALGMKSNFSLFDDTDQMALIKE | 100 |
| A0A060VJ91 | A0A060VJ91_KLEPN | 121 | AREMKERVGQTLGRKEARGLMISTFHTLGLDIIKREYAALGMKSNFSLFDDTDQVALLKE | 180 |
| A0A090V5M6 | A0A090V5M6_ESCVU | 60 | AREMKERVGQTLGRKEARGLMISTFHTLGLDIIKREYAALGMKSNFSLFDDTDQVALLKD | 119 |
| A0A083YZC2 | A0A083YZC2_CITAM | 60 | AREMKERVGQTLGRKEARGLMISTFHTLGLEVIKREYAALGMKSNFSLFDDTDQVALLKD | 119 |
| A0A0J6D7T8 | A0A0J6D7T8_SALDE | 60 | AREMKERVGQTLGRKEARGLMISTFHTLGLDIIKREYAALGMKSNFSLFDDTDQVALLKE | 119 |
| A0A085ITL8 | A0A085ITL8_RAOPL | 60 | AREMKERVGQTLGRKEARGLMISTFHTLGLDIIKREYAALGMKSNFSLFDDTDQVALLKE | 119 |
| E7T4Q1 | E7T4Q1_SHIBO | 60 | AREMKERVGQTLGRKEARGLMISTFHTLGLDIIKREYAALGMKVNFSLFDDTDQLALLKE | 119 |
| A0A085GMM2 | A0A085GMM2_9ENTR | 60 | AREMKERVAQTLGRKEARGLLISTFHTLGLEIIKREYAALGMKSNFSLFDDTDQTALLKD | 119 |
| A0A085HAK1 | A0A085HAK1_9ENTR | 41 | AREMKERVGQTLGRKEARGLMISTFHTLGLDIIKREYAALGMKSNFSLFDDTDQVALLKE | 100 |
| D4BE16 | D4BE16_9ENTR | 60 | AREMKERVGQTLGRKEARGLMISTFHTLGLDVIKREYAALGMKSNFSLFDDTDQVALLKE | 119 |
| A0A0H5PMJ7 | A0A0H5PMJ7_SALSE | 60 | AREMKERMAQTLGRKEARGLMISTFHTLGLDIIKREYAALGMKSNFSLFDDTDQVALLKE | 119 |
| A0A0J1JQT3 | A0A0J1JQT3_CITFR | 60 | AREMKERVAQTLGRKEARGLMISTFHTLGLEIIKREYNALGMKANFSLFDDTDQMALIKE | 119 |
| A0A0J8VI05 | A0A0J8VI05_9ENTR | 60 | AREMKERVGQTLGRKEARGLMISTFHTLGLDIIKREYAALGMKSNFSLFDDTDQVALLKE | 119 |
| F5S3F4 | F5S3F4_9ENTR | 60 | AREMKERVGQTLGRKEARGLMISTFHTLGLDIIKREYAALGMKSNFSLFDDTDQVALLKE | 119 |
| D2ZMA5 | D2ZMA5_9ENTR | 60 | AREMKERVAQTLGRKEARGLMISTFHTLGLEIIKREFAALGMKSNFSLFDDTDQVALLKE | 119 |
| A0A084ZTW9 | A0A084ZTW9_9E | 60 | AREMKERVGQTLGRKEARGLMISTFHTLGLDIIKREYAALGMKSNFSLFDDTDQVALLKE | 119 |
| A0A038CLT3 | A0A038CLT3_RAOOR | 60 | AREMKERVGQTLGRKEARGLMISTFHTLGLDIIKREYAALGMKSNFSLFDDTDQVALLKE | 119 |
| Q8Z385 | Q8Z385_SALTI | 60 | AREMKERVGQTLGRKEARGLMISTFHTLGLDIIKREYAALGMKSNFSLFDDTDQVALLKE | 119 |
| Q83IX8 | Q83IX8_SHIFL | 60 | AREMKERVGQTLGRKEARGLMISTFHTLGLDIIKREYAALGMKANFSLFDDTDQLALLKE | 119 |
| A0A0D5WYP4 | A0A0D5WYP4_9ENTR | 60 | AREMKERVSQTLGRKEARGLMISTFHTLGLEIIKREYAALGMKSNFSLFDDTDQTALLKE | 119 |
| A0A0H3FM31 | A0A0H3FM3 | 60 | AREMKERVGQTLGRKEARGLMISTFHTLGLDIIKREYAALGMKSNFSLFDDTDQVALLKE | 119 |
| A0A0H2WUK6 | A0A0H2WUK6_SALPA | 60 | AREMKERVGQTLGRKEARGLMISTFHTLGFDIIKREYAALGMKSNFSLFDDTDQVALLKE | 119 |
| A0A0H3H1F3 | A0A0H3H1F3_KLEOK | 60 | AREMKERVGQTLGRKEARGLMISTFHTLGLDIIKREYAALGMKSNFSLFDDTDQVALLKE | 119 |
| X7I146 | X7I146_CITFR | 60 | AREMKERVAQTLGRKEARGLMISTFHTLGLDIIKREYAALGMKSNFSLFDDTDQVALLKE | 119 |
| A0A0H3CTF5 | A0A0H3CTF5_ENTCC | 60 | AREMKERVGQTLGRKEARGLMISTFHTLGLDIIKREYAALGMKSNFSLFDDTDQVALLKE | 119 |
| D2TH67 | D2TH67_CITRI | 60 | AREMKERVGQTLGRKEARGLMISTFHTLGLEIIKREYAALGMKSNFSLFDDTDQLALLKE | 119 |
| Q3Z9V6 | Q3Z9V6_SHIDS | 60 | AREMKERVGQTLGRKEARGLMISTFHTLGLDIIKREYAALGMKANFSLFDDTDQLALLKE | 119 |
| W6J7C4 | W6J7C4_9ENTR | 60 | AREMKERVAQTLGRKEARGLMISTFHTLGLNIIKREPAALGMKSNFSLFDDTDQVALLKD | 119 |
| I2BE87 | I2BE87_SHIBC | 60 | AREMKERVAQTLGRKEARGLMISTFHTLGLEIIKREYAALGMKSNFSLFDDTDQLALIKD | 119 |
| B5EZ38 | B5EZ38_SALA4 | 60 | AREMKERVGQTLGRKEARGLMISTFHTLGLDIIKREYAALGMKSNFSLFDDTDQVALLKE | 119 |
| A0A0F5SGU2 | A0A0F5SGU | 60 | AREMKERVAQTLGRKEARGLMISTFHTLGLDVIKREYAALGMKSNFSLFDDTDQVALLKE | 119 |
| G9YY11 | G9YY11_9ENTR | 60 | AREMKERVAQTLGRKEARGLMISTFHTLGLDIIKREYAALGMKSNFSLFDDTDQVALLKE | 119 |
| A0A090UXU3 | A0A090UXU3_9ENTR | 60 | AREMKERVAQTLGRKEARGLMISTFHTLGLDVIKREYAALGMKSNFSLFDDTDQVALLKE | 119 |
| A9MJ31 | A9MJ31_SALAR | 60 | AREMKERVGQTLGRKEARGLMISTFHTLGLDIIKREYAALGMKSNFSLFDDTDQVALLKE | 119 |
| Q3YV16 | Q3YV16_SHISS | 60 | AREMKERVGQTLGRKEARGLMISTFHTLGLDIIKREYAALGMKANFSLFDDTDQLALLKE | 119 |
| D3RHE6 | D3RHE6_KLEVT | 60 | AREMKERVGQTLGRKEARGLMISTFHTLGLDIIKREYAALGMKSNFSLFDDTDQVALLKE | 119 |
| Q57HT8 | Q57HT8_SALCH | 93 | AYEMKERVGQTLGRKEARGLMISTFHTLGLDIIKREYAALGMKSNFSLFDSDQVALLKE | 152 |
| B5RFS5 | B5RFS5_SALG2 | 60 | AREMKERVGQTLGRKEARGLMISTFHTLGLDIIKREYKALGMKSNFSLFDDTDQVALLKE | 119 |
| A0A089Q204 | A0A089Q204_9ENTR | 60 | AREMKERVSQTLGRKEARGLMISTFHTLGLEIIKREYAALGMKSNFSLFDDTDQTALLKE | 119 |
| A0A0H3BNR1 | A0A0H3BNR1_SALNS | 60 | AREMKERVGQTLGRKEARGLMISTFHTLGLDIIKREYAALGMKSNFSLFDDTDQVALLKE | 119 |
| C9Y4T0 | C9Y4T0_SICTZ | 60 | AREMKERVAQTMGRKEARGLMISTFHTLGLEIIKREYVALGMKSNFSLFDDTDQMALIKE | 119 |
| B7LU77 | B7LU77_ESCF3 | 60 | AREMKERVGQTLGRKEARGLMISTFHTLGLDIIKREYAALGMKANFSLFDDTDQLALLKE | 119 |
| A0A0H3TAW8 | A0A0H3TAW8_SALEN | 60 | AREMKERVGQTLGRKEARGLMISTFHTLGLDIIKREYAALGMKSNFSLFDDTDQVALLKE | 119 |
| G2S5J6 | G2S5J6_ENTAL | 60 | AREMKERVGQTLGRKEARGLMISTFHTLGLDIIKREYAALGMKSNFSLFDDTDQVALLKE | 119 |
| A0A0F7JC30 | A0A0F7JC30_SALET | 60 | AREMKERVGQTLGRKEARGLMISTFHTLGLDIIKREYAALGMKSNFSLFDDTDQVALLKE | 119 |
| A7MQI4 | A7MQI4_CROS8 | 60 | AREMKERVAQTLGRKEARGLMISTFHTLGLEIIKREYAALGMKSNFSLFDDTDQMALIKE | 119 |
| L0M8J0 | L0M8J0_ENTBF | 60 | AREMKERVAQTLGRKEARGLMISTFHTLGLDIIKREYAALGMKSNFSLFDDTDQVALLKD | 119 |
| A0A0K0HFU2 | A0A0K0HFU2_SALBC | 60 | AREMKERVGQTLGRKEARGLMISTFHTLGLEIIKREYAALGMKSNFSLFDDTDQTALLKE | 119 |
| A8ACT1 | A8ACT1_CITK8 | 60 | AREMKERVGQTLGRKEARGLMISTFHTLGLDIIKREYAALGMKSNFSLFDDTDQVALLKE | 119 |

*Fig. 9B*

Domain 1B Target Residues

| ID | Name | Start | Sequence | End |
|---|---|---|---|---|
| P09980 | REP_ECOLI | 120 | LTEGL-IEDDKVLQQLISTISNWKNDLKTPSQAAASAIGERDRIFAHCYGLYDAHLKACNVDIDLL | 187 |
| O51889 | REP_BUCAP | 120 | ICSKS-IKNDTKLLKKLVPMISFWKNKFLTPLQVQLSAQSNLEKDFAFFYRQYTPHLRKS | 178 |
| P57654 | REP_BUCAI | 120 | ICKKE-IKNNIQLLKKLNPMISYWKNKFLTPLQVQLLAKSSQEKDFAYVVEQYTNYLYKA | 178 |
| P44804 | REP_HAEIN | 120 | LTADV-LKEDKDLLRELISVISNWKNDLISPKQAFALARDAKYQTFAKCYERYATQIRTY | 178 |
| Q9L6S1 | REP_SALTY | 120 | LTEGL-IEDDKVLQQLISTISNWKNDLKTPAQAAAGAKGERDRIFAHCYGLYDAHMKAC | 178 |
| A0A077ZIR6 | A0A077ZIR6_TRITR | 137 | LTEGL-IEDDKVLQQLISTISNWKNDLKTPSQAAASAIGERDRIFAHCYGLYDAHLKAC | 195 |
| S3IEG5 | S3IEG5_9EN | 120 | LTEGL-LENDKVLQQLISTISNWKNSLLTPAQAAAQAKGERDRIFAHCYGLYDTHLKSC | 178 |
| J1R585 | J1R585_9ENTR | 120 | LTEGL-IDDDKAVLQQLISTISNWKNDLLTPPQAAAQAKGERDRIFAHCYGLYDSHMKSC | 178 |
| K8ABZ8 | K8ABZ8_9ENTR | 101 | LTEGL-IENDKVLQQLISTISNWKNDLLSPPQAAARAIGERDRIFAHCYSLYDAHLKAC | 159 |
| A0A060VJ91 | A0A060VJ91_KLEPN | 181 | LTEGL-IEDDKVVLQQLISTISNWKNDLKTPAQAAAGAKGERDRIFAHCYGLYDAHMKAC | 239 |
| A0A090V5M6 | A0A090V5M6_ESCVU | 120 | LTEGL-IEDEKTILQQLISTISNWKNDLMTPAQAAAQARGERDRIFAHCYSLYDAHMKAC | 178 |
| A0A083YZC2 | A0A083YZC2_CITAM | 120 | LTEGL-IEDDKVILQQLISTISNWKNDLKTPAQAAAGAKGERDRIFAHCYGLYDAHMKAC | 178 |
| A0A0J6D7T8 | A0A0J6D7T8_SALDE | 120 | LTEGL-IEDDKVLQQLISTISNWKNDLKTPAQAAAGAKGERDRIFAHCYGLYDAHMKAC | 178 |
| A0A085ITL8 | A0A085ITL8_RAOPL | 120 | LTEGL-IDDDKVVLQQLISTISNWKNDLQTPAQAAAGAKGERDRIFAHCYGLYDGHMKAC | 178 |
| E7T4Q1 | E7T4Q1_SHIBO | 120 | LTEGL-IEDDKVLQQLISTISNWKNDLKTPSQAAASAIGERDRIFAHCYGLYDAHLKAC | 178 |
| A0A085GMM2 | A0A085GMM2_9ENTR | 120 | LTEGL-LEDDKTLLQQLISTISNWKNDLMSPSQAAAQAKGERDRIFAHCYGLYDTHLKSC | 178 |
| A0A085HAK1 | A0A085HAK1_9ENTR | 101 | LTEGL-IEDDKTVLQQLISTISNWKNDLMNPEQAAASKGERDRIFAHCYGLYNDHLKAC | 159 |
| D4BE16 | D4BE16_9ENTR | 120 | LTEGL-IEDDKLILQQLISTISNWKNDLMTPAQAAAGAKGERDRIFAHCYGLYDAHMKAC | 178 |
| A0A0H5PMJ7 | A0A0H5PMJ7_SALSE | 120 | LTEGL-IEDDKVLQQLISTISNWKNDLMTPAQAAASAKGERDRIFAHCYGLYDAHMKAC | 178 |
| A0A0J1JQT3 | A0A0J1JQT3_CITFR | 120 | LTEGL-IEDDKLILQQLISTISNWKNDLMTPAQAAASAKGERDRIFAHCYGLYDAHMKAC | 178 |
| A0A0J8VI05 | A0A0J8VI05_9ENTR | 120 | LTEGL-VENDKSLLQQLISTISNWKNDLLNPLQAAAQAKGERDRIFAHCYGLYDAHLKAC | 178 |
| F5S3F4 | F5S3F4_9ENTR | 120 | LTEGL-IEDDKVLQQLISTISNWKNDLMTPAQAAAGAKGERDRIFAHCYGLYDAHMKAC | 178 |
| D2ZMA5 | D2ZMA5_9ENTR | 120 | LTEGL-IEDDKTVLQQLISTISNWKNDLMTPSQAAAIAKGERDRIFAHCYGLYDAHMKAC | 178 |
| A0A084ZTW9 | A0A084ZTW9_9ENTR | 120 | LTEGL-IDDDKTLLQQLISTISNWKNDLLTPAQAAAQAKGERDRIFAHCYGLYDAHMKAC | 178 |
| A0A038CLT3 | A0A038CLT3_RAOOR | 120 | LTEGL-IDDDKVVLQQLISTISNWKNDLQTPAQAAAGAKGERERIFAHCYGLYDGHMKAC | 178 |
| Q8Z385 | Q8Z385_SALTI | 120 | LTEGL-IEDDKVLQQLISTISNWKNDLKTPAQAAAGAKGERDRIFAHCYGLYDAHMKAC | 178 |
| Q831X8 | Q831X8_SHIFL | 120 | LTEGL-IEDDKVLQQLISTISNWKNDLKTPSQAAASAIGERDRIFAHCYGLYDAHLKAC | 178 |
| A0A0D5WYP4 | A0A0D5WYP4_9ENTR | 120 | LTEGL-LENDKVLQQLISTISNWKNGLLSPAQAAAQAKGERDRIFAHCYGLYDTHLKSC | 178 |
| A0A0H3FM31 | A0A0H3FM31_ENTAK | 120 | LTEGL-IEDDKVVLQQLISTISNWKNDLMTPAQAAAGAKGERDRIFAHCYGLYDAHMKAC | 178 |
| A0A0H2WUK6 | A0A0H2WUK6_SALPA | 120 | LTEGL-IEDDKVLQQLISTISNWKNDLKTPAQAAAGAKGERDRIFAHCYGLYDAHMKAC | 178 |
| A0A0H3H1F3 | A0A0H3H1F3_KLEOK | 120 | LTEGL-IEDDKVVLQQLISTISNWKNDLQTPAQAAAGAKGERDRIFAHCYGLYDAHMKAC | 178 |
| X7I146 | X7I146_CITFR | 120 | LTEGL-IEDDKLILQQLISTISNWKNDLMTPAQAAAGAKGERDRIFAHCYGLYDAHMKAC | 178 |
| A0A0H3CTF5 | A0A0H3CTF5_ENTCC | 120 | LTEGL-IEDDKVLQQLISTISNWKNDLMTPAQAAAGAKGERDRIFAHCYGLYDAHMKAC | 178 |
| D2TH67 | D2TH67_CITRI | 120 | LTEGL-LEEDKVLQQLISTISNWKNDLQTPAQAAAGAKGERDRIFAHCYGLYDAHLKAC | 178 |
| Q329V6 | Q329V6_SHIDS | 120 | LTEGL-IEDDKVLQQLISTISNWKNDLKTPAQAAAEAKGERDRIFAHCYGLYDAHMKAC | 178 |
| W6J7C4 | W6J7C4_9ENTR | 120 | LTEGL-IDDDKVVLQQLISTISNWKNDLLTPPQAAARANGERDRIFAHCYGLYDAHMKAC | 178 |
| I2BE87 | I2BE87_SHIBC | 120 | LTEGL-LENDKVIYQQLISTISNWKNDLMGPDQAAAMARGERDRIFAHCYRLYYDHLKAC | 178 |
| B5EZ38 | B5EZ38_SALA4 | 120 | LTEGL-IEDDKVLQQLISTISNWKNDLKTPAQAAAGAKGERDRIFAHCYGLYDAHMKAC | 178 |
| A0A0F5SGU2 | A0A0F5SGU2_CITAM | 120 | LTEGL-IEDDKLILQQLISTISNWKNDLMTPAQAAAQAKGERDRIFAHCYGLYDAHMKAC | 178 |
| G9YY11 | G9YY11_9ENTR | 120 | LTEGL-LENDKVLQQLISTISNWKNDLMTPAQAAAQAKGERDRIFAHCYSLYDAHMKAC | 178 |
| A0A090UXU3 | A0A090UXU3_9ENTR | 120 | LTEGL-IEDDKLILQQLISTISNWKNDLMTPAQAAAQAKGERDRIFAHCYGLYDAHMKAC | 178 |
| A9MJ31 | A9MJ31_SALAR | 120 | LTEGL-IDDDKVVLQQLISTISNWKNDLKTPAQAAAGAKGERDRIFAHCYGLYDAHMKAC | 178 |
| Q3YV16 | Q3YV16_SHISS | 120 | LTEGL-IEDDKVLQQLISTISNWKNDLKTPSQAAASAIGERDRIFAHCYGLYDAHLKAC | 178 |
| D3RHB6 | D3RHB6_KLEVT | 120 | LTEGL-IEDDKVVLQQLISTISNWKNDLKTPAQAAAGAKGERDRIFAHCYGLYDAHMKAC | 178 |
| Q57HT8 | Q57HT8_SALCH | 153 | LTEGL-IEDDKVLQQLISTISNWKNDLKTPAQAAAGAKGERDRIFAHCYGLYDAHMKAC | 211 |
| B5RFS5 | B5RFS5_SALG2 | 120 | LTEGL-IEDDKVLQQLISTISNWKNDLKTPAQAAAGAKGERDRIFAHCYGLYDAHMKAC | 178 |
| A0A089 | A0A089Q204_9ENTR | 120 | LTEGL-LENDKVLQQLISTISNWKNGLLSPAQAAAQAKGERDRIFAHCYGLYDTHLKSC | 178 |
| A0A0H3BNR1 | A0A0H3BNR1_SALNS | 120 | LTEGL-IEDDKVLQQLISTISNWKNDLKTPAQAAAGAKGERDRIFAHCYGLYDAHMKAC | 178 |
| C9Y4T0 | C9Y4T0_SICTZ | 120 | LTEGL-VENDKVLQQLISTISNWKNDLLSPPQAAARAIGERERIFAHCYSLYDAHLKAC | 178 |
| B7LU77 | B7LU77_ESCF3 | 120 | LTEGL-IEDDKVLQQLISTISNWKNDLKTPAQAAAEAKGERDRIFAHCYGLYDSHLKAC | 178 |
| A0A0H3TAW8 | A0A0H3TAW8_SALEN | 120 | LTEGL-IEDDKVVLQQLISTISNWKNDLKTPAQAAAGAKGERDRIFAHCYGLYDAHMKAC | 178 |
| G2S5J6 | G2S5J6_ENTAL | 120 | LTEGL-IEDDKVLQQLISTISNWKNDLMTPAQAAAGAKGERDRIFAHCYSLYDAHMKAC | 178 |
| A0A0F7JC30 | A0A0F7JC30_SALET | 120 | LTEGL-IEDDKVLQQLISTISNWKNDLKTPAQAAAGAKGERDRIFAHCYGLYDAHMKAC | 178 |
| A7MQI4 | A7MQI4_CROS8 | 120 | LTEGL-VENDKVLQQLISTISNWKNDLLSPPQAAARAIGERERIFAHCYSLYDAHLKAC | 178 |
| L0M8J0 | L0M8J0_ENTBF | 120 | LTEGL-IEDDKVQLQQLISTISNWKNDLKSPAQAAAGAKGERDRIFAHCYGLYDAHMKAC | 178 |
| A0A0K0HFU2 | A0A0K0HFU2_SALBC | 120 | LTEGL-IEDDKILQQLISTISNWKNDLKTPAQAAAGAKGERDRIFAHCYGLYDAHMKAC | 178 |
| A8ACT1 | A8ACT1_CITK8 | 120 | LTDGL-IEDDKVILQQLISTISNWKNDLMTPAQAAAGAKGERDRIFAHCYGLYDAHLKAC | 178 |

*Fig. 9C*

Domain 2B
Target Residues

```
P09980          REP_ECOLI           359  EKFLMQNRIPYKISGGTSFFSRPEIKDLI AYLRVLTNPDDDSAF LRIVNTPKREIGPATL  418
O51889          REP_BUCAP           359  EKTFLKKNIPYDISTNSSFPSRPEIKDLL SYLRLIVNPDDNHAF IRILNIPHRQIGLTTL  418
P57654          REP_BUCAI           359  EKALIKENIPYNISEKSSFPSRPEIKDLL SYLRVINRDDNHAF MRIVNIPSRQIGKTTL  418
P44804          REP_HAEIN           359  EKVLMQNRIPYKISGGTSFFSRAEIKDMM AYLRLVVNQDDDAAF LRIVNTPKREIGTATL  418
Q9L6S1          REP_SALTY           359  EKFLMQNRIPYKISGGTSFFSRPEIKDLL AYLRVLTNPDDDSAF LRIVNTPKREIGPATL  418
A0A077ZIR6      A0A077ZIR6_TRITR    376  EKFLMQNRIPYKISGGTSFFSRPEIKDLI AYLRVLTNPDDDSAF LRIVNTPKREIGPATL  435
S3IEG5          S3IEG5_9ENTR        359  EKMLMQNRIPYHISGGTSFFSRPEIKDLI AYLRVLTNPDDDSAF LRIVNTPKREIGPATL  418
J1R585          J1R585_9ENTR        359  EKFLMQNRIPYKISGGTSFFSRPEIKDLI AYLRVLTNTEDDSAF LRIVNTPKREIGSATL  418
K8ABZ8          K8ABZ8_9ENTR        340  EKMLMQNRIPYRISGGTSFFSRPEIKDLI AYLRVLTNPDDDSAF LRIVNTPKREIGPATL  399
A0A060VJ9       A0A060VJ9_KLEPN     420  EKMLMQNRIPYKISGGTSFFSRPEIKDLI AYLRVLTNPDDDSAF LRIVNTPKREIGPATL  479
A0A090V5M6      A0A090V5M6_ESCVU    359  EKFLMQNRIPYRISGGTSFFSRPEIKDLI AYLRVLTNPDDDSAF LRIVNTPKREIGPATL  418
A0A083YZC2      A0A083YZC2_CITAM    359  EKFLMQNRIPYKISGGTSFFSRPEIKDLI AYLRVLTNPDDDSAF LRIVNTPKREIGPATL  418
A0A0J6D7T8      A0A0J6D7T8_SALDE    359  EKFLMQNRIPYKISGGTSFFSRLEIKDLI AYLRVLTNPDDDSAF LRIVNTPKREIGPATL  418
A0A085ITL8      A0A085ITL8_RAOPL    359  EKMLMQNRIPYKISGGTSFFSRPEIKDLI AYLRVLTNPDDDSAF LRIVNTPKREIGPATL  418
E7T4Q1          E7T4Q1_SHIBO        359  EKFLMQNRIPYKISGGTSFFSRPEIKDLI AYLRVLTNPDDDSAF LRIVNTPKREIGPATL  418
A0A085GMM2      A0A085GMM2_9ENTR    359  EKMLMQNRIPYRISGGTSFFSRPEIKDLI AYLRVLTNPDDDSAF MRIVNTPKREIGSATL  418
A0A085HAK1      A0A085HAK1_9ENTR    340  EKMLMQNRIPYKISGGTSFFSRPEIKDLI AYLRVLTNPDDDSAF LRIVNTPKREIGPATL  399
D4BE16          D4BE16_9ENTR        359  EKFLMQNRIPYKISGGTSFFSRPEIKDLI AYLRVLSNPDDDSAF LRIVNTPKREIGSATL  418
A0A0H5PMJ7      A0A0H5PMJ7_SALSE    359  EKFLMQNRIPYKISGGTSFFSRPEIKDLI AYLRVLTNPDDDSAF LRIVNTPKREIGPATL  418
A0A0J1JQT3      A0A0J1JQT3_CITFR    359  EKFLMQNRIPYKISGGTSFFSRPEIKDLI AYLRVLSNPDDDSAF LRIVNTPKREIGPATL  418
A0A0J8VI05      A0A0J8VI05_9ENTR    359  EKLLMQNRIPYRISGGTSFFSRPEIKDLI AYLRVLTNPDDDSAF LRIVNTPKREIGPATL  418
F5S3F4          F5S3F4_9ENTR        359  EKMLMQNRIPYKISGGTSFFSRPEIKDLI AYLRVLTNPDDDSAF LRIVNTPKREIGPATL  418
D2ZMA5          D2ZMA5_9ENTR        359  EKMLMQNRIPYKISGGTSFFSRPEIKDLI AYLRVLTNPDDDSAF LRIVNTPKREIGPATL  418
A0A084ZTW9      A0A084ZTW9_9ENTR    359  EKMLMQNRIPYKISGGTSFFSRPEIKDLI AYLRVLTNPDDDSAF LRIVNTPKREIGPATL  418
A0A038CLT3      A0A038CLT3_RAOOR    359  EKFLMQNRIPYKISGGTSFFSRPEIKDLI AYLRVLTNPDDDSAF LRIVNTPKREIGPATL  418
Q8Z385          Q8Z385_SALTI        359  EKFLMQNRIPYKISGGTSFFSRPEIKDLI AYLRVLTNPDDDSAF LRIVNTPKREIGPATL  418
Q83IX8          Q83IX8_SHIFL        359  EKFLMQNRIPYKISGGTSFFSRPEIKDLI AYLRVLTNPDDDSAF LRIVNTPKREIGPATL  418
A0A0D5WYP4      A0A0D5WYP4_9ENTR    359  EKMLMQNRIPYRISGGTSFFSRPEIKDLI AYLRVLTNPDDDSAF LRIVNTPKREIGPATL  418
A0A0H3FM31      A0A0H3FM31_ENTAK    359  EKMLMQNRIPYKISGGTSFFSRPEIKDLI AYLRVLTNPDDDSAF LRIVNTPKREIGPATL  418
A0A0H2WUK6      A0A0H2WUK6_SALPA    359  EKFLMQNRIPYKISGGTSFFSRPEIKDLI AYLRVLTNPDDDSAF LRIVNTPKREIGPATL  418
A0A0H3H1F3      A0A0H3H1F3_KLEOK    359  EKMLMQNRIPYKISGGTSFFSRPEIKDLI AYLRVLTNPDDDSAF MRIVNTPKREIGSATL  418
X71146          X71146_CITFR        359  EKFLMQNRIPYKISGGTSFFSRPEIKDLI AYLRVLSNPDDDSAF LRIVNTPKREIGPATL  418
A0A0H3CTF5      A0A0H3CTF5_ENTCC    359  EKMLMQNRIPYKISGGTSFFSRPEIKDLI AYLRVLTNPDDDSAF LRIVNTPKREIGPATL  418
D2TH67          D2TH67_CITRI        359  EKFLMQNRIPYKISGGTSFFSRPEIKDLI AYLRVLTNPDDDSAF LRIVNTPKREIGPATL  418
Q329V6          Q329V6_SHIDS        359  EKFLMQNRIPYKISGGTSFFSRPEIKDLI AYLRVLTNPDDDSAF LRIVNTPKREIGPATL  418
W6J7C4          W6J7C4_9ENTR        359  EKFLMQNRIPYKISGGTSFFSRPEIKDLI AYLRVLTNTDDDSAF LRIVNTPKREIGSATL  418
I2BE87          I2BE87_SHIBC        359  EKMLMQNRIPYKISGGTSFFSRPEIKDLI AYLRVLTNPDDDSAF LRIVNTPRREIGPATL  418
B5EZ38          B5EZ38_SALA4        359  EKFLMQNRIPYKISGGTSFFSRPEIKDLI AYLRVLTNPDDDSAF LRIVNTPKREIGPATL  418
A0A0F5SGU2      A0A0F5SGU2_CITAM    359  EKFLMQNRIPYKISGGTSFFSRPEIKDLI AYLRVLSNPDDDSAF LRIVNTPKREIGPATL  418
G9YY11          G9YY11_9ENTR        359  EKMLMQNRIPYKISGGTSFFSRPEIKDLI AYLRVLTNPDDDSAF LRIVNTPKREIGPATL  418
A0A090UXU3      A0A090UXU3_9ENTR    359  EKMLMQNRIPYKISGGTSFFSRPEIKDLI AYLRVLSNPDDDSAF LRIVNTPKREIGPATL  418
A9MJ31          A9MJ31_SALAR        359  EKFLMQNRIPYKISGGTSFFSRPEIKDLI AYLRVLTNPDDDSAF LRIVNTPKREIGSATL  418
Q3YV16          Q3YV16_SHISS        359  EKFLMQNRIPYKISGGTSFFSRPEIKDLI AYLRVLTNPDDDSAF LRIVNTPKREIGPATL  418
D3RHB6          D3RHB6_KLEVT        359  EKMLMQNRIPYKISGGTSFFSRPEIKDLI AYLRVLTNPDDDSAF LRIVNTPKREIGPATL  418
Q57HT8          Q57HT8_SALCH        392  EKFLMQNRIPYKISGGTSFFSRPEIKDLI AYLRVLTNPDDDSAF LRIVNTPKREIGPATL  451
B5RFS5          B5RFS5_SALG2        359  EKFLMQNRIPYKISGGTSFFSRPEIKDLI AYLRVLTNPDDDSAF LRIVNTPKREIGPATL  41
A0A089Q204      A0A089Q204_9ENTR    359  EKMLMQNRIPYRISGGTSFFSRPEIKDLI AYLRVLTNPDDDSAF LRIVNTPKREIGPATL  418
A0A0H3BNR1      A0A0H3BNR1_SALNS    359  EKFLMQNRIPYKISGGTSFFSRPEIKDLI AYLRVLTNPDDDSAF LRIVNTPKREIGPATL  418
C9Y4T0          C9Y4T0_SICTZ        359  EKMLMQNRIPYRISGGTSFFSRPEIKDLI AYLRVLTNPDDDSAF LRIVNTPKREIGPATL  418
B7LU77          B7LU77_ESCF3        359  EKFLMQNRIPYKISGGTSFFSRPEIKDLI AYLRVLTNPDDDSAF LRIVNTPKREIGPATL  418
A0A0H3TAW8      A0A0H3TAW8_SALEN    359  EKFLMQNRIPYKISGGTSFFSRPEIKDLI AYLRVLTNPDDDSAF LRIVNTPKREIGPATL  418
G2S5J6          G2S5J6_ENTAL        359  EKMLMQNRIPYKISGGTSFFSRPEIKDLI AYLRVLTNPDDDSAF LRIVNTPKREIGPATL  418
A0A0F7JC30      A0A0F7JC30_SALET    359  EKFLMQNRIPYKISGGTSFFSRPEIKDLI AYLRVLTNPDDDSAF LRIVNTPKREIGPATL  418
A7MQ14          A7MQ14_CROS8        359  EKMLMQNRIPYRISGGTSFFSRPEIKDLI AYLRVLTNPDDDSAF LRIVNTPKREIGPATL  418
L0M8J0          L0M8J0_ENTBF        359  EKFLMQNRIPYKISGGTSFFSRPEIKDLI AYLRVLTNPDDDSAF LRIVNTPKREIGAATM  418
A0A0K0HFU2      A0A0K0HFU2_SALBC    359  EKFLMQNRIPYKISGGTSFFSRPEIKDLI AYLRVLTNPDDDSAF LRIVNTPKREIGPATL  418
A8ACT1          A8ACT1_CITK8        359  EKFLMQNRIPYKISGGTSFFSRPEIKDLI AYLRVLTNPDDDSAF LRIVNTPKREIGPATL  418
```

*Fig. 9D*

**Domain 2B
Target Residues**

| | | | | |
|---|---|---|---|---|
| P09980 | REP_ECOLI | 419 | KKLGEWAMTRNKSMFTASFDMGLSQTLSGRGYEALTRFTHWLAEIQRLAEREPIAAVRD | 477 |
| O51889 | REP_BUCAP | 419 | NKLEELASKKNKSLFQISNDIEIKKTILRERTVKKTKDFIYWIKKTTK-LSLLKEDIILDK | 477 |
| P57654 | REP_BUCAI | 419 | KKIEEWANKKHVSLFQASNNIEIKKFLNENTIKKIKNFISKIEKFTA-WSCLKPSNIIDD | 477 |
| P44804 | REP_HAEIN | 419 | QKIGELAQEKHISLFEAIFEFELIQRITPKAYDSLQKFGRWIVELNDEIQRSEPERAVRS | 478 |
| Q9L6S1 | REP_SALTY | 419 | QKIGEWAMTRNKSLFTASFDMGLSQKLTGRGYDSLTRFTHWLGEIQR-LAEREPVAAVRD | 477 |
| A0A077ZIR6 | A0A077ZIR6_TRITR | 436 | KKLGEWAMTRNKSMFTASFDMGLSQTLSGRGYEALTRFTHWLAEIQR-LAEREPIAAVRD | 494 |
| S3IEG5 | S3IEG5_9ENTR | 419 | QKIGEWATQRNKSLLTASFDMGLSQTLSGRGLESLQRFTHWLREVAT-LAEREPVAAVRD | 477 |
| J1R585 | J1R585_9ENTR | 419 | QKIGEWAMLRNKSLFAASFDVGLNQTLTGRGYESLTRFQWLGDVQQ-LSEREPIAAVRD | 477 |
| K8ABZ8 | K8ABZ8_9ENTR | 400 | QKIGEWATQRNKSLFTASFDMGLSQSLTGRGYESLTRFQWLQEVAV-LSEREPVAAVRD | 458 |
| A0A060VJ91 | A0A060VJ91_KLEPN | 480 | QKIGEWAMGRNKGLFTASFDMGLSQTLTGRGYESLTRFTHWLREIQQ-LAEREPVNAVRD | 538 |
| A0A090V5M6 | A0A090V5M6_ESCVU | 419 | QKIGEWANSRNKGLFAASFDMGLTQTLSGRGYESLTRFTHWLSEVQR-LSEREPIAAVRD | 477 |
| A9A083YZC2 | A0A083YZC2_CITAM | 419 | QKIGEWAMTRNKSLFTASFDLGLSQTLTGRGYDSLTRFTHWLGEVQR-LAEREPIAAVRD | 477 |
| A0A0J6D7T8 | A0A0J6D7T8_SALDE | 419 | QKIGEWAMTRNKSLFTASFDMGLSQKLTGRGYDSLTRFTHWLGEIQR-LAEREPVAAVRD | 477 |
| A0A085ITL8 | A0A085ITL8_RAOPL | 419 | QKIGEWAMTRNKSLFTASFDMGLNQTLTGRGYDALTGFTQWLADIQR-LAEREPVAAVRD | 477 |
| E7T4Q1 | E7T4Q1_SHIBO | 419 | KKLGEWAMTRNKSMFTASFDMGLSQTLSGRGYEALTRFTHWLAEIQR-LAEREPIAAVRD | 477 |
| A0A085GMM2 | A0A085GMM2_9ENTR | 419 | QKIGAWAMQRNKGLFLSSFDMGLSQTLSGRGLESLQRFTHWLREVAT-LAEREPVAAVRD | 477 |
| A0A085HAK1 | A0A085HAK1_9ENTR | 400 | QKIGEWAMTRNKSLLTASFDMGLSHTLTGRGYESLTRFTHWLREIQQ-LSEREPIAAVRD | 458 |
| D4BE16 | D4BE16_9ENTR | 419 | QKIGEWAMTRNKSLFTASFDMGLSQTLTGRGYDSLTRFTHWLGEIQR-LAEREPVAAVRD | 477 |
| A0A0H5PMJ7 | A0A0H5PMJ7_SALSE | 419 | QKIGEWAMTRNKSLFTASFDMGLSQKLTGRGYDSLTRFTHWLGEIQR-LAERE PVAAVRD | 477 |
| A0A0J1JQT3 | A0A0J1JQT3_CITFR | 419 | QKIGEWAMTRNKSLFTASFDMGLSQTLTGRGYDSLTRFTHWLGEIQR-LAEREPVAAVRD | 477 |
| A0A0J8VI05 | A0A0J8VI05_9ENTR | 419 | QKIGEWAMSRNKSLFTASFDMGLSQTLTGRGYDSLTRFTHWLGEVAR-LSEREPVAAVRD | 477 |
| F5S3F4 | F5S3F4_9ENTR | 419 | QKIGEWAMTRNKSLFTASFDMGLSQTLTGRGYDALTRFTHWLGEVQR-LAEREPVAAVRD | 477 |
| D2ZMA5 | D2ZMA5_9ENTR | 419 | QKIGEWAMTRSKSMFTASFDMGLSQTLTGRGYDNLTRFTHWLGEVQR-LAEREPVAAVRD | 477 |
| A0A084ZTW9 | A0A084ZTW9_9ENTR | 419 | QKIGEWASTRNKSLFTASFDVGLTQTLSGRGYDALTRFTHWLGEIQR-LSEREPVAAVRD | 477 |
| A0A038CLT3 | A0A038CLT3_RAOOR | 419 | QKIGEWAMTRNKSLFTASFDMGLNQTLTGRGYDALTGFTQWLADIQR-LAEREPVAAVRD | 477 |
| Q8Z385 | Q8Z385_SALTI | 419 | QKIGEWAMTRNKSLFTASFDMGLSQKLTGRGYDSLTRFTHWLGEIQR-LAEREPVAAVRD | 477 |
| Q831X8 | Q831X8_SHIFL | 419 | KKLGEWAMTRNKSMFTASFDMGLSQTLSGRGYEALTRFTHWLAEIQR-LAEREPIAAVRD | 477 |
| A0A0D5WYP4 | A0A0D5WYP4_9ENTR | 419 | QKIGEWAMQRNKGLFTASFDMGLSQTLSGRGLDALQRFTHWLRDVAT-LAEREPVAAVRD | 477 |
| A0A0H3FM31 | A0A0H3FM31_ENTAK | 419 | QKIGEWAMSRNKGLFTASFDMGLSQTLTGRGYESLTRFTHWLREIQQ-LAEREPVNAVRD | 477 |
| A0A0H2WUK6 | A0A0H2WUK6_SALPA | 419 | QKIGEWAMTRNKSLFTASFDMGLSQKLTGRGYDSLTRFTHWLGEIQR-LAEREPVAAVRD | 477 |
| A9A0H3H1F3 | A0A0H3H1F3_KLEOK | 419 | KKLGEWAMGRNKSMFTASFDMGLTQTLNGRGYESLTRFTHWLREIQQ-LAEREPVAAVRD | 477 |
| X7I146 | X7I146_CITFR | 419 | QKIGEWAMTRNKSLFTASFDMGLSQTLTGRGYDSLTRFTHWLGEVQR-LAEREPVAAVRD | 477 |
| A0A0H3CTF5 | A0A0H3CTF5_ENTCC | 419 | QKIGEWAMTRNKSLFTASFDMGLSQTLTGRGYESLTRFTHWLGEVQR-LAEREPVAAVRD | 477 |
| D2TH67 | D2TH67_CITRI | 419 | QKIGEWAMTRNKSLFTASFDLGLAQTLTGRGYESLTRFTHWLGEVQR-LAEREPVAAVRD | 477 |
| Q329V6 | Q329V6_SHIDS | 419 | KKLGEWAMTRNKSMFTASFDMGLSQTLSGRGYEALTRFTHWLAEIQR-LAEREPIAAVRD | 477 |
| W6J7C4 | W6J7C4_9ENTR | 419 | QKIGEWAMLRNKSLFAASFDVGLNQTLTGRGYDALTRFTHWLGEVQR-LSEREPIAAVRD | 477 |
| I2BE87 | I2BE87_SHIBC | 419 | QKIGEWALQRNKSMFTASFDLGLSQTLTGRGYEALTRFTHWLGEVAR-LSEKEPVAAVRD | 477 |
| B5EZ38 | B5EZ38_SALA4 | 419 | QKIGEWAMTRNKSLFTASFDMGLSQKLTGRGYDSLTRFTHWLGEIQR-LAEREPVAAVRD | 477 |
| A0A0F5SGU2 | A0A0F5SGU2_CITAM | 419 | QKIGEWAMTRNKSLFTASFDMGLSQTLTGRGYDSLTRFTHWLGDIQR-LAEREPVAAVRD | 477 |
| G9YY11 | G9YY11_9ENTR | 419 | QKIGEWAMTRSKSMFTASFDMGLSHLLPGRGYESLTRFTHWLGEVQR-LSEREPIAAVRD | 477 |
| A0A090UXU3 | A0A090UXU3_9ENTR | 419 | QKIGEWAMTRNKSLFTASFDMGLSQTLTGRGYESLTRFTHWLGEIQR-LAEREPVAAVRD | 477 |
| A9MJ31 | A9MJ31_SALAR | 419 | QKIGEWAMTRNKSLFTASFDMGLSQKLTGRGYDSLTRFTHWLGEIQR-LAEREPVAAVRD | 477 |
| Q3YVI6 | Q3YVI6_SHISS | 419 | KKLGEWAMTRNKSMFTASFDMGLSQTLSGRGYEALTRFTHWLAEIQR-LAEREPIAAVRD | 477 |
| D3RHB6 | D3RHB6_KLEVT | 419 | QKIGEWAMGRNKGLFTASFDMGLSQTLTGRGYESLTRFTHWLREIQQ-LAEREPVNAVRD | 477 |
| Q57HT8 | Q57HT8_SALCH | 452 | QKIGEWAMTRNKSLFTASFDMGLSQKLTGRGYDSLTRFTHWLGEIQR-LAEREPVAAVRD | 510 |
| B5RFS5 | B5RFS5_SALG2 | 419 | QKIGEWAMTRNKSLFTASFDMGLSQKLTGRGYDSLTRFTHWLGEIQR-LAEREPVAAVRD | 477 |
| A0A089Q204 | A0A089Q204_9ENTR | 419 | QKIGEWAMQRNKGLFTASFDMGLSQTLSGRGLDSLQRFTHWLRDVAT-LAEREPVAAVRD | 477 |
| A0A0H3BNR1 | A0A0H3BNR1_SALNS | 419 | QKIGEWAMTRNKSLFTASFDMGLSQKLTGRGYDSLTRFTHWLGEIQR-LAEREPVAAVRD | 477 |
| C9Y4T0 | C9Y4T0_SICTZ | 419 | QKIGEWANQRNKSLPTASFDMGLAQTSGRGYESLTRFTSWLQDVAV-LSEREPVAAVRD | 477 |
| B7LU77 | B7LU77_ESCF3 | 419 | KKLGEWAMTRNKSMFTASFDMGLSQTLSGRGYEALTRFTHWLAEIQR-LAEREPIAAVRD | 477 |
| A0A0H3TAW8 | A0A0H3TAW8_SALEN | 419 | QKIGEWAMTRNKSLFTASFDMGLSQKLTGRGYDSLTRFTHWLGEIQR-LAEREPVAAVRD | 477 |
| G2S5J6 | G2S5J6_ENTAL | 419 | QKIGEWAMTRNKSLFTASFDMGLSQTLTGRGYDSLTRFTHWLGEVQR-LAEREPVAAVRD | 477 |
| A0A0F7JC30 | A0A0F7JC30_SALET | 419 | QKIGEWAMTRNKSLFTASFDMGLSQKLTGRGYDSLTRFTHWLGEIQR-LAEREPVAAVRD | 477 |
| A7MQI4 | A7MQI4_CROS8 | 419 | QKIGEWANQRNKSLFTASFDMGLAQTLTGRGYESLTRFTSWLQEVAV-LSEREPVAAVRD | 477 |
| L0M8J0 | L0M8J0_ENTBF | 419 | QKIGEWAMTRNKSLFAASFDMGLTQTLSGRGYESLTRFQWLAEVQR-LSEREPIAAVRD | 477 |
| A0A0K0HPU2 | A0A0K0HPU2_SALBC | 419 | QKIGEWAMTRSKSLFTASFDMGLSQTLTGRGYDALTRFTHWLAEIQR-LAEREPVAAVRD | 477 |
| A8ACT1 | A8ACT1_CITK8 | 419 | QKIGEWAMTRNKSLFTASFDVGLNQTLTGRGYDSLTRFTHWLGEIQR-LSEREPIAAVRD | 477 |

*Fig. 9E*

Domain 2B Target Residues

| Accession | Name | Start | Sequence | End |
|---|---|---|---|---|
| P09980 | REP_ECOLI | 478 | LIHGMDYESWLYETSPSPKAAEMRMKNVNQLFSWMTEMLEGSELDEPMTLTQVVTRFTLR | 537 |
| O51889 | REP_BUCAP | 478 | IINDIKYELWLTKILKEPKKIKTSINNIYTLSNWLKEMLRQNEFEKPMNLLQIVKKMTLR | 537 |
| P57654 | REP_BUCAI | 478 | IVDDLEYEKWLSKFLKDPNKIKNSINNVHTLSQWFKNMLKQDDFEKPMTLPQIVTRMTIR | 537 |
| P44804 | REP_HAEIN | 479 | MLSAIHYEEYLYEYATSPKAAEMQSKNVATLFDWVADMLKQDETNEPMNLNQVVTRLTLR | 538 |
| Q9L6S1 | REP_SALTY | 478 | LIHGIDYESWLYETSPSPKAAEMRMKNVNQLFSWMTEMLEGNELDEPMTLTQVVTRFTLR | 537 |
| A0A077ZIR6 | A0A077ZIR6_TRITR | 495 | LIHGMDYESWLYETSPSPKAAEMRMKNVNQLFSWMTEMLEGSELDEPMTLTQVVTRFTLR | 554 |
| S3IEG5 | S3IEG5_9ENTR | 478 | LIHGIDYESWLYETSPSPKAAEMRMKNVNQLFSWMTEMLEASDLDEPMTLVQVVTRFTLR | 537 |
| J1R585 | J1R585_9ENTR | 478 | LIHGIDYESWLFETSPSPKAAEMRMKNVNTLFGWMTEMLEGSELDEPMTLAEVVTRFTLR | 537 |
| K8ABZ8 | K8ABZ8_9ENTR | 459 | LIRGIDYEAWLFETSPSPKAAEMRMKNVNQLFSWMTEMLEGTDLDEPMTLTQVVTRFTLR | 518 |
| A0A060VJ91 | A0A060VJ91_KLEPN | 539 | LIRGIDYESWLYETSPSPKAAEMRMKNVNQLFTWMTEMLEGSEIDEPMTLTQVVTRFTLR | 598 |
| A0A090V5M6 | A0A090V5M6_ESCVU | 478 | LIHGIDYESWLFETSPSPKAAEMRMKNVNTLFSWMTEMLEGSEIDEPMTLTQVVTRFTLR | 537 |
| A0A083YZC2 | A0A083YZC2_CITAM | 478 | LIHGIDYESWLYETSPSPKAAEMRMKNVNQLFSWMTEMLEGSELDEPMTLTQVVSRFTLR | 537 |
| A0A0J6D7T8 | A0A0J6D7T8_SALDE | 478 | LIHGIDYESWLYETSPSPKAAEMRMKNVNQLFSWMTEMLEGNELDEPMTLTQVVTRFTLR | 537 |
| A0A085ITL8 | A0A085ITL8_RAOP | 478 | LIRGVDYESWLYETSPSPKAAEMRMKNVNQLFSWMTEMLEGSDIDEPMTLTQVVTRFTLR | 537 |
| E7T4Q1 | E7T4Q1_SHIBO | 478 | LIHGMDYEFWLYETSPSPKAAEMRMKNVNQLFSWMTEMLEGSELDEPMTLTQVVTRFTLR | 537 |
| A0A085GMM2 | A0A085GMM2_9ENTR | 478 | LIHGIDYESWLYETSPSQKAAEMRMKNVNTLFSWMTEMLEGSEIDEPMTLTQVVTRFTLR | 537 |
| A0A085HAK1 | A0A085HAK1_9ENTR | 459 | LIRGIDYESWLYETSASPKAAEMRMKNVNQLFSWMTEMLEGSDIDEPMTLTQVVTRFTLR | 518 |
| D4BE16 | D4BE16_9ENTR | 478 | LIHGIDYESWLYETSPSPKAAEMRMKNVNTLFGWMTEMLEGSELEEPMTLTQVVTRFTLR | 537 |
| A0A0H5PMJ7 | A0A0H5PMJ7_SALSE | 478 | LIHGIDYESWLYETSPSPKAAEMRMKNVNQLFSWMTEMLEGNELDEPMTLTQVVTRFTLR | 537 |
| A0A0J1JQT3 | A0A0J1JQT3_CITFR | 478 | LIHGIDYESWLYETSPSPKAAEMRMKNVNTLFSWMTEMLEGSELEEPMTLTQVVTRFTLR | 537 |
| A0A0J8VI05 | A0A0J8VI05_9ENTR | 478 | LIHGIDYEAWLYETSPSQKAAEMRMKNVNQLFSWMTEMLEGTELDEPMTLTQVVTRFTLR | 537 |
| F5S3F4 | F5S3F4_9ENTR | 478 | LIHGIDYESWLYETSASPKAAEMRMKNVNQLFSWMTEMLEGSEIDEPMTLTQVVTRFTLR | 537 |
| D2ZMA5 | D2ZMA5_9ENTR | 478 | LIHGIDYESWLYETSASPKAAEMRMKNVNQLFSWMTEMLEGSEIDEPMTLTQVVTRFTLR | 537 |
| A0A084ZTW9 | A0A084ZTW9_9ENTR | 478 | LIHGIDYESWLFETSPSPKAAEMRMKNVNQLFSWMTEMLEGSELDEPMTLTQVVTRFTLR | 537 |
| A0A038CLT3 | A0A038CLT3_RAOOR | 478 | LIRGVDYESWLYETSPSPKAAEMRMKNVNQLFSWMTEMLEGSDIDEPMTLTQVVTRFTLR | 537 |
| Q8Z385 | Q8Z385_SALTI | 478 | LIHGIDYESWLYETSPSPKAAEMRMKNVNQLFSWMTEMLEGNELDEPMTLTQVVTRFTLR | 537 |
| Q831X8 | Q831X8_SHIFL | 478 | LIHGMDYESWLYETSPSTKAAEMRMKNVNQLFSWMTEMLEGSELDEPMTLTQVVTRFTLR | 537 |
| A0A0D5WYP4 | A0A0D5WYP4_9ENTR | 478 | LIHGIDYESWLYETSPSPKAAEMRMKNVNQLFSWMTEMLEGSDLDEPMTLTQVVTRFTLR | 537 |
| A0A0H3PM31 | A0A0H3PM31_ENTAK | 478 | LIRGIDYESWLYETSPSPKAAEMRMKNVNQLFTWMTEMLEGSEIDEPMTLTQVVTRFTLR | 537 |
| A0A0H2WUK6 | A0A0H2WUK6_SALPA | 478 | LIHGIDYESWLYETSPSPKAAEMRMKNVNQLFSWMTEMLEGNELDEPMTLTLVVTRFTLR | 537 |
| A0A0H3H1F3 | A0A0H3H1F3_KLEOK | 478 | LIRGVDYESWLYETSPSPKAAEMRMKNVNTLFTWMTEMLEGSEIDEPMTLTQVVTRFTLR | 537 |
| X7I146 | X7I146_CITFR | 478 | LIHGIDYESWLYETSPSPKAAEMRMKNVNTLFSWMTEMLEGSELEEPMTLTQVVTRFTLR | 537 |
| A0A0H3CTF5 | A0A0H3CTF5_ENTCC | 478 | LIHGIDYESWLYETSASPKAAEMRMKNVNQLFSWMTEMLEGSEIDEPMTLTQVVTRFTLR | 537 |
| D2TH67 | D2TH67_CITRI | 478 | LIHGIDYESWLYETSPSPKAAEMRMKNVNQLFSWMTEMLEGSELDEPMTLTQVVTRFTLR | 537 |
| Q329V6 | Q329V6_SHIDS | 478 | LIHGMDYESWLYETSPSPKAAEMRMKNVNQLFSWMTEMLEGSELDEPMTLTQVVTRFTLR | 537 |
| W6J7C4 | W6J7C4_9ENTR | 478 | LIHGIDYESWLFETSASPKAAEMRMKNVNTLFGWMTEMLEGSELDEPMTLAEVVTRFTLR | 537 |
| I2BE87 | I2BE87_SHIBC | 478 | LIHGIDYESWLFETSPSPKAAEMRMKNVNQLFTWMTEMLEGSDLDEPMTLTQVVTRFTLR | 537 |
| B5EZ38 | B5EZ38_SALA4 | 478 | LIHGIDYESWLYETSPSPKAAEMRMKNVNQLFSWMTEMLEGNELDEPMTLTQVVTRFTLR | 537 |
| A0A0F5SGU2 | A0A0F5SGU2_CITAM | 478 | LIHGIDYESWLYETSPSPKAAEMRMKNVNTLFSWMTEMLEGSELEEPMTLTQVVTRFTLR | 537 |
| G9YY11 | G9YY11_9ENTR | 478 | LIHGIDYESWLFETSPSPKAAEMRMKNVNQLFSWMTEMLEGSELEEPMTLTQVVTRFTLR | 537 |
| A0A090UXU3 | A0A090UXU3_9ENTR | 478 | LIHGIDYESWLYETSPSPKAAEMRMKNVNQLFSWMTEMLEGSEIDEPMTLTQVVTRFTLR | 537 |
| A9MJ31 | A9MJ31_SALAR | 478 | LIHGIDYESWLYETSPSPKAAEMRMKNVNQLFSWMTEMLEGNELNEPMTLTQVVTRFTLR | 537 |
| Q3YV16 | Q3YV16_SHISS | 478 | LIHGMDYESWLYETSPSPKAAEMRMKNVNQLFSWMTEMLEGSELDEPMTLTQVVTRFTLR | 537 |
| D3RHB6 | D3RHB6_KLEVT | 478 | LIRGIDYESWLYETSPSPKAAEMRMKNVNQLFTWMTEMLEGSEIDEPMTLTQVVTRFTLR | 537 |
| Q57HT8 | Q57HT8_SALCH | 511 | LIHGIYYESWLYETSPSPKAAEMRMKNVNQLFSWMTEMLEGNELDEPMTLTQVVTRFTLR | 570 |
| B5RFS5 | B5RFS5_SALG2 | 478 | LIHGIDYESWLYETSPSPKAAEMRMKNVNQLFSWMTEMLEGNELDEPMTLTQVVTRFTLR | 537 |
| A0A089Q204 | A0A089Q204_9ENTR | 478 | LIHGIDYESWLYETSPSPKAAEMRMKNVNQLFSWMTEMLEGSDLDEPMTLTQVVTRFTLR | 537 |
| A0A0H3BNR1 | A0A0H3BNR1_SALNS | 478 | LIHGIDYESWLYETSPSPKAAEMRMKNVNQLFSWMTEMLEGNELDEPMTLTQVVTRFTLR | 537 |
| C9Y4T0 | C9Y4T0_SICTZ | 478 | LIRGIDYEAWLFETSPSPKAAEMRMKNVNQLFSWMTEMLEGTDLDEPMTLTQVVTRFTLR | 537 |
| B7LU77 | B7LU77_ESCF3 | 478 | LIHGMDYESWLYETSPSPKAAEMRMKNVNQLFSWMTEMLEGSELDEPMTLTQVVTRFTLR | 537 |
| A0A0H3TAW8 | A0A0H3TAW8_SALEN | 478 | LIHGIDYESWLYETSPSPKAAEMRMKNVNQLFSWMTEMLEGNELDEPMTLTQVVTRFTLR | 537 |
| G2S5J6 | G2S5J6_ENTAL | 478 | LIHGIDYESWLYETSASPKAAEMRMKNVNQLFSWMTEMLEGSEIDEPMTLTQVVTRFTLR | 537 |
| A0A0F7JC30 | A0A0F7JC30_SALET | 478 | LIHGIDYESWLYETSPSPKAAEMRMKNVNQLFSWMTEMLEGNELDEPMTLTQVVTRFTLR | 537 |
| A7MQ14 | A7MQ14_CROS8 | 478 | LIRGIDYEAWLFETSPSPKAAEMRMKNVNQLFSWMTEMLEGTDLDEPMTLTQVVTRFTLR | 537 |
| L0M8J0 | L0M8J0_ENTBF | 478 | LIHGIDYESWLFETSASPKAAEMRMKNVNTLFGWMTEMLEGSEIDEPMTLTQVVTRFTLR | 537 |
| A0A0K0HFU2 | A0A0K0HFU2_SALBC | 478 | LIHGIDYESWLYETSPSPKAAEMRMKNVNQLFGWMTEMLEGSDIDEPMTLTQVVTRFTLR | 537 |
| A8ACT1 | A8ACT1_CITK8 | 478 | LIHGIDYESWLYETSPSPKAAEMRMKNVNQLFSWMTEMLEGNELDEPMTLTQVVTRFTLR | 537 |

*Fig. 9F*

Target Residues

```
Q9RTI9   Q9RTI9_DEIRA   61   LAVTFTNKAAAEMRERAGHLVPG--AGDLWMSTFHSAGVRILRTYGEHIGLRRGPVIYDD   118  ⎫
P03018   UVRD_ECOLI     58   MAVTFTNKAAAEMRHRIGQLMGTS-QGGMWVGTFHGLAHRLLRAHHMDANLPQDFQILDS   116  ⎪ Domain 1A
P56255   PCRA_GEOSE     60   LAITFTNKAAREMRERVQSLLGGA-AEDVWISTFHSMCVRILRRDIDRIGINRNFSTLDP   118  ⎪
P09980   REP_ECOLI      51   AAVTFTNKAAREMKERVGQTLGRKEARGLMISTFHTLGLDIIKREYAALGMKANPSLFDD   110  ⎭
                             *:******* **:.*       :        :.***   :::    :  *  : *

Q9RTI9   Q9RTI9_DEIRA   179  EAYRRYEVRKKGQNAIDFGDLITETVRLFKEVPGYLDKVQNKAKFIHVDEYQDTNRAQYE   238  ⎫
P03018   UVRD_ECOLI     172  KVYQAYQEACDRAGLVDFAELLLRAHELWLNKPHILQHYRERFTNILVDEFQDTNNIQYA   231  ⎪ Domain 1B
P56255   PCRA_GEOSE     175  DVYQEYQQRLLRHSLDFDDLMTTIQLFDRVPDVLHYYQYKFQYIHIDEYQDTNRAQYT   234  ⎪
P09980   REP_ECOLI      166  HCYGLYDAHLKACNVLDFDDLILLPTLLQRNEEVRKRWQNKIRYLLVDEYQDTNSQYE   225  ⎭
                              . * *:     :** :*:    *   ,  :  . ::   : :**:****  **

Q9RTI9   Q9RTI9_DEIRA   358  AILYRTNAQSRVIEESLRRVQIPARIVGGVGFYDRREIRDILAYARLALNPADDVALRRI   417  ⎫
P03018   UVRD_ECOLI     351  AILYRSNAQSRVLEEALLQASMPYRIYGGMRFFERQEIKDALSYLRLIANRNDDAAFERV   410  ⎪
P56255   PCRA_GEOSE     355  AVLYRTNAQSRVMEEMLLKANIPYQIVGGLKFYDRKEIKDILAYLRVIANPDDDLSLLRI   414  ⎪
P09980   REP_ECOLI      346  AILYRGNHQSRVFEKFLMQNRIPYKISGGTSFFSRPEIKDLLAYLRVLTNPDDDSAFLRI   405  ⎭
                             *:*** * *****:*  *  :   *  **  *  .  **:* ::*  *:  **  *:

Q9RTI9   Q9RTI9_DEIRA   418  IGRPRRGIGDTALQKIMEWARTHHTSVLTACANAAE-QNILDRGAHKATEFAGLMEAMSE   476  ⎫
P03018   UVRD_ECOLI     411  VNTPTRGIGDRTLDVVRQTSRDRQLTLWQACRELLQEKALAGRAASALQRFMELIDALAQ   470  ⎪
P56255   PCRA_GEOSE     415  INVPKRGIGASTIDKLVRYAADHELSLFEALGELEM-IGLCAKAAGALAAPRSQLEQWTQ   473  ⎪ Domain 2B
P09980   REP_ECOLI      406  VNTPKREIGPATLKKLGEWAMTRNKSMFTASFDMGLSQTLSGRGYEALTRFHWLAEIQR   465  ⎭
                             :  *  ::  :: *:    :   *,  :  *   ::  :  :     *  :  .

Q9RTI9   Q9RTI9_DEIRA   477  AADNYEPAAFLRFVMETSGYLDLLR----QEGQEGQVRLENLEELVSAAEEWSQLEANV-G   532  ⎫
P03018   UVRD_ECOLI     471  ETADMPLHVQTDRVIKDSGLRTM-YEQE-KGEKGQTRIENLEELVTATRQFSYNEEDEDL   528  ⎪
P56255   PCRA_GEOSE     474  LQEYVSVTELVEEVLDKSGYREM--LKAE-RTIEAQSRLENLDEFLSVTKHFENVSDDKSL   531  ⎪
P09980   REP_ECOLI      466  LAEREPIAAVRDL--HGMDYESWLYETSPSPKAAEMRMKNVNQLFSWMTEMLEGSELDEP   524  ⎭
                                                          ,:  *:*::*::.,:

Q9RTI9   Q9RTI9_DEIRA   533  GSIADFLDDAARLSSVDDMRTKAENKGAPEDAVTLMTLHNAKGLEFPVVFIVGVEQGLLP   592
P03018   UVRD_ECOLI     529  MPLQAFLSHAALEA-------GEG---QADTWQDAVQLMTLHSAKGLEFPQVFIVGMEEGMFP   581
P56255   PCRA_GEOSE     532  IAF----LTDLALISDLELDGT---EQAAEGDAVMLMTLHAAKGLEFPYVFLIGMEEGIFP   586
P09980   REP_ECOLI      525  MRLTQVVTRPTL---RDMMERG--ESEEELDQVQLMTLHASKGLEFPYVYMVGMEEGFLP   579
                             :    :*       :   :  * * ***** :*****  *::*:*:*
```

Fig. 9G

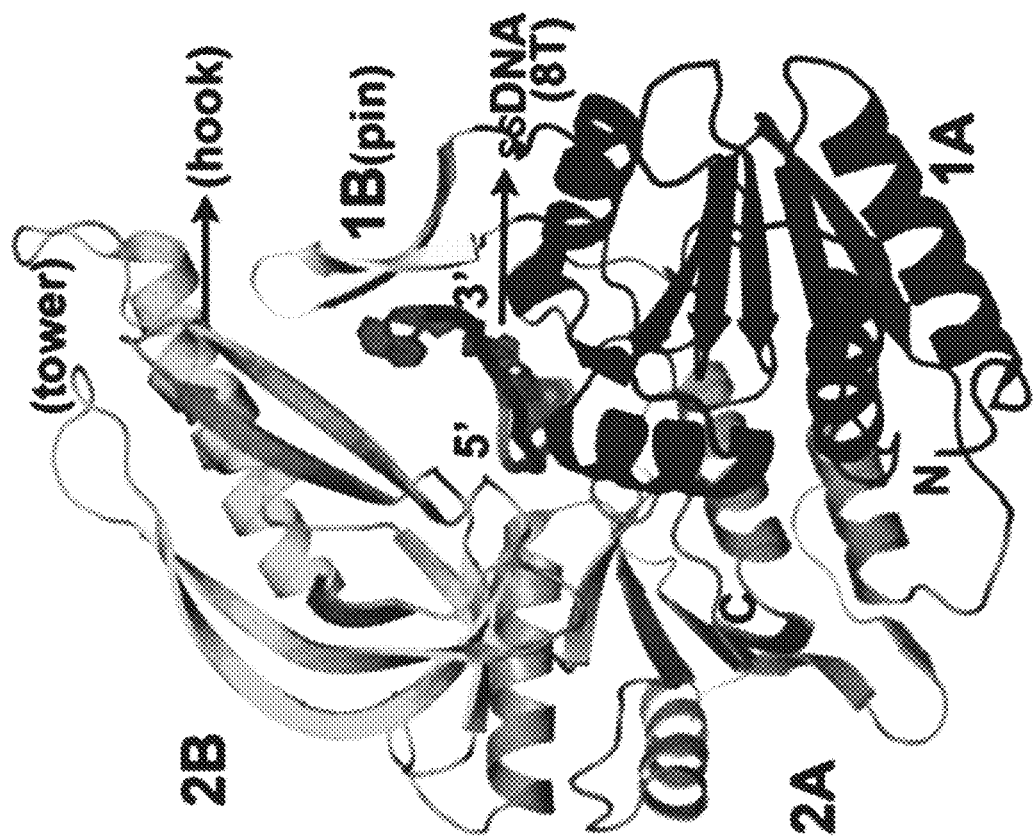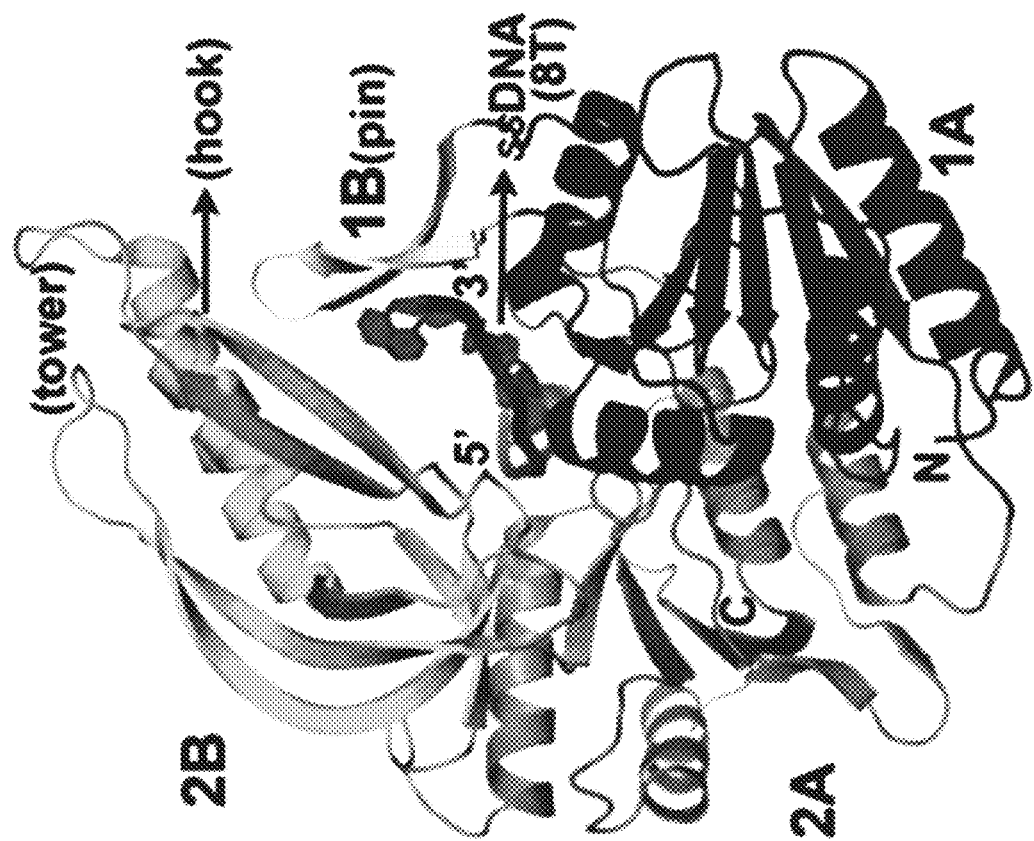
Fig. 16

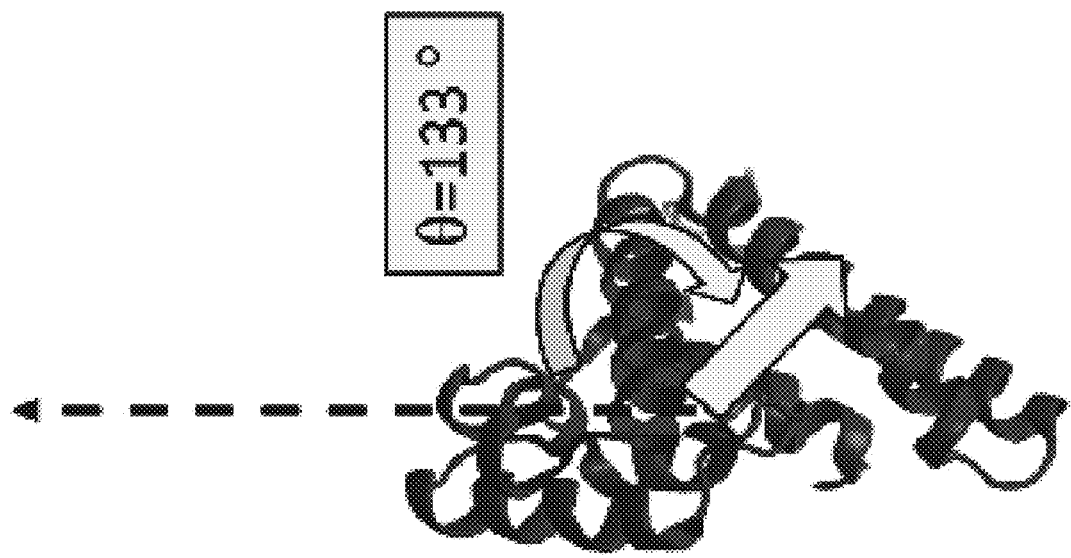
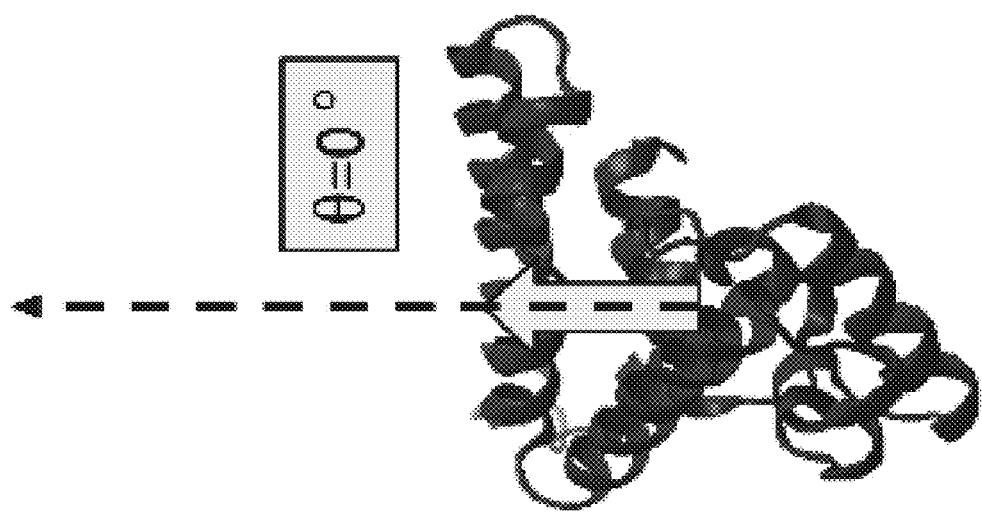
Fig. 17

BIO-ENGINEERED HYPER-FUNCTIONAL "SUPER" HELICASES

RELATED APPLICATIONS

This application is a continuation of U.S. patent application Ser. No. 15/526,905, filed May 15, 2017, which is a 35 U.S.C. § 371 of International Patent Application No. PCT/US2015/060693, filed Nov. 13, 2015, which claims the benefit of U.S. Provisional Application No. 62/079,183, filed Nov. 13, 2014, the disclosures of which are incorporated herein by reference in their entirety.

STATEMENT REGARDING FEDERALLY SPONSORED RESEARCH OR DEVELOPMENT

This invention was made with government support under GM065367 awarded by the National Institutes of Health. The United States Government has certain rights in the invention.

SEQUENCE LISTING

The instant application contains a Sequence Listing which has been submitted electronically in ASCII format and is hereby incorporated by reference in its entirety.

FIELD OF THE INVENTION

The present disclosure relates to compositions and methods for helicase-mediated DNA unwinding activity.

BACKGROUND

A traditional definition of a helicase is an enzyme that catalyzes the reaction of separating/unzipping/unwinding the helical structure of nucleic acid duplexes (DNA, RNA or hybrids) into single-stranded components, using nucleoside triphosphate (NTP) hydrolysis as the energy source (such as ATP). However, it should be noted that not all helicases fit this definition anymore. A more general definition is that they are motor proteins that move along the single-stranded or double stranded nucleic acids (usually in a certain direction, 3' to 5' or 5 to 3, or both), i.e. translocases, that can or cannot unwind the duplexed nucleic acid encountered. In addition, some helicases simply bind and "melt" the duplexed nucleic acid structure without an apparent translocase activity.

Helicases exist in all living organisms and function in all aspects of nucleic acid metabolism. Helicases are classified based on the amino acid sequences, directionality, oligomerization state and nucleic-acid type and structure preferences. The most common classification method was developed based on the presence of certain amino acid sequences, called motifs. According to this classification helicases are divided into 6 super families: SF1, SF2, SF3, SF4, SF5 and SF6. SF1 and SF2 helicases do not form a ring structure around the nucleic acid, whereas SF3 to SF6 do. Superfamily classification is not dependent on the classical taxonomy.

DNA helicases are responsible for catalyzing the unwinding of double-stranded DNA (dsDNA) molecules to their respective single-stranded nucleic acid (ssDNA) forms. Although structural and biochemical studies have shown how various helicases can translocate on ssDNA directionally, consuming one ATP per nucleotide, the mechanism of nucleic acid unwinding and how the unwinding activity is regulated remains unclear and controversial (T. M. Lohman, E. J. Tomko, C. G. Wu, "Non-hexameric DNA helicases and translocases: mechanisms and regulation," Nat Rev Mol Cell Biol 9:391-401 (2008)). Since helicases can potentially unwind all nucleic acids encountered, understanding how their unwinding activities are regulated can lead to harnessing helicase functions for biotechnology applications.

BRIEF SUMMARY OF THE INVENTION

The present invention is based on the discovery of novel modified helicases that show dramatically enhanced helicase activity and increased strength as compared to unmodified helicases. As described further herein, it has been surprisingly discovered that, by controlling the conformation of certain subdomains such that the helicase remains in a closed form (e.g., by covalently crosslinking the 2B domain to the 1A domain or the 1B domain in a Rep helicase), a highly active and strong form of the helicase is achieved.

In one aspect, a composition for catalyzing an unwinding reaction on double-stranded DNA is provided that includes a conformationally-constrained helicase.

In another aspect, a method of catalyzing an unwinding reaction of a double-stranded DNA is provided. The method includes the step of contacting the double-stranded DNA with a conformationally-constrained helicase in the presence of ATP.

In another aspect, an isolated nucleic acid that encodes a helicase polypeptide having the capability to be constrained in a conformation by an intramolecular crosslinking agent is provided.

In another aspect, a modified helicase comprising a first subdomain having a first amino acid and a second subdomain having a second amino acid is provided. Said first amino acid is at least about 30 Å from said second amino acid when the helicase is in an inactive conformation, and said first amino acid is less than about 20 Å from said second amino acid when the helicase is in an active conformation. A side chain of the first amino acid is covalently crosslinked to a side chain of the second amino acid with a linker to form an active, conformationally-constrained helicase.

In certain exemplary embodiments, the modified helicase is a Super Family 1 (SF1) helicase (e.g., an SF1A or an SF1B helicase) or a Super Family 2 (SF2) helicase.

In certain exemplary embodiments, the first amino acid is less than about 20 Å, about 19 Å, about 18 Å, about 17 Å, about 16 Å, about 15 Å, about 10 Å, about 9 Å, about 8 Å, about 7 Å, about 5 Å, or about 4 Å from the second amino acid when the helicase is in an active conformation.

In certain exemplary embodiments, the first amino acid is at least about 30 Å, about 40 Å, about 50 Å, about 55 Å, about 60 Å, about 65 Å, about 70 Å, about 75 Å, about 80 Å or about 85 Å from the second amino acid when the helicase is in an inactive conformation.

In certain exemplary embodiments, the helicase is selected from the group consisting of a Rep helicase (e.g., from *E. coli*), a UvrD helicase (e.g., from *E. coli*) and a PcrA helicase (e.g., from *B. stearothermophilus*).

In certain exemplary embodiments, the first amino acid is at any one of positions 84-116 or 178-196 of the modified helicase amino acid sequence, and the helicase is a Rep, PcrA or UvrD helicase, or homolog thereof.

In certain exemplary embodiments, the first amino acid is at any one of positions 92-116 or 178-196 of the modified helicase amino acid sequence, and the helicase is a PcrA helicase, or homolog thereof.

In certain exemplary embodiments, the first amino acid is at any one of positions 84-108 or 169-187 of the modified helicase amino acid sequence, and the helicase is a Rep helicase, or homolog thereof.

In certain exemplary embodiments, the first amino acid is at any one of positions 90-114 or 175-193 of the modified helicase amino acid sequence, and the helicase is a UvrD helicase, or homolog thereof.

In certain exemplary embodiments, the first amino acid at position 178 of the modified helicase amino acid sequence, and the helicase is a Rep helicase, or homolog thereof.

In certain exemplary embodiments, the first amino acid is at position 187 of the modified helicase amino acid sequence, and the helicase is a PcrA helicase, or homolog thereof.

In certain exemplary embodiments, the first amino acid is present in an amino acid sequence having at least 20% amino acid sequence identity to SEQ ID NO:13 or SEQ ID NO:14, and the helicase is a Rep helicase, or homolog thereof.

In certain exemplary embodiments, the second amino acid is present in an amino acid sequence having at least 20% amino acid sequence identity to SEQ ID NO:15 or SEQ ID NO:16, and the helicase is a Rep helicase, or homolog thereof.

In certain exemplary embodiments, the second amino acid residue is at any one of positions 388-411, 422-444 and 518-540 of the modified helicase amino acid sequence, and the helicase is a Rep, PcrA or UvrD helicase, or homolog thereof.

In certain exemplary embodiments, the second amino acid is at any one of positions 397-411, 431-444 or 526-540 of the modified helicase amino acid sequence, and the helicase is a PcrA helicase, or homolog thereof.

In certain exemplary embodiments, the second amino acid is at any one of positions 388-402, 422-435 or 519-531 of the modified helicase amino acid sequence, and the helicase is a Rep helicase, or homolog thereof.

In certain exemplary embodiments, the second amino acid is at any one of positions 393-407, 427-440 or 523-540 of the modified helicase amino acid sequence, and the helicase is a UvrD helicase, or homolog thereof.

In certain exemplary embodiments, the second amino acid is at position 400 of the modified helicase amino acid sequence, and the helicase is a Rep helicase, or homolog thereof.

In certain exemplary embodiments, the second amino acid is at position 409 of the modified helicase amino acid sequence, and the helicase is a PcrA helicase, or homolog thereof.

In certain exemplary embodiments, the first amino acid is at any one of positions 60-82 of the modified helicase amino acid sequence, and the helicase is a Rep helicase, or homolog thereof. In certain exemplary embodiments, the first amino acid is at any one of positions 68-79 of the modified helicase amino acid sequence, and the helicase is a Rep helicase, or homolog thereof.

In certain exemplary embodiments, the first amino acid is at any one of positions 69-89 of the modified helicase amino acid sequence, and the helicase is a PcrA helicase, or homolog thereof. In certain exemplary embodiments, the first amino acid is at any one of positions 77-87 of the modified helicase amino acid sequence, and the helicase is a PcrA helicase, or homolog thereof.

In certain exemplary embodiments, the first amino acid is at any one of positions 67-87 of the modified helicase amino acid sequence, and the helicase is a UvrD helicase, or homolog thereof. In certain exemplary embodiments, the first amino acid is at any one of positions 75-85 of the modified helicase amino acid sequence, and the helicase is a UvrD helicase, or homolog thereof.

In certain exemplary embodiments, the second amino acid is at any one of positions 509-536 of the modified helicase amino acid sequence, and the helicase is a Rep helicase, or homolog thereof. In certain exemplary embodiments, the second amino acid is at any one of positions 519-525 of the modified helicase amino acid sequence, and the helicase is a Rep helicase, or homolog thereof.

In certain exemplary embodiments, the second amino acid is at any one of positions 516-534 of the modified helicase amino acid sequence, and the helicase is a PcrA helicase, or homolog thereof. In certain exemplary embodiments, the second amino acid is at any one of positions 526-532 of the modified helicase amino acid sequence, and the helicase is a PcrA helicase, or homolog thereof.

In certain exemplary embodiments, the second amino acid is at any one of positions 513-531 of the modified helicase amino acid sequence, and the helicase is a UvrD helicase, or homolog thereof. In certain exemplary embodiments, the second amino acid is at any one of positions 523-529 of the modified helicase amino acid sequence, and the helicase is a UvrD helicase, or homolog thereof.

In certain exemplary embodiments, said first subdomain and said second subdomain comprise no more than a total of two cysteine residues.

In certain exemplary embodiments, the helicase comprises one cysteine residue and/or is from a bacterium selected from the group consisting of *Deinococcus geothermalis, Meiothermus sp., Marinithermus hydrothermalis, Marinithermus hydrothermalis* and *Oceanithermus profundus*.

In certain exemplary embodiments, the helicase comprises one cysteine residue or no cysteine residues and/or is from a bacterium selected from the group consisting of *Thermococcus sp.* EXT9, *Thermococcus sp.* IRI48, *Thermococcus sp.* IRI33, *Thermococcus* sp. AMT7, *Thermococcus nautili, Thermococcus onnurineus* (strain NA1), *Thermococcus kodakarensis* (strain ATCC BAA-918/JCM 12380/KOD1) (*Pyrococcus kodakaraensis* (strain KOD1)), *Thermococcus sibiricus* (strain MM 739/DSM 12597), *Thermococcus paralvinellae, Thermus aquaticus* Y51MC23, *Thermus aquaticus* Y51MC23, *Thermus aquaticus* Y51MC23, *Thermus sp.* RL, *Thermus sp.* RL, *Thermus sp.* 2.9, *Salinisphaera hydrothermalis* C41B8, *Thermus filiformis, Meiothermus ruber, Thermus sp.* NMX2.A1, *Thermus thermophilus* JL-18, *Thermus scotoductus* (strain ATCC 700910/SA-01), *Thermus scotoductus* (strain ATCC 700910/SA-01), *Oceanithermus profundus* (strain DSM 14977/NBRC 100410/VKM B-2274/506), *Oceanithermus profundus* (strain DSM 14977/NBRC 100410/VKM B-2274/506), *Oceanithermus profundus* (strain DSM 14977/NBRC 100410/VKM B-2274/506), *Oceanithermus profundus* (strain DSM 14977/NBRC 100410/VKM B-2274/506), *Oceanithermus profundus* (strain DSM 14977/NBRC 100410/VKM B-2274/506), *Thermus oshimai* JL-2, *Thermus oshimai* JL-2, *Thermus oshimai* JL-2, *Thermomonospora curvata* (strain ATCC 19995/DSM 43183/JCM 3096/NCIMB 10081), *Thermodesulfatator indicus* (strain DSM 15286/JCM 11887/CIR29812), *Geobacillus stearothermophilus* (*Bacillus stearothermophilus*), *Coprothermobacter proteolyticus* (strain ATCC 35245/DSM 5265/BT), *Meiothermus silvanus* (strain ATCC 700542/DSM 9946/VI-R2) (*Thermus silvanus*), *Anaerolinea thermophila* (strain DSM 14523/JCM 11388/NBRC 100420/UNI-1), *Thermoanaero-*

*bacterium thermosaccharolyticum* M0795, *Meiothermus ruber* (strain ATCC 35948/DSM 1279/VKM B-1258/21) (*Thermus ruber*), *Meiothermus ruber* (strain ATCC 35948/DSM 1279/VKM B-1258/21) (*Thermus ruber*), *Deinococcus radiodurans* (strain ATCC 13939/DSM 20539/JCM 16871/LMG 4051/NBRC 15346/NCIMB 9279/R1/VKM B-1422), *Thermodesulfobium narugense* DSM 14796, *Thermus thermophilus* (strain HB8/ATCC 27634/DSM 579), *Dictyoglomus thermophilum* (strain ATCC 35947/DSM 3960/H-6-12), *Thermus thermophilus* (strain SG0.5JP17-16), *Thermus thermophilus* (strain SG0.5JP17-16), *Thermus thermophilus* (strain SG0.5JP17-16), *Thermus sp.* CCB_US3_UF1, *Deinococcus geothermalis* (strain DSM 11300), *Thermus thermophilus* (strain HB27/ATCC BAA-163/DSM 7039), *Thermus thermophilus* (strain HB27/ATCC BAA-163/DSM 7039), *Marinithermus hydrothermalis* (strain DSM 14884/JCM 11576/T1).

In certain exemplary embodiments, the first amino acid and the second amino acid are each independently an unnatural amino acid or a natural amino acid.

In certain exemplary embodiments, one or more of an amino acid of the helicase is substituted with an unnatural amino acid or a natural amino acid (e.g., a cysteine or a homocysteine).

In certain exemplary embodiments, said helicase comprises a sequence selected from SEQ ID NOs:4 and 12.

In certain exemplary embodiments, the first amino acid is covalently crosslinked to the second amino acid by a disulfide bond or by a chemical crosslinker (e.g., a chemical crosslinker having a length of from about 6 Å to about 25 Å).

In certain exemplary embodiments, the chemical crosslinker is a bis-maleimide crosslinker.

In certain exemplary embodiments, the chemical crosslinker is selected from the group consisting of

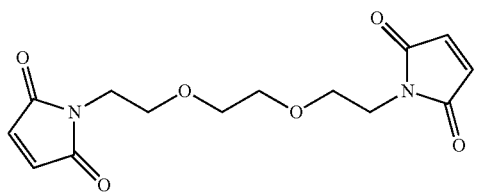

1-[2-[2-[2-(2,5-dioxopyrrol-1-yl)ethoxy]ethoxy]ethyl]pyrrole-2,5-dione,

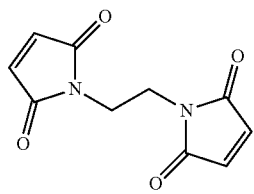

1-[2-(2,5-dioxopyrrol-1-yl)ethyl]pyrrole-2,5-dione,

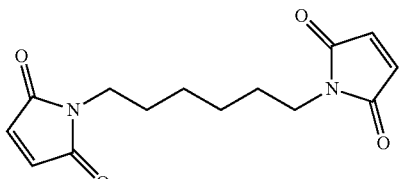

1-[6-(2,5-dioxopyrrol-1-yl)hexyl]pyrrole-2,5-dione,

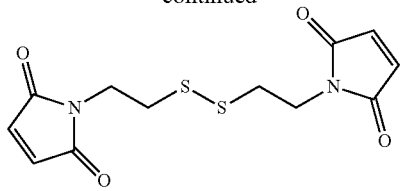

1-[2-[2-(2,5-dioxopyrrol-1-yl)ethyldisulfanyl]ethyl]pyrrole-2,5-dione,

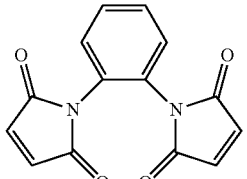

1-[2-(2,5-dioxopyrrol-1-yl)phenyl]pyrrole-2,5-dione, and

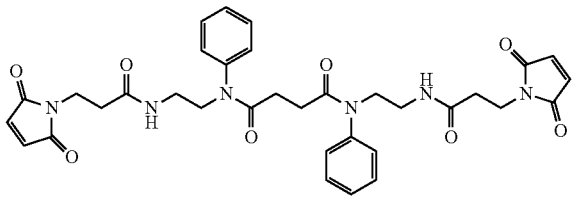

N,N'-bis[2-[3-(2,5-dioxopyrrol-1-yl)propanoylamino]ethyl]-N,N'-diphenylbutanediamide.

In certain exemplary embodiments, the chemical crosslinker is

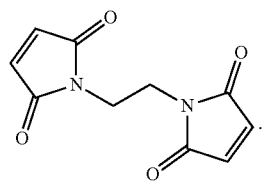

1-[2-(2,5-dioxopyrrol-1-yl)ethyl]
pyrrole-2,5-dione

In one aspect, a modified helicase comprising a first subdomain having a first amino acid and a second subdomain having a second amino acid, wherein said first amino acid is at least about 30 Å from said second amino acid when the helicase is in an inactive conformation, and said first amino acid is less than about 20 Å from said second amino acid when the helicase is in an active conformation, and wherein a side chain of the first amino acid is chemically crosslinked to a side chain of the second amino acid using

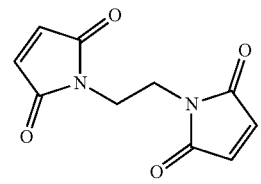 [SMILES: O=C1C=CC(=O)N1CCN1C(=O)C=CC1=O]

1-[2-(2,5-dioxopyrrol-1-yl)ethyl]pyrrole-2,5-dione to form an active, conformationally-constrained helicase is provided.

In another aspect, a modified Rep, PcrA or UvrD helicase or homolog thereof, comprising a first subdomain having a first amino acid at any one of positions 84-116 and a second subdomain having a second amino acid at any one of positions 388-411, 422-444 and 518-540, wherein a side chain of the first amino acid is covalently crosslinked to a side chain of the second amino acid with a linker to form an active, conformationally-constrained Rep, PcrA or UvrD helicase, or homolog thereof is provided.

In another aspect, a modified Rep helicase or homolog thereof comprising an amino acid at position 178 covalently crosslinked to an amino acid at position 400 to form an active, conformationally-constrained Rep helicase or homolog thereof is provided.

In another aspect, a modified Rep helicase or homolog thereof comprising an amino acid at position 187 covalently crosslinked to an amino acid at position 409, to form an active, conformationally-constrained helicase is provided.

In another aspect, a modified helicase comprising a first subdomain having a first amino acid and a second subdomain having a second amino acid, wherein said first amino acid is at least about 30 Å from said second amino acid when the helicase is in an inactive conformation, and said first amino acid is less than about 20 Å from said second amino acid when the helicase is in an active conformation, and wherein a side chain of the first amino acid is covalently crosslinked to a side chain of the second amino acid with a chemical crosslinker to form an active, conformationally-constrained helicase, and wherein one or more of an amino acid of the helicase is substituted with an unnatural amino acid or a natural amino acid is provided.

In one aspect, a method of making an active, conformationally-constrained helicase is provided. The method includes the steps of selecting in a helicase a first amino acid in a first subdomain that is at least about 30 Å from a second amino acid in a second subdomain when the helicase is in an inactive conformation, and the first amino acid is less than about 20 Å from the second amino acid when the helicase is in an active conformation, and covalently crosslinking the first amino acid to the second amino acid when the helicase is in an active conformation to form an active, conformationally-constrained helicase.

In a certain exemplary embodiment, the method includes two steps. The first step includes expressing a helicase polypeptide having the capability to be constrained in a conformation by an intramolecular crosslinking agent from an isolated nucleic acid selected from a group consisting of SEQ ID NOs: 2, 3, 5 and 6. The second step includes reacting the helicase polypeptide with an intramolecular crosslinking agent to form the conformationally-constrained helicase.

In certain exemplary embodiments, the modified helicase is a Super Family 1 (SF1) helicase (e.g., SF1A or SF1B) or a Super Family 2 (SF2) helicase.

In certain exemplary embodiments, the first subdomain comprises a 1A subdomain or a 1B subdomain and the second subdomain comprises a 2B subdomain.

In certain exemplary embodiments, the first amino acid is less than about 20 Å, about 19 Å, about 18 Å, about 17 Å, about 16 Å, about 15 Å, about 10 Å, about 9 Å, about 8 Å, about 7 Å, about 5 Å, or about 4 Å from the second amino acid when the helicase is in an active conformation.

In certain exemplary embodiments, the first amino acid is at least about 30 Å, about 35 Å, about 40 Å, about 45 Å, about 50 Å, about 55 Å, about 60 Å, about 65 Å, about 70 Å, about 75 Å, about 80 Å or about 85 Å from the second amino acid when the helicase is in an inactive conformation.

In certain exemplary embodiments, the helicase is selected from the group consisting of a Rep helicase, a UvrD helicase and a PcrA helicase.

In certain exemplary embodiments, the helicase comprises a sequence selected from SEQ ID NOs:4 and 12.

In certain exemplary embodiments, the first amino acid is covalently linked to the second amino acid by a disulfide bond or a chemical crosslinker.

In another aspect, a method of catalyzing an unwinding reaction of a double-stranded DNA, comprising contacting the double-stranded DNA with a modified helicase comprising a first subdomain having a first amino acid and a second subdomain having a second amino acid is provided. Said first amino acid is at least about 30 Å from said second amino acid when the helicase is in an inactive conformation, and said first amino acid is less than about 20 Å from said second amino acid when the helicase is in an active conformation. A side chain of the first amino acid is covalently crosslinked to a side chain of the second amino acid with a linker to form an active, conformationally-constrained helicase.

In certain exemplary embodiments, the conformationally-constrained helicase comprises SEQ ID NO: 4 or SEQ ID NO:12.

In certain exemplary embodiments, the conformationally-constrained helicase is chemically crosslinked.

In certain exemplary embodiments, the linker comprises an alkyl having a length in the range from C7 to C23 or from C8 to C13.

In another aspect, a method of performing isothermal DNA amplification, comprising combining a DNA template, the conformationally-constrained helicase described above and amplification reagents. under conditions compatible for performing isothermal DNA amplification.

In certain exemplary embodiments, the method includes two steps. The first step includes forming a mixture. The mixture includes a double-stranded DNA template having a first strand and a second strand; a conformationally-constrained helicase; a DNA-dependent DNA polymerase; a first oligonucleotide primer complementary to a portion of the first strand; a second oligonucleotide primer complementary to a portion of the second strand; and an amplification buffer cocktail. The second step includes incubating the mixture at a temperature compatible for activating the conformationally-constrained helicase and DNA-dependent DNA polymerase.

In certain exemplary embodiments, the conformationally-constrained helicase comprises SEQ ID NO:4 or 12. In certain exemplary embodiments, the DNA-dependent DNA polymerase is selected from a group consisting of *E. coli* DNA Pol I, *E. coli* DNA Pol I Large Fragment, Bst 2.0 DNA Polymerase, Bst DNA Polymerase, Bst DNA Polymerase Large Fragment, Bsu DNA Polymerase I Large Fragment, T4 DNA Polymerase, T7 DNA polymerase, PyroPhage® 3173 DNA Polymerase and phi29 DNA Polymerase.

In certain exemplary embodiments, the conformationally-constrained helicase is chemically crosslinked.

In certain exemplary embodiments, the chemical crosslinker comprises a length in the range from about 6 Å to about 25 Å.

In certain exemplary embodiments, the chemical crosslinker comprises an alkyl having a length in the range from C7 to C23 or from C8 to C13.

In another aspect, a kit for performing helicase dependent amplification is provided. The kit includes a conformationally-constrained helicase and amplification reagents (e.g., an amplification buffer cocktail).

In certain exemplary embodiments, the conformationally-constrained helicase is selected from SEQ ID NOs: 4 and 12.

In certain exemplary embodiments, the kit further comprising a DNA-dependent DNA polymerase, e.g., selected from a group consisting of E. coli DNA Pol I, E. coli DNA Pol I Large Fragment, Bst 2.0 DNA Polymerase, Bst DNA Polymerase, Bst DNA Polymerase Large Fragment, Bsu DNA Polymerase I Large Fragment, T4 DNA Polymerase, T7 DNA polymerase, PyroPhage® 3173 DNA Polymerase and phi29 DNA Polymerase.

In one aspect, an isolated nucleic acid encoding a modified helicase described herein is provided.

In certain exemplary embodiments, the isolated nucleic acid is selected from the group consisting of SEQ ID NOs: 2, 3, 10 and 11.

In one aspect, a modified E. coli. Rep helicase comprising a first subdomain having a first amino acid, a second subdomain having a second amino acid, and an axis vector defined by the alpha carbon of ILE371 from which the vector originates and the alpha carbon of SER280 or the alpha carbon of ALA603, wherein theta is an angle of rotation of said first amino acid and said second amino acid around the axis vector is provided. A first theta between said first amino acid and said second amino acid is between about 60 degrees and about 155 degrees when the helicase is in an inactive conformation, and a second theta between said first amino acid and said second amino acid is between about 355 degrees and about 25 degrees when the helicase is in an active conformation. A side chain of the first amino acid is covalently crosslinked to a side chain of the second amino acid with a linker to form an active, conformationally-constrained helicase.

In certain exemplary embodiments, the first theta is about 133 degrees and/or the second theta is about 0 degrees.

In certain exemplary embodiments, the axis vector is defined by the alpha carbon of ILE371 and the alpha carbon of SER280.

In certain exemplary embodiments, the first amino acid is at any one of positions 84-108 or 169-187 or at position 178 of the modified helicase amino acid sequence. In certain exemplary embodiments, the first amino acid is present in an amino acid sequence having at least 20% amino acid sequence identity to SEQ ID NO:13 or SEQ ID NO:14. In certain exemplary embodiments, the first amino acid is at any one of positions 60-82 of the modified helicase amino acid sequence. In certain exemplary embodiments, the first amino acid is at any one of positions 68-79 of the modified helicase amino acid sequence.

In certain exemplary embodiments, the second amino acid is at any one of positions 388-402, 422-435 or 519-531 or at position 400 of the modified helicase amino acid sequence. In certain exemplary embodiments, the first amino acid is present in an amino acid sequence having at least 20% amino acid sequence identity to SEQ ID NO:15 or SEQ ID NO:16. In certain exemplary embodiments, the second amino acid is at any one of positions 509-536 of the modified helicase amino acid sequence. In certain exemplary embodiments, the second amino acid is at any one of positions 519-525 of the modified helicase amino acid sequence.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 4A illustrates a consensus sequence alignment of TxGx motif for 27 organisms within 10 out 11 families, wherein Cys is present at position 96. Leuconostocaceae family species have an alanine at this position. Figure discloses SEQ ID NOS 109-142, respectively, in order of appearance.

FIG. 4B illustrates a consensus sequence alignment of motif III for 27 organisms within 10 families, wherein Cys is present at position 247. Leuconostocaceae family species have an alanine at this position. Figure discloses SEQ ID NOS 143-176, respectively, in order of appearance.

FIG. 9A shows target residues in Rep (SEQ ID NO: 32), PcrA (SEQ ID NO: 177) and UvrD (SEQ ID NO: 178), for-X form crosslinking, calculated based on the criteria and crystal structures in open (inactive) and closed (active) conformations. One residue is chosen from 1A or 1B domain (shaded), and another from 2B (shaded).

FIG. 9B shows 56 representative Rep homologs/orthologs with 90% identity to and 80% overlap, and the corresponding region of domain 1A where crosslinking residues can be chosen. FIGS. 9B-9C disclose SEQ ID NOS 179-235, respectively, in order of appearance.

FIG. 9C shows 56 representative Rep homologs/orthologs with 90% identity to and 80% overlap, and the corresponding region of domain 1B where crosslinking residues can be chosen.

FIG. 9D shows 56 representative Rep homologs/orthologs with 90% identity to and 80% overlap, and the corresponding region of domain 2B where crosslinking residues can be chosen. FIGS. 9D-9F disclose SEQ ID NOS 236-292, respectively, in order of appearance.

FIG. 9E shows 56 representative Rep homologs/orthologs with 90% identity to and 80% overlap, and the corresponding region of domain 2B where crosslinking residues can be chosen in addition to those shown in FIG. 9D.

FIG. 9F shows 56 representative Rep homologs/orthologs with 90% identity to and 80% overlap, and the corresponding region of domain 2B where crosslinking residues can be chosen in addition to those shown in FIG. 9E.

FIG. 9G shows target residues in drUvrD, Rep, PcrA and UvrD, for-X form crosslinking, calculated based on the criteria and crystal structures in open (inactive) and closed (active) conformations. One residue is chosen from 1A or 1B domain (shaded), and another from 2B (shaded). Figure discloses SEQ ID NOS 293-304, respectively, in order of appearance.

FIG. 16 shows a stereo view of a ribbon diagram of a 5'-3' SF1 superhelicase (T4 Dda).

FIG. 17 shows Rep helicase's 2B domain structure in two different orientations that differ through a rotation around an axis coming out of the plane of the paper. 2B domain orientation can be described by the rotation angle $\theta$ with respect to the closed form. $\theta=0$ when the helicase is in the closed form, and $\theta$ is 133 degrees when the 2B rotates to the open form.

DETAILED DESCRIPTION

Figure 1A:
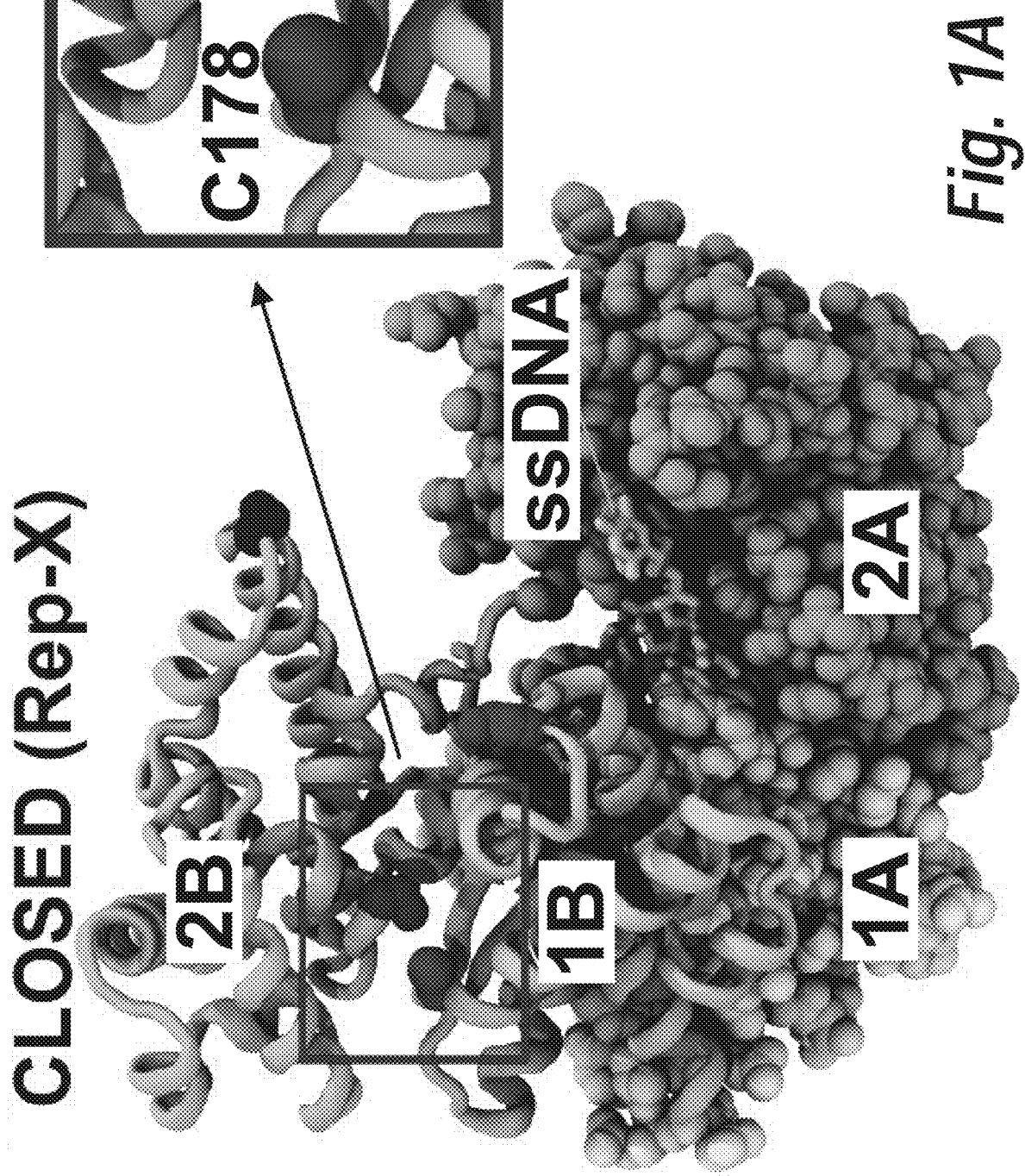
FIG. 1A depicts the closed form Rep crystal structure (PDB entry 1UAA), wherein subdomains are colored and named accordingly and 3' end of the ssDNA (gray) is visible. Residues that were mutated to cysteine and crosslinked to lock the conformation are shown as pink, blue and red van der Waals spheres in both conformations as reference. Boxed area is magnified view showing the two residues that were crosslinked for engineering Rep-X.
Figure 1B:
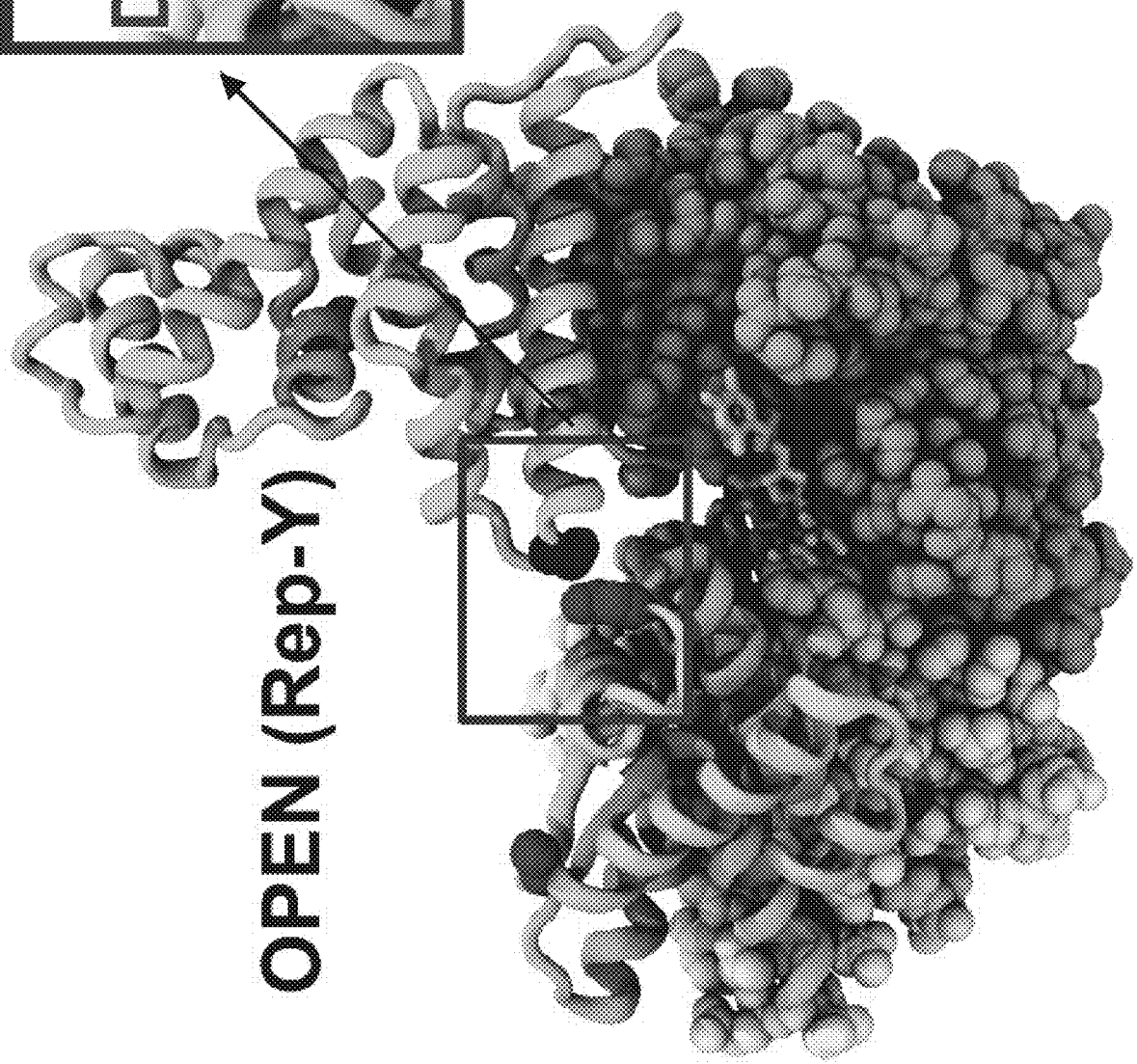
FIG. 1B depicts the open form Rep crystal structure (PDB entry 1UAA), wherein subdomains are colored and named accordingly and 3' end of the ssDNA (gray) is visible. Residues that were mutated to cysteine and crosslinked to lock the conformation are shown as pink, blue and red van der Waals spheres in both conformations as reference. Boxed area is magnified view showing the two residues that were crosslinked for engineering Rep-Y.

The present disclosure provides details of the discovery of robust enzymes of the superfamily 1 helicases. The helicase enzymes are engineered as crosslinked, conformationally-constrained monomeric configurations providing enhanced unwinding activity on dsDNA substrates. The "super" helicases display inherently strong physical properties having superior characteristics to all presently known natural helicases. The disclosed helicases have utility in isothermal PCR and helicase-dependent amplification processes, as well as in next generation sequencing applications, including nanopore sequencing methods and the like.

Terminology and Definitions

The terminology used herein is for the purpose of describing particular embodiments only, and is not intended to be limiting. With respect to the use of plural and/or singular terms herein, those having skill in the art can translate from the plural as is appropriate to the context and/or application. The various singular/plural permutations may be expressly set forth herein for the sake of clarity.

Terms used herein are intended as "open" terms (e.g., the term "including" should be interpreted as "including but not limited to," the term "having" should be interpreted as "having at least," the term "includes" should be interpreted as "includes but is not limited to," etc.).

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into sub-ranges.

A range includes each individual member. Thus, for example, a group having 1-3 members refers to groups having 1, 2, or 3 members. Similarly, a group having 1-6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

The present invention provides modified helicases that have enhanced enzymatic activity. As used herein, a "helicase" refers to a class of enzymes that function as motor proteins which move directionally along a nucleic acid phosphodiester backbone, separating two annealed nucleic acid strands (i.e., DNA, RNA, or RNA-DNA hybrid) using energy derived from ATP hydrolysis. Helicases are often used to separate strands of a DNA double helix or a self-annealed RNA molecule using the energy from ATP hydrolysis, a process characterized by the breaking of hydrogen bonds between annealed nucleotide bases. They also function to remove nucleic acid-associated proteins and catalyze homologous DNA recombination. Metabolic processes of RNA such as translation, transcription, ribosome biogenesis, RNA splicing, RNA transport, RNA editing, and RNA degradation are all facilitated by helicases. Helicases move incrementally along one nucleic acid strand of the duplex with a directionality and processivity specific to each particular enzyme.

Six super families of helicases are known in the art that are classified based on their shared sequence motifs. Helicases not forming a ring structure are classified in Super Families 1 (SF1) and 2 (SF2). Ring-forming helicases form Super Families 3 (SF3), 4 (SF4), (SF5) and 6 (SF6).

SF1 is further subdivided into SF1 Å and SF1B helicases. In this group, helicases can have either 3'-5' (SF1 Å subfamily) or 5'-3'(SF1B subfamily) translocation polarity. SF1 Å helicases include, but are not limited to are Rep and UvrD in gram-negative bacteria and PcrA helicase from gram-positive bacteria. SF1B helicases include, but are not limited to RecD and Dda helicases.

SF2 is the largest family of helicases, which are involved in varied cellular processes. They are characterized by the presence of nine conserved motifs: Q, I, Ia, Ib, and II through VI. This family primarily comprises DEAD-box RNA helicases ("DEAD" disclosed as SEQ ID NO: 18). Other helicases in SF2 family are the RecQ-like family and Snf2-like enzymes. Most of the SF2 helicases are type A, with a few exceptions such as the XPD family.

SF3 comprises helicases encoded mainly by small DNA viruses and some large nucleocytoplasmic DNA viruses. They have a 3'-5' translocation directionality (therefore they are all type A helicases). SF3 helicase include viral helicases such as the papilloma virus E1 helicase.

SF4 helicases have a type B polarity (5'-3'), and function in bacterial or bacteriophage DNA replication. Gp4 from bacteriophage T7 is an SF4 helicase.

SF5 helicases have a type B polarity (5'-3'), and include only the bacterial termination factors Rho.

SF6 helicases contain the core AAA+ that is not included in the SF3 classification. SF6 helicases include, but are not limited to, Mini Chromosome Maintenance (MCM), RuvB, RuvA, and RuvC.

Exemplary helicases according to the invention include, but are not limited to RecD, Upfl, PcrA, Rep, UvrD, Hel308, Mtr4, XPD, NS3, Mssl 16, Prp43, RecG, RecQ, TIR, RapA, Hef, RecB, Pifl, Dna2, Dda, Ul5, RecD2, Tral, Senlp, SETX, IBP160, ZNFX1, Upflp, UPF1, Hes1p, IGHMBP2, Dna2p, DNA2, Mttlp, MOV10, MOV10L1, HELZ, PR285, ptMRDFL1 and the like.

In certain embodiments of the invention, a helicase comprises subdomains. For example, SF1 helicases comprise subdomains 1A, 1B, 2A and 2B. The 2B subdomain has been shown to rotate between an open conformation and a closed conformation.

As used herein, an "open conformation" refers to the inactive conformation of a helicase in which minimal or no helicase activity occurs. As used herein, a "closed conformation" refers to the active form of a helicase which has helicase activity. Crystal structures depicting the open and/or closed conformations of many helicases have been published in the art.

As described further herein, it has been discovered that, by stabilizing the active (i.e., closed) conformation and destabilizing the inactive (i.e., open) conformation, a modified helicase can be obtained having greatly enhanced helicase activity and strength relative to the corresponding unmodified helicase. According to certain embodiments of the invention, a modified helicase that stabilizes the active (i.e., closed) conformation and destabilizes the inactive (i.e., open) conformation can be generated by covalently linking one or more amino acids in the 2B subdomain to one or more amino acids in the 1A and/or the 1B domain of the helicase. Such a modified helicase is referred to herein as an "active, conformationally constrained helicase" or a "helicase-x polypeptide." Exemplary helicase-x polypeptides include, but are not limited to, Rep-x, PcrA-x and UvrD-x. In certain embodiments, a helicase-x polypeptide forms a loop around a target nucleic acid sequence (e.g., a DNA sequence). In other embodiments, a helicase-x polypeptide does not form a loop around a target nucleic acid sequence (e.g., a DNA sequence).

In other embodiments, a helicase is provided that is stabilized in its inactive (i.e., open) conformation and destabilized in its active (i.e., closed) conformation. Such a helicase is referred to as an "inactive, conformationally constrained helicase" or a "helicase-Y polypeptide." Helicase-Y polypeptides exhibit little or no helicase activity.

In certain embodiments, a helicase-x polypeptide has an increased nucleic acid (e.g., DNA) unwinding activity relative to a corresponding unmodified helicase. In certain aspects, the number of base pairs that can be unwound by a helicase-x polypeptide is increased by about 1000%, about 10,000%, about 100,000% or more (or any ranges or points within the ranges) relative to a corresponding unmodified helicase.

In certain embodiments, a helicase-x polypeptide can unwind at least about 500 base pairs, about 1000 base pairs, about 1500 base pairs, about 2000 base pairs, about 2500 base pairs, about 3000 base pairs, about 3500 base pairs, about 4000 base pairs, about 4500 base pairs, about 5000 base pairs, about 5500 base pairs, about 6000 base pairs, about 6500 base pairs, about 7000 base pairs, about 7500 base pairs, about 8000 base pairs, about 8500 base pairs, about 9000 base pairs, about 9500 base pairs, about 10,000 base pairs or more (or any ranges or points within the ranges) without dissociating from the nucleic acid sequence (e.g., DNA).

In certain embodiments, a helicase-x polypeptide is stronger that the corresponding unmodified helicase, withstanding opposing forces of at least about 10 pN, about 15 pN, about 20 pN, about 25 pN, about 30 pN, about 35 pN, about 40 pN, about 45 pN, about 50 pN, about 55 pN, about 60 pN, or more (or any ranges or points within the ranges).

In certain embodiments, a helicase-x polypeptide comprises a first subdomain comprising a first amino acid and a second subdomain comprising a second amino acid, wherein the first amino acid is at least about 35 Å from the second amino acid when the helicase is in an inactive conformation, and wherein the first amino acid is less than about 25 Å from the second amino acid when the helicase is in an active conformation. In certain embodiments, the first amino acid is at least about 40 Å, about 45 Å, about 50 Å, about 55 Å, about 60 Å, about 65 Å, about 70 Å, about 75 Å, about 80 Å, about 85 Å, or more from the second amino acid (or any ranges or points within these ranges) when the helicase is in an inactive (i.e., open) conformation. In certain embodiments, the first amino acid is at most about 20 Å, about 15 Å, about 10 Å, about 9 Å, about 8 Å, about 7 Å, about 6 Å, about 5 Å, about 4 Å, or less from the second amino acid (or any ranges or points within the ranges) when the helicase is in an active (i.e., closed) conformation. In certain embodiments, the linker in a helicasex polypeptide has a length in the range from about 6 Å to about 25 Å.

In certain embodiments, the first amino acid of a helicase-x polypeptide is present in a 1 Å or a 1B subdomain and the second amino acid of a helicasex polypeptide is present in a 2B subdomain.

In certain embodiments, the Rep-x polypeptide forms a loop around the target nucleic acid (e.g., DNA) sequence. In certain embodiments, the first amino acid of a Rep-x polypeptide that forms a loop is at any one of positions 84-108 or 169-187, or at position 178 of the Rep amino acid sequence. In certain embodiments, the second amino acid of a Repx polypeptide that forms a loop is at any one of positions 388-402, 422-435 or 519-536, or at position 400 of the Rep amino acid sequence.

In certain embodiments, the PcrA-x polypeptide forms a loop around the target nucleic acid (e.g., DNA) sequence. In certain embodiments, the first amino acid of a PcrA-x polypeptide that forms a loop is at any one of positions 92-116 or 178-196, or at position 187 of the PcrA amino acid sequence. In certain embodiments, the second amino acid of a PcrA-x polypeptide that forms a loop is at any one of positions 397-411, 431-444 or 526-540, or at position 409 of the PcrA amino acid sequence.

In certain embodiments, the UvrD-x polypeptide forms a loop around the target nucleic acid (e.g., DNA) sequence. In certain embodiments, the first amino acid of a UvrD-x polypeptide that forms a loop is at any one of positions 90-114 or 175-193 of the UvrD amino acid sequence. In certain embodiments, the second amino acid of a UvrD-x polypeptide that forms a loop is at any one of positions 393-407, 427-440 or 523-540 of the UvrD amino acid sequence.

In certain embodiments, the Rep-x polypeptide does not form a loop around the target nucleic acid (e.g., DNA) sequence. In certain embodiments, the first amino acid of the Rep-x polypeptide that does not form a loop is at any one of positions 60-82 (i.e., at any one of AREMKERVGQTL-GRKEARGLMIS (SEQ ID NO: 19)), or at any one of positions 68-79 (i.e., at any one of GQTLGRKEARGL (SEQ ID NO: 20)) of the Rep amino acid sequence. In certain embodiments, the second amino acid of the Rep-x polypeptide that does not form a loop is at any one of positions 509-536 (i.e., at any one of FSWMTEM-LEGSELDEPMTLTQVVTRFTL (SEQ ID NO: 21)), or at any one of positions 519-525 (i.e., at any one of SELDEPM (SEQ ID NO: 22)) of the Rep amino acid sequence.

In certain embodiments, the PcrA-x polypeptide does not form a loop around the target nucleic acid (e.g., DNA) sequence. In certain embodiments, the first amino acid of the PcrA-x polypeptide that does not form a loop is at any one of positions 69-89 (i.e., at any one of AREMRERVQSLLG-GAAEDVWI (SEQ ID NO: 23)), or at any one of positions 77-87 (i.e., at any one of QSLLGGAAEDV (SEQ ID NO: 24)) of the PcrA amino acid sequence. In certain embodiments, the second amino acid of the PcrA-x polypeptide that does not form a loop is at any one of positions 516-534 (i.e., at any one of LSVTKHFENVSDDKSLIAF (SEQ ID NO: 25)), or at any one of positions 526-532 (i.e., at any one of SDDKSLI (SEQ ID NO: 26)) of the PcrA amino acid sequence.

In certain embodiments, the UvrD-x polypeptide does not form a loop around the target nucleic acid (e.g., DNA) sequence. In certain embodiments, the first amino acid of the UvrD-x polypeptide that does not form a loop is at any one of positions 67-87 (i.e., at any one of AAEMRH-RIGQLMGTSQGGMWV (SEQ ID NO: 27)), or at any one of positions 75-85 (i.e., at any one of GQLMGTSQGGM (SEQ ID NO: 28)) of the UvrD amino acid sequence. In certain embodiments, the second amino acid of the UvrD-x polypeptide that does not form a loop is at any one of positions 513-531 (i.e., at any one of VTATRQFSYNEED-EDLMPL (SEQ ID NO: 29)), or at any one of positions 523-529 (i.e., at any one of EEDEDLM (SEQ ID NO: 30)) of the UvrD amino acid sequence.

In certain embodiments, the first amino acid and/or the second amino acid of a helicase-x polypeptide is present in a particular amino acid sequence having at least about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98% or about 99% or more sequence identity to that of a reference sequence (e.g., a Rep helicase, A PcrA helicase, a UvrD helicase, or a homolog or ortholog thereof).

In certain embodiments, the first amino acid is present in a Rep helicase at an amino acid sequence having at least about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98% or about 99% or more amino acid sequence identity (or any ranges or points within the ranges) to FHTLGLDIIKREYAALGM-KANFSLF (SEQ ID NO:13). In certain embodiments, the first amino acid is present in a Rep helicase at an amino acid sequence having at least about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98% or about 99% or more amino acid sequence identity (or any ranges or points within the ranges) to GLYDAHLKACNVLDFDDLI (SEQ ID NO:14).

In certain embodiments, the second amino acid is present in a Rep helicase at an amino acid sequence having at least about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98% or about 99% amino acid sequence identity (or any ranges or points within the ranges) to AYLRVLTNPDDDSAF (SEQ ID NO:15). In certain embodiments, the second amino acid is present in a Rep helicase at an amino acid sequence having at least about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98% or about 99% amino acid sequence identity (or any ranges or points within the ranges) to GEWAMTRNKSMFTA (SEQ ID NO:16).

Suitable amino acid positions for modifying to engineer helicase-x polypeptides (and homologs and orthologs thereof) according to the invention can be identified by one of ordinary skill in the art using this disclosure and well-known local sequence alignment tools.

Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986) Nucl. Acids Res. 14:6745. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.).

One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by.dbd.HIGH SCORE; Databases=non-redundant, GenBank+EMBL+DDBJ+PDB+GenBank CDS translations+Swiss protein+Spupdate+PIR. Details of these programs can be found at the NCBI/NLM web site.

In certain embodiments of the invention, a helicase is provided that is conformationally-constrained. The term "conformationally-constrained" refers to a conformation having a least one degree of freedom (that is, motion or range of motion) that is less than a reference conformation. In certain embodiments, a conformationally-constrained helicase has a least one degree of freedom that is less than a helicase that is not conformationally constrained.

In certain embodiments of the invention, a helicase is constrained via a covalent linkage between two or more amino acids of the helicase. A covalent linkage is a chemical linkage between two atoms or radicals formed by the sharing of a pair of electrons (i.e., a single bond), two pairs of electrons (i.e., a double bond) or three pairs of electrons (i.e., a triple bond). Covalent linkages are also known in the art as electron pair interactions or electron pair bonds.

In embodiments, a covalent linkage is formed via a crosslink between the side chains of two (or more) amino acids of a polypeptide (e.g., between two (or more) amino acids of a modified helicase).

As used herein the term "crosslink" refers to the joining of two or more molecules by a covalent bond. Crosslinking can occur via disulfide bonds, e.g., between cysteine residues. Crosslinking can occur via the use of crosslinking reagents (or chemical crosslinkers), which are molecules that contain two or more reactive ends capable of chemically attaching to specific functional groups (primary amines, sulfhydryls, etc.) on proteins or other molecules.

The terms "intramolecular crosslinking agent" and "chemical crosslinking agent" refer to a compound that can form covalent bonds via specific functional groups (e.g., primary amines, sulfhydryls, etc.) on proteins or other molecules. An example of an intramolecular or chemical crosslinking agent includes a compound having two bifunctional groups in its structure.

Chemical crosslinkers are known in the art, and are commercially available (e.g., from Thermo Fisher Scientific, Waltham, MA). In certain embodiments, a crosslinker is cleavable (e.g., by reducing one or more of the functional groups of the crosslinker). In other embodiments, a crosslinker is not cleavable.

Examples of chemical crosslinkers include, but are not limited to, those having the following functional groups: maleimide, active esters, succinimide, azide, alkyne (such as dibenzocyclooctynol (DIBO or DBCO), difluoro cycloalkynes and linear alkynes), phosphine (such as those used in traceless and non-traceless Staudinger ligations), haloacetyl (such as iodoacetamide), phosgene type reagents, sulfonyl chloride reagents, isothiocyanates, acyl halides, hydrazines, disulphides, vinyl sulfones, aziridines and photoreactive reagents (such as aryl azides, diaziridines). Reactions between amino acids and functional groups may be spontaneous, such as cysteine/maleimide, or may require external reagents, such as Cu(I) for linking azide and linear alkynes.

Linkers can comprise any molecule that stretches across the distance required. Linkers can vary in length from one carbon (phosgene-type linkers) to many Angstroms. In certain embodiments, the linker includes an alkyl having a length in the range from $C_7$ to $C_{23}$. In some embodiments, the linker includes an alkyl having a length in the range from $C_8$ to $C_{13}$.

Examples of linear molecules include but are not limited to, polyethyleneglycols (PEGs), polypeptides, polysaccharides, deoxyribonucleic acid (DNA), peptide nucleic acid (PNA), threose nucleic acid (TNA), glycerol nucleic acid (GNA), saturated and unsaturated hydrocarbons, and polyamides. These linkers may be inert or reactive, in particular they may be chemically cleavable at a defined position, or may be themselves modified with a ligand. In certain embodiments, the linker is resistant to dithiothreitol (DTT).

Examples of crosslinkers include, but are not limited to 2,5-dioxopyrrolidin-1-yl 3-(pyridin-2-yldisulfanyl)propanoate, 2,5-dioxopyrrolidin-1-yl 4-(pyridin-2-yldisulfanyl)butanoate and 2,5-dioxopyrrolidin-1-yl 8-(pyridin-2-yldisulfanyl)octananoate, di-maleimide PEG 1k, di-maleimide PEG 3.4k, di-maleimide PEG 5k, di-maleimide PEG 10k, bis(maleimido)ethane (BMOE), bis-maleimidohexane (BMH), 1,4-bis-maleimidobutane (BMB), 1,4 bis-maleimidyl-2,3-dihydroxybutane (BMDB), BM[PEO]2 (1,8-bis-maleimidodiethyleneglycol), BM[PEO]3 (1, 11-bis-maleimidotriethylene glycol), tris[2-maleimidoethyl]amine (TMEA), dithiobismaleimidoethane (DTME), bis-maleimide PEG3, bis-maleimide PEGU, DBCO-maleimide, DBCO-PEG4-maleimide, DBCO-PEG4-NH2, DBCO-PEG4-NHS, DBCO-NHS, DBCO-PEG-DBCO 2.8 kDa, DBCO-PEG-DBCO 4.0 kDa, DBCO-15 atoms-DBCO, DBCO-26 atoms-DBCO, DBCO-35 atoms-DBCO, DBCO-PEG4-S—S-PEG3-biotin, DBCO-S-S-PEG3-biotin, DBCO-S-S-PEGI 1-biotin and (succinimidyl 3-(2-pyridyldithio)propionate (SPDP).

In certain embodiments, a covalent linkage refers to the linkage between two or more amino acids. One or more of the linked amino acids may be naturally occurring or non-naturally occurring. One or more of the linked amino acids may be chemically modified.

As used herein, a "natural amino acid" refers to the twenty genetically encoded alpha-amino acids. See, e.g., Biochemistry by L. Stryer, 3$^{rd}$ ed. 1988, Freeman and Company, New York, for structures of the twenty natural amino acids.

As used herein, an "unnatural amino acid," "modified amino acid" or "chemically modified amino acid" refers to any amino acid, modified amino acid, or amino acid analogue other than the twenty genetically encoded alpha-amino acids. Unnatural amino acids have side chain groups that distinguish them from the natural amino acids, although unnatural amino acids can be naturally occurring compounds other than the twenty proteinogenic alpha-amino acids. In addition to side chain groups that distinguish them from the natural amino acids, unnatural amino acids may have an extended backbone such as beta-amino acids.

Non-limiting examples of unnatural amino acids include selenocysteine, pyrrolysine, homocysteine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an a-hydroxy containing acid; an amino thio acid containing amino acid; an α,α disubstituted amino acid; a β-amino acid; and a cyclic amino acid other than proline. In an embodiment of the helicases described herein, one or more amino acids of the helicase are substituted with one or more unnatural amino acids and/or one or more natural amino acids.

In certain embodiments, a helicase-X is a closed form, conformationally-constrained helicase monomer generated from a helicase polypeptide that was reacted with an intramolecular crosslinking agent. In certain embodiments, a helicase-Y is an open form, conformationally-constrained helicase monomer generated from a helicase polypeptide that was reacted with an intramolecular crosslinking agent.

The chemical structures described herein are named according to IUPAC nomenclature rules and include art-accepted common names and abbreviations where appropriate. The IUPAC nomenclature can be derived with chemical structure drawing software programs, such as ChemDraw® (PerkinElmer, Inc.), ChemDoodle® (iChemLabs, LLC) and Marvin (ChemAxon Ltd.). The chemical structure controls in the disclosure to the extent that an IUPAC name is misnamed or otherwise conflicts with the chemical structure disclosed herein. E. coli Rep mutants can be engineered that are intramolecularly crosslinked to constrain the 2B subdomain in open or closed conformations. Residues for the cysteine substitution mutagenesis and the length of the bis-maleimide crosslinkers were selected such that when crosslinked, the 2B subdomain cannot rotate appreciably, effectively locking the protein in one conformation (FIG. 1A, B). The closed form of a helicase that is crosslinked in a constrained conformation is denoted with the suffix "-X", and the open form of a helicase that is crosslinked in a constrained conformation is denoted with the suffix "-Y." For Rep, Rep-X and Rep-Y represent the conformationally-constrained closed and open forms, respectively. Enzymatic activities of Rep-X and Rep-Y monomers were studied in single molecule and ensemble assays employing fluorescence resonance energy transfer (FRET), total internal reflection fluorescence (TIRF) microscopy, and optical tweezers force spectroscopy.

The Rep mutant sequences used to generate Rep-X and Rep-Y include those nucleotide and amino acid sequences identified in Table 1.

TABLE 1

Amino Acid and Nucleotide Sequences for exemplary Rep-X and Rep-Y proteins

| Polypeptide/DNA/RNA (SEQ ID NO:_) | 5'→3' (nucleotide sequence) N→C (amino acid sequence) |
|---|---|
| Wild type Rep helicase (gene sequence) >gi\|556503834:3960677-3962698 Escherichia coli str. K-12 substr. MG1655, complete genome (SEQ ID NO: 31) | ATGCGTCTAAACCCCGGCCAACAACAAGCTGTCGAATTCGTT ACCGGCCCCTGCCTGGTGCTGGCGGGCGCGGGTTCCGGTAAA ACTCGTGTTATCACCAATAAAATCGCCCATCTGATCCGCGGTT GCGGTTATCAGGCGCGGCACATTGCGGCGGTGACCTTTACTA ATAAAGCAGCGCGCGAGATGAAAGAGCGTGTAGGGCAGACG CTGGGGCGCAAAGAGGCGCGTGGGCTGATGATCTCCACTTTC CATACGTTGGGGCTGGATATCATCAAACGCGAGTATGCGGCG CTTGGGATGAAAGCGAACTTCTCGTTGTTTGACGATACCGATC AGCTTGCTTTGCTTAAAGAGTTGACCGAGGGGCTGATTGAAG ATGACAAAGTTCTCCTGCAACAACTGATTTCGACCATCTCTAA CTGGAAGAATGATCTCAAAACACCGTCCCAGGCGGCAGCAAG TGCGATTGGCGAGCGGGACCGTATTTTTGCCCATTGTTATGGG CTGTATGATGCACACCTGAAAGCCTGTAACGTTCTCGACTTCG ATGATCTGATTTTATTGCCGACGTTGCTGCTGCAACGCAATGA AGAAGTCCGCAAGCGCTGGCAGAACAAAATTCGCTATCTGCT GGTGGATGAGTATCAGGACACCAACACCAGCCAGTATGAGCT GGTGAAACTGCTGGTGGGCAGCCGCGCGCGCTTTACCGTGGT GGGTGACGATGACCAGTCGATCTACTCCTGGCGCGGTGCACG TCCGCAAAACCTGGTGCTGCTGAGTCAGGATTTTCCGGCGCTG AAGGTGATTAAGCTTGAGCAGAACTATCGCTCTTCCGGGCGT ATTCTGAAAGCGGCGAACATCCTGATCGCCAATAACCCGCAC GTCTTTGAAAAGCGTCTGTTCTCCGAACTGGGTTATGGCGCGG |

TABLE 1 -continued

Amino Acid and Nucleotide Sequences for exemplary Rep-X and Rep-Y proteins

| Polypeptide/DNA/RNA (SEQ ID NO:_) | 5'→3' (nucleotide sequence) N→C (amino acid sequence) |
|---|---|
| | AGCTAAAAGTATTAAGCGCGAATAACGAAGAACATGAGGCTG<br>AGCGCGTTACTGGCGAGCTGATCGCCCATCACTTCGTCAATAA<br>AACGCAGTACAAAGATTACGCCATTCTTTATCGCGGTAACCAT<br>CAGTCGCGGGTGCTTGAAAAATTCCTGATGCAAAACCGCATC<br>CCGTACAAAATATCTGGTGGTACGTCGTTTTTCTCTCGTCCTG<br>AAATCAAGCACTTGCTGGCTTATCTGCGCGTGCTGACTAACCC<br>GGACGATGACAGCGCATTTCTGCGTATCGTTAACACGCCGAA<br>GCGAGAGATTGGCCCGGCTACGCTGAAAAAGCTGGGTGAGTG<br>GGCGATGACGCGCAATAAAAGCATGTTTACCGCCAGCTTTGA<br>TATGGGCCTGAGTCAGACGCTTAGCGGACGTGGTTATGAAGC<br>ATTGACCCGCTTCACTCACTGGTTGGCAGAAATCCAGCGTCTG<br>GCGGAGCGGGAGCCGATTGCCGCGGTGCGTGATCTGATCCAT<br>GGCATGGATTATGAATCCTGGCTGTACGAAACATCGCCCAGC<br>CCGAAAGCCGCCGAAATGCGCATGAAGAACGTCAACCAACTG<br>TTTAGCTGGATGACGGAGATGCTGGAAGGCAGTGAACTGGAT<br>GAGCCGATGACGCTCACCCAGGTGGTGACGCGCTTTACTTTGC<br>GCGACATGATGGAGCGTGGTGAGAGTGAAGAAGAGCTGGATC<br>AGGTGCAACTGATGACTCTCCACGCGTCGAAAGGGCTGGAGT<br>TTCCTTATGTCTACATGGTCGGTATGGAAGAAGGGTTTTTGCC<br>GCACCAGAGCAGCATCGATGAAGATAATATCGATGAGGAGCG<br>GCGGCTGGCCTATGTCGGCATTACCCGCGCCCAGAAGGAATT<br>GACCTTTACGCCTGTGTAAAGAACGCCGTCAGTACGGCGAACT<br>GGTGCGCCCGGAGCCGAGCCGCTTTTTGCTGGAGCTGCCGCA<br>GGATGATCTGATTTGGGAACAGGAGCGCAAAGTGGTCAGCGC<br>CGAAGAACGGATGCAGAAAGGGCAAAGCCATCTGGCGAATCT<br>GAAAGCGATGATGGCGGCAAAACGAGGGAAATAA |
| Wild type Rep helicase (amino acid sequence) >gi\|48994965\|gb AAT48209.1\|DNA helicase and single-stranded DNA-dependent ATPase [*Escherichia coli* str. K-12 substr. MG16] (SEQ ID NO: 32) | MRLNPGQQQAVEFVTGPCLVLAGAGSGKTRVITNKIAHLIRGCG<br>YQARHIAAVTFTNKAAREMKERVGQTLGRKEARGLMISTFHTLG<br>LDIIKREYAALGMKANFSLFDDTDQLALLKELTEGLIEDDKVLLQ<br>QLISTISNWKNDLKTPSQAAASAIGERDRIFAHCYGLYDAHLKAC<br>NVLDFDDLILLPTLLLQRNEEVRKRWQNKIRYLLVDEYQDTNTS<br>QYELVKLLVGSRARFTVVGDDDQSIYSWRGARPQNLVLLSQDFP<br>ALKVIKLEQNYRSSGRILKAANILLANNPHVFEKRLFSELGYGAEL<br>KVLSANNEEHEAERVTGELIAHHFVNKTQYKDYAILYRGNHQSR<br>VFEKFLMQNRIPYKISGGTSFFSRPEIKDLLAYLRVLTNPDDDSAF<br>LRIVNTPKREIGPATLKKLGEWAMTRNKSMFTASFDMGLSQTLS<br>GRGYEALTRFTHWLAEIQRLAEREPIAAVRDLIHGMDYESWLYE<br>TSPSPKAAEMRMKNVNQLFSWMTEMLEGSELDEPMTLTQVVTR<br>FTLRDMMERGESEEELDQVQLMTLHASKGLEFPYVYMVGMEEG<br>FLPHQSSIDEDNIDEERRLAYVGITRAQKELTFTLCKERRQYGELV<br>RPEPSRFLLELPQDDLIWEQERKVVSAEERMQKGQSHLANLKAM<br>MAAKRGK |
| Rep-x polypmtide[1] (SEQ ID NO: 1) | MRLNPGQQQAVEFVTGPLLVLAGAGSGKTRVITNKIAHLIRGSG<br>YQARHIAAVTFTNKAAREMKERVGQTLGRKEARGLMISTFHTLG<br>LDIIKREYAALGMKANFSLFDDTDQLALLKELTEGLIEDDKVLLQ<br>QLISTISNWKNDLKTPSQAAASAIGERDRIFAHVYGLYDAHLKAC<br>NVLDFDDLILLPTLLLQRNEEVRKRWQNKIRYLLVDEYQDTNTS<br>QYELVKLLVGSRARFTWGDDDQSIYSWRGARPQNLVLLSQDFP<br>ALKVIKLEQNYRSSGRILKAANILIANNPHVFEKRLFSELGYGAEL<br>KVLSANNEEHEAERVTGELLAHHFVNKTQYKDYAILYRGNHQSR<br>VFEKFLMQNRIPYKISGGTSFFSRPEIKDLLAYLRVLTNPDDDCAF<br>LRIVNTPKREIGPATLKKLGEWAMTRNKSMFTASFDMGLSQTLS<br>GRGYEALTRFTHWLAEIQRLAEREPIAAVRDLIHGMDYESWLYE<br>TSPSPKAAEMRMKNVNQLFSWNTEMLEGSELDEPMTLTQVVTR<br>FTLRDMMERGESEEELDQVQLMTLHASKGLEFPYVYMVGMEEG<br>FLPHQSSIDEDNIDEERRLAYVGITRAQKELTFTLAKERRQYGELV<br>RPEPSRFLLELPQDDLIWEQERKVVSAEERMQKGQSHLANLKAM<br>MAAKRGK |
| Rep-x DNA[2] (SEQ ID NO: 2) | ATGCGTCTAAACCCCGGCCAACAACAAGCTGTCGAATTCGTT<br>ACCGGCCCCTTGCTGGTGCTGGCGGGCGCGGGTTCCGGTAAA<br>ACTCGTGTTATCACCAATAAAATCGCCCATCTGATCCGCGGTA<br>GCGGGTACCAGGCGCGGCACATTGCGGCGGTGACCTTTACTA<br>ATAAAGCAGCGCGCGAGATGAAAGAGCGTGTAGGGCAGACG<br>CTGGGGCGCAAAGAGGCGCGTGGGCTGATGATCTCCACTTTC<br>CATACGTTGGGGCTGGATATCATCAAACGCGAGTATGCGGCG<br>CTTGGGATGAAAGCGAACTTCTCGTTGTTTGACGATACCGATC<br>AGCTTGCTTTGCTTAAAGAGTTGACCGAGGGGCTGATTGAAG<br>ATGACAAAGTTCTCCTGCAACAACTGATTTCGACCATCTCTAA<br>CTGGAAGAATGATCTCAAAACACCGTCCCAGGCGGCAGCAAG<br>TGCGATTGGCGAGCGGGACCGTATTTTTGCCCATGTTTATGGG<br>CTGTATGATGCACACCTGAAAGCCTGTAACGTTCTCGACTTCG |

TABLE 1-continued

Amino Acid and Nucleotide Sequences for exemplary Rep-X and Rep-Y proteins

| Polypeptide/DNA/RNA (SEQ ID NO:_) | 5'→3' (nucleotide sequence) N→C (amino acid sequence) |
|---|---|
| | ATGATCTGATTTTATTGCCGACGTTGCTGCTGCAACGCAATGA<br>AGAAGTCCGCAAGCGCTGGCAGAACAAAATTCGCTATCTGCT<br>GGTGGATGAGTATCAGGACACCAACACCAGCCAGTATGAGCT<br>GGTGAAACTGCTGGTGGGCAGCCGCGCGCGCTTTACCGTGGT<br>GGGTGACGATGACCAGTCGATCTACTCCTGGCGCGGTGCACG<br>TCCGCAAAACCTGGTGCTGCTGAGTCAGGATTTTCCGGCGCTG<br>AAGGTGATTAAGCTTGAGCAGAACTATCGCTCTTCCGGGCGT<br>ATTCTCAAAGCGGCGAACATCCTGATCGCCAATAACCCGCAC<br>GTCTTTGAAAAGCGTCTGTTCTCCGAACTGGGTTATGGCGCGG<br>ACTCTAAAAGTATTAAGCGCGAATAACGAAGAACATGAGGCTG<br>AGCGCGTTACTGGCGAGCTGATCGCCCATCACTTCGTCAATAA<br>AACGCAGTACAAAGATTACGCCATTCTTTATCGCGGTAACCAT<br>CAGTCGCGGGTGTTTGAAAAATTCCTGATGCAAAACCGCATC<br>CCGTACAAAATATCTGGTGGTACGTCGTTTTTCTCTCGTCCTG<br>AAATCAAGGACTTGCTGGCTTATCTGCGCGTGCTGACTAACCC<br>GGACGATGACTGCGCATTTCTGCGTATCGTTAACACGCCGAA<br>GCGAGAGATTGGCCCGGCTACGCTGAAAAAGCTGGGTGAGTG<br>GGCGATGACGCGCAATAAAAGCATGTTTACCGCCAGCTTTGA<br>TATGGGCCTGAGTCAGACGCTTAGCGGACGTGGTTATGAAGC<br>ATTGACCCGCTTCACTCACTGGTTGGCAGAAATCCAGCGTCTG<br>GCGGAGCGGGAGCCGATTGCCGCGGTGCGTGATCTGATCCAT<br>GGCATGGATTATGAATCCTGGCTGTACGAAACATCGCCCAGC<br>CCGAAAGCCGCCGAAATGCGCATGAAGAACGTCAACCAACTG<br>TTTAGCTGGATGACGGAGATGCTGGAAGGCAGTGAACTGGAT<br>GAGCCGATGACGCTCACCCAGGTGGTGACGCGCTTTACTTTGC<br>GCGACATGATGGAGCGTGGTGAGAGTGAAGAAGAGCTGGATC<br>AGGTGCAACTGATGACTCTCCACGCGTCGAAAGGGCTGGAGT<br>TTCCTTATGTCTACATGGTCGGTATGGAAGAAGGGTTTTTGCC<br>GCACCAGAGCAGCATCGATGAAGATAATATCGATGAGGAGCG<br>GCGGCTGGCCTATGTCGGCATTACCCGCGCCCAGAAGGAATT<br>GACCTTTACGCTGGCTAAAGAACGCCGTCAGTACGGCGAACT<br>GGTGCGCCCGGAGCCGAGCCGCTTTTTGCTGGAGCTGCCGCA<br>GGATGATCTGATTTGGGAACAGGAGCGCAAAGTGGTCAGCGC<br>CGAAGAACGGATGCAGAAAGGGCAAAGCCATCTGGCGAATCT<br>GAAAGCGATGATGGCGGCAAAACGAGGGAAATAA |
| Rep-$_X$ RNA[3]<br>(SEQ ID NO: 3) | AUGCGUCUAAACCCCGGCCAACAACAAGCUGUCGANUUCGU<br>UACCGGCCCCUUGCUGGUGCUGGCGGGCGCGGGUUCCGGUA<br>AAACUCGUGUUAUCACCAAUAAAAUCGCCCAUCUGAUCCGC<br>GGUAGCGGGUACCAGGCGCGGCACAUUGCGGCGGUGACCUU<br>UACUAAUAAAGCAGCGCGCGAGAUGAAAGAGCUGUAGGGGC<br>AGACGCUGGGGCGCAAAGAGGCGCGUGGGCUGAUGAUCUCC<br>ACUUUCCAUACGUUGGGGCUGGAUAUCAUCAAACGCGAGUA<br>UGCGGCGCUUGGGAUGAAAGCGAACUUCUCGUUGUUUGACG<br>AUACCGAUCAGCUUGCUUUGCUUAAAGAGUUGACCGAGGGG<br>CUGAUUGAAGAUGACAAAGUUCUCCUGCAACAACUGAUUUC<br>GACCAUCUCUAACUGGAAGAAUGAUCUCAAAACACCGUCCC<br>AGGCGGCAGCAAGUGCGAUUGCGAGCGGGACCGUAUUUUU<br>GCCCAUGUUUAUGGGCUGUAUGAUGCACACCUGAAAGCCUG<br>UAACGUUCUCGACUUCGAUGAUCUGAUUUUAUUGCCGACGU<br>UGCUGCUGCAACGCAAUGAAGAAGUCCGCAAGCGCUGGCAG<br>AACAAAAUUCGCUAUCUGCUGGUGGAUGAGUAUCAGGACAC<br>CAACACCAGCCAGUAUGAGCUGGUGAAACUGCUGGUGGGCA<br>GCCGCGCGCUUUACCGUGGUGGGUGACGAUGACCAGUCG<br>AUCUACUCCUGGCGCGGUGCACGUCCGCAAAACCUGGUGCU<br>GCUGAGUCAGGAUUUUCCGGCGCUGAAGGUGAUUAAGCUUG<br>AGCAGAACUAUCGCUCUUCCGUGCGUAUUCUGAAAGCGGCG<br>AACAUCCUGAUCGCCAAUAACCCGCACGUCUUUGAAAAGCG<br>UCUGUUCUCCGAACUGGGUUAUGGCGCGGAGCUAAAAGUAU<br>UAAGCGCGAAUAACGAAGAACAUGAGGCUGAGCGCGUUACU<br>GGCGAGCUGAUCGCCCAUCACUUCGUCAAUAAAACGCAGUA<br>CAAAGNUUACGCCAUUCUUUAUCGCGGUAACCAUCAGUCGC<br>GGGUGUUUGAAAAAUUCCUGAUGCAAAACCGCAUCCCGUAC<br>AAAAUAUCUGGUGGUACGUCGUUUUUCUCUCGUCCUGAAAU<br>CAAGGACUUGCUGGCUUAUCUGCGCGUGCUGACUAACCCGG<br>ACGAUGACUGCGCAUUUCUGCGUAUCGUUAACACGCCGAAG<br>CGAGAGAUUGGCCCGGCUACGCUGAAAAAGCUGGGUGAGUG<br>GGCCAUGACGCGCAAUAAAAGCAUGUUUACCGCCAGCUUUG<br>AUAUGGGCCUGAGUCAGACGCUUAGCGGACGUGGUUAUGAA<br>GCAUUGACCCGCUUCACUCACUGGUUGGCAGAAAUCCAGCG<br>UCUGGCGGAGCGGGAGCCGAUUGCCGCGGUGCGUGAUCUGA<br>UCCAUGGCAUGGAUUAUGAAUCCUGGCUGUACGAAACAUCG<br>CCCAGCCCGAAAGCCGCCGAAAUGCGCAUGAAGAACGUCAA<br>CCAACUGUUUAGCUGGAUGACGGAGAUGCUGGAAGGCAGUG |

TABLE 1 -continued

Amino Acid and Nucleotide Sequences for exemplary Rep-X and Rep-Y proteins

| Polypeptide/DNA/RNA (SEQ ID NO:_) | 5'→3' (nucleotide sequence) N→C (amino acid sequence) |
|---|---|
| | AACUGGAUGAGCCGAUGACGCUCACCCAGGUGGUGACGCGC UUUACUUUGCGCGACAUGAUGGAGCGUGGUGAGAGUGAAG AAGAGCUGGAUCAGGUGCAACUGAUGACUCUCCACGCGUCG AAAGGGCUGGAGUUUCCUUAUGUCUACAUGGUCGGUAUGG AAGAAGGGUUUUUGCCGCACCAGAGCAGCAUCGAUGAAGAU AAUAUCGAUGAGGAGCGGCGGCUGGCCUAUGUCGGCAUUAC CCGCGCCCAGAAGGAAUUGACCUUUACGCUGGCUAAAGAAC GCCGUCAGUACGGCGAACUGGUGCGCCCGGAGCCGAGCCGC UUUUUGCUGGAGCUGCCGCAGGAUGAUCUGAUUUGUGAACA GGAGCGCAAAGUGGUCAGCGCCGAAGAACGGAUGCAGAAAG GGCAAAGCCAUCUGGCGAAUCUGAAAGCGAUGAUGGCGGCA AAACGAGGGAAAUAA |
| Rep-X polypeptide[4] (SEQ ID NO: 4) | SEQ ID NO: 1 and formula no 2 in Table 2 (1-[2-(2,5-dioxopyrrol-1-yl)ethyl]pyrrole-2, 5-dione) |
| Rep-Y polypeptide[5] (SEQ ID NO: 5) | MRLNPGQQQAVEFVTGPLLVLAGAGSGKTRVITNKIAHLIRGSG YQARHIAAVTFTNKAAREMKERVGQTLGRKEARGLMISTFHTLG LDIIKREYAALGMKANFSLFDDTDQLALLKELTEGLIEDDKVLLQ QLISTISNWKNDLKTPSQAAASAIGERDRIFAHVYGLYDAHLKAC NVLDFDDLILLPTLLLQRNEEVRKRWQNKIRYLLNDEYQDTNTS QYELVKLLVGSRARFTVVGDDDQSIYSWRGARPQNLVLLSQDFP ALKVIKLEQNYRSSGRILKAANILIANNPHVFEKRLFSELGYGAEL KVLSANNEEHEAERVTGELIAHHFVNKTQYKDYAILYRGNHQSR VFEKFLMQNRIPYKISGGTSFFSRPEIKDLLAYLRVLTNPDDDCAF LRIVNTPKREIGPATLKKLGEWAMTRNKSMFTASFDMGLSQTLS GRGYEALTRFTHWLAEIQRLAEREPIAAVRDLIHGMDYESWLYE TSPSPKAAEMRMKNVNQLFSWMTEMLEGSELDEPMTLTQVVTR FTLRDMMERGESEEELDQVQLMTLHASKGLEFPPYVYMVGMEEG FLPHQSSIDEDNIDEERRLAYVGITRAQKELTFTLAKERRQYGELV RPEPSRFLLELPDDLIWEQERKVVSAEERMQKGQSHLANLKAM MAAKRGK |
| Rep-Y DNA[6] (SEQ ID NO:6) | ATGCGTCTAAACCCCGGCCAACAACAAGCTGTCGAATTCGTT ACCGGCCCCTTGCTGGTGCTGGCGGGCGCGGGTTCCGGTAAA ACTCGTGTTATCACCAATAAAATCGCCCATCTGATCCGCGGTA GCGGGTACCAGGCGCGGCACATTGCGGCGGTGACCTTTACTA ATAAAGCAGCGCGCGAGATGAAAGAGCGTGTAGGGCAGACG CTGGGGCGCAAAGAGGCGCGTGGGCTGATGATCTCCACTTTC CATACGTTGGGGCTGGATATCATCAAACGCGAGTATGCGGCG CTTGGGATGAAAGCGAACTTCTCGTTGTTTGACGATACCGATC AGCTTGCTTTGCTTAAAGAGTTGACCGAGGGGCTGATTGAAG ATGACAAAGTTCTCCTGCAACAACTGATTTCGACCATCTCTAA CTGGAAGAATGATCTCAAAACACCGTCCCAGGCGGCAGCAAG TGCGATTGGCGAGCGGGACCGTATTTTTGCCCATGTTTATGGG CTGTATGATGCACACCTGAAAGCCTGTAACGTTCTCGACTTCG ATGATCTGATTTTATTGCCGACGTTGCTGCTGCAACGCAATGA AGAAGTCCGCAAGCGCTGGCAGAACAAAATTCGCTATCTGCT GGTGGATGAGTATCAGGACACCAACACCAGCCAGTATGAGCT GGTGAAACTGCTGGTGGGCAGCCGCGCGCGCTTTACCGTGGT GGGTGACGATGACCAGTCGATCTACTCCTGGCGCGGTGCACG TCCGCAAAACCTGGTGCTGCTGAGTCAGGATTTTCCGGCGCTG AAGGTGATTAAGCTTGAGCAGAACTATCGCTCTTCCGGGCGT ATTCTGAAAGCGGCGAACATCCTGATCGCCAATAACCCGCAC GTCTTTGAAAAGCGTCTGTTCTCCGAACTGGGTTATGGCGCGG AGCTAAAAGTATTAAGCGCGAATAACGAAGAACATGAGGCTG AGCGCGTTACTGGCGAGCTGATCGCCCATCACTTCGTCAATAA AACGCAGTACAAAGATTACGCCATTCTTTATCGCGGTAACCAT CAGTCGCGGGTGTTTGAAAAATTCCTGATGCAAAACCGCATC CCGTACAAAATATCTGGTGGTACGTCGTTTTTCTCTCGTCCTG AAATCAAGGACTTGCTGGCTTATCTGCGCGTGCTGACTAACCC GGACGATGACTGCGCATTTCTGCGTATCGTTAACACGCCGAA GCGAGAGATTGGCCCGGCTACGCTGAAAAAGCTGGGTGAGTG GGCGATGACGCGCAATAAAAGCATGTTTACCGCCAGCTTTGA TATGGGCCTGAGTCAGACGCTTAGCGGACGTGGTTATGAAGC ATTGACCCGCTTCACTCACTGGTTGGCAGAAATCCAGCGTCTG GCGGAGCGGGAGCCGATTGCCGCGGTGCGTGATCTGATCCAT GGCATGGATTATGAATCCTGGCTGTACGAAACATCGCCCAGC CCGAAAGCCGCCGAAATGCGCATGAAGAACGTCAACCAACTG TTTAGCTGGATGACGGAGATGCTGGAAGGCAGTGAACTGGAT GAGCCGATGACGCTCACCCAGGTGGTGACGCGCTTTACTTTGC GCGACATGATGGAGCGTGGTGAGAGTGAAGAAGAGCTGGATC AGGTGCAACTGATGACTCTCCACGCGTCGAAAGGGCTGGAGT |

TABLE 1-continued

Amino Acid and Nucleotide Sequences for exemplary Rep-X and Rep-Y proteins

| Polypeptide/DNA/RNA (SEQ ID NO:_) | 5'→3' (nucleotide sequence) N→C (amino acid sequence) |
|---|---|
| | TTCCTTATGTCTACATGGTCGGTATGGAAGAAGGGTTTTTGCC<br>GCACCAGAGCAGCATCGATGAAGATAATATCGATGAGGAGCG<br>GCGGCTGGCCTATGTCGGCATTACCCGCGCCCAGAAGGAATT<br>GACCTTTACGCTGGCTAAAGAACGCCGTCAGTACGGCGAACT<br>GGTGCGCCCGGAGCCGAGCCGCTTTTTGCTGGAGCTGCCGCA<br>GGATGATCTGATTTGGGAACAGGAGCGCAAAGTGGTCAGCGC<br>CGAAGAACGGATGCAGAAAGGGCAAAGCCATCTGGCGAATCT<br>GAAAGCGATGATGGCGGCAAAACGAGGGAAATAA |
| Rep-Y RNA[7]<br>(SEQ ID NO: 7) | AUGCGUCUAAACCCCGGCCAACAACAAGCUGUCGAAUUCGU<br>UACCGGCCCCUUGCUGGUGCUGGCGGGCGCGGGUUCCGGUA<br>AAACUCGUGUUAUCACCAAUAAAAUCGCCCAUCUGAUCCGC<br>GGUAGCGGGUACCAGGCGCGGCACAUUGCGGCGGUGACCUU<br>UACUAAUAAAGCAGCGCGCGAGAUGAAAGAGCGUGUAGGGC<br>AGACGCUGGGGCGCAAAGAGGCGCGUGGGCUGAUGAUCUCC<br>ACUUUCCAUACGUUGGGGCUGGAUAUCAUCAAACGCGAGUA<br>UGCGGCGCUUGGGAUGAAAGCGAACUUCUCGUUGUUUGACG<br>AUACCGAUCAGCUUGCUUUGCUUAAAGAGUUGACCGAGGGG<br>CUGAUUGAAGAUGACAAAGUUCUCCUGCAACAACUGAUUUC<br>GACCAUCUCUAACUGGAAGAAUGAUCUCAAAACACCGUCCC<br>AGGCGGCAGCAAGUGCGAUUGGCGAGCGGGACCGUAUUUUU<br>GCCCAUGUUUAUGGGCUGUAUGAUGCACACCUGAAAGCCUG<br>UAACGUUCUCGACUUCGAUGAUCUGNUUUUAUUGCCGACGU<br>UGCUGCUGCAACGCAAUGAAGAAGUCCGCAAGCGCUGGCAG<br>AACAAAAUUCGCUAUCUGCUGGUGGAUGAGUAUCAGGACAC<br>CAACACCAGCCAGUAUGAGCUGGUGAAACUGCUGGUGGGCA<br>GCCGCGCGCUUUACCGUGGUGGGUGACGAUGACCAGUCG<br>AUCUACUCCUGGCGCGGUGCACGUCCGCAAAACCUGGUGCU<br>GCUGAGUCAGGAUUUUCCGGCGCUGAAGGUGAUUAAGCUUG<br>AGCAGAACUAUCGCUCUUCCGGGCGUAUUCUGAAAGCGGCG<br>AACAUCCUGAUCGCCAAUAACCCGCACGUCUUUGAAAAGCG<br>UCUGUUCUCCGAACUGGGUUAUGGCGCGGAGCUAAAAGUAU<br>UAAGCGCGAAUAACGAAGAACAUGAGGCUGAGCGCGUUACU<br>GGCGAGCUGAUCGCCCAUCACUUCGUCAAUAAAACGCAGUA<br>CAAAGAUUACGCCAUUCUUUAUCGCGGUAACCAUCAGUCGC<br>GGGUGUUUGAAAAAUUCCUGAUGCAAAACCGCAUCCCGUAC<br>AAAAUAUCUGGUGGUACGUCGUUUUUCUCUCGUCCUGAAAU<br>CAAGGACUUGCUGGCUUAUCUGCGCGUGCUGACUAACCCGG<br>ACGAUGACUGCGCAUUUCUGCGUAUCGUUAACACGCCGAAG<br>CGAGAGAUUGGCCCGGCUACGCUGAAAAAGCUGGGUGAGUG<br>GGCGAUGACGCGCAAUAAAAGCAUGUUUACCGCCAGCUUUG<br>AUAUGGGCCUGAGUCAGACGCUUAGCGGACGUGGUUAUGAA<br>GCAUUGACCCGCUUCACUCACUGGUUGGCAGAAAUCCAGCG<br>UCUGGCGCAGCGGCAGCCGAUUGCCGCGGUGCGUGAUCUGA<br>UCCAUGGCAUGGAUUAUGAAUCCUGGCUGUACGAAACAUCG<br>CCCAGCCCGAAAGCCGCCGAAAUGCGCAUGAAGAACGUCAA<br>CCAACUGUUUAGCUGGAUGACGGAGAUGCUGGAAGGCAGUG<br>AACUGGAUGAGCCGAUGACGCUCACCCAGGUGGUGACGCGC<br>UUUACUUUGCGCGACAUGAUGGAGCGUGGUGAGAGUGAAG<br>AAGAGCUGGAUCAGGUGCAACUGAUGACUCUCCACGCGUCG<br>AAAGGGCUGGAGUUUCCUUAUGUCUACAUGGUCGGUAUGG<br>AAGAAGGGUUUUUGCCGCACCAGAGCAGCAUCGAUGAAGAU<br>AAUAUCCAUGAGGAGCGGCGGCUGGCCUAUGUCGGCAUUAC<br>CCGCGCCCAGAAGGAAUUGACCUUUACGCUGGCUAAAGAAC |

TABLE 1-continued

Amino Acid and Nucleotide Sequences for exemplary Rep-X and Rep-Y proteins

| Polypeptide/DNA/RNA (SEQ ID NO:_) | 5'→3' (nucleotide sequence) N→C (amino acid sequence) |
|---|---|
| | GCCGUCAGUACGGCGAACUGGUGCGCCCGGAGCCGAGCCGC UUUUUGCUGGAGCUGCCGCAGGAUGAUCUGAUUUGGGAACA GGAGCGCAAAGUGGUCAGCGCCGAAGAACGGAUGCAGAAAG GGCAAAGCCAUCUGGCGAAUCUGAAAGCGAUGAUGGCGGCA AAACGAGGGAAAUAA |
| Rep-Y polypeptide[8] (SEQ ID NO: 8) | SEQ ID NO: 5 and formula no 2 in Table 2 (1-[2-(2,5-dioxopyrrol-1-yl)ethyl]pyrrole-2, 5-dione). |

[1]This Rep mutant encodes mutations removing natural cysteine residues found in the wild-type Rep and include further amino acid mutations to facilitate intramolecular crosslinking to an intramolecular crosslinking agent to generate the Rep-x polypeptide.
[2]The DNA sequence corresponds to the open reading frame that encodes the polypeptide of SEQ ID NO: 1.
[3]The RNA sequence corresponds to the open reading frame that encodes the polypeptide of SEQ ID NO: 1.
[4]The Rep-X polypeptide closed foim monomer following reaction of Repx polypeptide (SEQ ID NO: 1) with an intramolecular crosslinking agent:
[5]This Rep mutants encodes mutations that remove natural cysteine residues found in the wild-type Rep and include further amino acid mutations to facilitate intramolecular crosslinking to an intramolecular crosslinking agent to generate the Rep-y polypeptide.
[6]The DNA sequence corresponds to the open reading frame that encodes the polypeptide of SEQ ID NO: 5.
[7]The RNA sequence corresponds to the open reading frame that encodes the polypeptide of SEQ ID NO: 5.
[8]The Rep-Y polypeptide open forui monomer following reaction of Repy polypeptide (SEQ ID NO: 5) with an intramolecular crosslinking agent:

The intramolecular crosslinking agents suitable for generating versions of Rep-x and Rep-Y include those identified in Table 2.

TABLE 2

Exemplary intramolecular crosslinking agents for generating Rep-$X$ and Rep-$Y$

| Formula No. | Compound Structure (IUPAC Name) |
|---|---|
| 1 | 1-[2-[2-[2-(2,5-dioxopyrrol-1-yl)ethoxy]ethoxy]ethyl]pyrrole-2,5-dione |
| 2 | 1-[2-(2,5-dioxopyrrol-1-yl)ethyl]pyrrole-2,5-dione |

TABLE 2-continued

Exemplary intramolecular crosslinking agents for generating Rep-$_X$ and Rep-$_Y$

| Formula No. | Compound Structure (IUPAC Name) |
|---|---|
| 3 | 1-[6-(2,5-dioxopyrrol-1-yl)hexyl]pyrrole-2,5-dione |
| 4 | 1-[2-[2-(2,5-dioxopyrrol-1-yl)ethyldisulfanyl]ethyl]pyrrole-2,5-dione |
| 5 | 1-[2-(2,5-dioxopyrrol-1-yl)phenyl]pyrrole-2,5-dione |
| 6 | N,N'-bis[2-[3-(2,5-dioxopyrrol-1-yl)propanoylamino]ethyl]-N,N'-diphenylbutanediamide |

These intramolecular crosslinking agents yield intramolecular crosslinked monomer structures when reacted with Rep-X and Rep-Y polypeptides. The linkers can have a length in the range from about 6 Å to about 25 Å. These types of linkers have an alkyl length in the range corresponding from about $C_7$ to about $C_{20}$, wherein highly preferred linkers have a length in the range from about $C_{10}$ to about $C_{12}$. Methods and conditions for generating intramolecular crosslink formation in proteins are well known in the art for these types of intramolecular crosslinking agents, and such methods and conditions are applicable to the helicases of this disclosure.

Figure 1C:
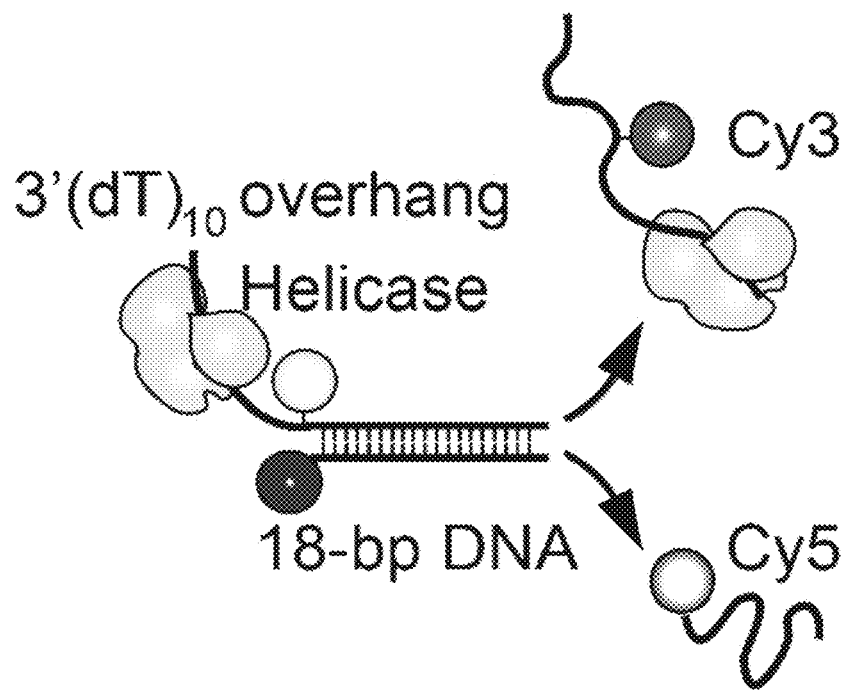
FIG. 1C depicts a schematic showing that helicase-catalyzed unwinding of a DNA labeled with a donor and an acceptor would convert high FRET efficiency ($E_{FRET}$) to low $E_{FRET}$. Shading level of the donor and acceptor color represents the relative intensity changes. Figure discloses "$(dT)_{10}$" as SEQ ID NO: 33.
Figure 1D:
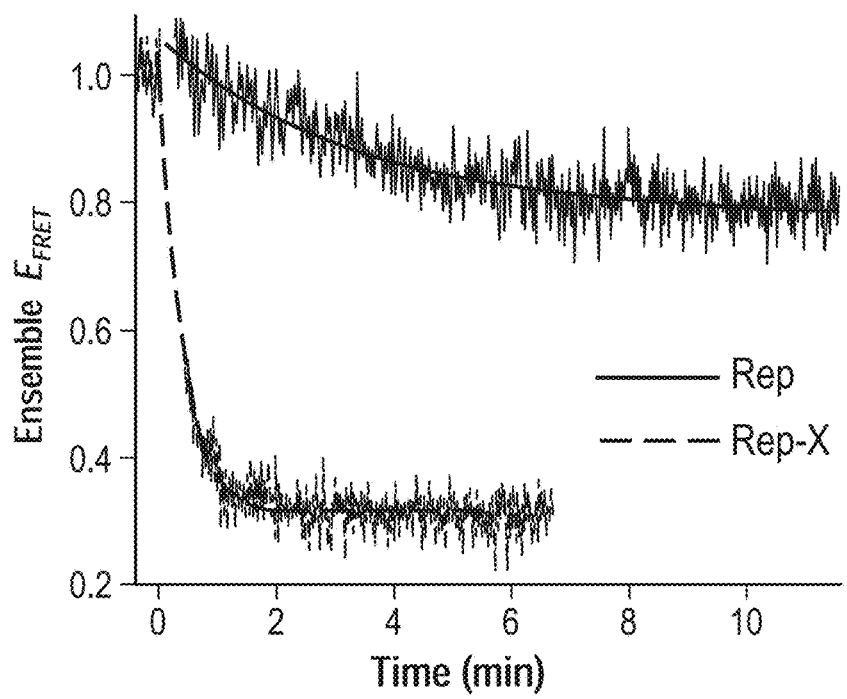
FIG. 1D depicts an ensemble unwinding kinetics of DNA from FIG. 1C by Rep and Rep-X shows the enhanced helicase activity of Rep-X over Rep as measured via ensemble $E_{FRET}$. Solid lines are fitted exponential decay curves as guides to the eye.

Rep-x would be inefficient in DNA unwinding even at high concentrations that make the wild type Rep active if the closed form is inactive for unwinding. In multiple turnover ensemble unwinding reactions using FRET-labeled DNA (see, for example, FIG. 1C), however, Rep-X unwound an 18-bp substrate with a 3'-(dT)$_{10}$ overhang (SEQ ID NO: 33) at a much faster rate and higher reaction amplitude than the wild type Rep (FIG. 1D). In contrast, Rep-Y unwinding rates were similar to that of Rep (FIG. 1E), indicating that the dramatic unwinding enhancement is specifically achieved in the closed conformation. Because the large enhancement in unwinding activity observed in bulk solution can result from the activation of a monomer or from enhanced oligomerization, single molecule FRET (smFRET) experiments were performed to test if a single Rep-X can unwind DNA.

Figure 2A:
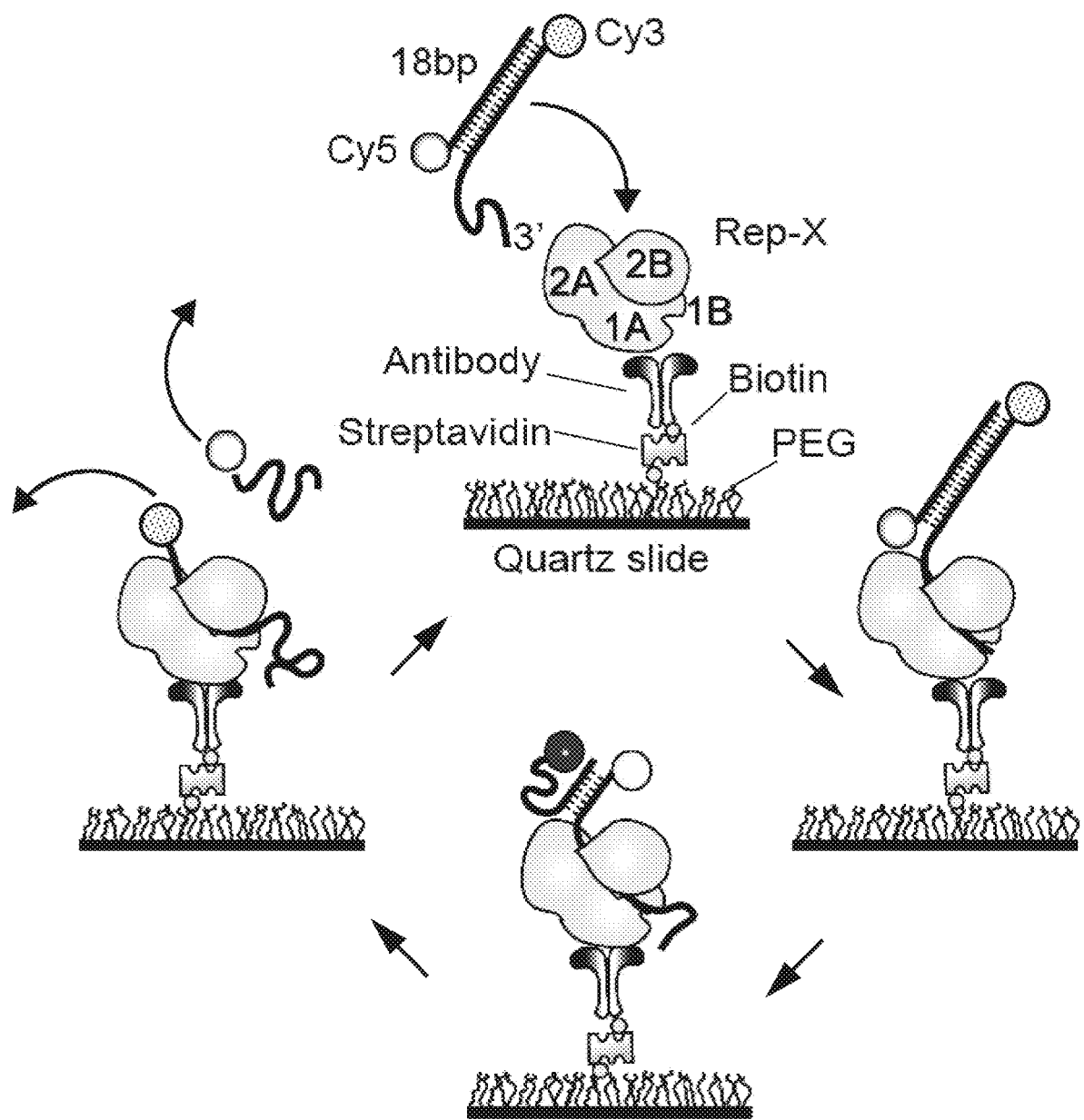
FIG. 2A depicts a schematic of unwinding stages of dual labeled DNA by a Rep-X monomer. Color lightness of the donor (green) and acceptor (red) on the DNA represents the change in the emission intensities as the unwinding progresses.
Figure 2B:
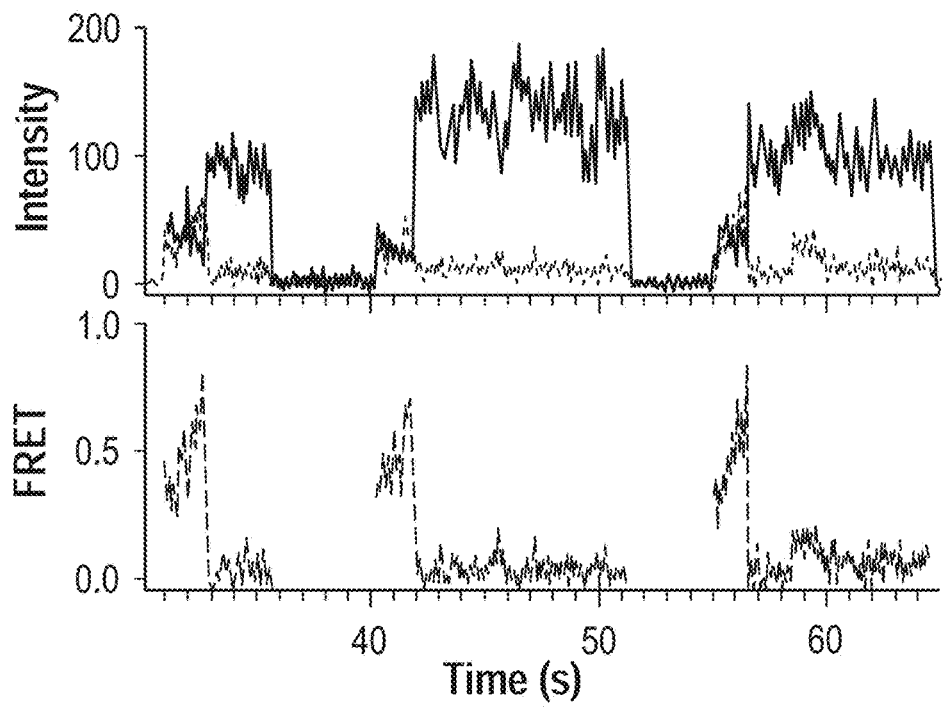
FIG. 2B depicts representative single molecule time traces show the DNA binding, unwinding and dissociation for the acceptor strand for Rep-X, wherein the donor fluorescence signal is in green, acceptor in red and $E_{FRET}$ in blue.
Figure 2C:
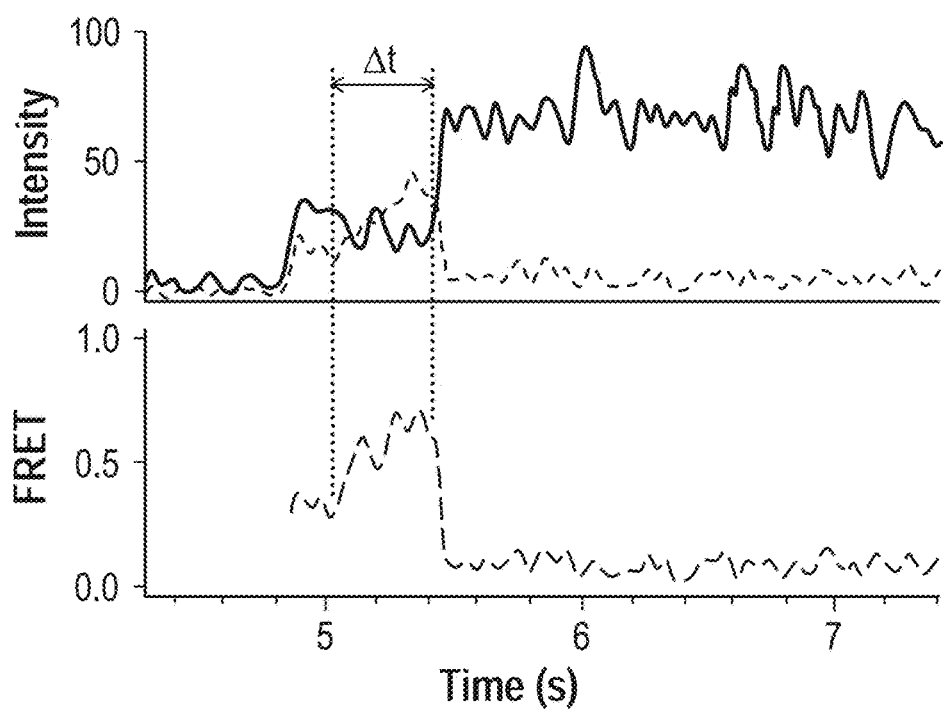
FIG. 2C depicts representative single molecule time traces showing the DNA binding, unwinding and dissociation for the donor strand for Rep-X, wherein the donor fluorescence signal is in green, acceptor in red and $E_{FRET}$ in blue. Unwinding period is denoted by Δt.
Figure 2D:
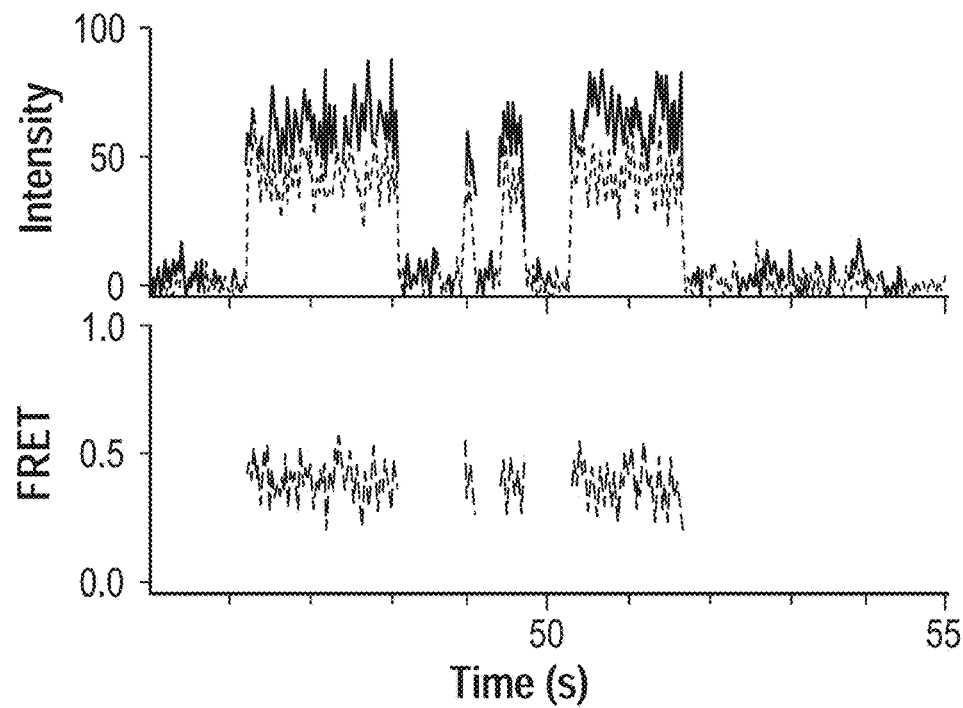
FIG. 2D depicts representative single molecule time traces showing the DNA binding and dissociation behavior for the donor strand for Rep, wherein the donor fluorescence signal is in green, acceptor in red and $E_{FRET}$ in blue.
Figure 2E:
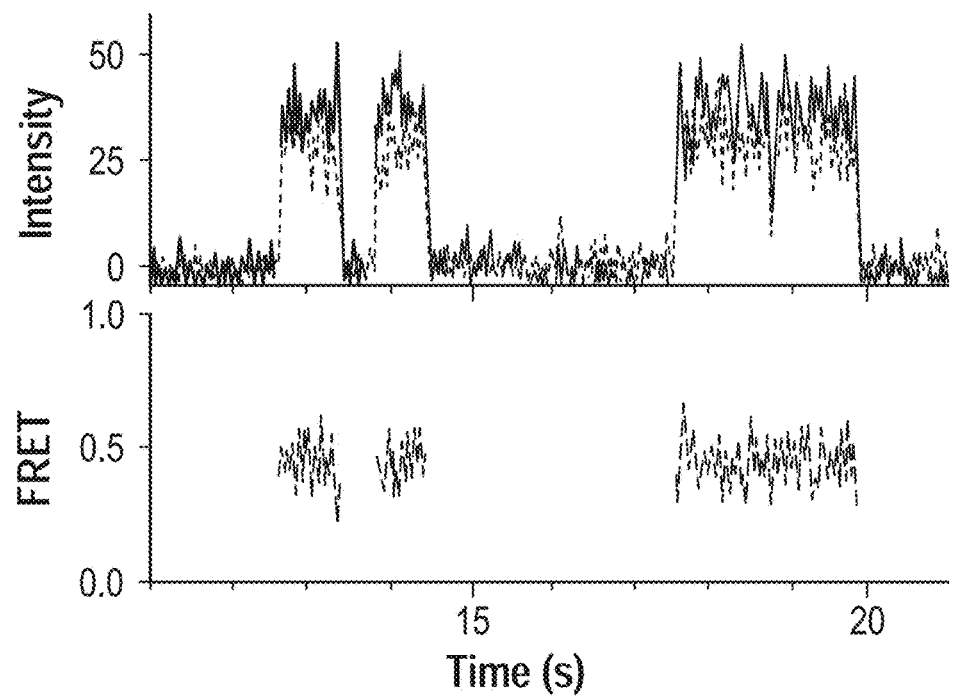
FIG. 2E depicts representative single molecule time traces showing the DNA binding and dissociation behavior for the donor strand for Rep-Y, wherein the donor fluorescence signal is in green, acceptor in red and $E_{FRET}$ in blue.
Figure 2F:
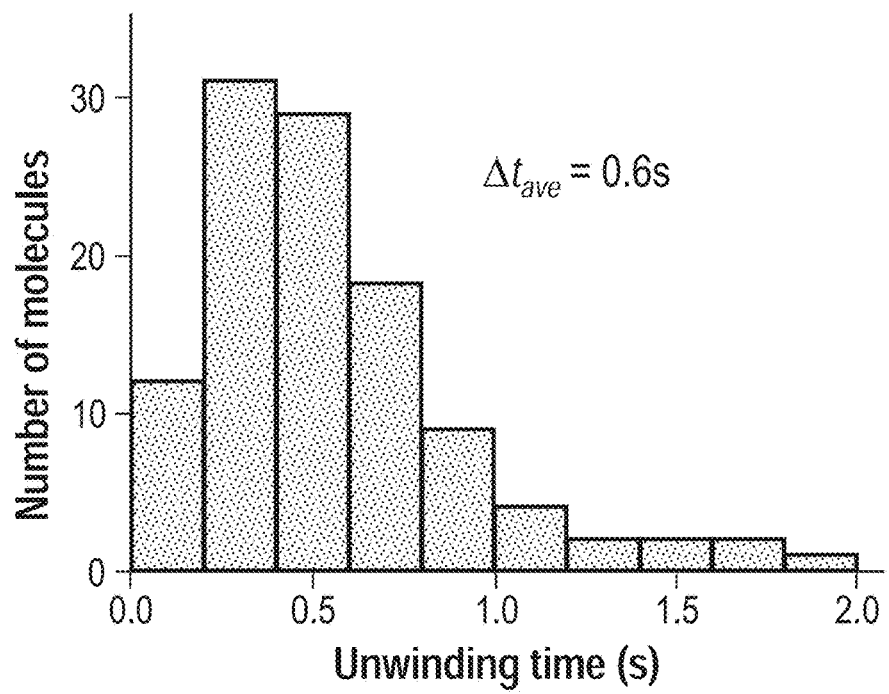
FIG. 2F depicts a representative distribution of Rep-X unwinding period Δt.
Figure 2G:
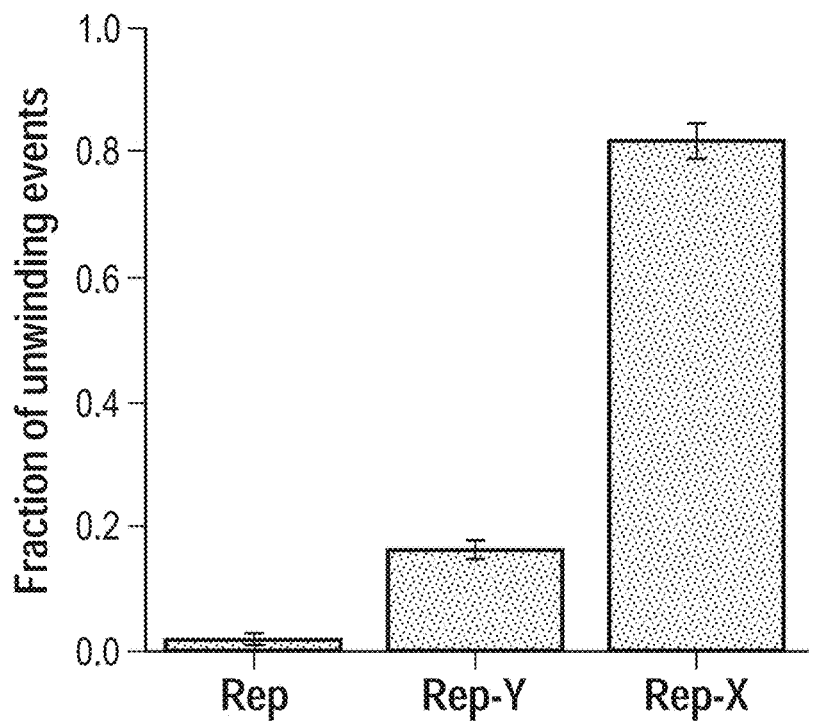
FIG. 2G depicts fractions of DNA binding events that led to unwinding (i.e. exhibited an $E_{FRET}$ increase phase) in smFRET experiments for Rep, Rep-Y and Rep-X. Error bars represent 95% confidence bounds.

Rep and Rep-X monomers were immobilized to a polymer-passivated quartz surface using antibodies against the N-terminal hexa-histidine-tag (SEQ ID NO: 36) on the protein (FIG. 2A) to ensure that the observed activity belonged to monomers (T. Ha et al., Initiation and re-initiation of DNA unwinding by the *Escherichia coli* Rep helicase. *Nature* 419, 638-641 (2002)). For the unwinding substrate, we used a 18-bp duplex DNA with a 3'-(dT)$_{20}$ overhang (SEQ ID NO: 37) labeled with a donor (Cy3) and an acceptor (Cy5) at two opposite ends of the DNA duplex, allowing us to identify unwinding reactions as increases in FRET efficiency ($E_{FRET}$)(FIG. 2A) (G. Lee, M. A. Bratkowski, F. Ding, A. Ke, T. Ha, Elastic Coupling Between RNA Degradation and Unwinding by an Exoribonuclease. *Science* (New York, N.Y 336, 1726-1729 (2012)). When the DNA and ATP were added to the reaction chamber, we could observe the capture of a single DNA molecule by a single protein as the sudden appearance of fluorescence signal (FIG. 2B-E). Subsequent DNA unwinding generated ssDNA strands that coil up due to high flexibility and $E_{FRET}$ increased (M. C. Murphy, I. Rasnik, W. Cheng, T. M. Lohman, T. Ha, Probing single-stranded DNA conformational flexibility using fluorescence spectroscopy. *Biophysical journal* 86, 2530-2537 (2004)). Once the duplex was completely unwound, the acceptor-labeled strand was released, which was marked by sudden disappearance of the acceptor signal and recovery of the donor signal. The donor-labeled strand then dissociated, resulting in complete loss of fluorescence. The mean duration of unwinding measured from the $E_{FRET}$ increase to acceptor strand release was ~0.6 s, giving a lower limit on the unwinding speed of 30 bp/s for the 18-bp substrate (FIG. 2F). About 82% of the DNA molecules (661 out of 809) that initially bound to Rep-X monomers were unwound (FIG. 2G). In contrast, only 2% of the DNA molecules (13 out of 847) that bound to Rep (i.e. without crosslinking) showed unwinding, and the unwinding yield for Rep-Y was 16% (357 out of 2212) (FIG. 2G), showing that constraining Rep into the closed form selectively activates the unwinding activity of a monomer. The nonzero amplitude of unwinding for Rep and Rep-Y may be due to conformational constraints caused by surface tethering in a small fraction of molecules.

Figure 3A:
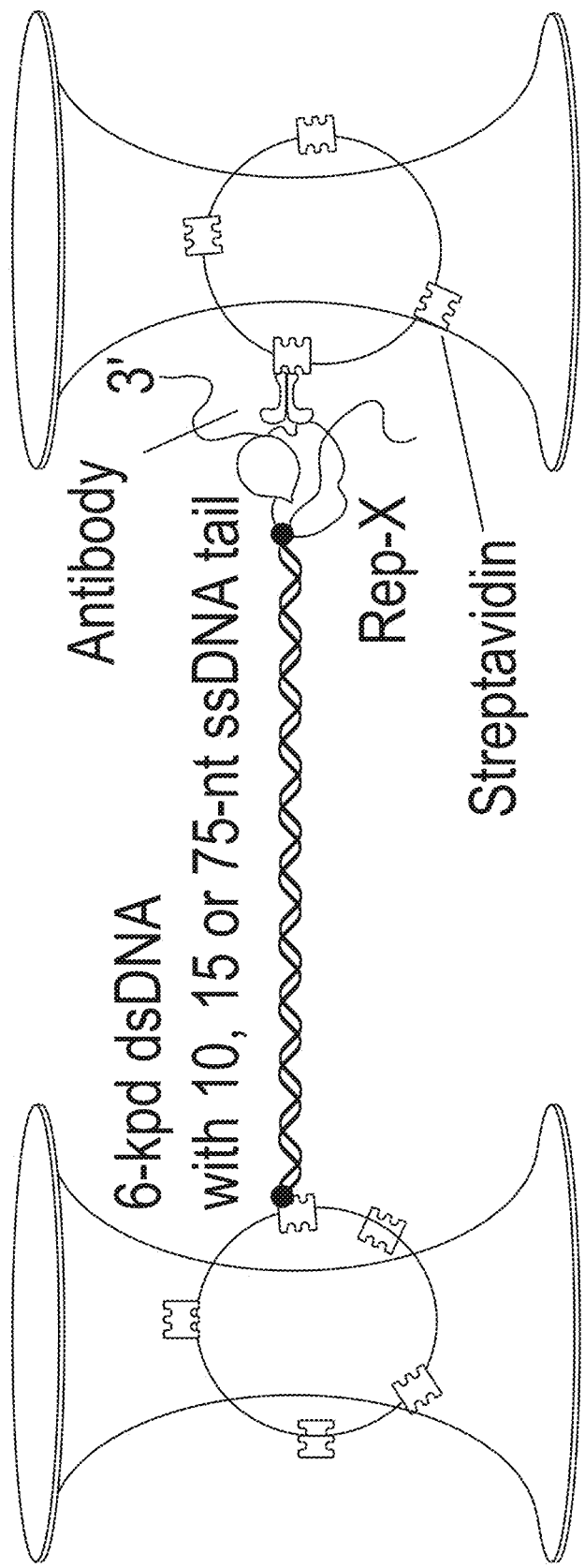
FIG. 3A depicts a schematic of the optical tweezers assay depicts a Rep-X molecule tethered to the bead surface that just loaded on the free ssDNA overhang and started to unwind the 6-kbp DNA=.
Figure 3B:
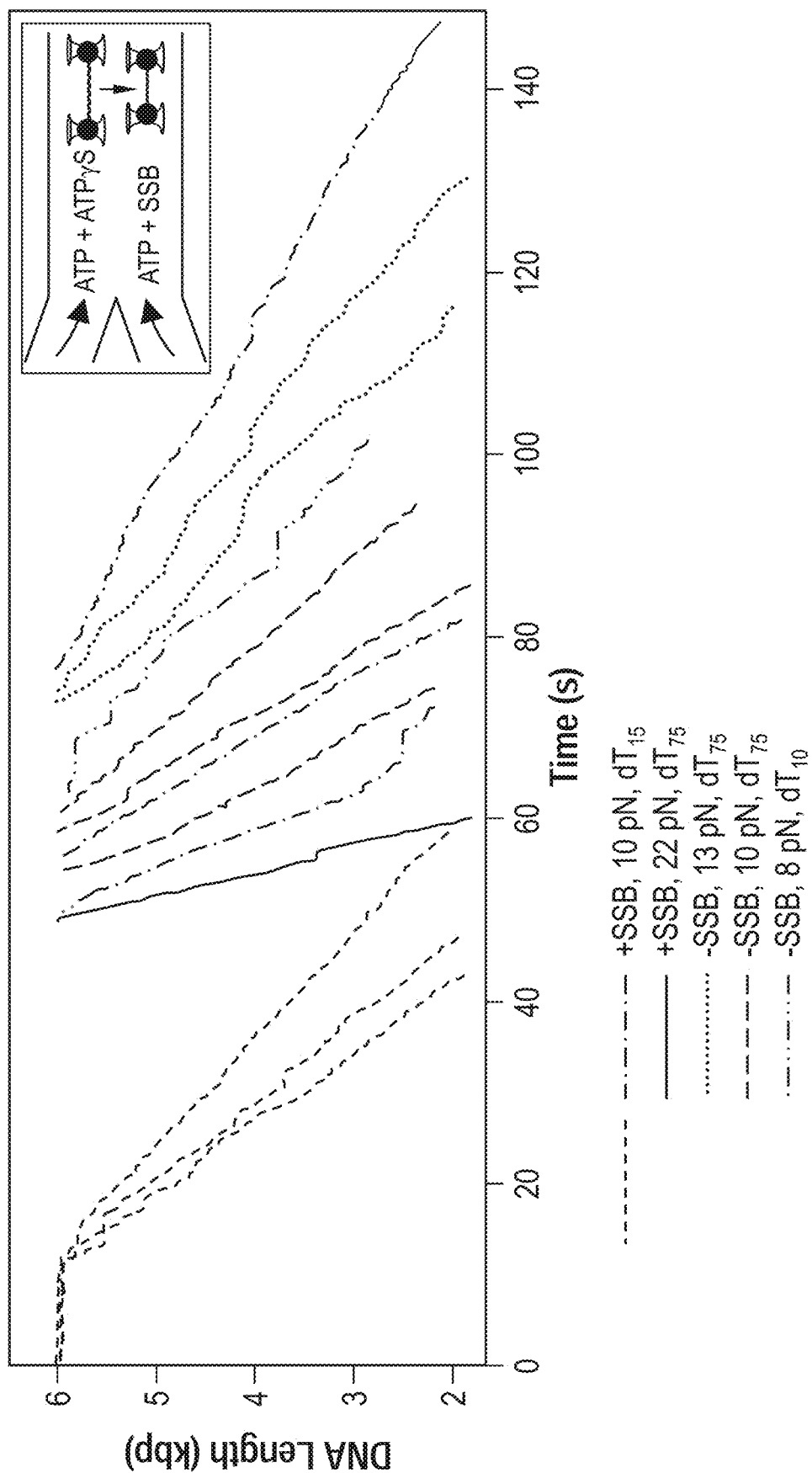
FIG. 3B depicts unwinding traces showing the extent of processive unwinding by Rep-X on the 6-kbp DNA (colored according to conditions of overhang length, SSB and force, and offset for clarity). Background is color coordinated with the inset to show the two laminar flows.
Figure 3C:
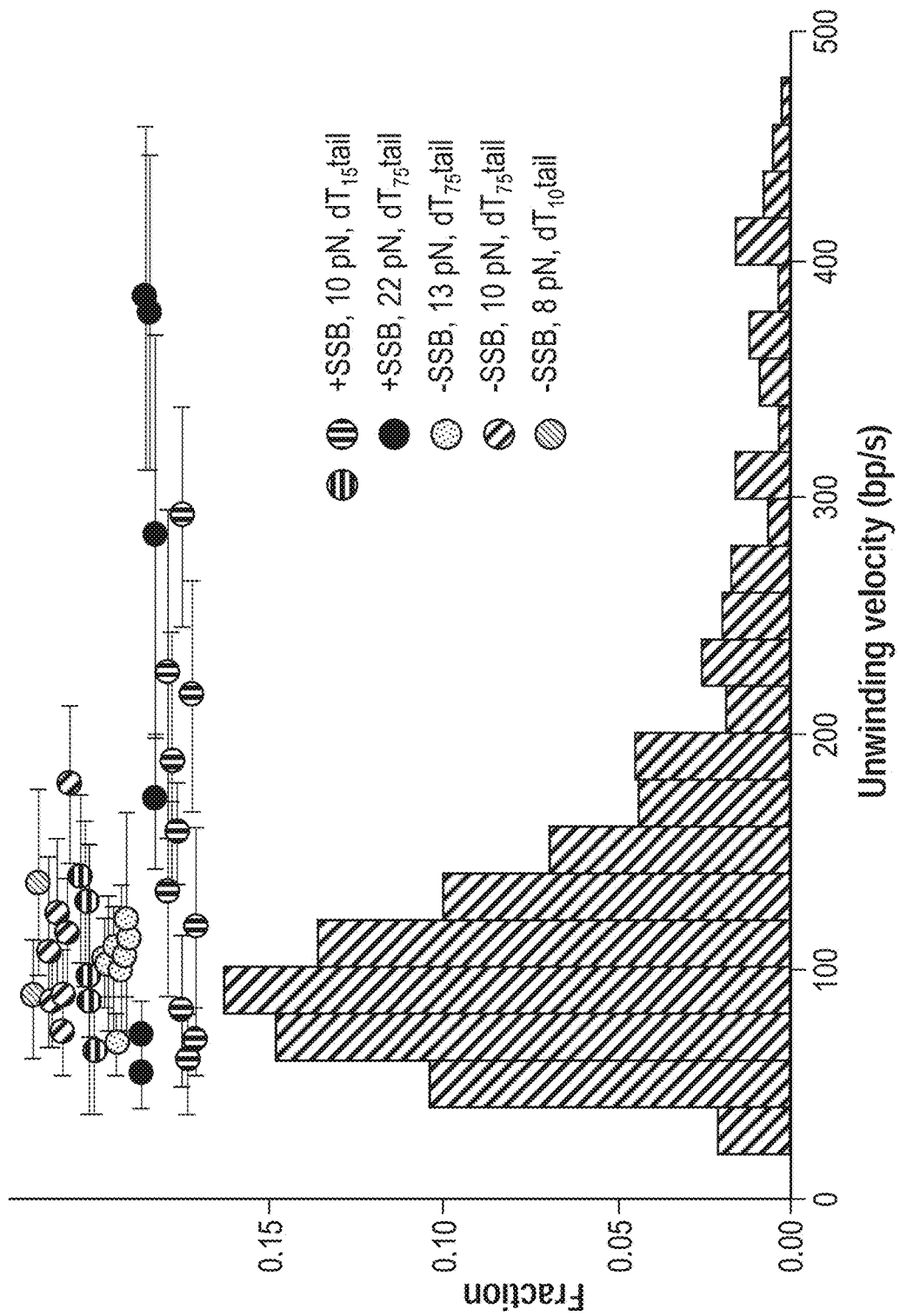
FIG. 3C depicts an exemplary distribution of Rep-X unwinding velocities (N=38). Mean velocity of unwinding and the standard deviation for each molecule were plotted above (colors as in B). Figure discloses "$(dT)_{10}$," "$(dT)_{15}$" and "$(dT)_{75}$" as SEQ ID NOS 33-35, respectively.
Figure 3D:
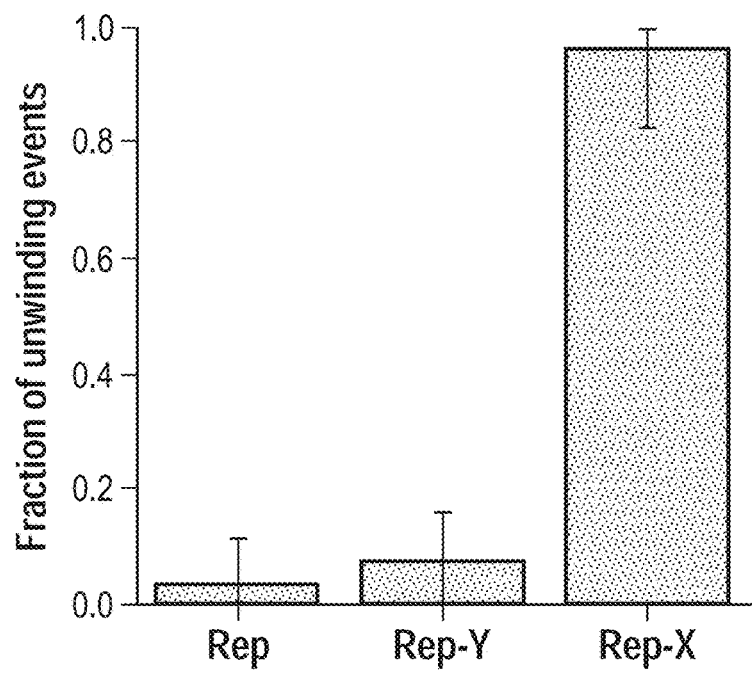
FIG. 3D depicts exemplary data comparing the fraction of the complete DNA binding events for Rep, Rep-Y and Rep-X. Error bars represent the 95% confidence bounds.

In vitro studies have shown that the unwinding processivity of Rep and related helicases is limited even in their oligomeric forms, ranging from 30-50 bp (A. Niedziela-Majka, M. A. Chesnik, E. J. Tomko, T. M. Lohman, *Bacillus stearothermophilus* PcrA monomer is a single-stranded DNA translocase but not a processive helicase in vitro. *The Journal of biological chemistry* 282, 27076-27085 (2007); Ha et al. (2008) supra; J. A. Ali, T. M. Lohman, Kinetic measurement of the step size of DNA unwinding by *Escherichia coli* UvrD helicase. *Science* (New York, N.Y 275, 377-380 (1997)). In order to investigate the processivity of Rep-X, we employed a dual optical tweezers assay (FIG. 3A; J. R. Moffitt et al., Intersubunit coordination in a homomeric ring ATPase. *Nature* 457, 446-450 (2009)) that can monitor unwinding amplitudes and speeds over thousands of base pairs of DNA. The two traps held two streptavidin functionalized sub-micron sized polystyrene beads. The first was coated with 6-kbp dsDNA attached via a biotin on the blunt end and containing a 3' poly-dT ssDNA overhang on the other end ((dT)$_{10}$ (SEQ ID NO: 33), (dT)$_{15}$ (SEQ ID NO: 34), and (dT)$_{75}$ (SEQ ID NO: 35) see Example 7)). The other bead was coated with Rep-X molecules via biotinylated antibody against the hexa-histidine-tag (SEQ ID NO: 36). A laminar flow cell with two parallel streams of buffer was created for controlling the initiation of the unwinding reaction (inset of FIG. 3B; L. R. Brewer, P. R. Bianco, Laminar flow cells for single-molecule studies of DNA-protein interactions. *Nature methods* 5, 517-525 (2008)). When the two beads were brought in proximity in the first laminar stream (Buffer C with 100 µM ATP and 100 µM ATP-γS), a single Rep-X binding to the 3' overhang of the DNA formed a tether between the two beads without initiating unwinding. When the tethered beads were moved to the second laminar stream (Buffer C and 1 mM ATP), the DNA tether between the beads progressively shortened as the Rep-X monomer unwound and pulled the DNA. Unless otherwise stated, SSB was added to the second laminar stream in order to prevent any subsequent interaction of unwound ssDNA with other Rep-X on the bead surface. The optical tweezers experiments that were performed without SSB yielded the same Rep-X behavior (Example 7). By operating the trap under force feedback control, the tension was maintained on the DNA at 10-22 pN, as indicated. Additional controls and considerations ascertained that the observed activity stemmed from a single Rep-X regardless of the 3'-tail length and inclusion/omission of SSB (Example 7). Remarkably, 95% (38 out of 40) of the Rep-X-DNA complexes tethered through a 3'-tail unwound the entire 6-kbp DNA in a processive manner (FIG. 3B, D) and the average pause-free speed was 136 bp/s (FIG. 3C). In comparison, only 3% (2 out of 61 at 4 pN tension, none at higher forces) of wild type Rep and 7% (5 out of 70) of Rep-Y complexes displayed such processive unwinding events (FIG. 3D). Rep-X may have even greater processivity than 6-kbp, currently only limited by the length of the DNA used. The processive activity of a crosslinked Rep-X monomer shows the innate potential of these helicases that can be harnessed via conformational control.

Figure 3E:
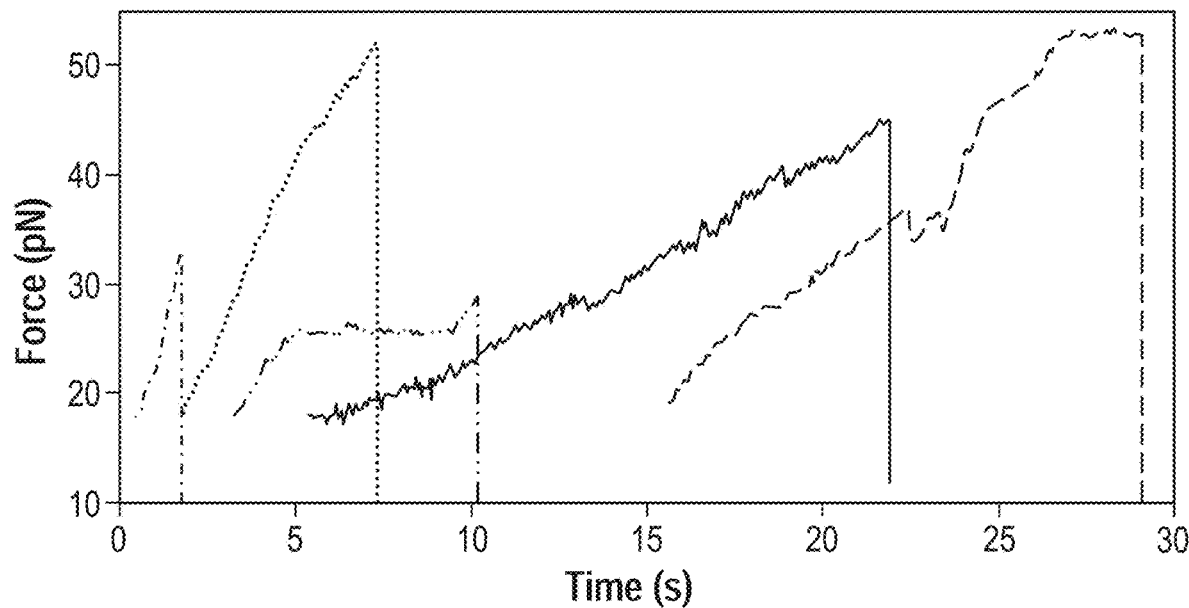
FIG. 3E depicts unwinding by five representative Rep-X molecules in the fixed trap assay are plotted. Pulling force increases during unwinding as the Rep-X pulls the beads closer. Tether breaks appear as sudden force drops.

The amount of force Rep-x can generate during unwinding was evaluated by performing measurements without the force feedback. Fixing trap positions led to a rapid build-up of force on the Rep-x in the opposite direction of unwinding until the measurement was terminated due to the breakage of connection between the two beads (FIG. 3E). The highest loads achieved in this experiment were not enough to stall the helicase permanently. More detailed analysis showed that the pause free unwinding rate of Rep-x was not impeded by increasing loads up to the limits of the linear regime of our trap (FIG. 3F), approximately 60 pN. These results suggest that the engineered Rep-X is the strongest helicase known to date (T. T. Perkins, H. W. Li, R. V. Dalal, J. Gelles, S. M. Block, Forward and reverse motion of single RecBCD molecules on DNA. *Biophysical journal* 86, 1640-1648 (2004); J. G. Yodh, M. Schlierf, T. Ha, Insight into helicase mechanism and function revealed through single-molecule approaches. *Quarterly reviews of biophysics* 43, 185-217 (2010)) In order to test if generation of a super active helicase can be reproduced for other helicases, thereby providing additional evidence of the conformational control mechanism, a PcrA-X helicase was engineered from *Bacillus stearothermophilus* PcrA. The Rep mutant sequences used to generate PcrA-x include those nucleotide and amino acid sequences identified in Table 3.

TABLE 3

Amino Acid and Nucleotide Sequences for exemplary PcrA-$_X$ proteins

| Polypeptide/DNA/RNA (SEQ ID NO:_) | 5'→3' (nucleotide sequence) N→C (amino acid sequence) |
|---|---|
| Wild type PcrA helicase (gene sequence) >gi\|696477066:c17795-15621 *Geobaciilus stearothermophilus* ATCC 7953 GBScontig0000036_2, whole genome shotgun sequence (SEQ ID NO: 38) | ATGAACTTTTTATCGGAACAGCTGCTCGCCCATTTAAACAAAG<br>AGCAACAAGAAGCCGTCAGGACGACGGAAGGCCCGCTGCTCA<br>TTATGGCGGGGCGGGAAGCGGGAAAACGCGGGTGTTGACGC<br>ACCGCATCGCCTATTTGATGGCGGAAAAGCATGTGGCGCCGT<br>GGAACATTTTGGCCATTACGTTTACGAACAAGGCGGCGCGCG<br>AAATGCGGGPACGTGTGCAGTCGCTCTTAGGTGGGGCGGCGG<br>AAGACGTCTGGATTTCGACGTTCCACTCGATGTGCGTCCGCAT<br>TTTGCGCCGCGACATTGACCGCATCGGCATCAACCGCAATTTT<br>TCCATCCTTGATCCGACGACCAGCTTTCAGTCATGAAAACGA<br>TTTTAAAAGAAAAAAACATAGACCCGAAAAAATTTGAGCCGC<br>GGACGATTTTAGGCACGATCAGCGCGGCGAAAAACGAGCTGT<br>TGCCTCCGGAGCAATTCGCGAAGCGGGCCTCGACGTATTACG<br>AAAAAGTCGTCAGCGATGTGTATCAAGAATACCAACAGCGCC<br>TGCTTCGCAATCATTCGCTCGATTTTGACGATTTGATCATGAC<br>GACGATCCAACTGTTTGACCGCGTGCCGGATGTGCTTCACTAT<br>TACCAATATAAGTTTCAGTACATTCATATTGATGAGTACCAGG<br>ATACGAACCGCGCTCAATATACGCTGGTCAAAAAGCTGGCGG<br>AACGCTTTCAAAACATTTGCGCCGTCGGCGACGCCGACCAAT<br>CGATTTATCGGTGGCGCGGGGCGGACATCCAAAACATTTTGTC<br>GTTCGAGCGCGACTATCCGAACGCAAAAGTCATTTTGCTTGAA<br>CAAAACTACCGCTCGACGAAGCGCATTTTGCAAGCGGCGAAC<br>GAAGTCATCGAGCATAACGTCAACCGGAAGCCGAAACGGCTT<br>TGGACGGAAAACCCGGAAGGAAAGCCGATTCTTTATTATGAG<br>GCGATGAACGAAGCGGACGAAGCGCAGTTTGTCGCTGGACGC<br>ATCCGCGAGGCGGTGGAGCGCGGCGAACGCCGCTACCGTGAT<br>TTTGCTGTCTTGTACCGGACGAACGCCCAGTCGCGTGTCATGG<br>AGGAAATGTTGCTGAAAGCGAACATTCCGTATCAAATTGTCG<br>GCGGCTTAAAGTTCTATGACCGGAAAGAAATTAAAGACATTC<br>TCGCCTATTTGCGCGTCATTGCCAATCCGGACGATGATTTAAG<br>CTTGCTTCGCATCATTAACGTGCCAAAACGCGGCATTGGCGCC<br>TCGACGATCGACAAACTCGTCCGCTATGCAGCCGATCATGAG<br>CTGTCCTTGTTTGAGGCGCTCGGCGAGCTAGAGATGATCGGGC<br>TTGGCGCCAAAGCGGCCGGGGCGCTCGCCGCGTICCGCAGCC<br>AGCTCGAGCAATGGACACAGCTGCAAGAATACGTCTCCGTCA<br>CCGAACTCGTCGAAGAAGTGCTCGACAAATCGGGCTACCGCG<br>AGATGCTCAAGGCGGAGCGGACGATTGAAGCACAAAGCCGG<br>CTCGAGAACTTGGATGAGTTTTTGTCGGTGACGAAGCATTTTG<br>AAAATGTGAGCGACGATAAATCGCTCATCGCCTTTTTAACCGA<br>CTTGGCGCTCATTTCCGATTTGGACGAGCTGAACGGGACGGA<br>ACAGGCCGCTGAAGGAGATGCCCGTCATGTTGATGACGTTGCA<br>TGCCGCCAAAGGGCTCGAGTTTCCGGTCGTCTTTTTGATCGGC<br>ATGGAAGAAGGCATTTTCCCGCACAACCGCTCTCTCGAGGAT<br>GACGATGAGATGGAAGAAGAACGGCGGCTGGCGTACGTCGG<br>CATCACCCGCGCGGAGGAAGAACTTGTGCTGACGAGCGCGCA<br>AATGCGGACGTTGTTTGGCAACATCCAAATGAACCCGCCGTC<br>GCGCTTTTTGAATGAAATTCCGGCGCATTTGCTTGAGACAGCC<br>TCGCGCCGCCAAGCGGGCGCCTCCCGCCCGGCCGTTTCGCGCC<br>CGCAGGCAAGCGGCGCCGTGGGATCGTGGAAAGTCGGCGATC<br>GGGCGAATCACCGGAAATGGGGCATCGGCACCGTCGTCAGCG<br>TCCGCGGCGGCGGCGACGACCAAGAGCTCGACATCGCCTTCC<br>CGAGCCCGATCGGCATTAAACGGTTGCTTGCCAAATTTGCGCC<br>GATTGAGAAAGTGTAG |
| Wild type PcrA helicase (amino acid sequence) >gi\|696477065\|ref\| WP_033016687.1 ATP-dependent DNA helicase PcrA [*Geobaciilus stearothermophilus*] (SEQ ID NO: 39) | MNFLSEQLLAHLNKEQQEAVRTTEGPLLIMAGAGSGKTRVLTHR<br>IAYLMAEKHVAPWNILAITFTNKAAREMRERVQSLLGGAAEDV<br>WISTHSMCVRILRRDIDRIGINRNFSILDPTDQLSVMKTILKEKNI<br>DPKKFEPRTILGTISAAKNELLPPEQFAKRASTYYEKVVSDVYQE<br>YQQRLLRNHSLDFDDLIMTTIQLFDRVPDVLHYYQYKYFQYIHIDE<br>YQDTNRAQYTLVKKLAERFQNICAVGDADQSIYRWRGADIQNIL<br>SFERDYPNAKVILLEQNYRSTKRILQAANEVIEHNVNRKPKRLWT<br>ENPEGKPILYYEAMNEADEAQFVAGRIREAVERGERRYRDFAVL<br>YRTNAQSRVMEEMLLKANIPYQIVGGLKFYDRKEIKDILAYLRVI<br>ANPDDDLSLLRIINVPKRGIGASTIDKLVRYAADHELSLFEALGEL |

TABLE 3 -continued

Amino Acid and Nucleotide Sequences for exemplary PcrA-$_X$ proteins

| Polypeptide/DNA/RNA (SEQ ID NO:_) | 5'→3' (nucleotide sequence) N→C (amino acid sequence) |
|---|---|
| | EMIGLGAKAAGALAAFRSQLEQWTQLQEYVSVTELVEEVLDKS GYREMLKAERTIEAQSRLENLDEFLSVTKHFENVSDDKSLIAFLT DLALISDLDELNGTEQAAEGDAVMLMTLHAAKGLEFPVVFLIGM EEGIFPHNRSLEDDDEMEEERRLAYVGITRAEEELVLTSAQMRTL FGNIQMNPPSRFLNEIPAHLLETASRRQAGASRPAVSRPQASGAV GSWKVGDRANHRKWGIGTVVSVRGGGDDQELDIAFPSPIGIKKL LAKFAPIEKV |
| PcrA-$_X$ polypeptide[1] (SEQ ID NO: 9) | MNFLSEQLLAHLNKEQQEAVRTTEGPLLIMAGAGSGKTRVLTHR IAYLMAEKHVAPWNILAITFTNKAAREMRERVQSLLGGAAEDV WISTFPHSMAVRILRRDIDRIGINRNFSILDPTDQLSVMKTILKEKNI DPKKFEPRTILGTISAAKNELLPPEQFAKRASTYYEKVVSDVYQE YQQRLLRCHSLDFDDLIMTTIQLFDRVPDVLHYYQYKFQYIHIDE YQDTNRAQYTLVKKLAERFQNIAAVGDADQSIYRWRGADIQNIL SFERDYPNAKVILLEQNYRSTKRILQAANEVIEHNVNRKPKRLWT ENPEGKPILYYEAMNEADEAQFVAGRIREAVERGERRYRDFAVL YRTNAQSRVMEEMLLLKANIPYQIVGGVKFYDRKEIKDILAYLRVI ANPDDDCSLLRIINVPKRGIGASTIDKLVRYAADHELSLFEALGEL EMIGLGAKAAGALAAFRSQLEQWTQLQEYVSVTELVEEVLDKS GYREMLKAERTIEAQSRLENLDEFLSVTKHFENVSDDKSLIAFLT DLALISDLDELNGTEQAAEGDAVMLMTLHAAKGLEFPVVFLIGM EEGIFPHNRSLEDDDEMEEERRLAYVGITRAEEELVLTSAQMRTL FGNIQMNPPSRFLNEIPAHLLETASRRQAGASRPAVSKPQASGAV GSWKVGDRANHRKWGIGTVVSVRGGGDDQELDIAFPSPIGIKRL LAKFAPIEKV |
| PcrA-$_X$ DNA[2] (SEQ ID NO: 10) | ATGAACTTTTTATCGGAACAGCTGCTCGCCCATTTAAACAAAG AGCAACAAGAAGCCGTCAGGACGACGGAAGGCCCGCTGcrcA TTATGGCGGGGGCGGGAAGCGGGAAAACGCGGGTGTTGACGC ACCGCATCGCCTATTTGATGGCGGAAAAGCATGTGGCGCCGT GGAACATTTTGGCCATTACGTTTACGAACAAGGCGGCGCGCG AAATGCGGGAACGTGTGCAGTCGCTCTTAGGTGGGGCGGCGG AAGACGTCTGGATTTCGACGTTCCACTCGATGGCCGTCCGCAT TTTGCGCCGCGACATTGACCGCATCGGCATCAACCGCAATTTT TCCATCCTTGATCCGACGGACCAGCTTTCAGTCATGAAAACGA TTTTAAAAGAAAAAAAACATAGACCCGAAAAAATTTGAGCCGC GGACGATTTTAGGCACGACAGCGCGGCGAAAAACGAGCTGT TGCCTCCGGAGCAATTCGCGAAGCGGGCCTCGACGTATTACG AAAAAGTCGTCAGCGATGTGTATCAAGAATACCAACAGCGCC TGCTTCGCTGTCATTCGCTCGATTTTGACGATTTGATCATGACG ACGATCCAACTGTTTGACCGCGTGCCGGATGTGCTTCACTATT ACCAATATAAGTTTCAGTACATTCATATTGATGAGTACCAGGA TACGAACCGCGCTCAATATACGCTGGTCAAAAAGCTGGCGGA ACGCTTCAAAACATTGCCGCCGTCGGCGACGCCGACCAATC GATTTATCGGTGGCGCGGGGCGGACATCCAAAACATTTTGTC GTTCGAGCGCGACTATCCGAACGCAAAAGTCATTTTGCTTGAA CAAAACTACCGCTCGACGAAGCGCATTTTGCAAGCGGCGAAC GAAGTCATCGAGCATAACGTCAACCGGAAGCCGAAACGGCTT TGGACGGAAAACCCGGAAGGAAAGCCGATTCTTTATTATGAG GCGATGAACGAAGCGGACGAAGCGCAGTTTGTCGCTGGACGC ATCCGCGAGGCGGTGGAGCGCGGCGAACGCCGCTACCGTGAT TTTGCTGTCTTGTACCGGACGAACGCCCAGTCGCGTGTCATGG AGGAAATGTTGCTGAAAGCGAACATTCCGTATCAAATTGTCG GCGGCGTAAAGTTCTATGACCGGAAAGAAATTAAAGACATTC TCGCCTATTTGCGCGTCATTGCCAATCCGGACGATGATTGCAG CTTGCTTCGCATCATTAACGTGCCAAAACGCGGCATTGGCGCC TCGACGATCGACAAACTCGTCCGCTATGCAGCCGATCATGAG CTGTCCTTGTTTGAGGCGCTCGGCGAGCTAGAGATGATCGGGC TTGGCGCCAAAGCGGCCGGGGCGCTCGCCGCGTTCCGCAGCC AGCTCGAGCAATGGACACAGCTGCAAGAATACGTCTCCGTCA CCGAACTCGTCGAAGAAGTGCTCGACAAATCGGGCTACCGCG AGATGCTCAAGGCGGAGCGGACGATTGAAGCACAAAGCCGG CTCGAGAACTTGGATGAGTTTTTGTCGGTGACGAAGCATTTTG AAAATGTGAGCGACGATAAATCGCTCATCGCCTTTTTAACCGA CTTGGCGCTCATTTCCGATTTGGACGAGCTGAACGGGACGGA ACAGGCCGCTGAAGGAGATGCCGTCATGTTGATGACGTTGCA TGCCGCCAAAGGGCTCGAGTTTCCGGTCGTCTTTTTGATCGGC ATGGAAGAAGGCATTTTCCCGCACAACCGCTCTCTCGAGGAT GACGATGAGATGGAAGAAGAACGGCGGCTGGCGTACGTCGG CATCACCCGCGCGGAGGAAGAACTTGTGCTGACGAGCGCGCA AATGCGGACGTTGTTTGGCAACATCCAAATGAACCCGCCGTC GCGCTTTTTGAATGAAATTCCGGCGCATTTGCTTGAGACAGCC TCGCGCCGCCAAGCGGGCGCCTCCCGCCCGGCCGTTTCGCGCC CGCAGGCAAGCGGCGCCGTGGGATCGTGGAAAGTCGGCGATC GGGCGAATCACCGGAAATGGCTGCATCGGCACCGTCGTCAGCG |

TABLE 3 -continued

Amino Acid and Nucleotide Sequences for exemplary PcrA-$_X$ proteins

| Polypeptide/DNA/RNA (SEQ ID NO:_) | 5'→3' (nucleotide sequence) N→C (amino acid sequence) |
|---|---|
| | TCCGCGGCGGCGGCGACGACCAAGAGCTCGACATCGCCTTCC<br>CGAGCCCGATCGGUATTAAACGGTTGCTTGCCAAATTTGCGCC<br>GATTGAGAAAGTGTAG |
| PcrA-$_X$ RNA[3]<br>(SEQ ID NO: 11) | AUGAACUUUUUAUCGGAACAGCUGCUCGCCCAUUUAAACAA<br>AGAGCAACAAGAAGCCGUCAGGACGACGGAAGGCCCGCUGC<br>UCAUUAUGGCGGGGGCGGGAAGCGGGAAAACGCGGGUGUU<br>GACGCACCGCAUCGCCUAUUUGAUGGCGGAAAAGCAUGUGG<br>CGCCGUGGAACAUUUUGGCCAUUACGUUUACGAACAAGGCG<br>GCGCGCGAAAUGCGGGAACGUGUGCAGUCGCUCUUAGGUGG<br>GGCGGCGGAAGACGUCUGGAUUUCGACGUUCCACUCGAUGG<br>CCGUCCGCAUUUUGCGCCGCGACAUUGACCGCAUCGGCAUC<br>AACCGCAAUUUUUCCAUCCUUGAUCCGACGGACCAGCUUUC<br>AGUCAUGAAAACGAUUUUAAAAGAAAAAAACAUAGACCCG<br>AAAAAAUUUGAGCCGCGGACGAUUUUAGGCACGAUCAGCGC<br>GGCGAAAAACGAGCUGUUGCCUCCGGAGCAAUUCGCGAAGC<br>GGGCCUCGACGUAUUACGAAAAAGUCGUCAGCGAUGUGUAU<br>CAAGAAUACCAACAGCGCCUGCUUCGCUGUCAUUCGCUCGA<br>UUUUGACGAUUUGAUCAUGACGACGAUCCAACUGUUUGACC<br>GCGUGCCGGAUGUGCUUCACUAUUACCAAUNUAAGUUUCAG<br>UACAUUCAUAUUGAUGAGUACCAGGAUACGAACCGCGCUCA<br>AUAUACGCUGGUCAAAAAGCUGGCGGAACGCUUUCAAAACA<br>UUGCCGCCGUCGGCGACGCCGACCAAUCGAUUUAUCGGUGG<br>CGCGGGGCGGACAUCCAAAACAUUUGUCGUUCGAGCGCGA<br>CUAUCCGAACGCAAAAGUCAUUUUGCUUGAACAAAACUACC<br>GCUCGACGAAGCGCAUUUUGCAAGCGGCGAACGAAGUCAUC<br>GAGCAUAACGUCAACCGGAAGCCGAAACGGCUUUGGACGGA<br>AAACCCGGAAGGAAAGCCGAUUCUUUAUUAUGAGGCGAUGA<br>ACGAAGCGGACGAAGCGCAGUUUGUCGCUGGACGCAUCCGC<br>GAGGCGGUGGAGCGCGGCGAACGCCGCUACCGUGAUUUUGC<br>UGUCUUGUACCGGACGAACGCCCAGUCGCGUGUCAUGGAGG<br>AAAUGUUGCUGAAAGCGAACAUUCCGUAUCAAAUUGUCGGC<br>GGCGUAAAGUUCUAUGACCGGAAAGAAAUUAAAGACAUUC<br>UCGCCUAUUUGCGCGUCAUUGCCAAUCCGGACGAUGAUUGC<br>AGCUUGCUUCGCAUCAUUAACGUGCCAAAACGCGGCAUUGG<br>CGCCUCGACGAUCGACAAACUCGUCCGCUAUGCAGCCGAUC<br>AUGAGCUGUCCUUGUUUGAGGCGCUCGGCGAGCUAGAGAUG<br>AUCGGGCUUGGCGCCAAAGCGGCCGGGGCGCUCGCCGCGUU<br>CCGCAGCCAGCUCGAGCAAUGGACACAGCUGCAAGAAUACG<br>UCUCCGUCACCGAACUCGUCGAAGAAGUGCUCGACAAAUCG<br>GGCUACCGCGAGAUGCUCAAGGCGGAGCGGACGAUUGAAGC<br>ACAAAGCCGGCUCGAGAACUUGGAUGAGUUUUUGUCGGUGA<br>CGAAGCAUUUUGAAAAUGUGAGCGACGAUAAAUCGCUCAUC<br>GCCUUUUUAACCGACUUGGCGCUCAUUUCCGAUUUGGACGA<br>GCUGAACGGGACGGAACAGGCCGCUGAAGGAGAUGCCGUCA<br>UGUUGAUGACGUUGCAUGCCGCCAAAGGGCUCGAGUUUCCG<br>GUCGUCUUUUUGAUCGGCAUGGAAGAAGGCAUUUUCCCGCA<br>CAACCGCUCUCUCGAGGAUGACGAUGAGAUGGAAGAAGAAC<br>GGCGGCUGGCGUACGUCGGCAUCACCCGCGCGGAGGAAGAA<br>CUUGUGCUGACGAGCGCGCAAAUGCGGACGUUGUUUGGCAA<br>CAUCCAAAUGAACCCGCCGUCGCGCUUUUUGAAUGAAAUUC<br>CGGCGCAUUUGCUUGAGACAGCCUCGCGCCGCCAAGCGGGC<br>GCCUCCCGCCCGGCCGUUUCGCGCCCGCAGUCAAGCGGCGCC<br>GUGGGAUCGUGGAAAGUCGGCGAUCGGGCGAAUCACCGGAA<br>AUGUGGCAUCGGCACCGUCGUCAGCGUCCGCGGCGGCGGCG<br>ACGACCAAGAGCUCGACAUCGCCUUCCCGAGCCCGAUCGGC<br>AUUAAACGGUUGCUUGCCAAAUUUGCGCCGAUUGAGAAAGU<br>GUAG |
| PerA-$_X$ polypeptide[4]<br>(SEQ ID NO: 12) | SEQ ID NO: 9 and formula no 1 in Table 2<br>(1-[2-[2-[2-(2,5-dioxopyrrol-1-<br>yl)ethoxy]ethoxy]ethyl]pyrrole-2,5-dime). |

[1]This PcrA mutant encodes mutations removing natural cysteine residues found in the wild-type PcrA and include further amino acid mutations to facilitate intramolecular crosslinking to an intramolecular crosslinking agent to generate the PcrA-$_X$ polypeptide.
[2]The DNA sequence corresponds to the open reading frame that encodes the polypeptide of SEQ ID NO: 9.
[3]The RNA sequence corresponds to the open reading frame that encodes the polypeptide of SEQ ID NO: 9.
[4]The PcrA-$_X$ polypeptide closed form monomer following reaction of PcrA-$_X$ polypeptide (SEQ ID NO: 9) with an intramolecular crosslinking agent.

Exemplary intramolecular crosslinking agents suitable for generating versions of PcrA-x include those identified in Table 2. Methods and conditions for generating intramolecular crosslink formation in proteins are well known in the art for these types of intramolecular crosslinking agents, and such methods and conditions are applicable to the PcrA helicases of this disclosure.

Figure 5A:
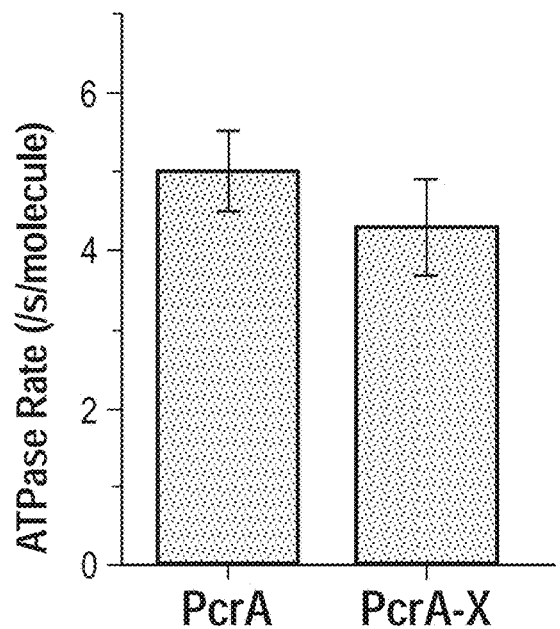
FIG. 5A depicts exemplary ATPase activity of mutant PcrA before ("PcrA") and after crosslinking ("PcrA-X"). Error bars represent standard deviation over multiple preparations.
Figure 5B:
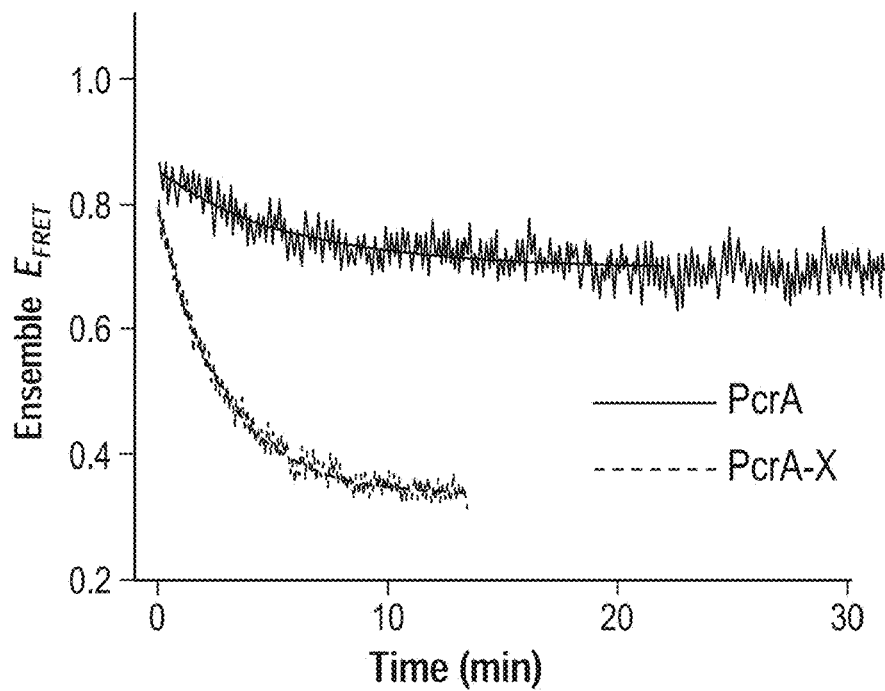
FIG. 5B depicts exemplary data of an ensemble unwinding assay for PcrA-X and wild type PcrA. Solid lines are fitted exponential decay curves as visual guides.
Figure 6A:
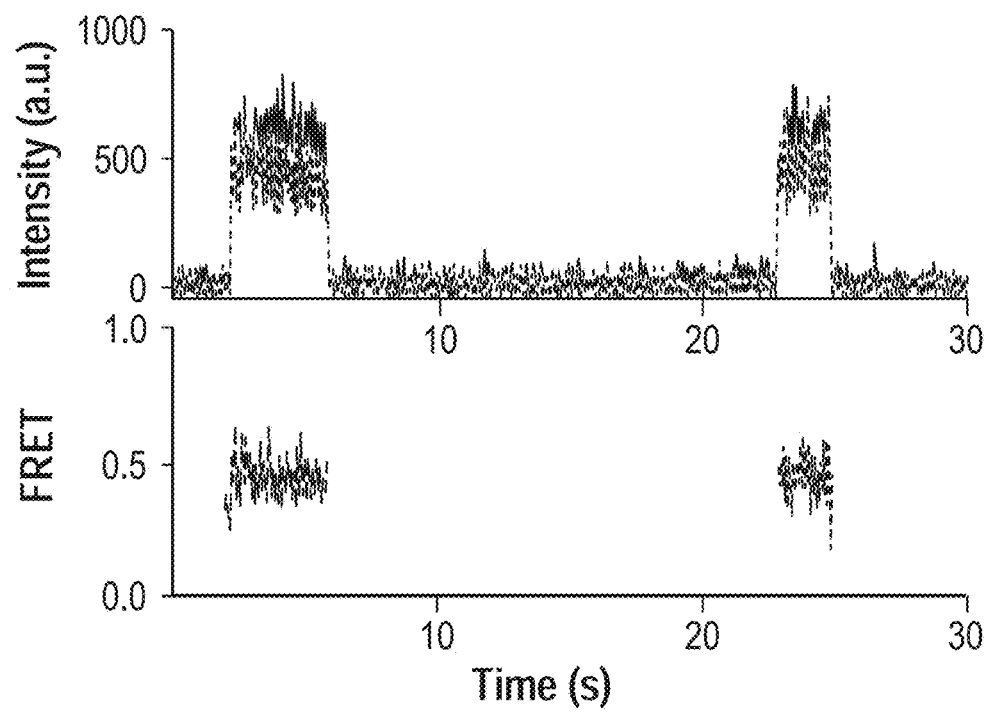
FIG. 6A depicts representative single molecule time traces for DNA binding and unwinding by PcrA-X monomers.
Figure 6B:
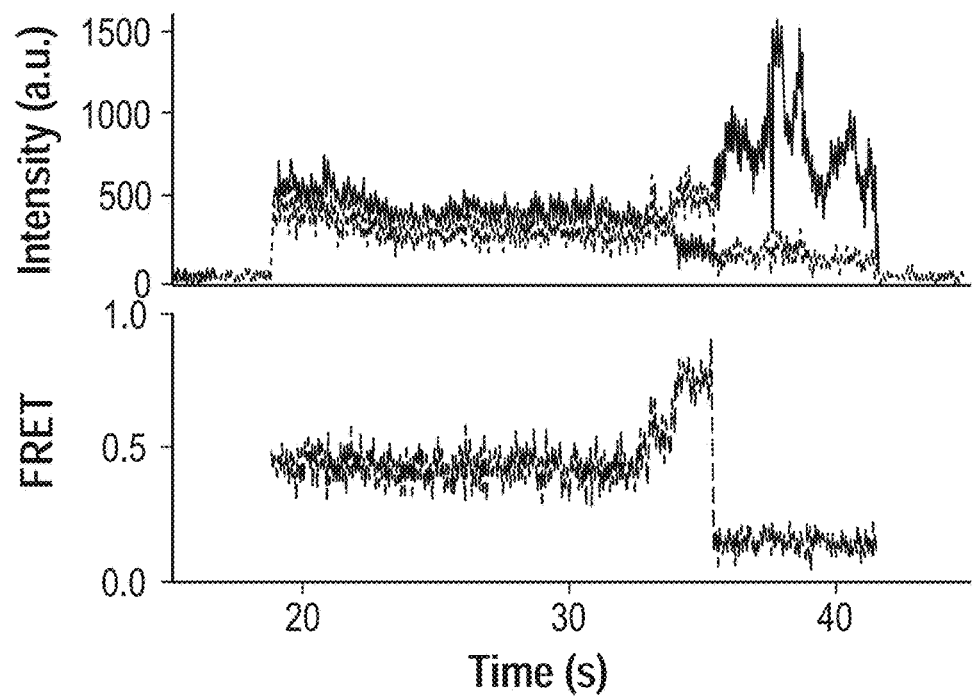
FIG. 6B depicts representative single molecule time traces for DNA binding and unwinding by t PcrA monomers, which are incapable of DNA unwinding.
Figure 6C:
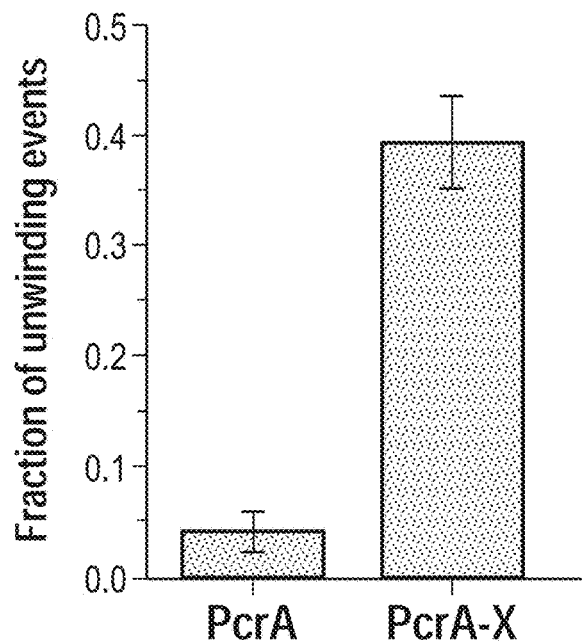
FIG. 6C depicts exemplary data of fractions of enzyme-DNA binding events that led to an unwinding phase for PcrA and PcrA-X in the smFRET assay. Error bars represent the 95% confidence bounds
Figure 6D:
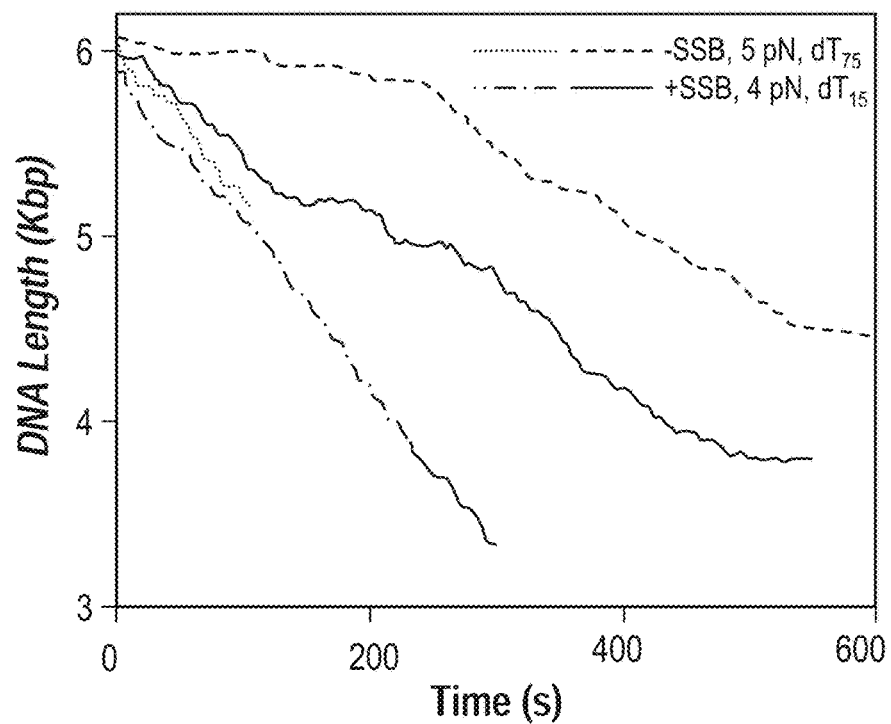
FIG. 6D depicts exemplary data showing processive unwinding of 6-kbp DNA by four representative PcrA-X molecules in the optical tweezers assay. Figure discloses "$(dT)_{15}$" and "$(dT)_{75}$" as SEQ ID NOS 34 and 35, respectively.
Figure 6E:
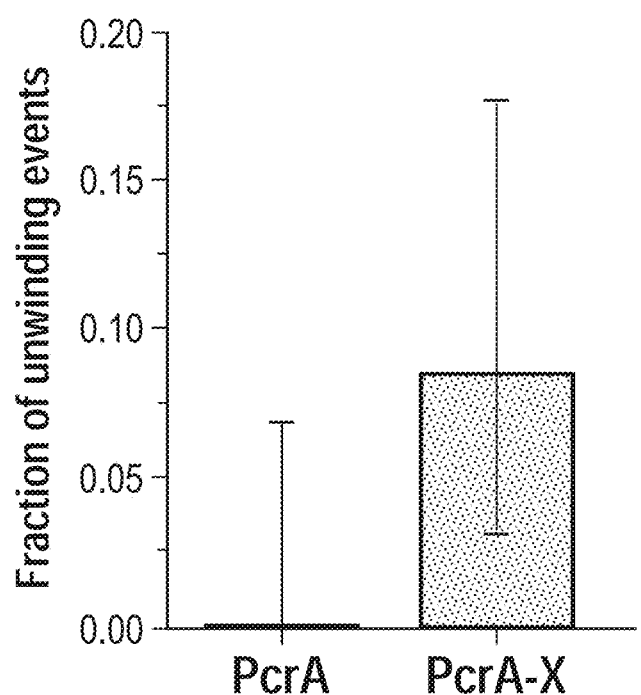
FIG. 6E depicts exemplary data for fractions of enzyme-DNA binding that led to the unwinding of 6-kbp DNA in the optical tweezers assay. Error bars represent the 95% confidence bounds

Mutations involved replacing two highly conserved Cys residues in this helicase (FIG. 4A, B) which reduced the apparent ssDNA-dependent ATPase activity from approximately 40 ATP/s (wild type) to 5 ATP/s. Upon crosslinking in the closed form, PcrA-x retained the low ATPase activity (4.3 ATP/s), but exhibited an enhanced helicase activity in comparison to both the wild type and non-crosslinked mutant in ensemble reactions (FIG. 5A, B). smFRET experiments showed that PcrA-X monomers can unwind 39% (228 out of 578) of the 18-bp dsDNA they bind compared to only 4% (26 out of 617) for wild type PcrA (FIG. 6A-C). In the optical tweezers assay, PcrA-X monomers, like Rep-X, were capable of processively unwinding of 1-6 kbp long DNA, albeit at a much lower rate (2-15 bp/s, FIG. 6D) whereas no PcrA molecule (0 out of 51) was able to do the same (FIG. 6E). Despite the impaired activity levels of the PcrA mutant, conversion to PcrA-X made its monomers into highly processive helicases, thus indicating a general mechanism of conformational control for this class of helicases.

Figure 6F:
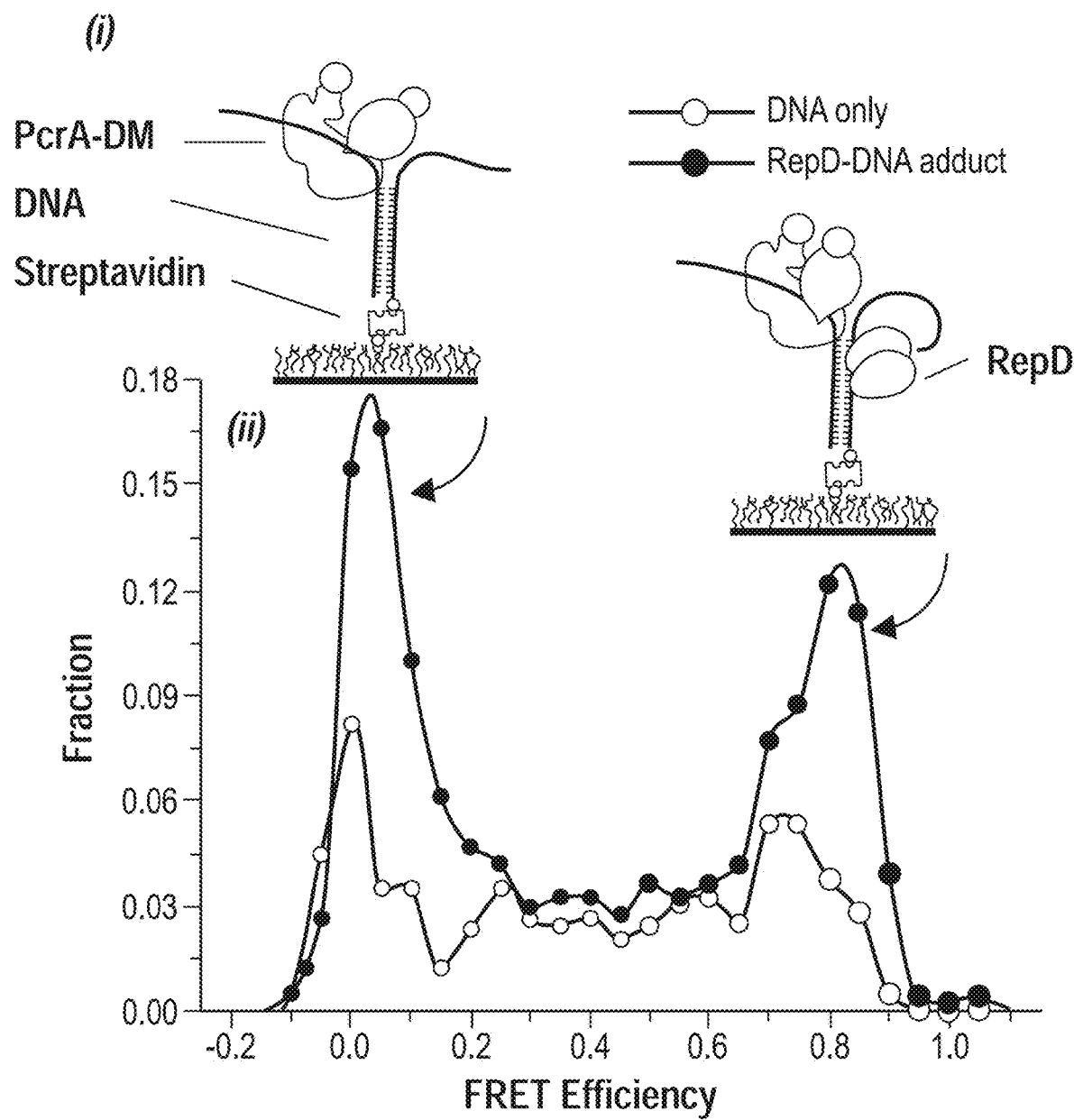
FIG. 6F depicts a schematic (in subpanel (i)) of the conformational effect of RepD, a stimulatory partner of PcrA, on PcrA as measured in a smFRET assay and $E_{FRET}$ histograms (sub-panel (ii)) showing that the PcrA bound to RepD adduct is biased toward the closed form (high $E_{FRET}$ population) compared to PcrA bound to the bare ori-D DNA.

Strong helicase activity of Rep-X and PcrA-X raises the possibility that the cellular partners of Rep or PcrA may switch on the powerful unwinding activity intrinsic to these enzymes by constraining them in the closed conformation. One such partner of PcrA is RepD, a plasmid replication initiator protein from *Staphylococcus aureus* that recognizes and forms a covalent adduct with the oriD sequence of the plasmid, and then recruits PcrA for highly processive unwinding (A. F. Slatter, C. D. Thomas, M. R. Webb, PcrA helicase tightly couples ATP hydrolysis to unwinding double-stranded DNA, modulated by the initiator protein for plasmid replication, RepD. *Biochemistry* 48, 6326-6334 (2009); W. Zhang et al., Directional loading and stimulation of PcrA helicase by the replication initiator protein RepD. *Journal of molecular biology* 371, 336-348 (2007); C. Machon et al., RepD-mediated recruitment of PcrA helicase at the *Staphylococcus aureus* pC221 plasmid replication origin, oriD. *Nucleic acids research* 38, 1874-1888 (2010)). Based on the similar results from PcrA-X and the homologous *E. coli* counterpart Rep-X, but not Rep-Y, we hypothesized that the RepD-induced PcrA activity enhancement is in fact the result of the conformational constraint of the helicase in the PcrA-X-like closed form. To test this prediction, we prepared an oriD DNA-RepD adduct, and measured the intramolecular conformation of PcrA bound to this adduct. We used a double cysteine mutant of PcrA, PcrA-DM1, stochastically labeled with a mixture of donor and acceptor fluorophores that would be expected to generate high $E_{FRET}$ in the closed form and low $E_{FRET}$ in the open form (J. Park et al., PcrA helicase dismantles RecA filaments by reeling in DNA in uniform steps. *Cell* 142, 544-555 (2010); (FIG. 6F). The $E_{FRET}$ distributions of PcrA-DM1 bound to the oriD DNA-RepD adduct and the oriD DNA alone are shown in FIG. 6F. Only the PcrA-DM1 molecules with a fluorescence active Cy3-Cy5 pair were included in the analysis. The results revealed that the presence of RepD indeed biases PcrA toward the closed high $E_{FRET}$ conformation. Without the invention being limited to any particular mechanism, the regulation mechanism of this class of helicases may involve in vivo partner proteins that constrain the conformation of 2B subdomain to the closed form to activate its function.

Figure 1E:
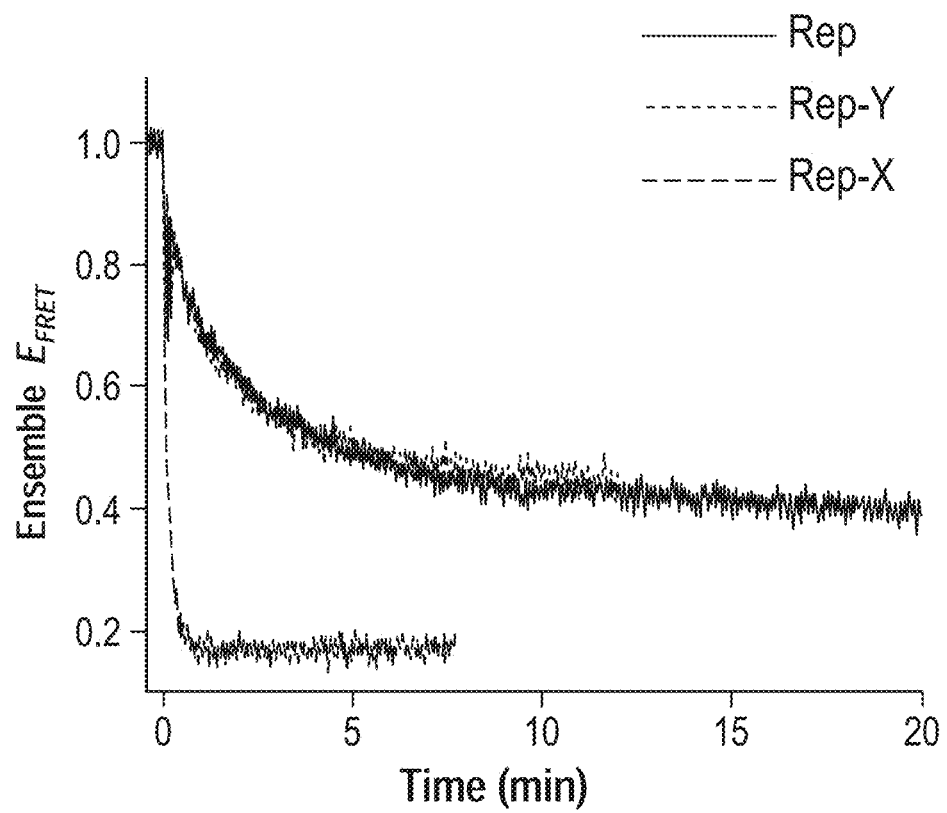
FIG. 1E depicts exemplary data of ensemble unwinding kinetics of the Rep-Y, Rep-X and non-crosslinked Rep using an assay containing 10 nM helicase, 5 nM 50-bp ensemble unwinding DNA with 3'-$(dT)_{30}$ (SEQ ID NO: 17) overhang in buffer D and 1 mM ATP).

The basis for constraining Rep and PcrA into the closed form that converts an enzyme with undetectable unwinding activity to a super helicase is unknown. One possibility is that the intrinsic unwinding activity itself requires the closed form, for example via the torque-wrench mechanism proposed for UvrD (J. Y. Lee, W. Yang, UvrD helicase unwinds DNA one base pair at a time by a two-part power stroke. *Cell* 127, 1349-1360 (2006)). Another possibility is that the open form inhibits helicase function and crosslinking to the closed form prevents this inhibitory mechanism. Without the invention being limited to any particular theory of operation, we prefer the latter for the following reasons. First, Rep-Y crosslinked in the open form does unwind DNA as well as the wild type when the protein is at high concentrations in excess of DNA (FIG. 1E). Therefore, the closed form per se is not absolutely required for unwinding activity. Second, using ultra-high resolution optical tweezers combined with smFRET capability, we found that UvrD assumes the closed conformation when it unwinds DNA but after it unwinds about 10 bp it switches to the open conformation and rewinds the DNA likely after strand switching. Therefore, we suggest that Rep-X becomes a highly processive super-helicase because crosslinking prevents the open conformation required for strand-switching and rewinding that have been observed for UvrD (M. N. Dessinges, T. Lionnet, X. G. Xi, D. Bensimon, V. Croquette, Single-molecule assay reveals strand switching and enhanced processivity of UvrD. *Proc. Natl. Acad. Sci., U.S.A.* 101, 6439-6444 (2004)) and BLM (J. G. Yodh, B. C. Stevens, R. Kanagaraj, P. Janscak, T. Ha, BLM helicase measures DNA unwound before switching strands and hRPA promotes unwinding reinitiation. *The EMBO journal* 28, 405-416 (2009)). The enhancement of unwinding activity via the deletion of 2B domain in Rep (W. Cheng et al., The 2B domain of the *Escherichia coli* Rep protein is not required for DNA helicase activity. *Proc. Natl. Acad. Sci., U.S.A.* 99, 16006-16011 (2002)) may also be due to inhibition of strand switching (M. J. Comstock, K. D. Whitley, H. Jia, T. M. Lohman, T. Ha and Y. R. Chemla, "Direct observation of structure-function relationship in a nucleic acid processing enzyme," *Science* 348: 352-354 (2015).

Most conformational control of protein functions demonstrated so far first locks the naturally active protein to an artificially inhibited conformation so that additional controls imposed by researchers can be used to recover the original activity (B. Choi, G. Zocchi, Y. Wu, S. Chan, L. Jeanne Perry, Allosteric control through mechanical tension. *Phys Rev Lett* 95, 078102 (2005); M. Tomishige, R. D. Vale, Controlling kinesin by reversible disulfide cross-linking. Identifying the motility-producing conformational change. *J Cell Biol* 151, 1081-1092 (2000); D. M. Veine, K. Ohnishi, C. H. Williams, Jr., Thioredoxin reductase from *Escherichia coli*: evidence of restriction to a single conformation upon formation of a crosslink between engineered cysteines. *Protein science: a publication of the Protein Society* 7, 369-375 (1998); B. X. Huang, H. Y. Kim, Interdomain conformational changes in Akt activation revealed by chemical cross-linking and tandem mass spectrometry. *Mol Cell Proteomics* 5, 1045-1053 (2006)). Our work is innovative and unique in that we found a conformational control that activates a naturally inhibited unwinding function, and the resulting enzyme is a super-helicase that has unprecedentedly high processivity for a single motor helicase. RecBCD, another SF-1 helicase, has similarly high processivity but contains two motors and associated nucleases. Moreover it is known to backslide at opposing forces below 10 pN whereas Rep-X can be active against forces as high as 60 pN (Perkins et al. (2004) supra). This super helicase with high processivity and high tolerance against load without nuclease activities may also be useful for biotechnological applications such as single molecule nanopore sequencing (D. Branton et al., The potential and challenges of nanopore sequencing. *Nature biotechnology* 26, 1146-1153 (2008); A. H. Laszlo et al., Decoding long nanopore sequencing reads of natural DNA. *Nature biotechnology*, (2014)) and isothermal DNA amplification (M. Vincent, Y. Xu, H. Kong, Helicase-dependent isothermal DNA amplification. *EMBO reports* 5, 795-800 (2004).

Figure 8:
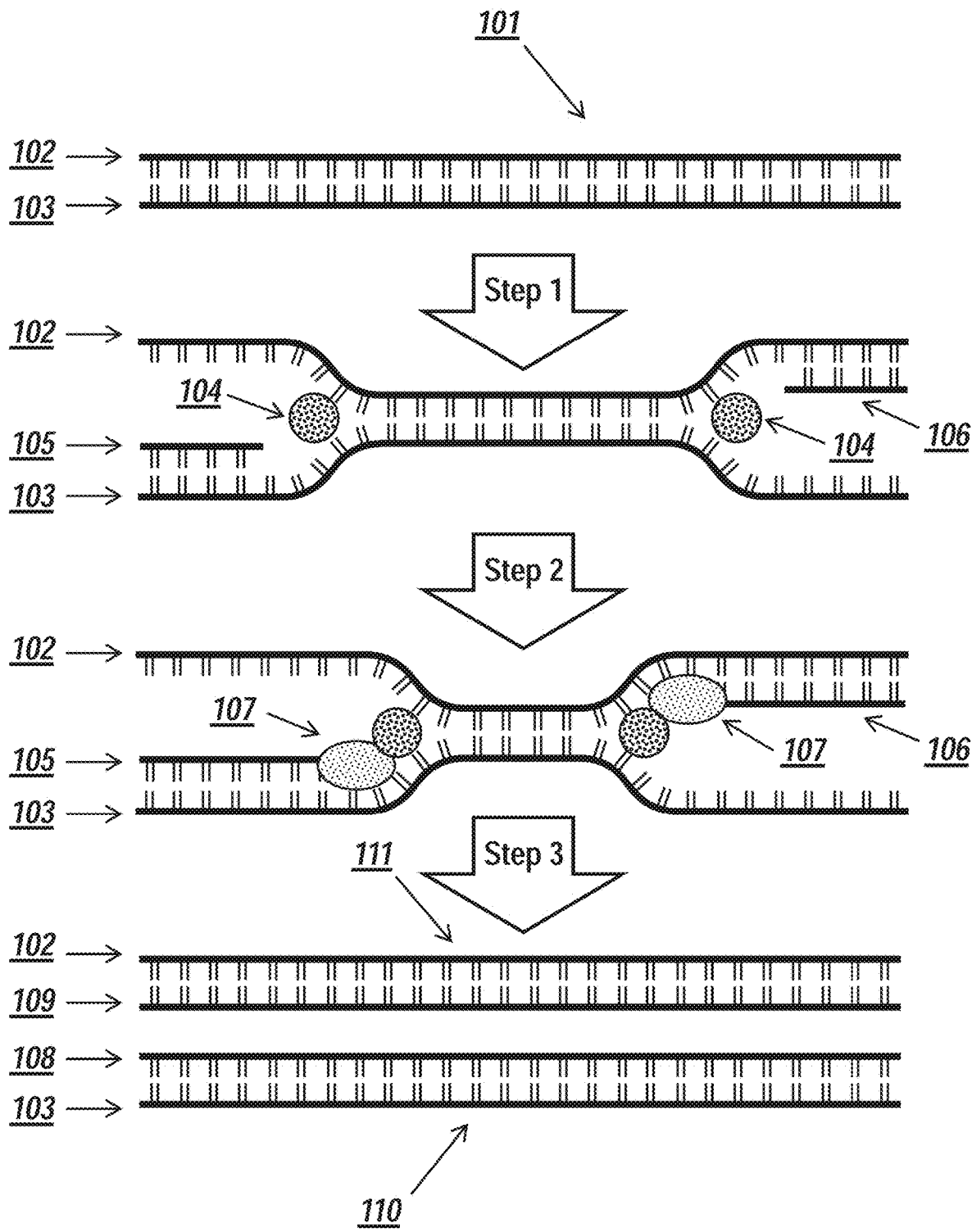
FIG. 8 depicts a schematic of an isothermal DNA amplification process called helicase dependent amplification, wherein in step 1: DNA helicase (104) contacts a double-stranded DNA (101) to unwind the first and second single strands (102 and 103) and first and second oligonucleotide primers (105 and 106) hybridize to the first and second single strands (102 and 103), respectively; in step 2: DNA-dependent DNA polymerases (107) bind to the 3'-termini of the first and second oligonucleotide primers (105 and 106) to initiate chain elongation of new strands (108 and 109); and in step 3: continued DNA polymerization results in DNA amplification and formation of new double-stranded DNA (110 and 111).

In this regard, one type of isothermal DNA amplification for which these super helicases have application include helicase dependent amplification. Referring to FIG. 8, the helicase dependent amplification can be characterized in three steps. In step 1, DNA helicase (104) contacts a double-stranded DNA (101) to unwind the first and second single strands (102 and 103) to provide the ability of first and second oligonucleotide primers (105 and 106) hybridize to the first and second single strands (102 and 103), respectively. In step 2: DNA-dependent DNA polymerases (107) bind to the 3'-termini of the first and second oligonucleotide primers (105 and 106) to initiate chain elongation of new strands (108 and 109). In step 3. continued DNA polymerization results in DNA amplification and formation of new double-stranded DNA (110 and 111).

Nucleic Acid Amplification

In certain exemplary embodiments, methods for amplifying nucleic acid sequences are provided. Exemplary methods for amplifying nucleic acids include the polymerase chain reaction (PCR) (see, e.g., Mullis et al. (1986) Cold Spring Harb. Symp. Quant. Biol. 51 Pt 1:263 and Cleary et al. (2004) Nature Methods 1:241; and U.S. Pat. Nos. 4,683,195 and 4,683,202), anchor PCR, RACE PCR, ligation chain reaction (LCR) (see, e.g., Landegran et al. (1988) Science 241:1077-1080; and Nakazawa et al. (1994) Proc. Natl. Acad. Sci. U.S.A. 91:360-364), self-sustained sequence replication (Guatelli et al. (1990) Proc. Natl. Acad. Sci. U.S.A. 87:1874), transcriptional amplification system (Kwoh et al. (1989) Proc. Natl. Acad. Sci. U.S.A. 86:1173), Q-Beta Replicase (Lizardi et al. (1988) BioTechnology 6:1197), recursive PCR (Jaffe et al. (2000) J. Biol. Chem. 275:2619; and Williams et al. (2002) J. Biol. Chem. 277: 7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA, or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, PCR: A Practical Approach and PCR 2: A Practical Approach (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., Nucleic Acids Research, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) Anal. Biochem., 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., Biotechniques, 26:112-126 (1999); Becker-Andre et al., Nucleic Acids Research, 17:9437-9447 (1989); Zimmerman et al., Biotechniques, 21:268-279 (1996); Diviacco et al., Gene, 122:3013-3020 (1992); Becker-Andre et al., Nucleic Acids Research, 17:9437-9446 (1989); and the like.

In one aspect of the invention, a method of performing isothermal DNA amplification is provided. The method can includes two steps. The first step includes forming a mixture. The mixture includes a double-stranded DNA template having a first strand and a second strand; a conformationally-constrained helicase; a DNA-dependent DNA polymerase; a first oligonucleotide primer complementary to a portion of the first strand; a second oligonucleotide primer complementary to a portion of the second strand; and an amplification buffer cocktail. The second step includes incubating the mixture at a temperature compatible for activating the conformationally-constrained helicase and DNA-dependent DNA polymerase. In some embodiments of this aspect, the conformationally-constrained helicase is selected from SEQ ID NOs: 4 and 12.

Nucleic Acid Sequencing

In certain exemplary embodiments, methods of determining the sequence identities of nucleic acid sequences are provided. Determination of the sequence of a nucleic acid sequence of interest can be performed using variety of sequencing methods known in the art including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. 2008/0269068; Porreca et al (2007) Nat. Methods 4:931), polymerized colony (POLONY) sequencing (U.S. Pat. Nos. 6,432,360, 6,485,944 and 6,511,803, and PCT/US05/06425), nanogrid rolling circle sequencing (ROLONY) (U.S. 2009/0018024), nanopore sequencing (using platforms such as those from Agilent, Oxford, Sequenom, Noblegen, NABsys, Genia), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa, ABI-SOLiD, ION Torrents, Complete Genomics, Pacific Bioscience, Helicos, Polonator platforms (Worldwide Web Site: Polonator.org), and the like, can also be utilized. High-throughput sequencing methods are described in U.S. 2010/0273164. A variety of light-based sequencing technologies are known in the art (Landegren et al. (1998) Genome Res. 8:769-76; Kwok (2000) Pharmocogenomics 1:95-100; and Shi (2001) Clin. Chem. 47:164-172).

In certain exemplary embodiments, the DNA-dependent DNA polymerase is selected from a group consisting of E. coli DNA Pol I, E. coli DNA Pol I Large Fragment, Bst 2.0 DNA Polymerase, Bst DNA Polymerase, Bst DNA Polymerase Large Fragment, Bsu DNA Polymerase I Large Fragment, T4 DNA Polymerase, T7 DNA polymerase, PyroPhage® 3173 DNA Polymerase and phi29 DNA Polymerase. In some embodiments, the conformationally-constrained helicase includes a helicase selected from superfamily 1, wherein the helicase has a first amino acid residue and a second amino acid reside, and wherein the first and second amino acid residues are in proximity. The conformationally-constrained helicase also includes a linker, wherein the linker comprises a first covalent bond with the first amino acid residue and a second covalent bond with the second amino acid residue. In some embodiments of this aspect, the conformationally-constrained helicase includes a crosslinked, closed form helicase monomer.

Expression of Helicase-X Polypeptides

The nucleic acids encoding the Rep-X and PcrA-X polypeptides can be adapted to suitable expression systems for producing the helicasex polypeptides for helicase-x production. For DNAs encoding helicasex genes, the representative genes can be operably-linked to suitable expression vectors for expressing the proteins in bacterial, fungal, insect or other suitable expression host. For RNAs encoding helicase-x polypeptides, the representative RNAs can be engineered for enabling efficient expression in vitro of the polypeptides in extract lysates produced from bacterial, fungal, insect or other suitable expression host sources. Such systems are well known in the art. Following expression, the helicase-x polypeptides can be purified by methods known in the art, including affinity-tag chromatography, SDS-PAGE, and size-exclusion chromatography, among others.

In certain exemplary embodiments, vectors such as, for example, expression vectors, containing a nucleic acid encoding one or more helicase-x polypeptides described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more helicase-x polypeptides described herein) in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence encoding one or more helicase-x polypeptides is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors described herein can be introduced into host cells to thereby produce proteins or portions thereof, including fusion proteins or portions thereof, encoded by nucleic acids as described herein (e.g., one or more helicasex polypeptides).

Recombinant expression vectors of the invention can be designed for expression of one or more encoding one or more helicase-x polypeptides in prokaryotic or eukaryotic cells. For example, one or more vectors encoding one or more helicase-x polypeptides can be expressed in bacterial cells such as *E. coli*, insect cells (e.g., using baculovirus expression vectors), yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40); pMAL (New England Biolabs, Beverly, Mass.); and pRIT5 (Pharmacia, Piscataway, N.J.) which fuse glutathione S-transferase (GST), maltose E binding protein, or protein A, respectively, to the target recombinant protein.

In another embodiment, the expression vector encoding one or more helicase-x polypeptides is a yeast expression vector. Examples of vectors for expression in yeast *S. cerevisiae* include pYepSec1 (Baldari, et. al., (1987) EMBO J. 6:229-234); pMFa (Kurjan and Herskowitz, (1982) Cell 30:933-943); pJRY88 (Schultz et al., (1987) Gene 54:113-123); pYES2 (Invitrogen Corporation, San Diego, Calif.); and picZ (Invitrogen Corporation).

Alternatively, one or more helicase-x polypeptides can be expressed in insect cells using baculovirus expression vectors. Baculovirus vectors available for expression of proteins in cultured insect cells (e.g., Sf9 cells) include the pAc series (Smith et al. (1983) Mol. Cell. Biol. 3:2156-2165) and the pVL series (Lucklow and Summers (1989) Virology 170: 31-39).

In certain exemplary embodiments, a nucleic acid described herein is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, adenovirus 2, cytomegalovirus and simian virus 40. For other suitable expression systems for both prokaryotic and eukaryotic cells see Green M., and Sambrook, J. Molecular Cloning: A Laboratory Manual. 4th, ed., Cold Spring Harbor Laboratory, Cold Spring Harbor Laboratory Press, Cold Spring Harbor, N.Y., 2012.

In certain exemplary embodiments, host cells into which a recombinant expression vector of the invention has been introduced are provided. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, one or more helicase-x polypeptides can be expressed in bacterial cells such as *E. coli*, viral cells such as retroviral cells, insect cells, yeast or mammalian cells (such as Chinese hamster ovary cells (CHO) or COS cells). Other suitable host cells are known to those skilled in the art.

Delivery of nucleic acids described herein (e.g., vector DNA) can be by any suitable method in the art. For example, delivery may be by injection, gene gun, by application of the nucleic acid in a gel, oil, or cream, by electroporation, using lipid-based transfection reagents, or by any other suitable transfection method.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN™ (Invitrogen Corp., San Diego, Calif.), LIPOFECTAMINE™ (Invitrogen), FUGENE™ (Roche Applied Science, Basel, Switzerland), JETPEI™ (Polyplus-transfection Inc., New York, N.Y.), EFFECTENE™ (Qiagen, Valencia, Calif.), DREAM-FECT™ (OZ Biosciences, France) and the like), or electroporation (e.g., in vivo electroporation). Suitable methods for transforming or transfecting host cells can be found in Green and Sambrook, et al. (Molecular Cloning: A Laboratory Manual. 4th, ed., Cold Spring Harbor Laboratory, Cold Spring Harbor Laboratory Press, Cold Spring Harbor, N.Y., 2012), and other laboratory manuals.

Kits

In another aspect, kits are contemplated in this disclosure. For example, a kit for performing helicase dependent amplification is provided. The kit can include a conformationally-constrained helicase and an optional amplification buffer cocktail. The conformationally-constrained helicase of the kit includes one or more helicasex polypeptides having a covalent linkage (e.g., reacted with a suitable intramolecular crosslinking agent) to form closed form helicase-x monomers having super helicase activity of the type described for Rep-X and PcrA-X. In particular, the conformationally-constrained helicase can be generated form reacting SEQ ID NOs:4 and 9 with a suitable intramolecular crosslinking agent. Representative conformationally-constrained helicases include those of SEQ ID NOs:4 and 12.

The kit can further include a DNA-dependent DNA polymerase. Exemplary DNA-dependent DNA polymerases for inclusion in kit include a polymerase selected from a group consisting of *E. coli* DNA Pol I, *E. coli* DNA Pol I Large Fragment, Bst 2.0 DNA Polymerase, Bst DNA Polymerase, Bst DNA Polymerase Large Fragment, Bsu DNA Polymerase I Large Fragment, T4 DNA Polymerase, T7 DNA polymerase, PyroPhage® 3173 DNA Polymerase, phi29 DNA Polymerase and the like.

EXAMPLES

Example 1. Mutagenesis and Purification of Protein

Preparation of pET expression plasmids containing cysteine-less rep (C18L, C43S, C167V, C178A, C612A) and pcrA (C96A/C247A) with N-terminal hexa-histidine-tags (SEQ ID NO: 36) were performed as described previously (Park et al. (2005) supra; I. Rasnik, S. Myong, W. Cheng, T. M. Lohman, T. Ha, DNA-binding orientation and domain conformation of the *E. coli* rep helicase monomer bound to a partial duplex junction: single-molecule studies of fluorescently labeled enzymes. *J. Mol. Biol.* 336, 395-408 (2004)). Site-directed mutations to introduce two Cys residues for crosslinking (Rep-X: A178C/S400C, Cys178 is a native cysteine in the wild type, Rep-Y: D127C/S494C, PcrA-X: N187C/L409C) were done using QuikChange Lightning kit (Life Technologies, Inc.) and mutagenic primer oligonucleotides (Integrated DNA Technologies Inc., Coralville, IA). Protein purifications were performed as described previously (Park et al. (2005) supra; Rasnik et al. (2004) supra). Catalytic activity levels of purified proteins as well as those of the crosslinked samples were determined in a ssDNA-dependent ATPase activity assay using the Invitrogen EnzChek phosphate assay kit (Life Technologies Inc.), the oligonucleotide (dT)$_{45}$ (SEQ ID NO: 305) and 1 mM ATP in buffer D (see ensemble FRET unwinding assay).

Wild type RepD from *Staphylococcus aureus* was purified as described in (Slatter et al. ((2009) supra; Zhang et al., (2007) supra) with the following differences. A wt-RepD encoding pET11m-RepD plasmid was constructed for expression in B834 (pLysS). The gene sequence contained silent mutations to introduce restriction sites for AgeI, PstI, SacI, and to modify the nick site (TCT'AAT to TCGAAT) to prevent premature cleavage by RepD during expression. An ammonium sulfate precipitated pellet (from 0.5 L culture) was resuspended and run through serially connected 5 ml Q-Sepharose (removed once the sample was through) and 5 ml heparin-Sepharose cartridges connected in series (GE Healthcare), and eluted on an AKTA purifier 10 FPLC system.

Example 2. Intra-Crosslinking of Rep and PcrA

Figure 10:
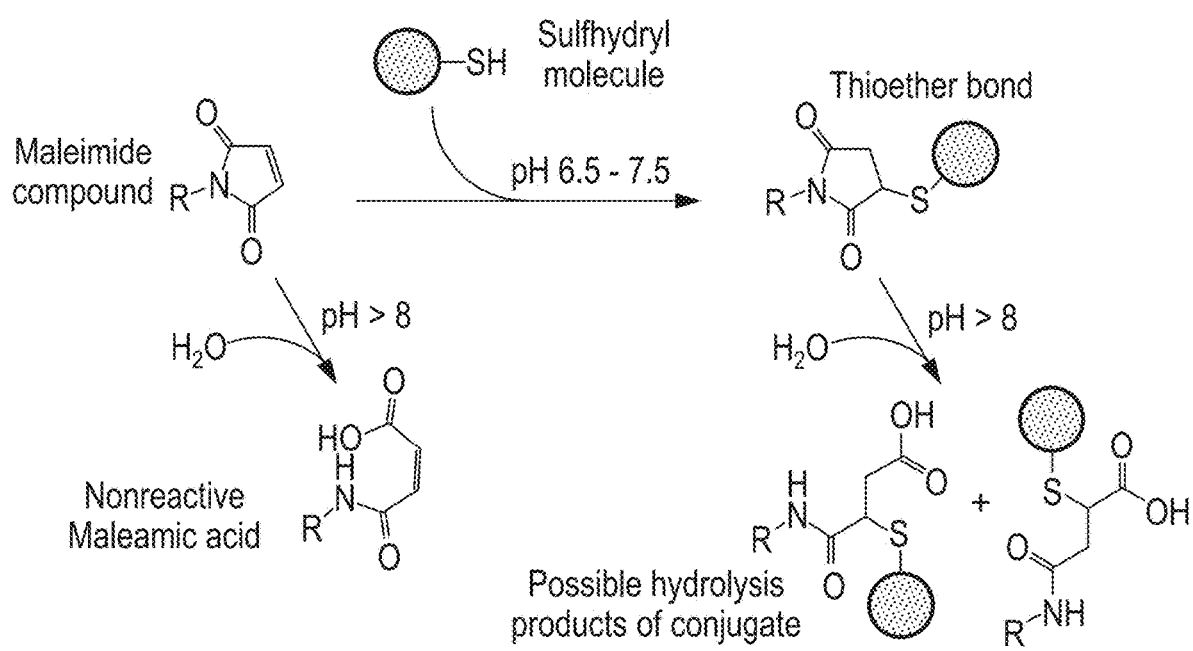
FIG. 10 shows the reaction of maleimide-activated compounds to sulfhydryl-bearing compounds.

Dual-cysteine Rep mutants were incubated overnight at 4° C. with 2- to 100-fold excess of bis-maleimide crosslinkers DTME (13 Å) and BMOE (8 Å) purchased from Thermo Fisher Scientific, Rockford, IL (FIG. 10). PcrA-X was crosslinked with DTME and BM(PEG)$_2$ (14.7 Å) from the same manufacturer. Excess crosslinkers were removed by Bio-Rad P-30 desalting column. Crosslinked Rep-X, Rep-Y and PcrA-X samples were stored at −20° C. or −80° C. as described (Park et al. (2005) supra; Rasnik et al. (2004) supra). Data presented in this manuscript used BMOE (8 Å), but other crosslinkers of various lengths gave similar results. DTME is a di-sulfide containing crosslinker that we reduced with β-mercaptoethanol (β-ME) or tris(2-carboxyethyl) phosphine (TCEP) to revert the crosslinked helicase to the non-crosslinked form for control purposes.

Figure 7A:
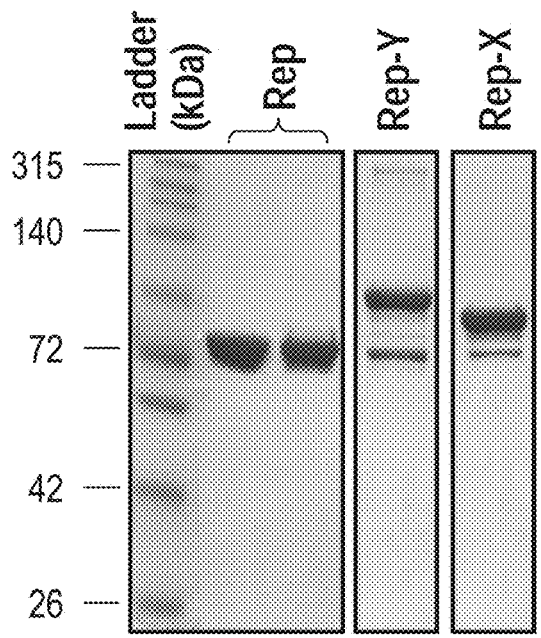
FIG. 7A shows an exemplary SDS-PAGE analysis of Rep-Y intra-crosslinking, wherein the typical three-band pattern on SDS polyacrylamide gels is evident. Rep-X intra-crosslinking pattern is shown for comparison, wherein the dominant middle band is slightly shifted for Rep-X compared with the corresponding band for Rep-Y. Lane designated as Rep is non-crosslinked Rep.
Figure 7B:
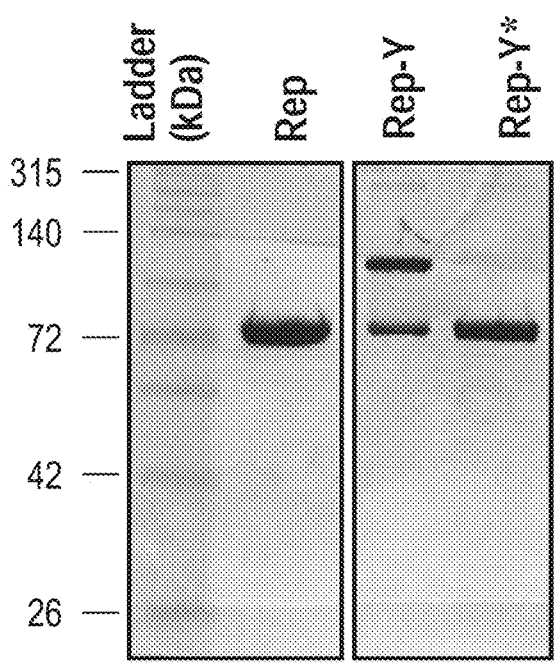
FIG. 7B shows an exemplary SDS-PAGE analysis of Rep-Y intra-crosslinking in comparison to uncrosslinked Rep ("Rep"). Lane denoted as Rep-Y*depicts (β-ME reduced Rep-Y (crosslinked with a di-sulfide crosslinker DTME).
Figure 7C:
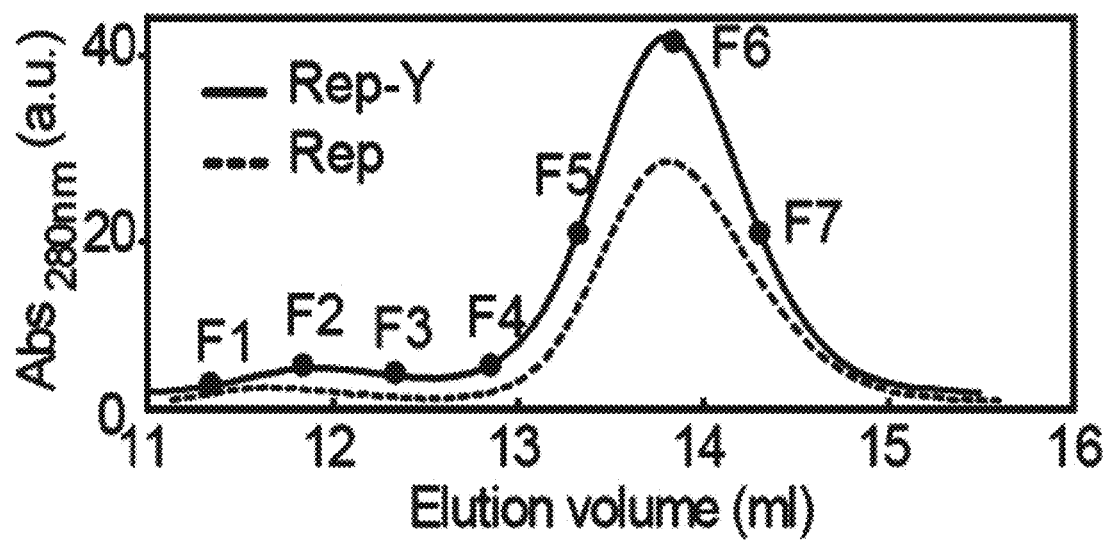
FIG. 7C shows an exemplary size exclusion chromatography (SEC) elution profile for Rep (dotted line) and the Rep-Y sample (solid line).
Figure 7D:
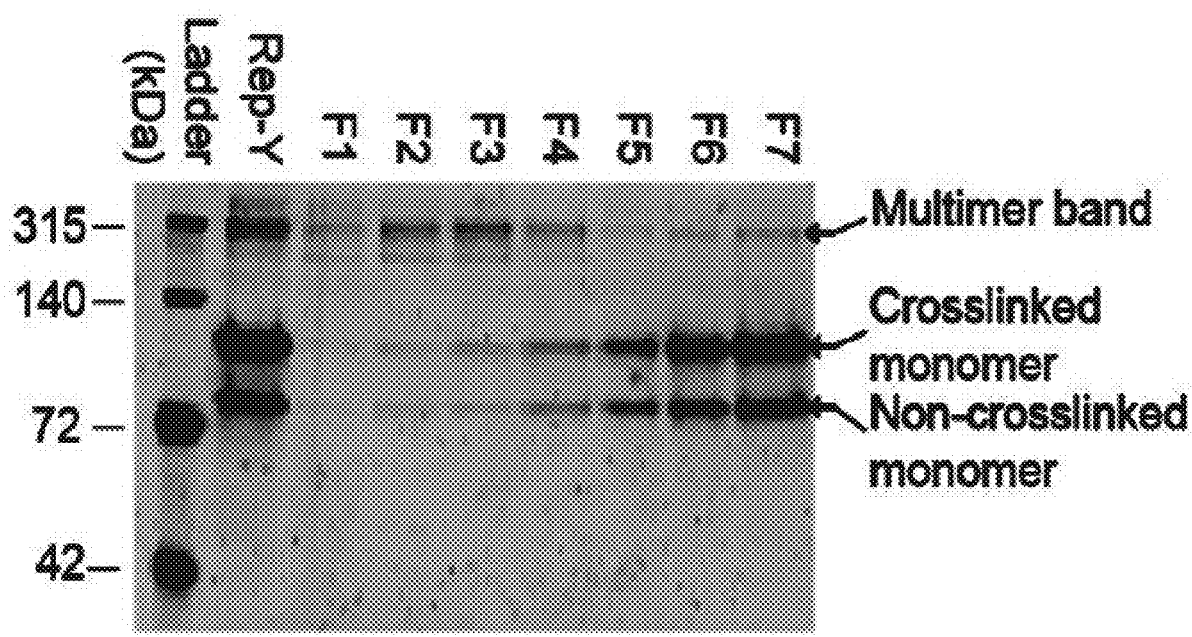
FIG. 7D shows an exemplary SDS-PAGE analysis of Rep-Y fractions, F1-F7, collected from SEC (FIG. 5C) in comparison with Rep-Y.
Figure 7E:
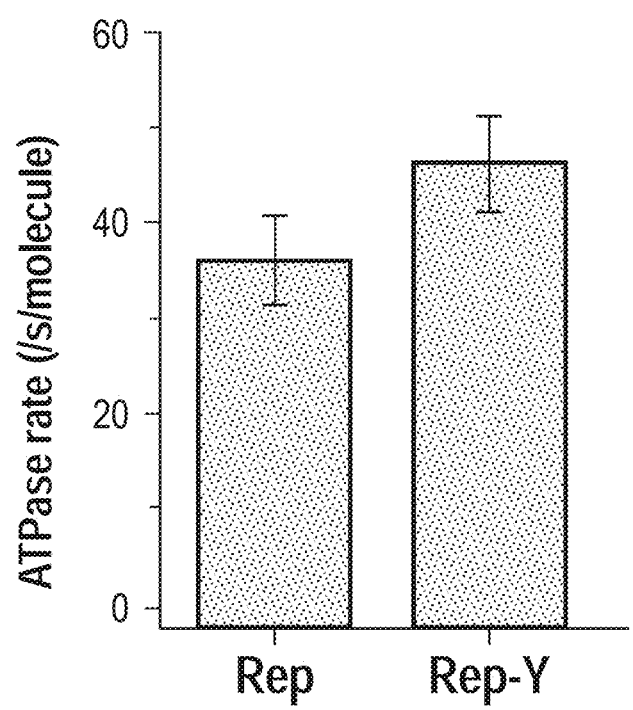
FIG. 7E depicts exemplary data of ssDNA dependent ATPase levels of Rep-Y and Rep. Error bars represent standard deviation over multiple preparations.

Crosslinking of the double Cys mutants with the bismaleimide linkers has the potential of producing covalently attached multimeric species, in addition to the intended internally crosslinked monomeric species. Sodium dodecyl sulfate polyacrylamide gel electrophoresis (SDS-PAGE) can distinguish these species from the non-crosslinked monomers (I. L. Urbatsch et al., Cysteines 431 and 1074 are responsible for inhibitory disulfide cross-linking between the two nucleotide-binding sites in human P-glycoprotein. *J Biol. Chem.* 276, 26980-26987 (2001)). Here we show a representative analysis of a crosslinked Rep-Y sample. Crosslinked Rep-X and Rep-Y produced three bands on a SDS polyacrylamide gel (FIG. 7A): a bottom band at ~76 kDa that was the same as the non-crosslinked Rep, a slightly retarded dominant middle band at ~100 kDa for Rep-Y and ~90 kDa for Rep-X and a much more slowly migrated, very faint top band at ~300 kDa. FIG. 7B shows three such bands of a Rep-Y sample (lane Rep-Y) crosslinked with a cleavable di-sulfide containing crosslinker (DTME). The dominant middle band and the fainter top band were the crosslinked species because they disappeared upon cleavage of the crosslinker using beta-mercaptoethanol (β-ME) (lane Rep-Y*). Relative shift between the middle bands of Rep-X and Rep-Y (FIG. 7A) was a strong indication of an internally crosslinked monomeric species, because the denatured Rep-X and Rep-Y would be likely to migrate at different rates due to the different size of peptide loops introduced by the internal crosslinker (denatured Rep-Y has a loop of 368 amino acids (aa) whereas Rep-X loop is 223 aa long). In order to ensure that the dominant middle band is not multimeric but is the intramolecularly crosslinked monomeric species, a Rep-Y sample was fractionated according to molecular size on a Superdex 200 size exclusion chromatography (SEC) column controlled by an FPLC apparatus. Elution profiles of Rep-Y and non-crosslinked Rep are shown in the FIG. 7C. Eluted fractions were analyzed on an SDS polyacrylamide gel (FIG. 7D, lanes F1-F7). The multimeric species that was eluted in the early SEC fractions (11-13 ml) displayed only the top band whereas the dominant middle band was eluted together with the non-crosslinked Rep monomer in the SEC analysis, showing that the middle band represents the intramolecularly crosslinked species and the top band is multimeric. After establishing that the intra-crosslinked protein shows up as a retarded band compared to the non-crosslinked form on the SDS polyacrylamide gels (such as the Rep-Y data presented here), we used this assay to check the efficiency of crosslinking reactions for Rep-X, Rep-Y and PcrA-X (86%, 73% and 58% respectively for the samples used in this manuscript). The Rep-Y form exhibited ATPase activity on par with non-crosslinked Rep (FIG. 7E).

Example 3. Size Exclusion Chromatography and SDS-PAGE Analysis

Crosslinked Rep and PcrA samples were separated from multimeric byproducts using Superdex 200 grade 10/300GL or HiLoad 16/600 gel filtration columns on an AKTA purifier 10 FPLC system. The crosslinking efficiency was monitored by SDS-PAGE analysis on 7.5-10% Tris-glycine gels (Bio-Rad). As needed for gel analysis, reduction of samples crosslinked with DTME was achieved by adding 5% (v/v) β-ME during the SDS denaturation step.

Example 4. Ensemble FRET Unwinding Assay

Multiple turnover ensemble unwinding kinetics was used to gauge the effect of the mutations and conformational modifications to the helicase activity. We used an 18-bp FRET labeled DNA substrate with a 3'-(dT)$_{10}$ overhang (SEQ ID NO: 33) (FIG. 1C), constructed by annealing complementary oligonucleotides DNA7 (Cy5-GCC TCG CTG CCG TCG CCA (SEQ ID NO: 40)) and amino-dT labeled DNA8 (TGG CGA CGG CAG CGA GGC-(T-Cy3)-T$_{10}$ (SEQ ID NO: 41)). Alternatively, another similarly labeled 50-bp DNA with a 3'-(dT)$_{30}$ overhang (SEQ ID NO: 17) was also used. This construct was made by annealing oligonucleotides DNA9 (Cy5-TCA ACT AGC AGT CAT AGG AGA AGT ATT AAC ATG CCT CGC TGC CGT CGC CA (SEQ ID NO: 42)) and amino-dT labeled DNA10 (TG GCG ACG GCA GCG AGG CAT GTT AAT ACT TCT CCT ATG ACT GCT AGT TGA (T-Cy3) T29 (SEQ ID NO: 43)). Unless otherwise stated, 5 nM ensemble FRET DNA was mixed with 50 nM helicase in buffer D (10 mM Tris-HCl [pH 8.0], 15 mM NaCl, 10 mM MgCl$_2$, 10% (v/v) glycerol, 0.1 mg/ml BSA) and 1 mM ATP was added to start the unwinding reaction in a quartz cuvette. A Cary Eclipse fluorescence spectrophotometer was used to measure the donor ($I_{555nm}$) and the acceptor signals ($I_{667}$ nm) under 545-nm excitation (5-nm slit, 2-10 Hz acquisition rate and 600-900V photomultiplier voltage). Unwinding of the substrate was monitored by the decrease in ensemble $E_{FRET}$ value, defined as $E_{FRET\text{-}ensemble}=I_{667nm}/(I_{555nm}-I_o+I_{667nm})$ where $I_o$ was the baseline donor signal of unpaired Cy3 prior to addition of ATP.

Example 5. smFRET Unwinding and RepD-PcrA Interaction Assays

All smFRET experiments were conducted on a custom-built prism type TIRF microscopy stage with an Andor EMCCD camera as described in R. Roy, S. Hohng, T. Ha, A practical guide to single-molecule FRET. *Nat Methods* 5, 507-516 (2008) and C. Joo, T. Ha, in *Cold Spring Harb Protoc*. (2012), vol. 2012. Reaction chambers were formed by quartz slides and glass coverslips passivated with polyethyleneglycol (PEG) and 1% biotinylated PEG (mPEG-SC and bio-PEG-SC, Laysan Bio, Arab, AL), followed by 5 min incubation with Neutravidin (Thermo Scientific, Newington, N.H.) for immobilization of biotinylated molecules on the chamber surface as described below.

For the smFRET unwinding experiments, the reaction chamber was first incubated with biotinylated anti penta-histidine tag (SEQ ID NO: 44) antibody (Qiagen, Valencia, CA), followed by 10-30 min incubation of His6-tagged (SEQ ID NO: 36) helicase sample (0.5-1 nM). The unwinding of the DNA was initiated by flowing 1 nM smFRET DNA and 1 mM ATP in the reaction buffer A (10 mM Tris-HCl [pH 8.0], 10 mM MgCl$_2$, 15 mM NaCl, 10% (v/v) glycerol, 1% (v/v) gloxy and 0.2% (w/v) glucose, an oxygen scavenging system (Y. Harada, K. Sakurada, T. Aoki, D. D. Thomas, T. Yanagida, Mechanochemical coupling in actomyosin energy transduction studied by in vitro movement assay. *J Mol. Biol.* 216, 49-68 (1990).) and 3-4 mM Trolox (T. Yanagida, M. Nakase, K. Nishiyama, F. Oosawa, Direct observation of motion of single F-actin filaments in the presence of myosin. *Nature* 307, 58-60 (1984); I. Rasnik, S. A. McKinney, T. Ha, Nonblinking and long-lasting single-molecule fluorescence imaging. *Nat Methods* 3, 891-893 (2006)). The smFRET DNA substrate was constructed by annealing the oligonucleotides DNA3 (Cy5-GCC TCG CTG CCG TCG CCA (SEQ ID NO: 40)) and DNA4 (Cy3-TGG CGA CGG CAG CGA GGC-T$_{20}$ (SEQ ID NO: 45)). The PcrA-RepD interaction assay involved preparation of the RepD-oriD DNA adduct as described in Slatter et al. (2009) supra. A biotinylated oriD DNA substrate was constructed by annealing oligonucleotides DNA1 (CTA ATA GCC GGT TAA GTG GTA ATT TTT TTA CCA CCC AAA GCC TGA AGA GCT AAT CGT TCG G (SEQ ID NO: 46)) and DNA2 (biotin-CCG AAC GAT TAG CTC TTC AGG CTT TGG GTG GTA AAA AAA TTA CCA CTT T15 (SEQ ID NO: 47)). In one chamber, only oriD DNA (50-100 µM) was immobilized on the surface. In a second chamber the RepD-oriD DNA adduct was immobilized. 100-500 µM dual labeled PcrA-DM1 was injected into the chambers in buffer B (10 mM Tris [pH7.5], 10% glycerol, 15 mM NaCl, 50 mM KCl, 5 mM MgCl$_2$, 3.4 mM Trolox, 1% (v/v) gloxy, 0.2% (w/v) glucose). Short movies of multiple chamber regions were recorded. Since the two Cys residues of PcrA-DM1 were randomly labeled with Cy3-Cy5 mixture, each movie contained a brief initial 633-nm laser excitation period to determine the molecules with a fluorescent Cy5, followed by turning on the 532-nm laser for Cy3 excitation. Only the PcrA-DM1 molecules with a colocalized donor-acceptor pair were factored in the $E_{FRET}$ histograms.

smFRET signals were acquired by an Andor EMCCD camera operated with a custom software at 16-100-ms time resolution. $E_{FRET}$ was calculated as described in R. Roy, S. Hohng, T. Ha, A practical guide to single-molecule FRET. *Nat Methods* 5, 507-516 (2008). Unwinding periods were measured as described in the text. The fraction of unwinding events was calculated as the proportion of the all DNA binding events that displayed an $E_{FRET}$ increase phase. Error bars were calculated according to Clopper-Pearson binomial proportion confidence interval method (C. J. Clopper, E. S. Pearson, The use of confidence or fiducial limits illustrated in the case of the binomial. *Biometrika* 26, 404-413 (1934)).

Example 6. Optical Tweezers Assay

The optical trap handle was a 6098-bp long DNA, amplified from k-phage DNA and flanked by a 5'-biotin and a 3'-(dT)$_{10,15,75}$ overhang (SEQ ID NOS 33-35, respectively) on the other end. First, a 5'-tailed 6083-bp fragment was amplified by the autosticky PCR reaction (J. Gal, R. Schnell, S. Szekeres, M. Kalman, Directional cloning of native PCR products with preformed sticky ends (autosticky PCR). *Mol Gen. Genet.* 260, 569-573 (1999)) using primers P1 (biotin-GGC AGG GAT ATT CTG GCA (SEQ ID NO: 48)) and P2 (GAT CAG TGG ACA GA-abasic-A AGC CTG AAG AGC TAA TCG TTC GG (SEQ ID NO: 49)). Subsequently the amplicon was annealed and ligated with oligonucleotide DNA5 (TTC TGT CCA CTG ATC-(T)$_{10,15,75}$ (SEQ ID NOS 50-52, respectively)) to create the 3'-overhang for the initial helicase binding (10, 15 or 75-nt, as specified in figures). DNA beads were prepared by adding biotinylated 6-kbp DNA to the streptavidin-coated polystyrene beads (0.79 µm in diameter, Spherotech, Lake Forest, IL), and incubated at 25° C. for 30 min. Protein samples were pre-incubated with biotinylated anti penta-histag (SEQ ID NO: 44) antibody (Qiagen, Valencia, CA) on ice for 1 hour. One microliter of this mixture, 1 µl of streptavidin beads, and 8 µl buffer (100 mM Tris-HCl [pH 7.5], 100 mM NaCl, 10% glycerol (v/v)) were mixed and incubated for 30 min on ice to make the protein coated beads. Reactions were performed in laminar flow chambers that were designed and assembled as described in Z. Qi, R. A. Pugh, M. Spies, Y. R. Chemla, Sequence-dependent base pair stepping dynamics in XPD helicase unwinding. *Elife* (Cambridge) 2, e00334 (2013). Reaction buffer C consisted of 100 mM Tris pH 8.0, 15 mM NaCl, 10% (v/v) glycerol, 10 mM MgCl$_2$, and an oxygen scavenging system (100 µg/ml glucose oxidase, 20 µg/ml catalase, and 4 mg/ml glucose) to reduce photo damage to the sample (M. P. Landry, P. M. McCall, Z. Qi, Y. R. Chemla, Characterization of photoactivated singlet oxygen damage in single-molecule optical trap experiments. *Biophysical journal* 97, 2128-2136 (2009)). The reaction chamber contained two laminar streams of buffer C with different ATP, ATP-γS and SSB concentrations as described in the text. The dual-trap optical tweezers were set up and calibrated as described in (C. Bustamante, Y. R. Chemla, J. R. Moffitt, *High-resolution dual-trap optical tweezers with differential detection*. Single-molecule techniques: a laboratory manual (Cold Spring Harbor Laboratory Press, Cold Spring Harbor, N.Y., 2008); K. Berg-Sorensen, H. Flyvbjerg, Power spectrum analysis for optical tweezers. *Review of Scientific Instruments* 75, 594-612 (2004)). All measurements were recorded at 100 Hz with a custom LabView software (8.2; National Instruments, Austin, TX) and smoothed with a 100 Hz boxcar filter. In the "force-feedback" mode, unwinding was allowed to occur against a constant force of 10-22 pN (as specified). The contour length of DNA was calculated from the measured force and end-to-end extension of the molecule and using the worm-like chain model (persistence length of 53 nm, stretch modulus of 1,200 pN and distance per base-pair of 0.34 nm). The velocity of DNA unwinding in the force feedback mode was determined from a linear fit of the contour length of DNA in a sliding window of 0.2 s (21 data points). Pauses longer than 0.2 s were removed and then the velocity was averaged in is bins. Error for the fraction of unwinding events per tether formation was calculated with the Clopper-Pearson binomial proportion confidence interval method (Clopper et al. (1934) supra)).

Figure 3F:
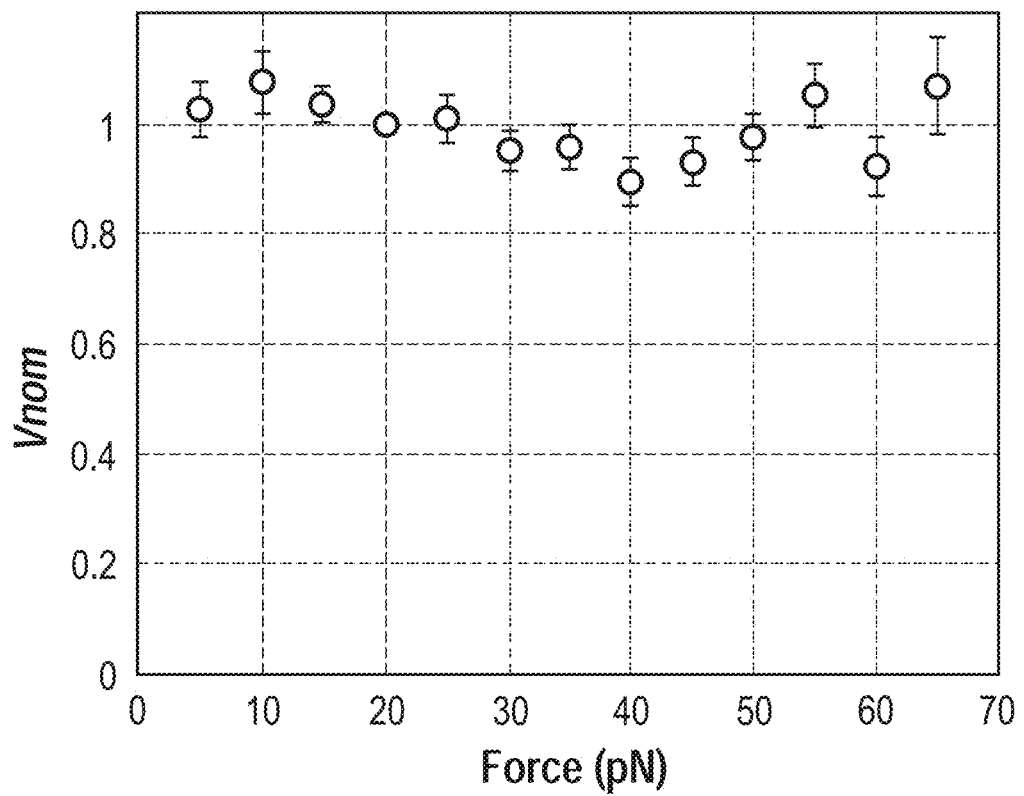
FIG. 3F depicts exemplary data showing the average of normalized unwinding velocities of 58 Rep-X molecules plotted against the pulling force that shows the high force tolerance of the engineered super-helicase Rep-X. Error bars represent standard error of the mean.

The force dependence of Rep-X unwinding activity was measured in the "fixed-trap" mode, by stopping the force feedback. The force data (100 Hz) was smoothed with a gaussian filter (by applying a 33-Hz moving average filter 10 times). Paused regions (velocity<10 bp/s) were removed. The pause-free unwinding velocities were calculated and normalized by the velocity at 20 pN for each molecule, and binned against the dynamic force values up to 60 pN to create the $V_{norm}$ vs. F plot (FIG. 3F). We previously found that the force response of our trap was linear against bead displacements up to 72 nm (determined in a separate experiment measuring where the force vs. extension curve of dsDNA started to deviate from the theoretical worm like chain. At a trap stiffness of 0.167 pN/nm, the deviation occurred above 12 pN). Hence we calculated the maximum reliable force to be at least 59 pN at a trap stiffness of 0.82 pN/nm.

Example 7. Ensuring Monomeric Rep-X Activity in Optical Tweezers Assay

We considered the possibility that the highly processive unwinding observed in our optical tweezers assay was caused by multiple Rep-X acting on the same DNA. If multimeric Rep-X had been required for highly processive unwinding, then the majority of binding events (i.e. formation of a tether) would not have displayed unwinding activity, because single Rep-X binding is the statistically the most probable event during the brief period of contact between the two beads. However, the majority of tethers formed displayed highly processive unwinding, suggesting that the processive unwinding is caused by a single Rep-X protein.

To further establish that the unwinding of the 6-kbp DNA was achieved by single Rep-X molecule, we repeated the experiment using beads incubated in lower concentrations of Rep-X, thus decreasing the number of Rep-X molecules per bead. Consequently, Rep-X binding (tether formation) took longer and required more trials of bumping the two beads. As the Rep-X concentration was lowered (20 nM, 4 nM and 0.4 nM) during the pre-incubation with 20 nM biotinylated antibody, the efficiency of tether formation was also reduced (7 out of 11, 9 out of 27 and 2 out of 16 beads, respectively). However, the subsequent unwinding was still the prevalent behavior (7 out of 7, 8 out of 9 and 2 out of 2 tethers, respectively).

As another test to ensure that the highly processive unwinding was due to a single Rep-X molecule, not multiple molecules, we compared the unwinding reaction of DNA with 75nt vs. 10- and 15-nt 3' overhangs. Since the footprint of Rep is reported to be 8-10 nt (S. Korolev, J. Hsieh, G. H. Gauss, T. M. Lohman, G. Waksman, Major domain swiveling revealed by the crystal structures of complexes of *E. coli* Rep helicase bound to single-stranded DNA and ADP. *Cell* 90, 635-647 (1997)), 10 or 15-nt overhang would increase the chance of single Rep-X binding. Rep-X exhibited the same highly processive behavior on the short overhang DNA molecules (17 out of 18 tethers formed with 10- and 15-nt overhang DNA vs. 21 out of 22 tethers formed with 75 nt overhang DNA, FIG. 3B, C), further indicating that the high processivity of unwinding is the property of a Rep-X monomer.

To test the possibility that the unwound ssDNA interacted with additional Rep-X on the bead surface, possibly increasing the processivity of unwinding, we added 66 nM of *E. coli* ssDNA binding protein (SSB) in the unwinding reaction stream in order to render the unwound ssDNA inaccessible to other Rep-X molecules. Inclusion of SSB did not change the highly processive behavior of unwinding (17 out of 18 tethers formed in the absence of SSB vs. 21 out of 22 tethers formed in the presence of SSB, FIG. 3B), suggesting that DNA unwinding by Rep-X is highly processive whether the unwound ssDNA is sequestered by SSB or not. This observation is probably due to the design of the dual optical tweezers assay, in which the DNA is under tension only between the "front runner" Rep-X molecule and the streptavidin on the other bead. Binding of a second Rep-X to the already unwound ssDNA should not affect the measurements because the second Rep-X, which is also tethered to the bead, cannot interact with the front runner that is tethered elsewhere on the bead.

Example 8. Selection of Crosslinking Sites and Crosslinker Length

Open (inactive) and closed (active) form crystal structures of Rep and similar helicases were used as a visual guide. The target residue pair for crosslinking and the crosslinker were selected based on these criteria.

One target residue of the target residue pair should be located on the mobile 2B domain and the other target residue should be located on the immobile body of the helicase (for example on 1B or 1A domains). Preferably, target residue pair should not be part of functional helicase motifs known in the literature to prevent detrimental effects of amino acid engineering. Preferably the target residue pair should not be conserved residues. Preferably the target residue pair should be as far away as possible from the ssDNA binding sites. These measures reduce the potentially detrimental effects of the target residue mutations and crosslinking on the basic translocation function of the helicase.

The target residues should be as close as possible to each other in the closed (active) conformation of 2B domain, and at the same time should be as far as possible from each other in the open (inactive) conformation. For example, the distance between the target residue pair should be less than 15 Å in the closed form (measured from alpha carbon coordinates) and should increase by more than 30 Å during transition to open form, so that a short crosslinker can prohibit the transition to an inactive (open) form. Residues that satisfy such criteria can be determined for helicases with known crystal structures in closed or open forms.

By sequence alignment, the corresponding crosslinking target residues can be found in helicases with unknown structures to convert those to superhelicases, as well. Sequence homology models can also be employed.

Target residues should be preferably on the surface of the protein, and their side chains should be facing outward and more preferably facing toward each other.

The crosslinker should be as short as possible, preferably only long enough to efficiently link the target residue pair in the desired conformation. Crosslinker length should be considerably shorter than the distance between the target residues in the unwanted conformation.

A representative 56 Rep homologs/orthologs with 90% identity to and 80% overlap are shown in Table 4, which are also shown in FIGS. 9A-G. The target residues of FIGS. 9A-G were selected from one residue from domain 1A or domain 1B, and one residue from domain 2B which satisfy the all these considerations. For PcrA, or a homolog thereof, the target residues are selected from residues 92-116 of domain 1A or 178-196 of domain 1B, and 397-411, 431-444 or 526-540 of domain 2B. For Rep, or a homolog thereof, the target residues are selected from 84-108 of domain 1A or 169-187 of domain 1B, and 388-402, 422-435 or 519-536 of domain 2B. For UvrD, or a homolog thereof, the target residues are selected from residues 90-114 of domain 1 Å or 175-193 of domain 1B, and 393-407, 427-440 or 523-540 of domain 2B.

TABLE 4

| Rep homolog | Organism |
| --- | --- |
| REP_BUCAP | *Buchnera aphidicola* subsp. *Schizaphis graminum* (strain Sg) |
| REP_BUCAI | *Buchnera aphidicola* subsp. *Acyrthosiphon pisum* (strain APS) (*Acyrthosiphon pisum* symbiotic bacterium) |
| REP_ECOLI | *Escherichia coli* (strain K12) |
| REP_HAEIN | *Haemophilus influenzae* (strain ATCC 51907/DSM 11121/KW20/Rd) |
| REP_SALTY | *Salmonella typhimurium* (strain LT2/SGSC1412/ATCC 700720) |
| A0A077ZIR6_TRITR | *Trichuris trichiura* (Whipworm) (*Trichocephalus trichiurus*) |
| S3IEG5_9ENTR | *Cedecea davisae* DSM 4568 |
| J1R585_9ENTR | *Kosakonia radicincitans* DSM 16656 |
| K8ABZ8_9ENTR | *Cronobacter muytjensii* 530 |
| A0A060VJ91_KLEPN | *Klebsiella pneumoniae* |
| A0A090V5M6_ESCVU | *Escherichia vulneris* NBRC 102420 |
| A0A083YZC2_CITAM | *Citrobacter amalonaticus* |
| A0A0J6D7T8_SALDE | *Salmonella derby* |
| A0A085ITL8_RAOPL | *Raoultella planticola* ATCC 33531 |
| E7T4Q1_SHIBO | *Shigella boydii* ATCC 9905 |
| A0A085GMM2_9ENTR | *Buttiauxella agrestis* ATCC 33320 |
| A0A085HAK1_9ENTR | *Leclercia adecarboxylata* ATCC 23216 = NBRC 102595 |
| D4BE16_9ENTR | *Citrobacter youngae* ATCC 29220 |
| A0A0H5PMJ7_SALSE | *Salmonella senftenberg* |
| A0A0J1JQT3_CITFR | *Citrobacter freundii* |
| A0A0J8VI05_9ENTR | *Cronobacter* sp. DJ34 |
| F5S3F4_9ENTR | *Enterobacter hormaechei* ATCC 49162 |
| D2ZMA5_9ENTR | *Enterobacter cancerogenus* ATCC 35316 |
| A0A084ZTW9_9ENTR | *Trabulsiella guamensis* ATCC 49490 |
| A0A038CLT3_RAOOR | *Raoultella ornithinolytica* (*Klebsiella ornithinolytica*) |
| Q8Z385_SALTI | *Salmonella typhi* |
| Q83IX8_SHIFL | *Shigella flexneri* |
| A0A0D5WYP4_9ENTR | *Klebsiella michiganensis* |
| A0A0H3FM31_ENTAK | *Enterobacter aerogenes* (strain ATCC 13048/DSM 30053/JCM 1235/KCTC 2190/NBRC 13534/NCIMB 10102/NCTC 10006) (*Aerobacter aerogenes*) |
| A0A0H2WUK6_SALPA | *Salmonella paratyphi* A (strain ATCC 9150/SARB42) |
| A0A0H3H1F3_KLEOK | *Klebsiella oxytoca* (strain ATCC 8724/DSM 4798/JCM 20051/NBRC 3318/NRRL B-199/KCTC 1686) |
| X7I146_CITFR | *Citrobacter freundii* UCI 31 |
| A0A0H3CTF5_ENTCC | *Enterobacter cloacae* subsp. *cloacae* (strain ATCC 13047/DSM 30054/NBRC 13535/NCDC 279-56) |
| D2TH67_CITRI | *Citrobacter rodentium* (strain ICC168) (*Citrobacter freundii* biotype 4280) |
| Q329V6_SHIDS | *Shigella dysenteriae* serotype 1 (strain Sd197) |
| W6J7C4_9ENTR | *Kosakonia sacchari* SP1 |
| I2BE87_SHIBC | *Shimwellia blattae* (strain ATCC 29907/DSM 4481/JCM 1650/NBRC 105725/CDC 9005-74) (*Escherichia blattae*) |
| B5EZ38_SALA4 | *Salmonella agona* (strain SL483) |
| A0A0F5SGU2_CITAM | *Citrobacter amalonaticus* |
| G9YY11_9ENTR | *Yokenella regensburgei* ATCC 43003 |
| A0A090UXU3_9ENTR | *Citrobacter werkmanii* NBRC 105721 |
| A9MJ31_SALAR | *Salmonella arizonae* (strain ATCC BAA-731/CDC346-86/RSK2980) |

TABLE 4-continued

| Rep homolog | Organism |
|---|---|
| Q3YVI6_SHISS | *Shigella sonnei* (strain Ss046) |
| D3RHB6_KLEVT | *Klebsiella variicola* (strain At-22) |
| Q57HT8_SALCH | *Salmonella choleraesuis* (strain SC-B67) |
| B5RFS5_SALG2 | *Salmonella gallinarum* (strain 287/91/NCTC 13346) |
| A0A089Q204_9ENTR | *Cedecea neteri* |
| A0A0H3BNR1_SALNS | *Salmonella newport* (strain SL254) |
| C9Y4T0_SICTZ | *Siccibacter turicensis* (strain DSM 18703/ LMG 23827/z3032) (*Cronobacter turicensis*) |
| B7LU77_ESCF3 | *Escherichia fergusonii* (strain ATCC 35469/ DSM 13698/CDC 0568-73) |
| A0A0H3TAW8_SALEN | *Salmonella enteritidis* |
| G2S5J6_ENTAL | *Enterobacter asburiae* (strain LF7a) |
| A0A0F7JC30_SALET | *Salmonella enterica* I |
| A7MQI4_CROS8 | *Cronobacter sakazakii* (strain ATCC BAA-894) (*Enterobacter sakazakii*) |
| L0M8J0_ENTBF | Enterobacteriaceae bacterium (strain FGI 57) |
| A0A0K0HFU2_SALBC | *Salmonella bongori* (strain ATCC 43975/ DSM 13772/NCTC 12419) |
| A8ACT1_CITK8 | *Citrobacter koseri* (strain ATCC BAA-895/ CDC 4225-83/SGSC4696) |

Use of shorter crosslinkers increase the efficiency of crosslinking reaction by favoring the intramolecularly cross-linked species rather than intermolecularly crosslinked multimeric species. These rules also ensure that the 2B domain is restricted to the active (closed) conformation, and cannot attain an open (inactive) conformation. Thus conformational control is achieved, and the possibility of 2B domain to swinging open to access an inactive (open) conformation is virtually eliminated.

Without being bound by theory, one possible explanation for the super activation would be the decreased dissociation rate due to the crosslinked protein encircling the ssDNA strand (indicated by the crystal structure, so that the protein cannot dissociate from the ssDNA easily. However, it was found that despite both Rep-X and Rep-Y encircling the ssDNA (as indicated by the crystal structure), only Rep-X was super-active. Thus, in order to create the super active helicase, immobilization of the correct conformational state of the 2B domain is necessary.

Example 9. Identifying Suitable Crosslinking Sites in Homologous Helicases

Based on the crosslinking target site selection criteria established in Example 8, potential crosslinking target residues in helicases were determined using known crystal structures. By sequence alignment and structural homology modeling, the corresponding crosslinking target residues are identified in helicases with unknown structures. Subsequently these helicases can be converted to superhelicase forms. For example, based on the criteria that the distance between the target residue pairs should be less than 15 Å in closed form and should increase by more than 30 Å in open form, we identified the residues in Rep, PcrA and UvrD helicases as shown in FIGS. 9A-G. Homologous helicases are identified, for example, by 50% sequence identity and 80% overlap to the helicase with the known structure. For example, we found 3147 such proteins homologous to *E. coli* Rep, 1747 proteins homologous to B. st PcrA, and 1209 proteins homologous to *E. coli* UvrD helicases were found (Tables 5-7, respectively). Then the corresponding crosslinking residues are identified in any of the homologs. For example, we chose an example of 56 Rep homologs (Table4), and found the regions where the crosslinking residues can be engineered (FIGS. 9A-G). Despite the fact that the three model superfamily 1 helicases, UvrD, Rep and PcrA, have only 35-40% sequence identity, they exhibit >90% structural homology according to their crystal structures. Hence it is reasonable to expect a highly similar structural homology from the proteins with 50% identity to and 80% overlap to the helicase with the known crystal structure; these are suitable candidates for crosslinking in the superhelicase (-X) form.

Figure 11:
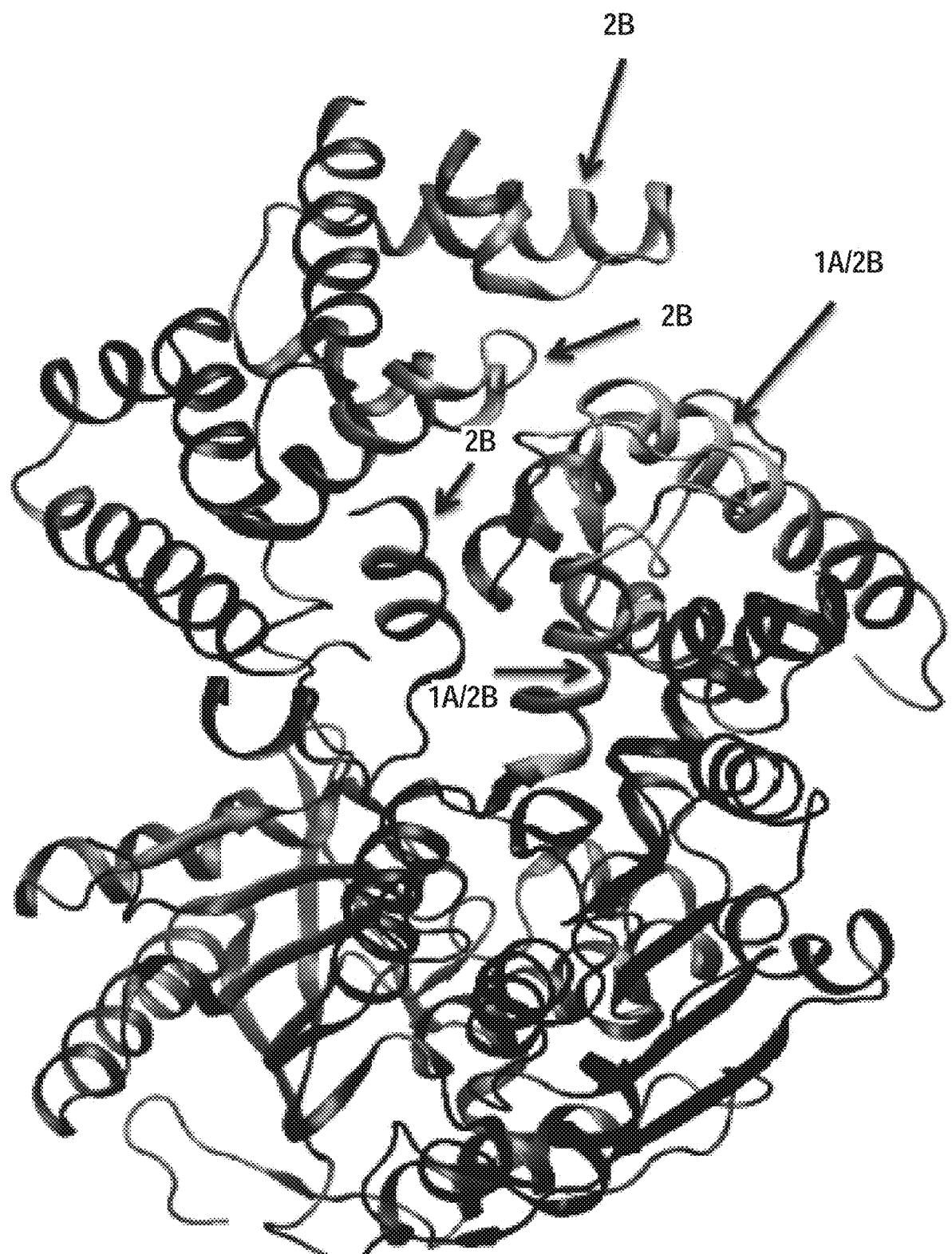
FIG. 11 shows a closed form crystal structure of *D. radiodurans* UvrD (drUvrD; Q9RTI9) with target crosslinking regions of domains 1A, 1B and 2B indicated by arrows.

*E. coli* UvrD (ecUvrD) has 33% sequence identity with *E. coli* Rep (ecRep) and 42% sequence identity with *Bacillus stearothermophillus* PcrA (bsPcrA). Highlighted regions in FIGS. 9A and 9G show the crosslinking sites obtained from the open form and closed form crystal structures and the criteria established in Example 8. These regions align well in the sequence showing that a sequence alignment can be used in helicases with unknown structures to determine the crosslinking target sites in helicases with unknown structures. For example, the crosslinking regions (boxed sequences of FIG. 9G) in *D. radiodurans* UvrD (drUvrD) were found by aligning its sequence to bsPcrA, ecRep and ecUvrD, 1A/1B residues: 92-116, 182-200, 2B residues: 400-414, 434-447 and 528-544. drUvrD (Q9RTI9) has 33%, 36% and 41% sequence identity to bsPcrA, ecUvrD and ecRep, respectively. These four proteins have 21% sequence identity as a group. Only closed form crystal structures of drUvrD are known. Boxed regions shown in FIG. 9G are shown in the crystal structure of drUvrD (FIG. 11) to demonstrate the suitability of the regions for crosslinking.

*D. radiodurans* UvrD (drUvrD, Q9RTI9_DEIRA) has only 1 Cys residue, and a crystal structure is known. drUvrD has 31 entries in the 50% identity cluster of the Uniprot database, some of which are mildly thermophilic (40° C.-68° C.; optimum growth at 60° C.), making them better candidates for helicase dependent nucleic acid amplifications. In certain exemplary embodiments, a suitable UvrD helicase is selected from following species: *Deinococcus geothermalis, Meiothermus sp., Marinithermus hydrothermalis, Marinithermus hydrothermalis, Oceanithermus profundus*. Selected thermophilic ortholog species of drUvrD are shown in Table 8.

In another embodiment, the helicase is selected from those shown in Tables 9 and Table 10.

TABLE 5

List of 3137 unique non-redundant helicases that have 50% sequence identity and 80% overlap with
E. coli Rep. (Uniref50_P09980 cluster, citable UniProtKB and UniParc accession numbers are shown).

| | | | | | | |
|---|---|---|---|---|---|---|
| P09980 | UPI00051877AD | UPI00050997D4 | A0A063KTD1 | W0QF97 | A0A0C3I5L6 |
| A0A0G3HMG0 | UPI0002CB7C3E | UPI00041BBC9F | A0A0F9UW26 | A3MZ01 | UPI0005EDEB6E |
| A0A069YUU2 | UPI0002CB6CB4 | Q31J65 | UPI00057A0DA3 | A0A0A7MFM3 | Q4F7B3 |
| A0A069XK09 | UPI0003EF7150 | UPI0004A7511F | UPI00042735E9 | UPI00037127A9 | H2IB31 |
| A0A090J554 | A0A0B5IRM0 | J3VUI0 | A0A0B2JU34 | W0QS54 | UPI00039DFE76 |
| J2LMP0 | UPI0005F8A649 | B3PF82 | A0Y242 | D9P8T6 | UPI0002D3CD90 |
| A0A0E1CLG8 | UPI00036A6E72 | W1J4L6 | G7F259 | B0BT27 | UPI00031FC355 |
| W8VIF4 | E7T4Q1 | A0A068QMH5 | F3BJI5 | E0EII5 | A0A034TPW5 |
| A0A0J2JAV4 | UPI000645DEF6 | UPI0002C94EDF | UPI0004641B09 | A0A011P892 | UPI0003B1A99F |
| A0A0H4Z590 | A0A0J1C9T2 | UPI0004A19D90 | W1Z619 | UPI0004795D5E | A0A090P8C9 |
| A0A0H4YMK4 | A0A024KL85 | A0A077P2A7 | N6W1D7 | W0QMN7 | U3AJD4 |
| A0A0H4ZZ54 | A0A029K3Y0 | A0A077PGN3 | G7EU46 | B3H0C1 | A0A0H0Y6H0 |
| W1HB14 | A0A029LST3 | A0A077Q5V6 | UPI0003F6330E | E0FKS8 | D0WV97 |
| A0A0H4ZHU7 | A0A074IDU1 | A0A0B6XFA1 | UPI0004175A32 | E0E690 | UPI00039CA46E |
| A0A0G3T252 | A0A070UMT6 | D3VHW6 | G7EBR9 | E8KIM6 | K5UKZ2 |
| A0A0H3GKB6 | A0A0H0NZ89 | N1NN52 | UPI0002317DDE | KOFXU5 | A0A061Q0T1 |
| A0A0K0GSG9 | UPI0004DACF34 | A0A0A8NWA1 | UPI000412695D | A0A0D6UGN8 | D0X594 |
| A0A0G8G0X7 | UPI000543FDCF | W1J8H9 | A0A099L6T2 | M9X512 | UPI0006814400 |
| A0A060VJ91 | A0A0H3MJI3 | A0A077NN58 | UPI0002DA5F7A | D9P4Y2 | UPI0006AA085C |
| W1HUU8 | UPI0002A2C4E1 | A0A068RA85 | UPI0003162143 | UPI0002556C8C | UPI00039C63E0 |
| W1EG06 | A0A0H0KMW7 | A0A0A8LWM3 | U1MBQ7 | A0A0B0HCL6 | UPI0005EFDC1A |
| W1HYL7 | F4NQI1 | A0A077PLN5 | U1JK11 | UPI00041A33FA | UPI00063C4F58 |
| W1EC12 | A0A0G9FGL3 | A0A077PEC1 | U1IZP2 | A0A081FYF7 | UPI0002B70576 |
| V0AP50 | UPI0005305422 | D3V6L9 | Q3IJF4 | A0A0B3BWV0 | UPI00023755B4 |
| W1E3B2 | I2X0N8 | A0A0J5FTN5 | E6RJ61 | A0A0B2DBM6 | UPI00069FBA0A |
| A0A080SZ33 | UPI0006C108B | A0A077N2X7 | Z9K3Y4 | UPI00337D905 | A7K6B6 |
| A6TGG4 | UPI00053AB8E4 | UPI00037EA902 | G7G5E8 | D2TCP1 | U4DZN2 |
| W1BG54 | UPI000390341B | A0A094NXP4 | UPI00034C744C | UPI0001960924 | L8XB50 |
| Q57HT8 | UPI0002C97E36 | F9QBX8 | A0A0F4PWX2 | V5Z3P5 | UPI0005975B9F |
| C0Q2V7 | T8JFG3 | UPI000364DEC7 | I3CJI7 | UPI00065FAA51 | UPI00039C5A41 |
| A0A0G2NT58 | A0A0J0IRL7 | A3V094 | A1T091 | UPI00054F6EBB | UPI0005F0AEC8 |
| V2QUW5 | J1GHC8 | UPI0002D3C2F3 | UPI00036133E4 | UPI000554232A | A7N1B5 |
| B5RFS5 | UPI0005EFAD7E | F9SI11 | A0A0A8UTG2 | UPI00044B0A82 | U4K9S4 |
| H3N5E4 | A0A0D7LCG7 | UPI00065FA69F | UPI0002624F9F | W0T2G5 | U3ATU8 |
| UPI00030AD7A3 | UPI0005EFAEC1 | UPI0003122A61 | UPI000465C470 | A0A014LYL5 | A0A0C1YTU5 |
| A0A0J2K868 | UPI00058EBC4A | UPI00030ED944 | UPI0004E14814 | E3DCZ6 | A6AVT6 |
| A0A0E2RBB6 | A0A0J5E886 | UPI0003151B6B | A3YC72 | UPI00069D7BD3 | UPI0003B1A0B5 |
| A0A0G3S4X6 | UPI0004D3B9EA | UPI0002EE9ECE | A0A0F4QZY4 | D8MKR6 | UPI0006A5B784 |
| A0A0H3H1F3 | UPI0005B485C4 | F6CZU1 | UPI00036B36CA | UPI00058F6E3E | A0A0D0JDJ7 |
| A0A068HB64 | V2SM85 | A6W1H3 | B5JVS4 | I3IF96 | UPI00069EC01E |
| A0A0J8Z8W0 | UPI0003AC5FE5 | X7E960 | M4U1U4 | UPI00066FB81F | UPI0006A5FC2D |
| UPI00066AC9B7 | UPI00057BEBAB | W1RWL7 | A0A0E4C1E5 | UPI0005866DF0 | UPI00026C4ED4 |
| H3MDG6 | A0A0C2ELY7 | UPI00037950B0 | C4K8X2 | UPI00037B74A6 | UPI0005EF44E2 |
| UPI0002F9F873 | U9Y0B8 | A0A0J8GYA3 | UPI0004762303 | V5VG28 | UPI0005EFA2F9 |
| A0A0A0FJZ3 | A0A0H0JVJ4 | UPI0003F7784F | UPI000558F88A | D0C9R6 | A0A0C1Z376 |
| A0A077ZIR6 | UPI0002CC3FC4 | I1E2U9 | A0A0E9M3L1 | A0A014AME8 | A0A061PWI7 |
| A0A0H7U3H0 | A0A0D1Q3M4 | Q0VLG2 | UPI000415F58C | A0A062IS38 | A0A090RFC6 |
| A0A0H7UZL4 | N2JD25 | B4X088 | UPI0003736C3A | A0A062RV86 | F7S1D5 |
| W1YGM8 | N3FAJ0 | A0A095S578 | UPI00047DD116 | A0A014QUN9 | UPI00037B6B31 |
| W1F515 | D7XDE9 | U7FXU8 | UPI00051B59BB | A0A0J1AD48 | UPI0004DB80FB |
| W1AVB8 | J1R585 | L0W9M5 | A3WIV3 | A0A011J490 | UPI0002559C1C |
| UPI00050B4286 | A0A063XPH7 | A0A095SJP8 | UPI00058ED431 | A0A009L4W9 | UPI0004226D1B |
| UPI000699BCA0 | UPI00046E61E1 | UPI0003096010 | A0A0B7IYA3 | A0A062ET27 | UPI0005A04CC3 |
| UPI0001BCF307 | UPI0005CFB922 | Q5QZ79 | A0A0D7FE58 | A0A062B4C4 | UPI00036751C4 |
| UPI000291E920 | F1ZPM5 | A0A0B4XU81 | N2J9F8 | K6NBZ9 | UPI0004A71315 |
| UPI0005CECD30 | E9Z170 | V4LHL4 | H0JBY0 | A0A062HCL9 | G7LUC7 |
| UPI000699485E | I2RDB4 | UPI00048D495E | UPI000307EC21 | U1UEQ4 | C6DHF7 |
| UPI0006995E89 | G9YY11 | UPI00066EC8FC | UPI00056B6FFA | N9HSF4 | A0A0G4JUN2 |
| A0A0H7XVC5 | UPI0005A8BE84 | A0A0E0Y6R4 | UPI000694928A | A0A009GJZ6 | UPI0003AAB78C |
| A0A0H7ZBU6 | B7N271 | F2G1X5 | W9SXN9 | A0A009HQM2 | UPI0003A1DD75 |
| A0A0H8QAW7 | A0A029IHD3 | S5C3L8 | G2E0G6 | L9NZJ0 | UPI0003AA3036 |
| T9GN10 | A0A029HDM3 | S5AI16 | H5V6K1 | A0A011IKX6 | UPI00039E8574 |
| U9YW53 | UPI00005EFD38 | UPI00057CAFFD | K8AD99 | A0A062FYV6 | UPI0003A8ECA5 |
| E1ITJ2 | UPI0005175495 | K0CYB3 | UPI0002F4EC6B | N8ZCZ6 | UPI0003A98BB4 |
| A0A029L915 | UPI0004D67711 | K0EB21 | K8AIR9 | A0A022JJ04 | UPI00039EFED1 |
| S0UVF6 | UPI00038F4A0A | A0A0B3Y7T5 | UPI0002F0AB46 | K1FLW5 | UPI000532BCE2 |
| I2SR57 | UPI0004ED858A | A0A075P1K0 | UPI0003747342 | N8UCZ4 | UPI0003AAAD9F |
| I4S298 | S1FND5 | UPI000509BB4B | A0A0D1MQD1 | A0A010EBV1 | U6ZJ94 |
| D7ZUA2 | S1LRE3 | F5Z5Y6 | F8FZI5 | A0A009SCE5 | UP10005539481 |
| A0A069X2C0 | S1CH47 | UPI0003556595 | UPI0004706F0C | N9GH50 | UPI00039F0A65 |
| F3WQ14 | L2VMG7 | A0A010PKS2 | UPI0004870A8C | A0A0J1AU91 | UPI00039CBB8 |
| E1I5T7 | UPI0005EDE9CE | A0A0C5ITU1 | UPI0005D7D9DE | A0A009JME7 | UPI00039E8082 |
| M9FM00 | UPI0002CA0423 | UPI0005D7D9DE | UPI0004838E3B | A0A062TQ97 | UPI00039A51A2 |
| S1HS46 | UPI0004E384CD | J2S9U8 | A0A0C5RPA5 | A0A009QEV1 | UPI00039E8236 |
| D7YBV4 | UPI000675EB35 | UPI0002E4097E | F0E436 | A0A010UBN4 | V3TUV7 |
| D7YG19 | V0Z8Q3 | UPI000641D99E | J3E3S1 | A0A062FMG3 | A0A0A8FH34 |
| V0RR51 | D7ZDM9 | J3D7I1 | T2HEW7 | A0A013G992 | UPI000532D788 |

TABLE 5-continued

List of 3137 unique non-redundant helicases that have 50% sequence identity and 80% overlap with
E. coli Rep. (Uniref50_P09980 cluster, citable UniProtKB and UniParc accession numbers are shown).

| | | | | | | |
|---|---|---|---|---|---|---|
| V0AF21 | V5B2V3 | J2T1B6 | B0KQ68 | A0A0J1A474 | D2BYS8 | |
| E9YLU8 | V1I8U1 | J3EAI0 | UPI00048196DC | N8YU24 | C6CGH3 | |
| I6CD40 | T9SAP6 | A0A0J6H1C3 | A0A084C8X6 | K6LHM0 | A0A089V9A1 | |
| E1HWT5 | A0A0I1J330 | J2MEX6 | A0A099E6T7 | A0A062DHL7 | A0A0A3ZID8 | |
| A0A070FCA9 | A0A0J3J6C1 | UPI0004653130 | A0A088NVW6 | A0A009TH79 | Q9K599 | |
| V0TJ44 | L0M8J0 | UPI000370037D | A0A0F7Y5R7 | A0A0J0ZSY5 | A0A0B2TLM6 | |
| S1H2A1 | UPI0002C957E6 | UPI00054B503C | A0A099N7M2 | F5I0P2 | E0SKR5 | |
| E6BNJ7 | UPI00033C37F9 | UPI0005A8A319 | V7DDK2 | A0A010K6Q8 | J8TIB8 | |
| D6I334 | UPI0003EF8387 | L1M697 | L0FS45 | F5IED5 | UPI00050455DF | |
| S1ESS4 | UPI00040AF69D | A0A0F4VBH8 | V9V750 | N9KF69 | A0A0B3XKC6 | |
| S1CGG8 | W8XM69 | J2XVS9 | A0A059V3S3 | S3TL87 | D0KC43 | |
| I2WCN5 | F0JWU2 | J2NB92 | B1J4P9 | A0A009MSS6 | A0A0H3IEB9 | |
| A0A070DIV3 | A0A0J2D6H5 | S6JBD8 | UPI000627A5A1 | A0A0J0ZPS4 | A0A0J5XQ16 | |
| A0A079D8A1 | L5GW15 | J2UYW0 | UPI0003A45A0C | A0A0J0GGU7 | UPI000505D45B | |
| A0A080I8Z6 | S1P4F9 | I4JZZ1 | UP10004901875 | A0A0J0ZKR3 | A0A0J6AFU6 | |
| L4IUS8 | UPI0006187646 | A0A0J8G475 | UPI000312CC5F | B0V8Y9 | A0A0B3Y0I6 | |
| L3IPS4 | UPI0002CA3627 | A0A038GJS8 | V6JD09 | A0A0E1PVY4 | UPI0004E7AD0D | |
| V6FPL2 | S1IH44 | J2NTP4 | A0A0C1IE71 | A0A0E0WM10 | UPI00005010995 | |
| F4T625 | UPI0001FB5104 | UPI00054BC40B | U5VL93 | A3M323 | A0A0E2ZQ64 | |
| A0A073VUA5 | UPI0006A60648 | A0A0J6JAQ4 | UPI0003B82996 | A0A0J0Z9E3 | A0A0J5UIH7 | |
| F4V8A1 | UPI000666D818 | A0A0J6I536 | A0A089YA93 | G2JCT3 | A0A093TZI5 | |
| K3KG62 | UPI00028CDADE | K0WMX7 | N9W558 | A0A0A8IQG4 | A0A0B2TAM5 | |
| M9E9G4 | UPI0005182B07 | UPI00069ECA48 | V9X4R6 | A0A0C0CBD9 | A0A086ER15 | |
| D6JH94 | UPI000246F098 | UPI0003D2AA53 | UPI0006836835 | A0A0C0CIL5 | J7L4K8 | |
| E0J414 | UPI0002CBC547 | A0A0C5ETI6 | S2KQL9 | UPI0003DF9CA6 | A0A0B2W727 | |
| W8U2K7 | A0A0A5IKM0 | A0A075PD74 | R9VCP0 | A0A062DT29 | A0A093S787 | |
| E8Y8U4 | UPI00046F99E1 | D7HTE0 | U2U6Q9 | N8VAV1 | Q6CZD7 | |
| A0A0E0U640 | UPI00066D2906 | S6JE83 | UPI000480BE0F | A0A0F3L889 | A0A0J5R7U1 | |
| A0A0E1SVC5 | A0A0G3QEH2 | J2LR66 | UPI00062A24F9 | V2VX37 | A0A094RXX6 | |
| A0A0E2TLG7 | W0AUJ4 | J2Q4M5 | UPI00040A96BC | V2TSL6 | UPI00057CA70B | |
| C6EG35 | UPI0006A5EC48 | UPI0003FAF552 | A0A0J8UZS6 | L9MEI1 | UPI00057CDC60 | |
| Q3YVI6 | R8WQW7 | UPI000289EE48 | I7BAY2 | A0A009ZWD9 | UPI0001A44592 | |
| J2YVU0 | S0XDU9 | UPI0006419BD9 | A0A0A7PUM7 | N9SD17 | UPI00057F7392 | |
| A7ZTX9 | UPI0002514D84 | UPI0006A612B6 | I3UUX4 | N9C3A1 | UPI000652BF86 | |
| A0A0E1M3S0 | UPI0005CF34C7 | A0A0F7A011 | A5WAY2 | UPI0004497B0F | UPI0002D49EE5 | |
| I6BAF2 | UPI0005AA6C75 | F3JF49 | Q88CB7 | UPI0002BB404B | U1LCU7 | |
| A0A090NEE8 | UPI0002CB348F | L7H1R3 | A0A0A7JV78 | UPI0004457216 | U1JRW9 | |
| A0A0A7A0X5 | UPI00039014F0 | Q500M3 | UPI000417E5AB | UPI00044C3A7B | A0A0F4P9F7 | |
| E2X573 | N2Q8R5 | S3NDD8 | Q1I2W2 | A0A0A7XTN0 | A0A0F4PG18 | |
| Q329V6 | UPI0003B29D20 | F3GZK5 | UPI0004A76E61 | A0A022ILU3 | A0A0C1LH68 | |
| F4TMM3 | UPI0005F81F2E | UPI0005CA31AB | A0A0E9ZS43 | A0A066PI57 | UPI00061D116D | |
| U9YTK0 | UPI0002CA5EAC | UPI00035D1EA1 | UPI000615E3F7 | A0A062G9S1 | A0Y9C9 | |
| B3X5G0 | UPI000462FEC5 | W0MPM6 | A0A0H5W4I1 | L9LZ08 | Q2S8F2 | |
| I6CYC2 | A0A070DGP2 | A0A0A1Z8J9 | A0A0H6ING7 | A0A010KUF7 | K2JN56 | |
| A0A0A0GP02 | S3IEG5 | W2DE98 | UPI00069F04C6 | K9BCT1 | UPI00067E742C | |
| F4SRI4 | UPI0002CC411A | A0A0F4TYK8 | UPI00053BC90E | A0A0E2G0N2 | A0A084IL47 | |
| UPI0006981AFC | UPI10005718CCF | UPI00041035FD | UPI00069E6D92 | A0A0E2GP36 | IJPT0006697E7E | |
| V0ST83 | UPI00036A6951 | F2ZPZ1 | A0A0H7D3K2 | UPI00044F9626 | C9PMC5 | |
| T8WTG6 | UPI0002A38058 | UPI00045100E9 | D2YQS5 | UPI00044ACF5B | UPI000402FD5E | |
| A0A071C0Z5 | A0A0I1VLP8 | UPI0006458FD3 | D2YET1 | UPI00044D2485 | UPI0004802687 | |
| V0XTH9 | UPI0002CB6DE1 | A0A098SWG7 | A0A085TFB6 | UPI0005AB250E | H0PYR0 | |
| D8C4A4 | T5NUB4 | A0A0D1NXC0 | UPI00051D019F | UPI00044F9882 | UPI0037C100B | |
| T9AU26 | A0A0D7F5Y8 | UPI000589F9C7 | A0A0F2IJ11 | A0A013NSE0 | UPI00067D4203 | |
| E1HNU3 | A0A070RX93 | UPI000614591D | UPI00050288CA | UPI0003558246 | UPI0002FE41B0 | |
| H4URG0 | H3MUT6 | UPI00370CF7F | A0A099MUD3 | A0A062L2N7 | UPI00005BC9A68 | |
| A0A070SPZ6 | A0A070H7B2 | UPI00061DB54E | UPI00042A59FC | A0A014DQT7 | A0A0J6NLY1 | |
| A0A073HDV7 | UPI00025B202A | UPI00048A25A1 | C9QBF3 | A0A014BGK8 | A0A0J6KGG3 | |
| S1HND8 | A0A064CY65 | UPI000463D380 | UPI00028D4D13 | A0A014E4S6 | UPI0005BBAD58 | |
| A0A079FCR6 | UPI0004D5922D | A0A0F4SXJ2 | A0A085PFD0 | UPI0002FB179F | B0UTK9 | |
| A0A073UI24 | UPI00038FE44C | E2Y0S2 | UPI0002F9A474 | A0A0B2XRW1 | Q0I2R4 | |
| V6FCI2 | UPI00057C0F18 | UPI00054B1EC3 | UPI0005C96744 | N8S5C9 | A0A0F6RAV7 | |
| W1BJG8 | UPI0004D7032E | A0A0J6KIB8 | A0A0H6I9T4 | UPI0004537654 | B7S2C9 | |
| A0A064T0J2 | A0A0J4XAT3 | UPI0004157785 | A0A0H3AKZ5 | UPI0004526A41 | H1G3C3 | |
| A0A070Y1X0 | UPI0002C8F3D6 | UPI00031D1029 | A0A0H3QD21 | A0A014CAF7 | UPI00048A6F57 | |
| A0A073GI88 | UPI00061449A9 | UPI00046A96D2 | Q9KVH9 | UPI00061AF1D4 | K2KA81 | |
| V8KBQ0 | A0A0F5SGU2 | UPI000287BEB4 | C3LQ06 | UPI000665B4E7 | UPI0005A75154 | |
| A0A070NWA9 | A0A0C1ZV53 | UP10004882B64 | UPI00053C3831 | N9IYA6 | A0A0F6KJ15 | |
| A0A071AHD9 | UPI0002CB0481 | UPI00004937205 | A0A0H6DK35 | A0A062KZU0 | UPI000538802DA | |
| A0A079GY22 | A0A029P5M4 | A0A0B8VQT6 | A0A0H6WUV7 | UPI0005A67365 | A0A0E2LUW8 | |
| A0A074HJN3 | UPI0002A43CB4 | UPI0004E6F9D0 | UPI0000F34C0E | A0A013IDC6 | K1JFB9 | |
| V1AR00 | C9Y4T0 | UPI0005B4FF04 | A0A0H6U8U2 | A0A013P0S9 | A0A023RRT0 | |
| A0A080HY13 | UPI00049ED8E4 | K9NS95 | UPI00069E3D50 | A0A009LQZ8 | UPI0005AA85F9 | |
| L3QA81 | R5WQS0 | J2QIN9 | UPI00069F740E | A0A062FFT3 | UPI0005AA6DC7 | |
| I2X3U6 | UPI0002C9A11F | S6I847 | UPI00069D81D6 | UPI00056E426A | UPI0005CE86ED | |
| L3K8G1 | UPI0003901F07 | A0A085URN7 | UPI000472B301 | A0A009EYA5 | K1K4T1 | |
| A0A080GHT9 | K8CHU4 | UPI0006762E20 | UPI0005B3F2F7 | Q6FDR1 | UPI0005C13448 | |
| A0A070PMD4 | F5VKN6 | A0A0D6C968 | UPI000419FA2F | A0A014CQR5 | UPI00068176EC | |

TABLE 5-continued

List of 3137 unique non-redundant helicases that have 50% sequence identity and 80% overlap with
E. coli Rep. (Uniref50_P09980 cluster, citable UniProtKB and UniParc accession numbers are shown).

| | | | | | |
|---|---|---|---|---|---|
| A0A079FM03 | A0A0J1M6F0 | A0A0D6BRV6 | UPI0019F6F0B | A0A014FSY6 | UPI0005A8197B |
| A0A071CG57 | A0A0J1MPE2 | UPI0004659D49 | D7HG42 | A0A014DDU2 | UPI0005EE918B |
| H1C5A6 | K0XCY3 | A0A0B7DG99 | UPI0006154522 | A0A062SQW5 | UPI0005A7CCE7 |
| A0A071DLR9 | UPI000483904F | UPI0005789654 | UPI0004E46C62 | A0A062MW11 | A0A091AMQ6 |
| V6E2G2 | UPI0002CA7454 | UPI0002887A69 | A0A0D1ESY4 | F0KFL5 | A0A0A5MTL6 |
| D8AZU3 | UPI0002CA7442 | UPI0004E363B2 | UPI0004A3DD97 | A0A010KWI7 | A0A070ARJ5 |
| I4J555 | UPI0002C8C519 | UPI0004711D03 | C2HS26 | A0A009GU89 | UPI0005B21AAA |
| D8AJN2 | UPI0002CAD3B5 | UPI0005AB8E86 | UPI0004939A0F | A0A009RTE6 | UPI0005B4D264 |
| L3NTU4 | UPI0005AB8E86 | A0A0C2R6G2 | UPI00041D5461 | A0A013S7D9 | UPI000206A54C |
| A0A017JGH1 | E3G401 | UPI000036390E5 | UPI0053C556B | A0A011KJ92 | UPI00057A9E387 |
| E6B0V7 | A0A0D6J066 | Q4K3U4 | UPI0006B26D10 | W3T1R8 | UPI00057A3319 |
| G0F684 | A0A0G3J3X1 | UPI000467F1C8 | UPI0003DDF141 | A0A013T0B3 | UPI00067160F8 |
| T5ZL14 | A0A0G2SEI1 | UPI00035F9085 | UPI00041C3DE6 | A0A062GLJ2 | UPI0005BE5278 |
| A0A023LHN8 | Q1R4G1 | S6MAY1 | D0IMK5 | A0A022KT37 | UPI0005B44CBF |
| B1LLV1 | A0A0H2Z4L9 | A0A0D0PI96 | UPI0004D45E01 | A0A013LNZ0 | A0A0A5LAX4 |
| A0A0G3KG39 | B7MGI8 | W8PZL5 | UPI00064AB4CA | R8YFJ5 | UPI0005A92C34 |
| A0A0E3N453 | A0A0E2KYV2 | A0A0A1HZQ3 | UPI00027344D7 | A0A010JTN9 | UPI0005AA862F |
| H9UYX9 | UPI0005AABAAC | A0A067A109 | UPI00157DCC7 | A0A062EII9 | UPI0005B93FB |
| W1WIT4 | UPI0005A9C3D7 | M4K6D4 | UPI00042503B9 | U4NIT0 | UPI00067ED86E |
| D2ABU8 | M8YJ27 | L7HM91 | UPI0004223C0C | A0A009MNG3 | UPI0005A81507 |
| UPI00050A88E3 | A0A084ZTW9 | UPI0003631017 | UPI000418E3F8 | A0A062M340 | UPI0005A6CF02 |
| I6FUG1 | V0V039 | Q3K4P8 | UPI0006A57310 | A0A009GIH8 | N9TZ36 |
| I6FTV3 | UPI00038FD937 | UPI000490BE66 | UPI00042555E5 | A0A013TVZ0 | UPI000305A965 |
| A0A0C7MGG8 | UPI0005436CE7 | A0A085VMC8 | UPI0019F31E6 | A0A010GR47 | UPI00051BB915 |
| Q83IX8 | UPI00063CF1BC | A0A0C1WQJ9 | F0LQ07 | D6JS35 | UPI00036C158E |
| A0A0G3KSI3 | A0A0D5WYP4 | V8QZB9 | UPI00041CEAFC | A0A062DGV2 | UPI0005A8ECB0 |
| A0A0F6EJW3 | UPI000448752F | A0A010RSD4 | UPI0006A6C949 | UPI00044710CI58 | V9ZTN7 |
| R4Y441 | A0A017I2W6 | UPI0005C45ABE | UPI0003575C86 | UPI00044634D9 | UPI0005BA54D7 |
| C8T0L2 | R8WJV4 | A0A0J6KKN8 | UPI000218F470 | UPI000571CB80 | UPI00029B427F |
| D3H3Y7 | UPI0003B8BA8 | V9R4G1 | UPI0004408ADF6 | A0A011BSP6 | UPI00044B3D00 |
| Q0SYW8 | F5P1M9 | A0A0B4EK54 | UPI0004E46B12 | UPI000449E802 | UPI0004633883 |
| A0A0F6MJB5 | UPI0002C91A03 | F3FQI2 | UPI000427E347 | B0VTE6 | UPI00028072AE |
| UPI0002DF73BD | UPI00064025BA | UPI000497D00B | UPI0003FAAAB1 | UPI00044AA4AB | UPI0005AB7E0E |
| D2TH67 | UPI0003EF0793 | UPI000069BD02D | UPI0002BC24BA | A0A0E2GQQ9 | A0KQV9 |
| A0A0J0GM61 | I2RVV7 | UPI00062AF47B | UPI00021A9545 | K9C7H8 | T0PHI0 |
| UPI000664EF6E | UPI00057A8D97 | A0A0A4GEX8 | UPI0053C5E2E | A0A010WGE0 | UPI000589CE10 |
| UPI0006656E52 | UPI00057BF87B | A0A0H5ABK2 | UPI000424C2A2 | A0A022J6H8 | UPI0005D91456 |
| UPI00062C1AFB | UPI0002CCC14E | UPI000579419A | UPI00046EF0F3 | UPI0004474D0C | UPI000666021A |
| UPI00046642F8 | A0A0H3XA26 | UPI0005CB3DAB | UPI0002A3539C | UPI000406B18C | UPI0006A60313 |
| UPI0004E14727 | UPI0005CC970C | W0H3A6 | UPI0004112BDB | A0A013J7P7 | UPI000372D3BE |
| A0A090UXU3 | UPI0004F91B50 | UPI0001E29EE7 | A0A072J517 | A0A013IEY9 | UPI0005B1DD9B |
| UPI000598D943 | UPI0005F03F71 | UPI0006435FC4 | A0A0DIGPU1 | A0A010LP37 | A0A0D0P607 |
| UPI0005893785 | UPI0005CD8DCC | A0A0C2A864 | A0A0D1F105 | A0A013V1J9 | UPI0004937CC6 |
| A0A0F0QX40 | H7EDJ9 | C3K451 | X7NM08 | A0A011IN70 | UPI00059B6C6A |
| Y1GHZ4 | UPI0002BA9774 | UPI0003031244 | A6B4T3 | A0A011GFN4 | A0A0A5Q092 |
| A0A0J0JWN6 | A0A073TQR6 | UPI000376837D | A0A0F6M2K0 | A0A009I9W9 | UPI0006996A18 |
| A0A0J0RY26 | A0A0J8XHE7 | A0A023C475 | A0A0E2PRB3 | A0A062JC54 | UPI0005A7E00F |
| A0A0F1BFH2 | A0A0D8LLA3 | A0A0J6GRZ4 | Q87TM8 | A0A062T611 | X5HRY7 |
| UPI000668CF1D | A8ACT1 | F3K6V6 | A0A0F6LVP7 | A0A062IXJ9 | A0A0G3BY85 |
| A0A0J0NMD9 | UPI0003EF7A22 | E7PGN6 | Z2EEI2 | N9BR66 | UPI00051C6305 |
| UPI0006AA4E04 | UPI0004D811CA | F3EC88 | A0A0A3VAZ6 | UPI00036B0A84 | UPI0005B1FBE6 |
| A0A0F0VNG6 | A0A0I2AP98 | Q48QC4 | Z2EDP1 | UPI000426CED1 | A0A023E407 |
| V3CMI1 | UPI0002328C93 | E7NYU2 | UPI0004A2C7E5 | V4N4Z7 | A0A081LLX9 |
| A0A0J5K4Z7 | UPI000369897B | J2RG73 | A0A0A3V6V0 | UPI0002836BF4 | UPI0005AA429F |
| UPI0006AC63C4 | A0A089VYB3 | J2UNX5 | UPI000472ADBC | A0A0K0HLP9 | UPI0003603F0F |
| UPI00041ACFD5 | UPI000541FC4B | UPI000069F8C81 | Z2EJN6 | J5N8B5 | A0A0J1M7R1 |
| A0A0F2AQL9 | UPI000579035F | A0A0F0EFQ7 | UPI00041561ED | J6CRI5 | UPI0006489688 |
| A0A0F5B4Y8 | I2BE87 | W2DRJ6 | UPI00021A9FCC | UPI0003D82FE7 | K1J828 |
| A0A0J1RFK1 | UPI0004E1359A | A0A089YRC6 | UPI0001BAD8BD | Q9CLZ0 | UPI0005AAFC0D |
| A0A0J0RJ15 | A0A085GMM2 | A0A0G3GBQ2 | UPI0053C3D1D | J4SJC5 | A0A0A5NK04 |
| A0A0066NY31 | UPI00039B2EBD | J3ICZ1 | UPI0005C160B8 | J6CUJ6 | UPI00051C9AF5 |
| A0A0J0LMR4 | UPI000540F32C | J2UE96 | UPI0004D7564A | UPI0002828EB6 | A4SHB5 |
| A0A0F1A8L1 | UPI00057BFF33 | J2U1B0 | UPI000541DCCF | UPI00025912D9 | R1GU16 |
| UPI00049A4378 | UPI0002C9F7CC | J0P5Y9 | A0A085T413 | UPI000256A08F | Q5YL02 |
| A0A0H3BNR1 | UPI0003FFEF4B | F3IWL2 | UPI0003591073 | UPI00061A7F96 | A0A0J5SCJ7 |
| UPI00036B51A5 | UPI0002CC6D1E | A0A0D0SPI8 | UPI0069CC245 | UPI0002F21178 | UPI0040E493E |
| A0A0F3ZKX7 | A0A0H3FM31 | Q88BA4 | UPI0069D2456 | UPI00056150A9 | UPI00026C7DD5 |
| A0A064DDL2 | UPI000463D3B8 | A0A0F0F2C4 | UPI0004E3009B | F2MWQ4 | UPI00034AEF0E |
| UPI0005EEABA8 | UPI0002A4658A | UPI0006425E29 | UPI000682B11B | H7EWN0 | K4KNG9 |
| A0A0F1B160 | UPI0006684CD5 | UPI00048CEACE | UPI0004D918FF | UPI00046225F6 | UPI0005916203 |
| A0A0J1VF42 | UPI0002CCBD72 | F2K6U9 | UPI00064977DD | A0A028VHX2 | Q1MXX3 |
| A0A0J1RH04 | A0A0JUQT3 | I4N769 | UPI00021A928F | A0A0F3G1C6 | R1J2K6 |
| UPI0003BDCA59 | Q8XAT6 | UPI00054B3B22 | A0A0H6V1C5 | A0A0F3G1H1 | A0A0F5ZTG2 |
| UPI0005F8E6D5 | R6U5R3 | UPI00034B3DE4 | UPI00041CDED6 | A0A0D7EEU5 | UPI0002D73F2D |
| A0A0F3YH15 | A0A0F6GUR2 | UPI00054BF274 | M5NBE2 | A0A0I9SHZ4 | UPI0002E30D8F |
| V3DS68 | M8JSN4 | UPI00035C9B5D | UPI0005A612B3 | I4CY47 | D0I4E4 |
| UPI00067FBCBD | UPI0005EF606F | UPI000466DC2D | A0A067BE00 | A0A098FXA5 | UPI0004826336 |

TABLE 5-continued

List of 3137 unique non-redundant helicases that have 50% sequence identity and 80% overlap with
E. coli Rep. (Uniref50_P09980 cluster, citable UniProtKB and UniParc accession numbers are shown).

| | | | | | | |
|---|---|---|---|---|---|---|
| A0A0H0BBR0 | C3SKS7 | A0A031J819 | A0A0E2KH36 | F8H8H9 | L0GNC3 | UPI0005F7AFD8 |
| W7NPC9 | H5E8V7 | A0A0E2JIS7 | A0A011RY08 | A0A0B5C9B4 | A1SAR2 | A0A0F7M0Q2 |
| UPI000237CAE2 | A0A073G4J2 | F3DX19 | UPI000218FD46 | A0A0H6I7N5 | UPI0004752163 | A0A067A0E9 |
| A0A0H0B833 | E9TMZ3 | S6WCS6 | UPI0004DF1506 | F6AK49 | S6JQB6 | UPI00056F77EF |
| X5GBQ8 | M9HCU8 | UPI00069D83B7 | UPI00040CF721 | UPI0005A6CCD1 | R8ASG1 | UPI000046459AD |
| UPI000480BC4B | N2GRQ0 | F3EY12 | UPI0002C171C1 | V4QKI1 | UPI00057A6730 | |
| UPI0003BF53EE | V8FGU6 | A0A024EDQ4 | UPI0003A5CF66 | S5IY40 | V4PVZ8 | UPI000647EC3B |
| UPI00043B1758 | W1G9Y1 | UPI000473172F | A0A0H6RK46 | A4XNW1 | X6QAT8 | |
| UPI0003288250 | D8E9I5 | UPI0004837A57 | UPI0003FCEE4D | UPI0005B96553 | A0A0E2Q742 | |
| A0A0F4B9X9 | A0A080FRF1 | A0A0D9A8H9 | D0HB12 | A0A0D0KWI3 | UPI00065DE691 | |
| UPI0005EA547A | A0A074HNG7 | M5R504 | A0A0H6U223 | UPI0004CF668E | UPI00029BA482 | |
| A0A0E1J7G4 | D6IG13 | J3FAA8 | A0A0H5V3D7 | UPI000027874F3 | D1P301 | |
| A9MJ31 | N3JTF2 | A0A0J6G1D6 | A0A0H6XKF0 | UPI000483B47F | W3YJP2 | |
| V1K9F5 | J7R7U6 | UPI00069EC1FC | UPI0003F7284F | UPI00066DB41B | B6XD39 | |
| A0A0H3CTF5 | A0A0A8UGH0 | A0A031GCP2 | M4RF91 | M2TXC8 | K8WDI3 | |
| A0A0J0I6K1 | A0A026UZB6 | U1SSX9 | UPI000290E44C | UPI000646559F | D4C425 | |
| A0A0H0C2Z0 | M8L4U0 | V7E1I4 | K6YD96 | A0A0H3YQ39 | K8WMJ7 | |
| A0A0J0K9E8 | F8XAU8 | A0A0A6DIW0 | UPI0005254C58 | UPI0006274DB0 | B2Q4K1 | |
| A0A0F0TB35 | I0VX84 | UPI0006465369 | C7R609 | A0A0A1YQ26 | I0DV03 | |
| UPI0003546D46 | M9GR01 | UPI000640671F | UPI000483BB31 | U2Z897 | K8WW49 | |
| A0A090ULL0 | A0A028CB68 | A0A077FGC9 | UPI00041E0643 | UPI00048929DA | A0A099DD54 | |
| V2HH02 | F4W233 | A0A077LKD4 | S6BLM3 | UPI0004CF0F54 | UPI0005B3D15C | |
| A0A0E2JMN1 | A0A073FPG7 | F3DEB8 | A0A0H2QE7 | A0A023WXA7 | A0A0A7ED48 | |
| A0A0J0LZB7 | V0XEM3 | A0A0F4TWU8 | A0A0H4HX48 | W6QPC3 | U1M4M6 | |
| A0A0J0TKA0 | H5J8G9 | W6VH72 | A0A0H4HA84 | A0A087F8M6 | UPI0005EAE7B0 | |
| A0A0J0CC39 | D8ERM8 | I4K9P3 | A0A0H4GYY0 | A0A061CNF1 | UPI0003813008 | |
| W0BFN6 | A0A079Y2M7 | UPI00069DE63B | Q7VNG5 | U3HS13 | N6X102 | |
| G8LKX8 | L4UZJ8 | G8Q5Z2 | A0A0H4GVY1 | UPI000306C138 | UPI0003A42C04 | |
| UPI0005CF9B3D | T6GRI5 | S6I6M5 | UPI000364DF85 | F4DXY8 | W0TMS6 | |
| UPI000665E6B2 | H5IRB6 | A0A0F4XJX5 | UPI000312E129 | A4VGV2 | U7HXH2 | |
| A0A023V5X5 | A0A027YRN5 | UPI0006257434 | U3B5Z6 | U2B4P9 | K0CFZ9 | |
| W1FX72 | G2AN10 | F3IN68 | UPI000429C1C2 | U1T3I8 | A0A071LPA7 | |
| A0A0G2MPB1 | L3PUX5 | A0A0D0N8H7 | V5HP10 | Q088M5 | UPI00041A839D | |
| A0A0H2WUK6 | V0Z4M2 | S6RD61 | A0A0B8QVA0 | K6YBB4 | A0A078MHY5 | |
| UPI0005ED7CE9 | L3C1G4 | S6T6P7 | UPI0002DF401C | UPI0003B45ED8 | UPI0005CA5673 | |
| UPI0005749AE1 | M2P3K5 | UPI0003770316 | L0DT46 | C2LKQ6 | A0A031MHW5 | |
| W8XNK6 | M8PIH5 | A0A083UT61 | UPI0005099D99 | B4F1V1 | UPI00048184EA | |
| G2S5J6 | I2UBA9 | A0A026RV20 | UPI00041EBC8E | V6MEX9 | UPI000480EBFA | |
| A0A0J4QGK6 | A0A0H3JJN7 | S2EZ50 | UPI0003B66AF2 | UPI00040DD930 | A0A0A7RZK1 | |
| A0A060UXG1 | A0A0G3JMJ8 | U7DPS2 | E6Q994 | A0A094VIT6 | UPI0006656150 | |
| V1SVN5 | A0A027TGI5 | J2XUG2 | B7J5H5 | A0A0G4QET2 | F9H319 | |
| A0A0C9GL09 | D3QX71 | A0A0E1ED74 | B5EKY0 | C0AS08 | UPI0002E7B4B9 | |
| A0A0C9GYL4 | A0A023Z524 | I2BSP5 | G0JPR1 | A0A0J1FDF2 | A0A0E1WIG4 | |
| Q8Z385 | A0A0H3EP47 | I4LAD3 | A0A060USE4 | A0A0G4QJK0 | UPI0002DA963E | |
| UPI000500230C | L9HY53 | A0A059KWW4 | A0A099KS81 | UPI000536EEA0 | UPI0000445EA18 | |
| A0A0J1UWJ0 | A0A0H3PQH4 | W6V2S0 | Q48A47 | UPI00066713AB | UPI0005BEB3B1 | |
| A0A0E2M7J9 | A0A027ZJD8 | UPI00037298BE | UPI000369C377 | UPI00053159BF | UPI0005BEAFC8 | |
| A0A0J4NUP9 | A0A0F6FEN5 | J2SK90 | A0A099L585 | UPI0005FB88C6 | UPI00068166C9 | |
| M7P8Y2 | A0A0F6CB93 | UPI00062A28D4 | A0A0J6IZ62 | UPI000538E59F | UPI000680F31D | |
| V3KJ47 | A0A028E3B5 | A0A0J6LHZ7 | A6VEA1 | J7TSU4 | A0A0E1SM32 | |
| X0NMP3 | A0A025G7Y1 | UPI00054BC3BF | A0A086BUA3 | A0A0A2R681 | A4N6A7 | |
| A0A0J0MEC2 | K4VYE7 | F3HE08 | UPI0000D7267E | A0A0H2RF05 | UPI0006699B6B | |
| UPI0002B9ECA4 | A0A025C056 | UPI0004855F80 | UPI0004CEE864 | UPI00066588BE | UPI000682D126 | |
| UPI0003A99D9E | B6I4B4 | A0A0E2UZ31 | UPI0005C9EB61 | UPI0004684BD5 | UPI0001A3F561 | |
| UPI0003BD7E08 | A0A0H4S0M7 | UPI0004B486C5 | UPI00059FF9E6 | M7CFP7 | UPI0005AEEC55 | |
| UPI00017C01C2 | W8ZQB1 | UPI000467E321 | L8MSN6 | UPI000509F66A | UPI0001545AFF | |
| A0A083YZC2 | C8UJG0 | A0A0D9APL4 | UPI00048D30BD | UPI00004148097 | UPI00062D80BD | |
| UPI000633E857 | A0A0E1ZWP5 | A0A0B1Z6A5 | UPI0005BD2953 | A0A0H2QVE0 | F9GRY7 | |
| A0A0H0B767 | A0A0A0F921 | A0A0C2I7D7 | UPI0005CFE450 | UPI00062C8767 | A4N0M7 | |
| UPI00049F603B | F4VLA2 | K2SWK1 | UPI00053E8C86 | UPI0004632748 | UPI000667602A | |
| A0A0J5L5Y8 | UPI0005CCA9B7 | S6RKJ9 | UPI0004633730 | A0A076LNV0 | I3DT46 | |
| UPI0004A7224E | UPI0005CF3F54 | K2TIC3 | W5IS76 | A0A034T5A5 | E7A6L1 | |
| UPI0002E3DC58 | A0A0F6VR07 | F3GZK6 | UPI00053D2EE8 | A0A0H4Y5C6 | UPI00049A786F | |
| V2LMA2 | A7MQI4 | A0A0E3K5L5 | UPI000281A7AB | D0Z969 | A0A0D0HPX5 | |
| UPI0006AC7A4B | UPI0003EF9AA0 | A0A0D5XSI5 | A0A024HPG4 | A0A0H3DLQ4 | F9H118 | |
| A0A0G2MI6 | UPI0004A0972A | F3GAT3 | A0A0H3QKK2 | A0A0E0YV25 | UPI00014FD51C | |
| A0A0H0DGX5 | V4B7H4 | U6ZWQ4 | A0A081YDT2 | C5BBB0 | UPI000039A987 | |
| A0A0J0STY6 | W1F1B8 | A0A0D0N1N0 | UPI00021202D8 | A0A0J7JPC0 | UPI0006667D95 | |
| A0A0J0B4N3 | UPI0002FA2529 | UPI000291716A | UPI00048B1910 | UPI0002819173 | M0QBY6 | UPI0005AF4057 |
| A0A0H0DLE1 | UPI00066D0413 | E0WUJ5 | UPI00053ECB14 | D4F9S6 | UPI0006658AEE | |
| A0A0J0TZE8 | UPI0002CB68C1 | UPI000586ABB4 | UPI0005D3900B | UPI0002FC6C68 | UPI00062DA742 | |
| A0A0J0DI84 | A0A0A1R5L6 | UPI00058FF140 | UPI0004CE44FE | UPI0002EC2B1F | UPI00066825F9 | |
| A0A0J0M6U1 | UPI0002CBCFF5 | A0A086D7H2 | A0A071KY05 | A0A0F7NRS6 | UPI00062DA3B5 | |
| V7UEQ3 | UPI0002CAB9DA | Q1QSL3 | W1MWV7 | I1YH83 | T2BJ41 | |
| A0A0J6MH73 | UPI0002CA9661 | UPI0006507055 | Z2DC34 | A0A0C9NZX6 | UPI00045A627C | |
| A0A089GCS8 | A0A0J2DYF8 | | | | | |
| UPI00057D22D2 | | | | | | |

TABLE 5-continued

List of 3137 unique non-redundant helicases that have 50% sequence identity and 80% overlap with
E. coli Rep. (Uniref50_P09980 cluster, citable UniProtKB and UniParc accession numbers are shown).

| | | | | | |
|---|---|---|---|---|---|
| A0A0J0DPX9 | V0VJI0 | K6ZDC1 | Q9HTQ8 | UPI0004814447 | A0A0D6FR93 |
| UPI0004DB41FA | L2X5H3 | G4QEW3 | A0A0H2ZJC9 | UPI000485F550 | A5UHE1 |
| UPI000647BC86 | T5TGV8 | A0A094ITY3 | V6ANV3 | UPI000481ED5E | UPI0001F36303 |
| UPI000464DFFA | A0A0J3V897 | A0A078KWA8 | A0A0E1B1Y8 | UPI000485C7E8F6 | UPI00066E1D5B |
| A0A0J0JNC2 | U9YXY7 | R9PLC1 | UPI000066A1682 | UPI000048C3840 | A4P0W5 |
| A0A0F1RDS8 | X7NZP7 | F9U5G0 | UPI000053CF5E1 | G8UU65 | E1W2I7 |
| V3ICZ9 | S0VJS5 | UPI0004214388 | UPI000483B998 | Q5ZRR4 | UPI00066D46C5 |
| UPI0002ED4344 | UPI000553AB9C | A0A085HDC4 | UPI000453754D | Q5WSZ4 | A0A0E3LZ36 |
| UPI0002BAF5C3 | UPI00038FBA14 | UPI0004899DBF | UPI000053E9238 | A0A0C9MYI5 | UPI00066C24A1 |
| A0A0F0RUW6 | UPI000069AF41C | A0A0G3CX27 | UPI000044B92FC | I7HM78 | UPI00066D30E4 |
| A0A0J5X4F1 | E9XUF9 | U2EN75 | UPI0004F243CA | UPI00048A337F | UPI0004763AF3 |
| A0A0J6MA72 | UPI000377C134 | F7RTH7 | UPI000281A2C7 | UPI0001E3CB67 | UPI00066D6A55 |
| A0A0J0EMG6 | UPI0006144C0E | UPI000560CC8C | UPI00025BA256 | UPI0005A659E8 | A0A0H3PBZ3 |
| A0A0F0Y3A8 | UPI0002C95440 | A9L5H2 | UPI0005B80B94 | UPI000489B225 | UPI00066EEC6E |
| V2L1P6 | UPI0002A387C3 | A3D9R5 | M4X2N2 | D5TAM2 | F0EQH8 |
| A0A038D4Q8 | UPI00028D7E4A | B8E891 | UPI000464F24C | A0A098GC77 | F9GLZ1 |
| V2AL75 | UPI0003EF002B | Q8E9F8 | UPI00053DFB5E | A0A0E3V4J7 | UPI00068332D3 |
| UPI0006AC6CB6 | UPI000675F6B9 | V1DQ01 | A0A0H3RZC1 | A0A0E2Z1G0 | P44804 |
| S5MWY3 | UPI0002CB1048 | B0TJQ2 | UPI00053F27B9 | Q3J9N2 | A0A0E1WD80 |
| UPI0005E6338A | UPI000666D01A | A0A073KJP1 | UPI000580BD50 | UPI0004E88D84 | D1NF27 |
| A0A0G3TQ60 | UPI0003917D4F | A8GZF1 | UPI0003B96CAA | D8K6Y2 | UPI00066786CF |
| V5KMV0 | M8S4Q2 | A0KS48 | UPI000627ABF2 | H8GKB8 | UPI0005BEB07A |
| A0A0H3TAW8 | A0A0F6TYB8 | Q0HQH5 | S6AK57 | UPI00045E6F7C | UPI00062D93E5 |
| A0A0K0IDI8 | UPI000667500F | UPI00005E53DE | U3HFM7 | G4E537 | H1LQ71 |
| UPI0006678805 | A0A0G9GD89 | UPI00048E027C | A0A0D6T1C3 | UPI000592722C | Q4QMR8 |
| UPI0005CFE58C | UPI0001E172D8 | UPI00057AE72B | A0A077K6N5 | A0A0D8CVB0 | F2BZJ0 |
| V3R0S0 | UPI0005A5D84A | E6XQS6 | UPI00036968F6 | UPI0037B7540 | D1NGE3 |
| UPI000667F205 | K4WL59 | UPI00048F743D | W9UTB0 | UPI0005A79D1F | D1NDK2 |
| UPI0003BCBEBD | UPI00057BF7EA | A4YBH4 | UPI0004074F9F | UPI00048C3DFE | UPI0005891512 |
| F5S3F4 | A0A0J4KMU3 | B8CHT8 | UPI00037EAC87 | I3D5Z6 | E1XAV0 |
| A0A089QXV4 | UPI0004D4223E | UPI0005CD4AEB | UPI0006868A78 | E4PK47 | I3BJY2 |
| UPI0005DE95D8 | UPI0002C9357C | Q12S77 | UPI0006853B62 | M7D8V7 | UPI0006ABC8FB |
| R0EH56 | A0A0A8KN31 | UPI00046EB07E | UPI0006853B62 | UPI00034BBD60 | UPI00066B7069 |
| A0A0A6H3D6 | B7L8B9 | UPI00015880E3 | UPI0006878394 | U7G1L2 | UPI00066AD24C |
| UPI0068B0F23 | A0A0E0Y664 | UPI000468006F | UPI000688C08A | U7NT63 | D3RTA9 |
| A0A0H3RA37 | A0A0D1BKY7 | G0ATX3 | UPI000687FD4C | A0A0J7J5V1 | UPI0005D3DD99 |
| A0A0G2NZC5 | E3PNW8 | UPI00005FDF28 | UPI00068620CA | R8AXS8 | A0A0D8PL98 |
| UPI000353D040 | N2IIK3 | I3Y6V4 | A0A081N6G5 | H8WDK4 | UPI0005314008 |
| UPI0005E5AEEC | S1HQ90 | E1VG66 | F3KEE2 | U7H536 | A0A0A2Y273 |
| A0A0J0WRS8 | K5BLY1 | M7PDW2 | UPI0005F86AB0 | U7NXR9 | A0A0A2XH45 |
| UPI00069B3A9E | T9CGI0 | A0A081N9R3 | W0SBD9 | A1TXU4 | A0A0A2YTN3 |
| A0A0G4BD19 | A0A0F1KJV2 | A6VM58 | UPI0003B7AAB8 | A0A072MY82 | UPI000530E664 |
| UPI0005C61441 | A0A0F6K2V6 | B8GLW7 | UPI000409CD7B | UPI000069EBA57 | UPI0005314059 |
| UPI0005F19921 | UPI0002A2036B | UPI000570B5D1 | UPI000410D42B | G6YNL9 | UPI0005531D6FE |
| A0A0J6D7T8 | UPI0003915B14 | UPI0005278D4D | W0HH80 | UPI00031A8E93 | A0A0A3A494 |
| V2AVQ0 | A0A0G9QFI5 | A8G0X8 | Q2NQB0 | UPI0005230701 | A0A0A3A7G2 |
| V1GTV0 | A0A0J1ZW66 | UPI00048BE683 | W0HNJ1 | F4AHB5 | U1I2Y4 |
| UPI0003FA6617 | V2S178 | A3Q9M9 | UPI0005609D73 | Q15ZT6 | F4HF21 |
| UPI000665C816 | N4NBQ8 | B1KQB1 | UPI0005C9970E | K6XTE6 | UPI0005310D73 |
| M4LS14 | N4NKF8 | A0A0C3QZI7 | UPI0003FDF7C7 | K7A404 | A0A0A2XIV9 |
| A0A0J5MXA1 | N4NZ19 | UPI00052F1E8D | UPI000484C7F7 | K6YMY3 | A0A0A2ZUW6 |
| UPI00051391FD | A0A080EIA1 | UPI0004908F35 | A6EZW9 | A1K1U9 | A0A0A3AZE6 |
| A0A0A5R3K5 | L2VFP6 | Q21PD1 | UPI00058F11A8 | G2FGY2 | A0A0A2Y9K8 |
| A0A0J0QVL7 | M9ER59 | O51889 | A0A0F9NYG7 | G2DBK1 | UPI0005313184 |
| A0A0J0R4I6 | U9ZQ00 | UPI000034A05A0 | Q478X4 | UPI000360CFDB | UPI000530C37C |
| A0A0F1HGA3 | N3NAA8 | G4SXF2 | Q2BRL8 | W0BEM2 | UPI00053223C9 |
| UPI0003298127 | M9JK23 | UPI0004E1B20E | UPI0004E83861 | W2V1F8 | A0A0F3KHK4 |
| A0A0H0A7S1 | N2JXH2 | A0A084T7P6 | UPI0004A193CB | A3JE71 | UPI0004272D7B |
| Q9L6S1 | A0A080EPX3 | A6D9P6 | U4SR36 | A0A0H4I8W3 | Q5P4B6 |
| A0A0D6TML9 | B7NF83 | A0A090S7S9 | U4SES2 | UPI00037E8B5D | UPI0006A9A723 |
| A0A0E8MKU3 | A0A0H2VE70 | A0A090SBH7 | U4S459 | M1FGB5 | UPI000411120A |
| V1L7R7 | UPI0002CACCD9 | G3IVH2 | UPI0002CBFAC9 | UPI000572A7F6 | UPI0004221DBE |
| A0A0J8M094 | N2RLH9 | UPI0004DF8545 | UPI0003AC4DB6 | UPI0004744F39 | UPI000485D7F1 |
| S4IGJ2 | A0A0J1LII8 | UPI00047F1C5C | UPI0004ED825E | A0A0F0DKQ4 | UPI0005EA9DE |
| S4JI21 | UPI0003DE3024 | UPI0001ECFED8 | U4RRC2 | V9HKH3 | B9YZ61 |
| V1PEP5 | A0A0A5RMD0 | P57654 | A0A063CT47 | C4L8M5 | G2J035 |
| A0A0J8MRJ4 | A0A085ITL8 | UPI0004B2EA54 | U4RTG0 | UPI000467E424 | UPI0004844892 |
| A0A0J8I253 | A0A038CLT3 | A9CX24 | A0A0E1RML1 | N6XTH8 | L8D9A1 |
| T2Q8L1 | UPI000699D02C | D4ZCT1 | B8F834 | N6X5A1 | UPI0005DDA656 |
| S4I960 | UPI00053015A9 | UPI0006860AC7 | A0A084EXM6 | S9ZLZ2 | UPI0002DE6662 |
| V7VTQ5 | UPI0006A5F9C7 | A0A080UY52 | U4SEE3 | N6YIH6 | Q8D1K7 |
| V1U623 | UPI0002C9392A | L7Z9H4 | UPI00049FFDBE | A0A0J8Q929 | UPI000267BACB |
| A0A0J8MLX1 | A0A090V5M6 | A8G826 | UPI0004DFBD5A | N6YW13 | UPI0002679FF8 |
| A0A0J8KIG6 | UPI0005F02BB9 | U2LS81 | A0A0F5EXR4 | C4ZMK0 | UPI00036F034D |
| A0A0J8LPE0 | A0A0G2XKH3 | UPI00020E94C4 | A0A0F5EPE0 | N6XY51 | A0A014M0T5 |
| A0A0J8JI45 | I6FIC7 | UPI0002DABF6B | S6EML5 | A0A0C3J2Q5 | A0A0B6P3H3 |
| A0A0J8NNW4 | E7SHA3 | L0MCV8 | UPI000376F3D1 | UPI00056F25D5 | A0A0E8XKA8 |

TABLE 5-continued

List of 3137 unique non-redundant helicases that have 50% sequence identity and 80% overlap with
E. coli Rep. (Uniref50_P09980 cluster, citable UniProtKB and UniParc accession numbers are shown).

| | | | | | | |
|---|---|---|---|---|---|---|
| A0A0J8M386 | I6DJI8 | A0A0G8B441 | UPI0004921C45 | E1SPI9 | UPI0003B58CFA | A0A0E1NWJ3 |
| S4KQN0 | B2TU14 | UPI0002A42D68 | UPI00036D6D23 | UPI0003B58CFA | A0A0H3B897 | A0A0H3B897 |
| A0A0J8HDW7 | E7TCP3 | UPI0006652A04 | UPI0006737FF4 | Q65VJ0 | A0A0H3QMK7 | |
| S4JDD8 | Q31UK7 | U2L789 | A0A0F9VQX3 | I3DJM6 | Q66G21 | |
| A0A0J8M6F4 | UPI0002C9AB91 | UPI00061B5F40 | A0A094MWI0 | UPI0005CAE678 | Q0WAE0 | |
| V2N1K8 | R9VPF2 | UPI000325C91D | A0A0C1MVM0 | UPI00069EE2BB | A0A0H2YE35 | |
| S4K7P0 | K8CWZ5 | UPI0006688668 | U1LW91 | UPI00069E268B | A0A0E8MJ70 | |
| A0A0J8LWR5 | UPI0002C99AA5 | A0A0J5CK09 | A0A0F4QKC2 | UPI00069D7318 | A0A088KV63 | |
| A0A0J8HEC7 | UPI00038FB95B | S5EBF4 | V4JJ09 | UPI0003FDFDBC | A0A0B6FKI9 | |
| A0A0J8JAK5 | UPI0002C96518 | A0A069CNT5 | A0A0F6A4M8 | A0A099KBQ4 | A0A0H5LYI6 | |
| A0A0H5PMJ7 | W9BJ58 | A0A087L2V7 | UPI0006270414 | UPI0003FBA996 | UPI0005DF0BEB | |
| V2NGI2 | A0A0I2BS34 | A0A086G6L5 | UPI0006271440 | UPI00048E7C37 | A0A0H5H7D3 | |
| V1SGL7 | W6J7C4 | W0L9M1 | UPI0003618E19 | UPI000482708E | UPI0006827E21 | |
| X5MWS2 | UPI000500BF0E | UPI00066770B0 | UPI0004BB1652 | UPI00051D9F62 | A0A0H5JCZ5 | |
| T2PQT7 | K8BQX4 | D4E004 | I3BQA3 | A0A0E9BPQ7 | A0A0H3NX30 | |
| A0A0J8KVX1 | UPI0002CBEEC2 | UPI0006615922 | H5TCX1 | UPI000495F3A1 | UPI00067863B0 | |
| A0A021WMC9 | A0A0J4V9J3 | UPI000408D809 | A0A0B7J8T9 | D4GGK8 | A0A0F6ZK05 | |
| A0A0J8J9B6 | A0A0B7GDH2 | A0A0F7HAB5 | A0A0C5WV68 | A0A0H3L1U7 | A0A0H5ETP1 | |
| V1I8P9 | Z5CRA3 | A0A0G9N4S7 | UPI0005CBA06D | UPI0004751 5EA | W0UFJ9 | |
| S4LIK5 | B5XYZ5 | A0A0F6KPT4 | D0Z154 | A0A0E9B357 | UPI0005E9ED67 | |
| V2A692 | D3RHB6 | A0A0J8P0E6 | A0A0D8MPB6 | A0A0E9BHY8 | UPI0005DD7BF8 | |
| A0A0J8L0F3 | UPI0004D7628C | S4YDU2 | F2PBR6 | UPI0000468BFB9 | UPI0005E79D67 | |
| V1MB85 | UPI0003A3F66F | A0A0J1YD25 | A0A066RXJ4 | A0A0A1B4E0 | C4U266 | |
| B3YF36 | A0A0J4SW69 | A0A0J5CHL9 | UPI000307D228 | A0A0A3YME8 | UPI0005DB455D | |
| S5ILC5 | UPI000616F32D | UPI00046870F9 | UPI00040F27C9 | U2MK51 | UPI0003029766 | |
| A0A098GZB1 | UPI0002CA634B | A0A084A575 | Q2C483 | E0M1J4 | A0A0H5IPV3 | |
| V1XST3 | UPI00061449AA | S0A849 | A0A0D8SB06 | A0A0F5XV05 | A1JI64 | |
| V8ME39 | UPI0006A97B14 | UPI00048AA12D | A0A0D8LLV6 | UPI00036D7981 | A0A0E1NPM1 | |
| V2JQQ7 | UPI0005762BA1 | UPI000487A67F | Q1ZK16 | UPI00034BF070 | W8U8V7 | |
| A0A0H3S2U0 | I6FYC6 | D3HNV7 | A0A0D8LUA2 | UPI0004E1A398 | UPI0005E99F5C | |
| X2KI94 | A0A0J8VI05 | C6C798 | A0A0J1GP27 | UPI000508FC34 | A0A0B5E00E96 | |
| A0A0H3SKK5 | UPI000699B795 | UPI0005615E14 | A0A090RJP1 | A0A0B1RCL6 | A0A0B6HTA5 | |
| B5EZ38 | C8TL39 | UPI00040FFE96 | A0A0J1H812 | A0A0A6YFE9 | UPI0005DDB975 | |
| A0A0H3ILF8 | K3PM43 | UPI0005684D6D | UPI0005D2DDB6 | UPI000534D94B | UPI000173969B | |
| A0A023N7J2 | A0A026HND2 | UPI0003754 0FD | UPI0005E822AD | A0A0D8YE92 | UPI0005E5EB23 | |
| V2P0B4 | B1ERC7 | A0A0J8YX51 | UPI0005E9034E | A0A059IDE0 | A0A0E8MKS9 | |
| A0A0H3NHT9 | S0TTI5 | UPI0005E8F2FE | A0A0D8QVE1 | U1TNM8 | A0A0H5NCP1 | |
| A0A0H4V1S8 | UPI0005309AD3 | Q605Y2 | A0A0J1H2I7 | E1SK66 | A0A0B6HCA7 | |
| V7RZ28 | K8BE03 | UPI000308B214 | A0A0B9GYU2 | J3D9Z5 | A0A0H5MV89 | |
| M7S3Q8 | UPI00044CED1F | UPI000413FA42 | L8J7D2 | UPI0002A6B5C9 | A0A0H5PMI9 | |
| V1GIN0 | K6KFS6 | UPI00037FCD36 | UPI0005959C45 | U3TSP9 | A0A0B6LTD8 | |
| S5HF97 | UPI0006662A0A | A0A068Z3I4 | UPI000509EA27 | A0A0F3LWH1 | C4UBW2 | |
| V0GNY3 | UPI000448B406 | E9CNV6 | N8QMA4 | UPI0005C52466 | UPI0005E9D7FF | |
| A0A0F0ITA3 | UPI0004207793 | A0A068RDD4 | N9Q5H1 | UPI00048B685F | A0A0H5MA43 | |
| A0A0E1CUB8 | UPI0004468690 | UPI00039B0A85 | S3TBN2 | UPI00069BBC9C | A0A0H4MX63 | |
| A0A0F7JC30 | A0A0G3PTV9 | A4BKH1 | N9PM38 | E6WHD3 | UPI0005E84131 | |
| G4C8N2 | A0A0J8ZB76 | UPI0002E7F8E9 | N9RHD1 | UPI00050F5F1D | C4T540 | |
| A0A0D5WN88 | A0A0J9AH95 | UPI00036F75F9 | A0A009KDR6 | A0A0F5FBT2 | UPI0005EA618B | |
| A0A0F2ZS42 | J5XNR1 | UPI0004772558 | N9MFP0 | UPI00025848BE | UPI0005E2712E | |
| V5ZRF3 | A0A0E0WT30 | D3SDE5 | A0A022IP23 | UPI0005358D4C | A7FD44 | |
| V2D3X3 | UPI000066507BD | UPI000363C2C3 | K9AX41 | UPI000067631F8 | C4SH32 | |
| B5Q5L3 | UPI000665B1C4 | UPI000381348D | A0A009KTD8 | UPI0005342DB0 | UPI0005E88594 | |
| V7IN29 | UPI000664F825 | UPI00036A352B | N8RGJ8 | A0A0A3YQZ0 | C4S2J8 | |
| E8XIM3 | X4BC54 | UPI0003638A7F | V2TJN5 | J2UWK2 | UPI0005E15072 | |
| A0A0F6B977 | UPI000517D3E6 | UPI0003638CFC7 | V2UWT0 | UPI00066187B2 | UPI0005DBB3AC | |
| G5QS67 | A0A0I0Y9Y8 | UPI00036636AC | N9QAE1 | H3RIT7 | W8G789 | |
| G5LVZ4 | A0A070TA81 | UPI00036 89D3E | N9KD21 | D4HUI5 | UPI0005E9DE69 | |
| UPI00067FCA22 | F3VD48 | UPI00035E83C6 | N9TJB8 | E5B0I1 | UPI0005E6D02E | |
| G5PV49 | H4V842 | UPI00036EBDFE | N9RBQ9 | A0A0J8YTF5 | A0A0B6GH85 | |
| G5RMY1 | K8ABZ8 | UPI00036CB07E | N8XKN2 | B2VG71 | UPI0005E21E25 | |
| G5SIZ2 | V5U423 | UPI000371CE96 | N9MQT1 | UPI0002CAE332 | C4ULT0 | |
| X3X6G6 | A0A085HAK1 | UPI00037E26A7 | N9N9M9 | A0A0A0ZCV1 | A0A085U6D1 | |
| UPI0003063B27 | H5A4A8 | UPI0003719672 | UPI000570AC25 | UPI00048B3568 | UPI0005E333BA | |
| G5PBC2 | F5N8S8 | UPI00056FCF90 | UPI0005C62CED | Q6LVY9 | UPI0005E682AA | |
| G5QW51 | A0A0J9AK28 | UPI0003734BC2 | N8VTA9 | Q1YVV5 | UPI0005E03B74 | |
| UPI0005E961AF | UPI00067DF499 | UPI0003714E69 | N8VZT9 | UPI00062F612F | C4SRN3 | |
| G5MQG3 | UPI0005CB2CD4 | UPI000422ADAE | N9TDU3 | A0A034U1R0 | UPI0005E51855 | |
| UPI0005F2CBD5 | X4JC12 | A0A0G3FYM1 | N8V910 | UPI000030424F2 | UPI00005788705 | |
| W1XLV9 | G5P130 | UPI00035DF508 | N8UMY4 | U5A599 | UPI00046D0E5D | |
| A0A0J0N6G9 | UPI0003BCE0F3 | UPI0003653619 | N8U6B7 | UPI0002F53240 | M4R9M0 | |
| V2IST2 | L0H0T7 | UPI00035F46DD | R9ATC8 | UPI0003081AE5 | UPI00046D66BE | |
| A0A0J8F6X7 | UPI000062107C5 | UPI00037A10E5 | A0A0B0KKN3 | UPI0002E72691 | W0R997 | |
| V1SFT8 | A0A0K0HP61 | UPI00035F39C1 | S7WVT1 | B7VH95 | A0A094IJP1 | |
| A0A0K0HFU2 | A0A097QXR9 | UPI000381010F | N9KJH2 | UPI0005F9EDF7 | H8Z171 | |
| UPI0005AB2AE4 | A0A0B8ZV63 | UPI000368288B | N9SJA9 | UPI00063A1E73 | C9R7F6 | |
| UPI00062081F9 | UPI0005837FE4 | UPI00036D136F | N8W759 | A0A0C1NZP7 | E6KV30 | |
| A0A0J5KVY8 | G9Y0Y6 | UPI00037F35BB | N8RKD0 | UPI00064760CF | UPI0005194C73 | |

TABLE 5-continued

List of 3137 unique non-redundant helicases that have 50% sequence identity and 80% overlap with
E. coli Rep. (Uniref50_P09980 cluster, citable UniProtKB and UniParc accession numbers are shown).

| | | | | | |
|---|---|---|---|---|---|
| UPI00029C3FF8 | A0A0C5VQS4 | UPI0035EC95C | V5C2I3 | A0A0F4NTM0 | U1S9B3 |
| A0A0J1VMC9 | W1FXH4 | UPI000367CCE4 | UPI0061832D7 | A0A0A5HSY9 | UPI000406D49B |
| D2ZMA5 | A0A085GZB9 | UPI000423C045 | A0A061JWL5 | A0A0A6T9A9 | UPI000660A603 |
| UPI0003A1A991 | UPI00062253DC | UPI000373D30C | UPI00036CBF04 | UPI0005E2F450 | G4A8W6 |
| D7XM77 | UPI0003A59E18 | UPI000036243F4 | W8QTS8 | F9RNX1 | G3Z8Y9 |
| UPI0002677FD2 | C9P8Z5 | UPI00037D0EF9 | A0A078LYT9 | A0A0F4NNJ4 | I1XRY3 |
| D4BE16 | F2JTM7 | UPI00037114DA | A0A099RR43 | E8LUB9 | UPI0006831C68 |
| UPI0005794143 | A4C7W3 | B5FCU9 | A0A0D9ATR1 | UPI0002E710F1 | G4AZ10 |
| UPI00260B9F8 | UPI00039F0D67 | Q5E1T0 | I4JQR3 | UPI00031D8F80 | L8UHA2 |
| UPI00028307CF | UPI0002558A91 | B6EP51 | I7A9J8 | F7YIE8 | UPI0067CF184 |
| UPI0006660AB8 | UPI0005B86EE4 | UPI000247865A | K5XG83 | A0A066UM26 | UPI0006815E34 |
| A0A0E0VC55 | A0A098G8R1 | A0A090IP02 | A0A0A1GK07 | F9S363 | H0KC96 |
| T8Z104 | UPI000326FBA0 | T2L6T4 | UPI00040F147B | UPI0003102D21 | A0A0E1YSI3 |
| S0YAD1 | UPI00037E68F8 | L9UDC2 | UPI0004194356 | A0A099LPD8 | X2JQA6 |
| S0X3V2 | UPI00034D7EBF | UPI00037E36DB | UPI0003B39C7B | UPI0003167DE1 | UPI00067FF093 |
| S1DN83 | UPI00056CF143 | A0A0D7UZT0 | UPI0005BA4855 | UPI0002E0F676 | C6AQX1 |
| S0XCC9 | A0A0B8V8Y9 | A0A0F9VK34 | UPI0005B7EB79 | A0A0C2P7J1 | UPI0006A71057 |
| S1E4M9 | U4TCI2 | A0A0D5LWG2 | A0A0C1EK43 | A0A0C2JL07 | G4ABR6 |
| T9IPB3 | A0A0H4R6J4 | G4F9U9 | U1AEW3 | UPI00031E1DE0 | L8UIY4 |
| T6LBU7 | A0A0B8USV8 | A0A0B1PVT1 | UPI000617AEB5 | A0A0A5I590 | Q7MYL0 |
| S1GJ06 | UPI000368EE93 | H0J1C6 | UPI0006182BB7 | UPI0003043227 | A0A022PH42 |
| D8ADY5 | A0A095VW14 | UPI00048842D1 | Q7NQR9 | U3BS43 | W3VA31 |
| S0VUC6 | A0A0C5UZZ5 | UPI0002D5FF35 | A0A0J6LGT4 | UPI000571B2B4 | A0A0A0CQ83 |
| B7LU77 | W8FU49 | UPI000556BD4F | A0A0D8ZDY8 | A0A086WW56 | UPI0006203273 |
| A0A070K818 | M5DYB2 | A0A0C3I966 | UPI0004907BDE | F9T770 | A0A0F7LMM1 |
| A0A062XSU2 | UPI0004843630 | C5BIA4 | UPI0005F11AED | UPI0005C23C6 | |
| UPT0002C9B880 | R4YVB5 | F7SNI3 | UPI0003800078 | UPI000699D72A | A0A0J9EYL2 |
| UPI000651920D | H2G1G7 | UPI0004AB49AE | UPI000382D783 | UPI0005F118D8 | C7BQK5 |
| A0A0F3TFS9 | UPI000379F9FB | A0A060B1U5 | UPI0004227F3C | A5L7N9 | U7R5K0 |
| A0A0E2U8U7 | UPI0001EC45E8 | A0A0D6EF56 | UPI000035C7304 | UPI0001F55149 | A0A081RWC7 |
| C8TYS8 | C6XCN5 | G9EBD3 | UPI000369273A | U0FTU6 | UPI0058BF6A9 |
| A0A0J2E1P9 | UPI00035FCCBC | A0A0F4RA35 | W8KPW4 | UPI00030715AD | T0PH03 |
| UPI0005B2C8D4 | UPI00058D9CB0 | W1N5Q2 | D5C0J9 | UPI0006303856 | A0A085JM95 |
| UPI0002C95CB8 | A0A0A0BIG5 | UPI0004CE4C17 | A0A0A3AKX9 | E3BPB4 | A0A095VZP6 |
| A4WG32 | UPI0002DE5ECC | A0A081K8A4 | UPI0006A9F0F0 | E8MCD7 | UPI00046F3C99 |
| UPI0003420E0F | F5T1S3 | UPI000477FE94 | F7NR22 | Q7MQG8 | UPI0004A3375F |
| UPI00036F08F6 | A0A0F9NIL3 | A0A094JA28 | A0A066T3V5 | A0A087IWU5 | A0A0F9VYU9 |
| UPI0005C4EB5F | C0N7C2 | A0A090KED5 | A0A080LJV3 | UPI0006A98AC0 | I1XM63 |
| UPI0002C91779 | F6DAI6 | A6FE65 | X2GZR9 | UPI0006A98232 | I2JF40 |
| A0A078L9V2 | UPI0005C9F562 | UPI00030A12FE | A0A0J5P3I3 | UPI0002482DB8 | F9ZY05 |
| UPI000512B6F1 | W0DYM2 | UPI0002DF92C0 | A0A0F2P6J6 | F9REI7 | A0A0F5V836 |
| UPI0002CC209C | UPI00022C089B | UPI000464C875 | W7R0N4 | UPI0004F5E7D9 | S6GDK2 |
| A0A0D7LJA0 | UPI0006844205 | UPI000427CAB0 | UPI0004752339 | UPI00031835E8 | S6HCZ4 |
| A0A073VC48 | W7QF72 | B9CXM2 | UPI0004E147DD | UPI00031E4412 | I8U5K5 |
| X7I146 | UPI00058DEE31 | C5RZQ1 | UPI000479BC17 | A0A0H2MLA0 | H3ZE84 |
| X7HFY3 | UPI000289826B | UPI00035CAB1A | UPI00047B5018 | UPI0006195856 | J1YGP6 |
| A0A089Q204 | U7NY76 | UPI0003B481E4 | W9V341 | UPI00067F4562 | H2IWS7 |
| UPI000675D9DD | A0A098RE99 | UPI0004212DE4 | UPI0005C15FEC | A0A097QPF1 | UPI0005D339A3 |
| UPI0004D8E29C | E1VCA4 | A0A0C4WTU2 | E0FET2 | A0A0H0Y092 | I0QQI6 |
| B7UMN3 | UPI00030B6E67 | C1DJY5 | UPI000248B5E1 | UPI0002F588B8 | UPI00038060C2 |
| H4I3H7 | UPI0006148CBA | M9YDT7 | J4TTN5 | A0A0G9M026 | H8NUJ7 |
| H4JUI7 | UPI0005B789BB | UPI0004E1F9C3 | S9YCL8 | UPI0002DD07EC | A0A0H3FLE0 |
| H4KPD2 | S2KK42 | W0E158 | I2NC81 | A0A0B4IM65 | UPI000554A929 |
| H4L565 | UPI0003674641 | A0A0F7K0Q6 | UPI00031355EC | A0A0A3EMP0 | A0A085G3A6 |
| H3KW73 | UPI000343B180 | UPI00048BF236 | E0F2E9 | K5V6E0 | UPI00041ABFF4 |
| H4LJK6 | UPI000376C869 | UPI000395D43A | E0F8J5 | UPI00066B2D3D | UPI0003089400 |
| H4IZH1 | S5T4K5 | UPI00046F29D9 | E0EW49 | UPI0005F9A9ED | UPI0004719479 |
| H4JFJ8 | K0C8L7 | A0A0F5ARC9 | E2P8X6 | M7RIV0 | UPI00058F6D4E |
| H4K9V6 | A0A0F9YVG2 | Z5XTJ6 | W0Q1J8 | K5TSH9 | C8NBT1 |
| E3XW38 | UPI0004057986 | UPI0002AA68F1 | UPI0005856421 | C9QC04 | UPI000660E94E |
| H4IIJ0 | D2TWS6 | A0A0F4S821 | A0A0B5BWF7 | A8T649 | |

TABLE 6

List of Bacillus stearothermophilus PcrA homologs that have 50% identity to and 80% overlap. 1747 members
of Uniref 50% identity cluster is shown (citable UniProtKB and UniParc accession numbers are shown).

| | | | | | |
|---|---|---|---|---|---|
| P56255 | J7M5U5 | T0TN09 | A0A0I6PI88 | R3VBE4 | UPI0005CD7F53 |
| S7T032 | A0A0H2UUM0 | F8LQ03 | A5LVX9 | E0G4K8 | UPI000417C0DE |
| UPI00051815BF | Q1JLF2 | C2LSM3 | UPI0005E41D7E | E6GJJ0 | UPI0005CD905E |
| A0A098L684 | UPI0003C7B0E5 | UPI00065FC663 | S7YIM5 | S4DY07 | G7SM20 |
| U2YC97 | UPI000254D55F | UPI00066E20BD | UPI00066CDBC6 | C2H162 | UPI0004062509 |
| G8N340 | Q1J6A6 | E3CPD8 | E1LG87 | R3D1M0 | UPI0004051F87 |
| T0Q4M4 | A0A0G2V0F7 | W3XXV6 | A0A0I6BPW7 | X6SFW2 | UPI000411FB5C |

TABLE 6-continued

List of *Bacillus stearothermophilus* PcrA homologs that have 50% identity to and 80% overlap. 1747 members of Uniref 50% identity cluster is shown (citable UniProtKB and UniParc accession numbers are shown).

| | | | | | |
|---|---|---|---|---|---|
| A0A063Z1I8 | M4YYG1 | T0T6T2 | A0A0I9JBK7 | X6RK63 | UPI0004022BA7 |
| L7ZT56 | A0A0G4DFH5 | UPI0002AEC4C7 | UPI0005E02B0B | R4CW85 | UPI0004188987 |
| V6VMU8 | UPI0001E10349 | UPI0065FB970 | UPI0005DC8263 | X6RKD4 | UPI0005CE22CD |
| Q5L3C0 | UPI0000D9968 | UPI0003167399 | UPI0005E61B75 | X6SVN5 | UPI000400A66B |
| UPI0005CD09ED | A0A0G3U9S6 | A0A0A1DXP2 | UPI0066DCA04 | R4DBG2 | UPI0005CD5B4A |
| A0A0D8BW89 | Q48T98 | A0A0F3HAQ8 | E0Q0Y1 | C7WG78 | UPI0005BE8F33 |
| A0A087LEV1 | UPI00038E29D2 | V6Q5R6 | UPI0066CD043 | C7W6F8 | UPI0005CC9805 |
| UPI00066FD17E | A0A0H3BYK1 | A0A0C2HKT0 | UPI0066D16C5 | R3EDY6 | UPI0005CC91DA |
| UPI00519CC89 | UPI00050BF55F | UPI0004E153F7 | UPI0005E1DA5A | E0GYA3 | G5L3H4 |
| A0A0G3XVN0 | UPI0004BE2C5F | UPI000288F7E6 | UPI0005E04403 | R3L6W4 | UPI00040C9E90 |
| A4IJY5 | UPI0004F92D8A | A0A031IBW4 | A0A0I6R2B8 | E6FGS3 | UPI0005CE3BAA |
| UPI0005CCA9FF | UPI00066C9AA9 | B1YJ16 | UPI0005E64F07 | UPI00031E170D | UPI0005CCD039 |
| S5YVH0 | E7PYJ1 | UPI0006AA2516 | UPI00066B4226 | E2Z449 | UPI0005CD5201 |
| UPI0004DF596F | UPI0004BE34CB | UPI00047948D2 | A0A0I7U0N9 | UPI0002F39C67 | UPI00040A255C |
| A0A0E0T7W1 | UPI0004BE2973 | UPI000683717C | UPI0005DBFF52 | E6IN81 | UPI00419AA26 |
| UPI0006A962ED | C5WGR7 | UPI0041CB696 | A0A081PQV0 | UPI00031A4BB4 | UPI00040A186C |
| UPI00017E56F4 | F5U8K1 | K0A8A5 | E8KBG6 | S4G3W1 | UPI0004221FBB |
| UPI0001D581E8 | A0A0E4B7C5 | U6BA96 | UPI00017C1A3F | S4FMR9 | UPI0005CDC9EE |
| UPI000424F449 | Q5XBW2 | UPI00047AE0FA | A0A0I8Y7H2 | C7VZ55 | UPI0004624A9B |
| A0A0J0V9H4 | Q1JGI8 | UPI0004D4D3 | UPI0005E6A918 | C7UKX9 | F4EF32 |
| A0A093UDD5 | UPI00044FEC83 | UPI0004792A31 | A0A0F2E3V6 | A0A0E1C082 | UPI0005CF3160 |
| UPI000539F1EA | K4Q9V2 | UPI0004494A958 | UPI0066DA31C | R1KTX5 | UPI00400B1DD |
| N4W917 | UPI000617EC21 | U7USF2 | UPI0002AF45D8 | UPI00045B8E48 | UPI00040B8112 |
| UPI00055386C0 | UPI0003C7BD0F | A0A0E0UWM6 | UPI00066EE4B6 | R2UDI9 | B9WTD9 |
| UPI0005590F34 | A0A0F5P2U0 | A0A0E1R8Q5 | A0A0I8ZZI4 | R3B3J0 | UPI0041EA41C |
| UPI00020D9901 | UPI0003C7D5B0 | A0A0E1Y218 | E0SZL7 | R3J9A8 | UPI0005CEFECB |
| I8UBH1 | UPI0006181569 | A0A0B8RF49 | UPI00025ABE1B | UPI00032DCFB5 | UPI0041FE6F0 |
| UPI000555B2C6 | I7WIP9 | UPI000035D23A | A0A0I7UZI3 | UPI00032F5E7D | UPI0005CE9E1B |
| UPI00059000A4 | A0A0G2V4A4 | UPI0001B43587 | UPI0002313C8F | A0A0H1TNE2 | UPI0005CED2C1 |
| A0A089XIR5 | I1ZL68 | UPI0003591B75 | UPI00066E2824 | R3C367 | UPI0004128A2C |
| T0TNV3 | E8K3X2 | UPI0005128D3B | A0A0I8XVX0 | R3VC46 | UPI0005CF2FFD |
| A0A0H1RMM4 | W1Y2G0 | UPI0003EC8641 | UPI0005E6A956 | V7ZS55 | UPI0003FA464B |
| D2BQM2 | W1VGX2 | A0A0H4NBP6 | X8KE98 | C7YF48 | UPI0005CDDD5E |
| A0A0A7T646 | UPI0002F353EC | A0A097B674 | UPI0027EA587 | R3W0C9 | UPI0005CD2C43 |
| T0W2G0 | F8DFS6 | A0A0F5Z989 | A0A0E7WHF5 | C7UTX1 | UPI0005CE703E |
| H5SYV7 | UPI00031E513E | E3ZRG0 | UPI0005E9B66A | C7UDZ4 | UPI0005B9BF22 |
| A0A0B8QL14 | E7SC56 | UPI0006282029 | A0A0I5V7V4 | C7WW04 | UPI0005CCB173 |
| G6FEQ4 | UPI00021BD63E | UPI00052F1B16 | UPI0005EA0304 | R3KHA0 | UPI0005CD2248 |
| Q9CGH6 | I2NTT3 | A0A0H0TBR3 | UPI00066ED988 | R3KQT9 | UPI0003F9DC72 |
| F2HJH7 | UPI00065F8C03 | UPI0001975CA4 | A0A0B7LAG3 | U7S5K0 | A0A075SIP2 |
| T0V8Q3 | UPI00066A6FE6 | UPI0003CA336 | M5K5E4 | R3Y2U6 | UPI0005CCB671 |
| U6EMQ9 | U5P378 | A0A0H3GCW7 | M5K8F4 | R3ATF7 | D5AH63 |
| A0A084A9A3 | A0A0F3H3Y1 | A0A0H3IUG2 | M3IAM8 | R1LJ35 | UPI0002195DB2 |
| Q02Z69 | W1VGW0 | UPI000431635A | D3H992 | R3NBA7 | UPI000367B16E |
| U5PKA6 | UPI00066BB1D3 | UPI000396C49F | UPI0005DADCC0 | R3PMA1 | UPI00040780E6 |
| A2RL58 | U5PAT9 | UPI00057E5CD1 | A0A081QTN0 | C7WTA5 | UPI00047DE9FC |
| T2F5M7 | UPI0004E25F53 | UPI000541B044 | A0A0F2DL31 | C7V916 | A0A0D6A4Q8 |
| K7VSC5 | UPI0006600922 | UPI00065E0E60 | E9FH57 | C7VLS1 | UPI0003079325 |
| T0VAM5 | UPI00066E3612 | UPI00059B4903 | K0ZJQ5 | R2VJF4 | W1SU53 |
| UPI0006172C2A | V8BFU1 | UPI00064CDA40 | UPI0005EA108D | C7VRD8 | K6DTK1 |
| G8P2F6 | UPI0006605290 | A0AJL2 | A0A0I8KXT3 | R3I2U9 | UPI00058D7294 |
| S6FGR2 | UPI00066EBF4B | UPI0004F3EE62 | G6R9C9 | R3I1C1 | UPI0005F025AA |
| UPI0005838B59 | F9M2F0 | UPI000570B4C0 | A0A0I8MDZ1 | U7SAR7 | UPI00055EBF2F |
| T0UFT5 | UPI00066C8E1F | H1G7W7 | X8HMR1 | R3DJQ9 | A0A0F3RNZ7 |
| Y1QH73 | UPI00066A3914 | UPI0004D59A43 | J4Q880 | R1JZF5 | UPI0005534922 |
| UPI000629DD6D | UPI00066CB902 | G2ZBE3 | W3XTS5 | R4ALC3 | E7FSU1 |
| Y1Q968 | E3CEE7 | A0A0G2WHH3 | UPI00066C1FD6 | R4B5K9 | G2SLV9 |
| UPI000376C4D7 | UPI00066DB632 | A0A0G2W8X5 | UPI00066BE89C | Q837V7 | A0A0G8G5N5 |
| A0A0D6DXQ0 | UPI00066D30C4 | Q92AP9 | UPI0005E8CD89 | A0A0E1RBS1 | R6S5W5 |
| R2SEZ2 | K8MRD3 | Q8Y6C9 | K1ABC3 | A0A0F5AWZ1 | A0A0G8G9A4 |
| UPI0003F7ADC6 | UPI00066D94ED | A0A0G2VQM3 | K1AGK6 | A0A059N1T2 | A0A0B4B1V1 |
| F9DT42 | UPI00066CDADB | A0A0G2VT50 | K0ZZ87 | S7U796 | F7R373 |
| UPI00054EA513 | A0A0F3HXT7 | UPI0001EBB745 | A0A0I6M9Y8 | D4EPU4 | UPT00062CB1C4 |
| UPI00030811AC | I7IYF1 | UPI00066D78F0 | UPI0005E36939 | U6RZD7 | UPI00040409F2F6 |
| UPI00036C3403 | UPI000345D943 | E6J2G2 | UPI0005E225FD | E6ISD3 | C0WZU5 |
| S0KSL1 | Q8ES83 | UPI0002FD7F0C | A0A0I7LKZ4 | J6NDX6 | A0A0G9GFB1 |
| A0A0A5GAU1 | R2R7H3 | W1TUK9 | A0A0F2DPD4 | S4GCT9 | V4X193 |
| UPI000414CEF0 | R2VFE1 | I0S6A8 | UPI0005E11B6C | C0X2D5 | A0A0F4HGR5 |
| A0A078MEE0 | R2RQ91 | UPI000660E090 | A0A081QG94 | J6PVS6 | U2HDV7 |
| UPI0004103FCF | S0RUY8 | F5U2X9 | I0SZR9 | J6ESY5 | D8IIP0 |
| M1Z7Z9 | UPI00051A74A9 | U2XKT4 | UPI0005E14969 | S4C6D0 | T0SLF0 |
| UPI0001850A35 | W9EJ23 | K8YYY0 | UPI00066A9D62 | J6GZ70 | D0DT13 |
| J1HTP8 | UPI00028D8F83 | T1ZV68 | A0A0E8P896 | E6H2K6 | R4RJL7 |
| F0ELG6 | K0IW42 | A0A0E2IST8 | UPI0005E5529F | E0GC91 | UPI000582B547 |
| UPI0002E3189C | UPI00059D08F4 | I0SM41 | A0A0B7M600 | E2YA71 | UPI0006657CCS |
| T2NS83 | E5WTD2 | UPI00066B626D | A0A0I8X1A0 | S4DTD6 | B2GDT0 |
| UPI00042432D9 | UPI00047A5B10 | UPI0003906A09 | UPI00066A9CD2 | E0HHS0 | A0A0G9GHB4 |

TABLE 6-continued

List of *Bacillus stearothermophilus* PcrA homologs that have 50% identity to and 80% overlap. 1747 members of Uniref 50% identity cluster is shown (citable UniProtKB and UniParc accession numbers are shown).

| | | | | | |
|---|---|---|---|---|---|
| S4E2N9 | A0A0J5YRT7 | J5H823 | I0STF6 | J6CZA7 | A6CTQ5 |
| UPI0004065D0D | UPI0006A9BD02 | F9P5H7 | UPI00066EB944 | E2YXC8 | UPI000468231D |
| S4B0D0 | UPI00031F0DBB | UPI0006612AD9 | A0A0H2UPX1 | J6F8R9 | A0A0A2TG25 |
| UPI0004080059 | W7KMF0 | UPI0003908243 | V8IKB2 | E6HPG5 | K9ECC9 |
| C8ZW14 | G5K2S6 | UPI00066D6CAA | B2IQ19 | J6LKR6 | UPI00048127F0 |
| G5ISN9 | I4X463 | G6A4N0 | A0A0E7X876 | J5ZVI4 | G2KVV1 |
| R2PGJ0 | UPI00052FEEE4 | UPI00023296C1 | UPI0005DD5C54 | J6QD02 | G5KC28 |
| C9CH47 | A0A098EQM7 | UPI00066A46EE | A0A0I9AQP0 | J5DL74 | F3L6C7 |
| C9A7W5 | W3AD61 | UPI00066A7CBF | S9RFX3 | J6EQP8 | UPI0003106D0B |
| T0UB13 | A0A0B4RAA8 | T1ZDX9 | UPI0005E228BC | J6NTK1 | UPI000419C333 |
| A0A0C2Y4G1 | UPI00069FBE5D | X8HC25 | UPI0005E426DE | J6PAC4 | UPI00047C345A |
| A0A0D0Z5K2 | F6CR29 | A0A0C1HWD2 | UPI0005E7453E | D4EZ78 | UPI00069F1374 |
| B4U2N2 | G8PE15 | UPI0001F606A4 | S7XP08 | E6IB45 | A0A0J6BIJ7 |
| UPI0005BB133A | V7HVC5 | U2YEQ3 | UPI0005E54BE5 | E6EW25 | UPI000345FA17 |
| C0MG96 | A0A0F4LU79 | UPI00066AA721 | UPI0005E4BCD8 | J6LYS0 | C0Z4D5 |
| A0A0D0ZF61 | C7XVU9 | A0A0E9EVC1 | A0A0B7L333 | E0GI65 | L5MLM9 |
| A0A0E1DXS1 | F6B7U9 | UPI00066A249D | R0N6B7 | C2DEW5 | J2ICT3 |
| A0A0D1AJJ8 | UPI0001FAE64A | A5MXJ1 | E6HGC1 | J2GML2 | |
| UPI0005BB6148 | UPI0004119D25 | A0A075QWT2 | UPI00066CEE14 | E6GUV7 | UPI00036424CF |
| A0A0G7A7Q1 | E1UN03 | UPI0003821CF7 | UPI000352C53C | E2YIL6 | A0A0H0SII0 |
| UPI0002175097 | A0A0A0TU62 | H0UC09 | A0A0I6M0R5 | T2P3G0 | UPI000673AC8A |
| C0M8W6 | UPI0006480DA4 | A0A0F7BZE | J0UC50 | J6R7F3 | UPI00037AD71B |
| A0A0G6YRU4 | I2C272 | UPI0005556E3B | F9PC08 | J6QBF0 | D6XYW2 |
| A0A072ELK0 | A0A0E1LP36 | UPI00029B0B59 | UPI0005E65946 | T2P2M8 | UPI0005A0C938 |
| UPI0005B9A818 | UPI000458757A | UPI0005A8DE74 | UPI0005DEEC80 | C2JPD9 | K0NSF0 |
| N1ZT17 | UPI0002458DDC | UPI0004936DE9 | UPI0005DB5FE3 | F3R2R2 | K0NWD9 |
| A0A062X6V6 | UPI000471D8DA | UPI0003104D4F | UPI0005DB0E2B | C2JPD8 | I7JV33 |
| UPI00046A8E16 | A0A0G3V8X1 | A0A0G2Z1V7 | A0A0E9A2L0 | J6F4X7 | UPI00039E5A1A |
| UPI000219434D | A0A0D1IMY3 | A0A0H1T5V3 | G6PSM2 | UPI000665D580 | UPI00066064E2 |
| UPI00054D6FB4 | U1YND2 | UPI0002BAE34A | A5MAN0 | UPI00053BEB7B | UPI00004959EB5 |
| Q5FLL5 | UPI00069E39D3 | K0JN87 | H7JF57 | W1VWC1 | UPI00020DA0D4 |
| A0A094K9S3 | UPI0002F6BFBB | UPI0002BAFF71 | D6ZSN4 | UPI0002FDF1DC | M7NB45 |
| UPI0006735FF0 | UPI00028966FC | UPI0002E84A37 | UPI00067E3BD1 | UPI00032EF110 | I4D367 |
| UPI0002F19FB8 | UPI0005F96F19 | A0A0H1VSP1 | I0Q912 | UPI00032ED949 | A0A0J1FQT |
| F8DMZ0 | A0A0G2YPJ5 | A0A0H1VST5 | J0VYU9 | UPI00032DF268 | UPI0005A135DF |
| A0A073K223 | M4KP62 | A0A0H1XJQ7 | A0A0I7N7X2 | UPI0006611725 | UPI000557D9AE |
| A0A081NN78 | UPI000467CBC2 | S8PCV2 | B2E1F7 | R3KQ79 | UPI00040DC1E5 |
| UPI0002DA8E1F | UPI0004E7B7B4 | S9B2B8 | G6S5S7 | UPI00032D8816 | G5JVH9 |
| S5N6B2 | UPI0002A11EAA | F8Y0Z9 | G6LMK2 | UPI00032F27BE | A0A061N7C8 |
| C0YY61 | A0A0G2LYN9 | S9MTU2 | C1CE74 | UPI0004244B9B | UPI0005525FE7 |
| A0A0H4L928 | UPI00046ED5B5 | S9CV37 | A0A0I9HKT6 | R3JUC0 | UPI00034C8C5C |
| A5VLG7 | UPI0006529B7C | S8FGZ3 | A0A0I9C672 | UPI00045A0DF5 | D5D9D8 |
| R9WGA8 | L8PVW0 | S9BAQ5 | UPI0005E5C16F | C7CXQ3 | G2RXJ7 |
| F8KEB4 | E0TU76 | E7S415 | UPI0005DF7A6C | I7BW34 | A0A0H4R638 |
| B3XPD6 | A0A0D5D2X4 | UPI00046CB8EA | UPI00066DA9B2 | A1HME8 | D5DWY1 |
| A0A0F4LTY8 | UPI0002B6EC1D | UPI0005E2BE93 | A0A0I7G3B6 | Q5WJ31 | A0A0F0J8P4 |
| UPI000487320D | UPI00002891107 | S8FZ09 | A0A0F7Y925 | UPI000FD32D5 | A0A0B6AB4 |
| D5WUX8 | D4G620 | A0A0H1GG85 | UPI00039C59B5 | UPI00067A2901 | UPI0005B4512E |
| UPI0002F118C8 | UPI0005AD3458 | Q8DZF9 | A0A0I5N723 | S2XF35 | UPI000682E43B |
| UPI0001E89712 | UPI0002865556 | A0A0H1WCN1 | A0A0E7ZAF0 | UPI000679FA7D | A0A0J5USU5 |
| A0A0J5GSJ3 | O34580 | A0A0H1YVD6 | UPI0005E318B4 | A0A0A8HNC8 | A0A0J1IVB0 |
| UPI00068A6D6D | G4EZ92 | UPI0002BE4DD4 | A0A081PXD6 | A0A069F1G6 | UPI0004733E51 |
| A0A062XR18 | A0A0A1LU02 | UPI0005DE829A | UPI0002735B06 | A0A085UDQ4 | UPI00047C38B4 |
| UPI00021964BD | L8ADL0 | A0A0H1IDA8 | UPI0005E614FB | UPI00036BDB49 | A0A0J6WUD7 |
| UPI000415247A | UPI00046730CE | A0A076YVH2 | A0A0I5WGP4 | A0A094WEU8 | A0A098ESM7 |
| V6Z3H5 | I0F1C0 | UPI000332E0DF | A5LMH1 | A4J705 | UPI000423B330 |
| UPI0004205ED9 | UPI0003A70724 | A0A0H1LVT6 | UPI0005E59371 | UPI0006527050 | UPI0003882373 |
| UPI0003817B64 | UPI000416C8D9 | UPI0002B9E962 | UPI0005E5CDC9 | UPI00053C5AB9 | A0A024QGT6 |
| A0A0J8G63 | A0A0F5MHF6 | UPI0002B9AAC1 | UPI00066E2A51 | A0A099YFE2 | UPI00036A8D74 |
| M3GSH8 | UPI0002A13E19 | S9MD09 | UPI00066DCBF7 | A0A0D4CNA9 | H1LDA8 |
| H7F3P6 | UPI0002416823 | S8NNN7 | UPI0005DAF614 | UPI0003FBD3F6 | UPI0002E51DEA |
| W7DTL5 | A0A0F0AC16 | S8P6Y4 | K8MSF0 | UPI000378183D | H3NEA0 |
| G0UES1 | I2HNA7 | S8QFS6 | C1C784 | UPI0002E4B790 | UPI00058BA923 |
| C5RBQ7 | UPI0002E6650E | A0A0H1NAH8 | UPI0005E0C55C | G5KGH3 | A0A0A3TV65 |
| D7UU99 | UPI00057C2EC9 | UPI0002F54753 | A0A081QQF8 | A0A0F3HRU1 | K8E0T1 |
| W7BIE4 | UPI0003872E1B | UPI00028CE135 | A0A0I6RW2 | J7TJ76 | UPI0003F5E34D |
| W7BQB1 | A7Z260 | UPI0002BE2494 | UPI0005E787E3 | F0I8F9 | A0A074LMV6 |
| A0A091BQ28 | S6G180 | A0A0H1HP61 | A0A081Q205 | F2CE01 | W7CP40 |
| B1SEW1 | UPI000398030A | S8P0E2 | UPI0005E3629B | E8KQC7 | N0AL42 |
| UPI0005C4C4A5 | UPI0003A660B0 | Q8E525 | UPI00023100D2 | A0A0F2CZP2 | J0L6J5 |
| S5RL61 | UPI0005C46508 | UPI000345B919 | A0A0H1DLQ4 | UPI0005E1CE26 | F2C6S2 | UPI0004915921 |
| UPI0005C46508 | UPI000665EEF6 | UPI0002E871D3 | A0A0I7RCB5 | N0CB15 | UPI00035FC8AB |
| H6PBJ7 | A0A0D7XRK8 | S8VI39 | UPI0005DADB38 | A8AXV7 | UPI000525E54F |
| UPI0005C676D5 | UPI00038048E7 | UPI00030AEE41 | UPI0005E20280 | UPI00066BA6D4 | R4KJT8 |
| T0UQQ7 | UPI0005A43216 | K0JMH9 | A0A0I6RJI8 | D0RVG1 | UPI00024669AD |
| A0A060RKS5 | UPI00057BD0DF | UPI0002B8C27C | B1IBM7 | F0IOL3 | A0A0A1IK06 |
| F5X182 | | | | F0FSG1 | Q9S3Q0 |

TABLE 6-continued

List of *Bacillus stearothermophilus* PcrA homologs that have 50% identity to and 80% overlap. 1747 members of Uniref 50% identity cluster is shown (citable UniProtKB and UniParc accession numbers are shown).

| | | | | | |
|---|---|---|---|---|---|
| UPI00066000C4 | UPI0005EBB97E | UPI0002F07C72 | UPI0002ADCFE5 | UPI0006B25214 | B1MXQ7 |
| F5X6S0 | UPI0006AE6F38 | A0A0H1Z5L | A0A081QYR3 | UPI00066A525C | A0A098BA44 |
| E0PDX9 | A0A0H3DY38 | I7ISP9 | UPI0005DF6E72 | A0A0F2CRI4 | H1WSK1 |
| A0A0E1XF14 | A0A080UNJ0 | A0A0H1T3F9 | UPI0005E41938 | A0A0B7GK35 | A0A069CV32 |
| H2A6M7 | UPI0022BA657 | A0A0H1MS35 | V8IC09 | F2BSX1 | UPI0005F00C2A |
| A0A081JHH2 | A0A0C2PX57 | A0A0H1V4C2 | A0A0B7L5V0 | UPI000660334B | A0A081BK49 |
| UPI00051C02C3 | UPI0002DC92B0 | S9APZ9 | I2J4H2 | UPI0006616F5F | A0A0A3HZB |
| UPI000410E728 | UPI00066FBF08 | S8FYF6 | A0A0I7VHR8 | F0IU30 | F4BLW5 |
| UPI0004D4E3B7 | G4NUA0 | S8HPX5 | UPI0005E06D6A | A0A0F5MJY5 | U5SAC6 |
| A0A091BNX2 | A0A068LM65 | UPI00046C8FD9 | UPI000318BEDD | F3UWM7 | A8U4Y8 |
| E8JNI7 | UPI00025F1BD8 | K9AHW3 | A0A064BXT9 | UPI0006603308 | UPI0005590D06 |
| UPI00040D1DBE | I3DZY5 | UPI000554B661 | A0A098ZS00 | F0INA4 | UPI0005550B1B9 |
| UPI00041D9E3E | A0A0F4M491 | C2E4W5 | S2UT89 | UPI0006605CF8 | UPI00054D85C0 |
| W7ZBP8 | UPI0005145490 | UPI0002FE2AC2 | UPI0005DBEB5A | UPI0001FBB9D8 | UPI000553C539 |
| A0A060M0P3 | A0A0F4LJ28 | A0A087QEX7 | UPI0005E44ED7 | A0A0F2CJE0 | UPI0005C4A619 |
| V6M8R1 | A0A0F4LIP7 | UPI000459CDE | UPI0067A8E24 | UPI0003D2BF73 | UPI0003B36792 |
| A0A075LMV5 | A0A089Y3J1 | A0A0A8B472 | UPI0005EA38C1 | A3CM74 | UPI0005CE4434 |
| U5L6Q7 | A0A0F4LHL3 | UPI00057E310A | UPI0005DFA93B | UPI00066124BC | I7LCW7 |
| Q2BBV3 | UPI00066D84FA | F7SF58 | UPI0005E43F38 | UPI000204C9B3 | UPI0004942515 |
| J9YKR2 | UPI00047168BE | UPI00069ED3EB | UPI0005EA228D | E8JTX8 | U1N3Z8 |
| B9E831 | UPI00031D0F4F | D0R5K3 | UPI0002D988F7 | F3SII1 | UPI0004DFB32B |
| A0A0A5GC60 | A0A033UAP9 | Q74I48 | UPI00016C30E9 | F3UBI9 | UPI000495DE5F |
| UPI00068F9B5A | UPI00065B9E05 | V5P429 | A0A0E9GYK1 | F0FE53 | C4L2B1 |
| D5XD67 | UPI00030B5B12 | F4AC33 | UPI0005DF5506 | F9E172 | A0A099DEL3 |
| S4D0X9 | R2S3I5 | UPI000660D235 | UPI00066C8BEE | F9HGV1 | UPI000554029F |
| UPI00040BD27E | UPI0005BB07E7 | UPI00066974FD | D2ER82 | F3URE9 | S3FYE4 |
| W4QBS4 | A0A0D1LT71 | UPI000665A968 | G6JAI2 | A0A0A0DGR7 | UPI0004787EFF |
| UPI0001E98CB8 | A0A0D1LUL0 | UPI0003421E15 | A0A0I8YKR7 | UPI00066B8271 | A0A069EVD4 |
| C8PBZ7 | UPI0002191623 | UPI0001A57BCC | A0A081R5K4 | W4F985 | UPI000426A771 |
| UPI0001E2B095 | D8MGK9 | D1YI75 | A0A0B7MAG0 | UPI0006A9F3B8 | S2KHH9 |
| UPI0001FDB18A | D5T1C2 | UPI00050F2122 | A0A0I9KK18 | UPI0052475A3 | Q1GBF8 |
| UPI0002072E3B | F6DPJ5 | UPI00050F4C6F | J1DH18 | A0A087N1S5 | UPI0006800765 |
| A0A0E1XZC6 | UPI0002E9BB91 | A0A0J7K5W0 | V8I629 | A0A078MFK8 | A0A061C4M6 |
| E3BTD7 | L0E9U7 | A0A0J7HHM3 | UPI0005E3DD18 | UPI0037E072F | E4SWU2 |
| G3YXZ2 | UPI000401406C | D3L7Q3 | UPI00066D82D8 | UPI0002F64287 | D8FRH5 |
| E1NV43 | A0A0A6NWI1 | Q04GN7 | E1LLK4 | UPI00040FF648 | F0HX91 |
| UPI0001FD875B | UPI00047166B2 | UPI00050F2BFE | A0A0I6S0N2 | UPI0002FBC45B | Q71HW2 |
| E1NLU9 | A0A0A1MVS7 | UPI00050DE508 | I0QC96 | S2XYX9 | UPI000510635 |
| UPI0001E5D8E8 | UPI000595B757 | UPI00050F1464 | UPI0005DCF59C | A0A0E4H7N7 | A0A061CFU6 |
| A0A061P6S2 | J3F9X4 | A0A0E2VR29 | A0A0D6J8D1 | UPI0004758748 | UPI0006829E76 |
| A0A061NMB4 | UPI000410FF91 | A0NL49 | UPI00066CDBD2 | T0BRJ1 | F0K0A9 |
| UPI000364DDD7 | UPI0002F4C1DE | UPI000277B8D1 | UPI0005E4C005 | UPI0004CECB95 | A0A061BVE6 |
| A0A0A3I330 | UPI00046A2EE8 | UPI00050FB3CA | J5GJF0 | UPI0002DA0189 | G6F4X4 |
| A0A0A3J757 | F0NVP6 | UPI000277B786 | UPI0005E2E74F | UPI0002E0B711 | UPI00032F7094 |
| UPI0003107DC7 | UPI0002DD6873 | UPI00050DA477 | A0A0E8AXP8 | UPI0037D657F | A0A061CH35 |
| UPI000465B065 | W5XDQ0 | UPI000277B3EF | F3VID1 | UPI0005B651F3 | A0A061BSV4 |
| UPI00062B59EE5 | UPI00046C96B8 | UPI00050EBFE8 | E0TNB3 | UPI00031B78EB | A0A061C0Y8 |
| UPI00031ED71B | C2KB80 | C2EVD7 | UPI00068136F1 | UPI0002DA8172 | G6EVU1 |
| UPI0004225966 | UPI0002E9360C | UPI0004953241 | UPI0005DD3E82 | UPI0002FE6543 | UPI00069A32A5 |
| UPI0002B55DD2 | UPI0001B2ADB8 | UPI0004256505 | A0A0I6F783 | UPI0002EB9E28 | UPI00034B89F3 |
| UPI00268A7D1 | D5H1T9 | R9TUH2 | UPI00060414A | UPI0003362867B | V4QC95 |
| UPI0002DD3475 | V5E0D8 | A0A0J6H039 | I0Q427 | E3CGX4 | UPI000287FE90 |
| UPI0003140F32 | U6FUY0 | A0A0D7XCT2 | UPI0005E1E1D9 | UPI0003675904 | UPI000493F21F |
| UPI0002DF577A | U6FDW7 | A0A0D7XAM9 | F9HM88 | UPI0002BE1554 | UPI0002F64068 |
| UPI0002B52183 | U4QEF3 | UPI000470EB15 | R0NC47 | UPI00036D9746 | G9ZMU8 |
| UPI00030AAF28 | C2ELL7 | A0A0H4X8R6 | UPI0005E3138C | UPI0031BD2D4 | I7JG80 |
| UPI0002B54D20 | F6CEU6 | T5HV53 | F9HDZ5 | U2KML1 | UPI0002490095 |
| UPI00030ED4DD | A0A0D5MK99 | Q65MR3 | UPI0005DF6040 | UPI0002F0FB31 | A0A069DTV4 |
| UPI000317D564 | U6F2P2 | UPI0003A92B3A | UPI00066DF5D2 | UPI0002DF3A61 | UPI0003718539 |
| UPI0002B5AC18 | A8YTZ2 | M5P7T2 | UPI0005E78EF0 | UPI000309D239 | A0A0A5GG76 |
| UPI0002B53160 | UPI000468D9FF | A0A0F5KXW3 | A0A0I7SUM9 | UPI0002E4AADA | UPI00040E6B55 |
| UPI0002B5578F | UPI000698FD57 | A0A0J6ENX9 | UPI000399E547 | UPI0002EFE60F | UPI0005CD2072 |
| UPI0002D5DE55 | F0TDD1 | A0A0J6ES4 | UPI0005E5D243 | UPI0003714975 | UPI000487D20C |
| UPI0002FFCB1B | F2M355 | UPI0005A16A5C | UPI0005DBEC58 | UPI0003773AA6 | UPI000370230I |
| UPI0002B50165 | R5ZGC9 | H6NTK0 | UPI0005E3FBD1 | UPI000375ABD2 | M3HNA0 |
| UPI0002B5E93C | E4SM94 | F8FKW5 | D4FT83 | UPI0002DE0320 | UPI00020CBEE6 |
| UPI0002B560C6 | C7XLR3 | UPI0003F50A86 | G6CA70 | UPI00035FC09C | A0A0A6UX77 |
| UPI0002B58B2 | J4BVM3 | G9WIE0 | A0A0B7LL60 | G5JQP7 | A0A0E2USS7 |
| A0A0E2ES03 | D0DI93 | UPI00054F4F52 | R0MM09 | UPI0002E29189 | F1Z0K5 |
| UPI00030C4A19 | K1MXE4 | A0A090IVN1 | Q8DPU8 | UPI0037CA55E | UPI00041B294C |
| UPI0004648E2C | U6FHU9 | A0A0D0FW99 | A0A0H2ZN88 | UPI000379270F | UPI000513CEDF |
| UPI0002B588C8 | F3MR07 | A0A0D0FHN9 | A0A0I5SPG | K8Z8B4 | G0VS69 |
| UPI0003111877 | W7YRH9 | A0A0D0F833 | E0PRK3 | A0A087EPN1 | UPI0004221C8D |
| UPI0002DA340C | W7Z816 | UPI0002195446 | UPI00066AC65D | A0A063B7B8 | UPI0004858886 |
| UPI0002EE7FD7 | V6J250 | J2ZKY4 | I2J7J6 | UPI00054DF8E8 | UPI000356EF52 |
| UPI0002D4555C | C0WSC1 | UPI0002192DE8 | F5W0L7 | UPI0006B251F7 | R7MZQ6 |
| UPI0002B513D0 | C2D3L0 | A0A0J1HWV3 | S3BFG0 | UPI0006B25740 | UPI000550AF6D |

TABLE 6-continued

List of *Bacillus stearothermophilus* PcrA homologs that have 50% identity to and 80% overlap. 1747 members of Uniref 50% identity cluster is shown (citable UniProtKB and UniParc accession numbers are shown).

| | | | | | |
|---|---|---|---|---|---|
| UPI0002B5E0D9 | C0XHM8 | R9BWL2 | E8K074 | UPI0006B25166 | A0A0B0IKT7 |
| UPI0002D9F995 | F5L444 | A0A073JY52 | UPI00066B28A6 | A0A0C2WKV7 | W4QVT6 |
| UPI0002E8D24F | A0A0G9MI18 | UPI000482AB97 | J1S8C6 | K0DDF5 | UPI00054D3339 |
| UPI0002B58C84 | Q03Q12 | A0A0E9GQ05 | UPI00066E5C86 | S0NID8 | F9VEL8 |
| UPI0002B53813 | U2PJH7 | UPI0002D32EA8 | F9PWL8 | UPI0003F6F988 | V8ANU3 |
| UPI0002B5E4B1 | M5AEL4 | G6LUK0 | UPI00066E06C6 | UPI00047D412F | UPI0006226EE6 |
| UPI0002EFF9CD | A0A0H4QAV4 | UPI00067AB63B | UPI00066CF5FD | UPI0004016A4F | UPI0002D66EB7 |
| UPI0002B58C9A | UPI0005B64156 | A0A0I8X5X0 | A0A0F3H5E8 | UPI00040AD781 | K2PIY1 |
| UPI0002B58360 | UPI0004882072 | UPI00066B62FD | UPI00066B0571 | G7SH52 | A0A098CN34 |
| A0A0E2EHS3 | A0A0C1PU47 | UPI0001DDD26E | A0A0F2DYG6 | UPI0003FB4C2E | UPI000266D5EF |
| UPI00030C12E8 | UPI00041E7D06 | UPI0005DB8FEA | A0A095ZC63 | UPI0005CE1998 | UPI0002FD1A27 |
| UPI0002B55BAC | J7LCK3 | UPI00066EE137 | A0A081SAK2 | UPI0005CD605D | UPI00031F2D35 |
| UPI0002B4E249 | A0A0A7U0Q8 | I0SAQ0 | UPI0005342342 | UPI0005CDF885 | UPI00031F5691 |
| UPI0002EC6AC7 | UPI00068191BE | F9MKL8 | A0A081Q0K0 | UPI0004424E658 | UPI0005AA507F |
| UPI000466520E | Q03YP2 | F2QD74 | UPI0005358034 | UPI0005CCF850 | UPI00040E6C2A |
| UPI0002B5A6DE | UPI0005A1E84F | A0A0F2DG50 | UPI00067A78F3 | UPI0003F512C0 | UPI000472C523 |
| UPI00046753B6 | C2KL56 | UPI00069CF310 | UPI00067BFD62 | UPI0005CCF8E5 | UPI000373D4CE |
| UPI00031B4772 | T0VWY9 | A0A0F2D2Q6 | H7QP48 | UPI0003FB972A | UPI000672387D |
| UPI00046312FB | UPI0002341443 | UPI0005EA00F8 | J1V408 | UPI0004079443 | E7RJR7 |
| UPI0002D7CB42 | UPI0005A6A464 | A0A0I8VWS0 | E1MA03 | UPI0004030821 | A0A0A2UWH4 |
| UPI000466DCC8 | UPI00046CA6CE | A0A0I6VM15 | UPI000411F965 | UPI00040E7BC1 | UPI0002880C4F |
| UPI0002B550C2 | UPI0006814228 | A0A0I8S594 | UPI00003751A95 | UPI0005CD07D9 | A0A075TVF2 |
| UPI0002B59082 | A0A0H4N937 | A0A081QA48 | C8P6C2 | UPI0005CDB669 | UPI00054E004D |
| UPI0002B5EB7C | A0A095AHY9 | A0A0I9J5Y7 | UPI000312AA9F | UPI0005CEAA59 | UPI0005A65B8B |
| UPI0004633B74 | UPI00037F25A9 | M5N794 | E3CAD3 | UPI0005CE6576 | W9ANP4 |
| UPI000264EF92 | B9DUG5 | UPI0005E67219 | UPI00021A3A73 | UPI000409F746 | M9LGB1 |
| UPI0002E7D773 | UPI00062028C1 | G0I9B0 | K0U2M0 | UPI0005D16915 | H3S9K5 |
| UPI0002D3B5B3 | UPI0006203F88 | A0A0E2P693 | U1ES89 | UPI0005CEBA00 | UPI000378CC96 |
| UPI0002B577F4 | A0A0F5I4J0 | F9NZH5 | UPI000660DA3F | UPI00040F513E | K2FNB3 |
| UPI0004662568 | A0A0F5HRS0 | UPI0005E921D9 | C8WTI7 | UPI0005CD9361 | UPI00067F085F |
| UPI0002FBB47E | Q5M4H1 | A0A0H5LNP6 | B7DQB4 | UPI0002322E59 | UPI0001E2EBD3 |
| UPI0002B5379E | UPI0002DE5460 | A0A0E0X8J2 | F8IDV6 | UPI0005CF78F9 | UPI0001FDB5AD |
| UPI0002B51579 | V8LWU0 | UPI0005E64E83 | UPI0005599D20 | R4NWS6 | D4W731 |
| UPI0002B4E9DA | E9DMH4 | F9LXX0 | UPI000509968E | UPI0005CEAB2F | UPI000490D40D |
| UPI000464DB1E | UPI0003121E5D | X8K6Y7 | UPI0005CABE96 | UPI00040E0B64 | UPI000255C522 |
| UPI0002B529E6 | J7T7E4 | I0T8M4 | A0A0J5S290 | UPI0005CD124C | A0A0F7D4N3 |
| UPI00046716B0 | UPI00031AFBDD | UPI0005E22D3B | A0A0J5WFP0 | U5UIJ5 | UPI00058E169D |
| UPI000319EA31 | E8KV65 | E1LS08 | A0A0J5YA29 | UPI00042996E4 | UPI000624F4AA |
| UPI0002FFFF03 | UPI0002E8600B | A0A024DEK7 | A0A06A9C586 | UPI00042A2929 | A0A0A8JEM1 |
| Q8DTY6 | F8HD36 | UPI0005E2SBC5 | C8NHG1 | A4VUA8 | UPI00047BFF10 |
| UPI0002B59757 | A0A0E2QHQ8 | UPI0005E30B11 | UPI0005874702 | A0A0H3MVK6 | I9B3V6 |
| UPI00035CDC0C | F8LX97 | E1M4S7 | UPI00066C1DCE | UPI0005CD2519 | A0A075K9S |
| A0A084GLL3 | A0A0F6BVJ6 | UPI0005E14CCC | D4YVQ1 | UPI000409C6E9 | I9NQ12 |
| A0A084H1D9 | A0A0E2RHF6 | F5VXC9 | E6FS51 | UPI0003FE3351 | UPI0004883363 |
| E6TWN0 | UPI000264F340 | A0A0E8T7V0 | UPI0002EA5AD2 | UPI0041E695A | S4NRZ4 |
| K1LG40 | UPI0000E563DC | E6KMR2 | S4CP69 | UPI0005CDA05A | J9W320 |
| F2F7J1 | UPI000660EC4F | UPI0005E76F14 | UPI0003FECF16 | UPI0004038E95 | F4FSH6 |
| J1GP52 | UPI00066C13CA | UPI0005E0C70E | F2MQT5 | UPI0005CE89C0 | UPI000403AE07 |
| F8HYK0 | F8LIZ1 | UPI0005E6F0D4 | UPI0002A3D37C | UPI0004018E0C | A0A084HBI0 |
| UPI00044D3C3A | G2GTJ2 | S7YYN6 | E0H8L5 | UPI000404D8AB | D3FTF3 |
| A0A0C6G2S0 | X8J9A0 | A0A0I8TLZ0 | R1W0H5 | UPI0041CFDD8 | U6SL82 |
| U2W3N6 | UPI00066AA528 | E9FJW6 | S4FW64 | UPI0005CDED2A | UPI000036426F2 |
| A0A0E1ENC5 | A0A074IU47 | UPI0005E93C3F | R3UP49 | UPI0005D236D1 | UPI00047A28D8 |
| Q99ZE1 | | | | | |

TABLE 7

List of *E. coli* PcrA homologs that have 50% identity to and 80% overlap. 1029 members of Uniref 50% identity cluster is shown (citable UniProtKB and UniParc accession numbers are shown).

| | | | | | |
|---|---|---|---|---|---|
| P03018 | K8BG21 | UPI0002C8F355 | UPI0005A9630D | UPI0003EF5338 | A0A0J0DJ77 |
| A0A0G3HMD3 | A0A060VDV3 | V1HN20 | A0A0A3YR40 | UPI0001F6648A | A0A0J0SUX3 |
| U9ZBE3 | A0A0E1CLV1 | UPI0002C9B17D | UPI0005EB7A8B | UPI000678B341 | A0A0J0M6S9 |
| A0A071CB77 | W8V249 | UPI0006811593 | UPI00058E54A4 | A0A0K0IDG2 | A0A0F0XZS7 |
| S1J559 | A0A0J2G3Q6 | A0A0J4VXC9 | H1C573 | UPI0002CC80BD | UPI0005D0A9E9 |
| V2S4E7 | A0A0H4Z3E1 | UPI00025C7C5C | UPI0005CD86D3 | A0A0J5K2Q0 | A0A0C8UHF8 |
| A0A073G662 | V0AU35 | UPI0005304A96 | UPI00044E7286 | A0A0H3MJV2 | A0A0C9HTD3 |
| I2SQY0 | A0A0H4YPU3 | UPI0002CAB12A | UPI00037EE7F7 | A0A0E0VDJ7 | Q8Z3B0 |
| B3X3W4 | A0A0H5AHT5 | UPI0005CCA08F | A0A0J0GVC5 | A0A0G2SID2 | A0A0E7LC59 |
| N2GY76 | W1HG62 | UPI000330B244 | A0A0H0CXK2 | UPI000542989F | W6J799 |
| W1F3C2 | A0A0H4ZLF1 | UPI0002CCBAB8 | V3PV69 | A0A070RYI3 | UPI0004DA823D |
| E1HNQ6 | W9BQA0 | F3WPX7 | A0A0D1KFS4 | H3MUW4 | V8MJC9 |
| A0A070SNS2 | A0A0H3GGJ9 | A0A0F6YD20 | H5V6H2 | A0A070H7E9 | UPI00049F5927 |
| H4URJ5 | A0A0K0GRR7 | K8DQF9 | D7YBR7 | UPI0003BC8E89 | N3EUQ7 |

TABLE 7-continued

List of *E. coli* PcrA homologs that have 50% identity to and 80% overlap. 1029 members of Uniref 50% identity cluster is shown (citable UniProtKB and UniParc accession numbers are shown).

| | | | | | |
|---|---|---|---|---|---|
| M9G7C2 | A6TGJ6 | K8C9V5 | UPI0002C8B609 | UPI0003910486 | UPI0004693D87 |
| N2IIQ0 | A0A0G8G1B7 | F5VR52 | UPI00063CD924 | A0A090UJD6 | UPI0002CCC2BC |
| S1HRC3 | UPI00058FD925 | A0A0D1QDQ1 | A0A0C2AR33 | UPI0004977D3D | F5N8N5 |
| D8E9M5 | UPI00058F49FC | A7MQJ8 | M9I6S8 | UPI0003EF3FD7 | UPI0006A5855E |
| A0A074HPP5 | W1HTQ0 | V5U5I0 | N3K330 | UPI0002CC54C7 | Q83IW7 |
| L2VEY2 | W0ZY91 | UPI0005187950 | I6CD07 | A0A0G3S4T9 | A0A0C7MG10 |
| K5CJK9 | F4T661 | K8D2A7 | E7SHD7 | A0A0H3HA95 | A0A0G3KPN2 |
| D7YG58 | F4V8D3 | UPI0002CA0405 | B2TUW9 | A0A0E0WSN3 | Q0SZ04 |
| W1BJG9 | F4TMH3 | A0A0J0I5H8 | UPI000390185B | A0A068H452 | D2ABY6 |
| N2QEY3 | A0A029LAE5 | UPI000579149A | UPI0005EEDAF9 | UPI0004A0FDEC | A0A0F6MJ85 |
| A0A069YVJ3 | U9YHH0 | UPI0006650689 | B5RFP5 | A0A0H0GX62 | F5P1J3 |
| A0A070Y0G0 | A0A080IB93 | N2J8A4 | UPI0004733206 | UPI0002CB804F | A0A0F6EK00 |
| A0A073GWJ7 | A0A083YZ93 | A0A063XKV2 | UPI00026721AF | UPI0002CB6B71 | I6BAB7 |
| V0RR87 | UPI0005C48DC6 | UPI0005C63608 | UPI0003A80309 | UPI0004D7856B | UPI00050B7641 |
| V0ACC7 | UPI0005A8BF01 | E7T4T6 | A8ACW1 | A0A084ZTZ9 | UPI00050B2FF7 |
| N2RS67 | UPI0003710649 | A0A0G2XIC2 | A0A0A5IRH8 | A0A062Y212 | I6FW66 |
| A0A069XHA8 | A4WG04 | I6DJM1 | A0A0F1WNC5 | A0A064DKM1 | UPI00067F497D |
| A0A079H1K8 | A0A0J8F6L5 | K0WUD4 | V3DAP7 | A0A080EWZ9 | UPI000530716C |
| A0A074IWT6 | UPI000666003A | E7TCS8 | A0A0E2K1D2 | UPI000668F9A7 | A0A0B1RCP6 |
| F8XAY4 | A0A0I1EMQ9 | Q31UH5 | UPI0004D8D514 | V5AU63 | B6I4F4 |
| A0A074HJR7 | A0A0J5U9E7 | A0A085HAH3 | UPI0003EF42B5 | UPI0002CC06C9 | E9TMV0 |
| V1BCC5 | A0A0J6MG09 | A0A0J5L085 | UPI0005A87CA8 | A0A0B1FRQ9 | UPI0004D72F99 |
| A0A080HWB3 | UPI0006684F9F | I2BE57 | UPI00016A0FB4 | S1FP27 | UPI0025ABCDF |
| I2X3X5 | UPI00058D9C39 | A0A0F1BI78 | UPI000496CFDD | S1L396 | UPI000627F480 |
| A0A070FA84 | A0A0A5RML6 | A0A0J0RXX3 | UPI0006ABEED8 | S1CI55 | UPI000326F8B9 |
| L3K8J5 | A0A085ITJ0 | Y1GM95 | UPI0004646130 | L2VN93 | A0A0F4HLT5 |
| A0A080GHX3 | A0A038CQJ1 | E8C7D9 | B7MR33 | A0A089U9W2 | T9FRL3 |
| A0A073FPS6 | A7ZU18 | V2JXK2 | A0A029IIQ6 | D2TV17 | H5E8S0 |
| S1GRU8 | UPI0002CA1DFD | V1LV18 | A0A029HFI5 | UPI000667BF5F | I4S2D3 |
| H5J8D4 | A0A0F3LUY4 | E8D343 | A0A0J9KSZ0 | UPI0006207A91 | V8FG33 |
| D8ERJ1 | UPI0002481DE4 | S4INC0 | A0A0H0KN67 | I2X271 | I2RVR0 |
| D6I369 | A0A0J8LYC2 | E7ZSL5 | UPI0002CB91AD | A0A0D6IZH2 | A0A070D8G2 |
| A0A071CFC4 | A0A0J8MSQ3 | A0A038D0Z4 | C3SKC2 | B7MH77 | A0A026UZE9 |
| M8SKZ8 | A0A0J8HX73 | E7YUD9 | A0A0H8C28 | A0A0E2KYP4 | A0A028CBA2 |
| S1EV38 | A0A0J8QFU8 | S4J0L5 | V0VC55 | UPI000512AED4 | V0U5F8 |
| S1CHB8 | A0A0J8KFX8 | E7YT71 | V0SS57 | UPI0002C8F6BF | H5A4E5 |
| I6CYG1 | A0A0J8IWX2 | E8F002 | T8ZCA9 | G9YXY2 | G2AN47 |
| H5IRF1 | A0A0J8NMQ9 | E8EDF3 | N4MZW5 | UPI0002CC829C | K3QIJ3 |
| I2WCK0 | A0A0J8JFF5 | G5LW37 | A0A070K8G3 | UPI0004B001CB | A0A070SY69 |
| A0A071DAV1 | A0A0J8M4K3 | E8FVB6 | W1BBJ0 | UPI0004E37056 | I2UC63 |
| A0A070DJ71 | A0A0J8HJM3 | E7VG83 | V0XWV9 | UPI0002C98364 | M9EF05 |
| A0A079D807 | A0A0J8M7Y3 | E8AMN0 | L2X7H9 | UPI000267F8CE | A0A027TGT7 |
| V0YB46 | A0A0J8LY21 | V1PEK5 | T8JFJ4 | UPI0002673104 | A0A0E1SZY6 |
| D8AZQ6 | A0A0J8K6V3 | E7ZUE1 | T5TRC8 | UPI0006D844D | A0A0E2U398 |
| L3IME4 | A0A0J8JD30 | E8B3Y5 | H4I3L1 | UPI0005083EE7 | A0A027ZJG3 |
| I4J587 | A0A0J8KYA0 | G5PV87 | A0A0J3V9C5 | UPI0002CABCFF | C8TL04 |
| T9CEL0 | A0A0J8M2A9 | T2Q2W7 | N4NRN6 | UPI0002C94803 | A0A028E3K3 |
| A0A070ULP7 | A0A0J8KZU2 | E7VUY1 | U9Z163 | UPI0005309A93 | A0A026HN93 |
| H4V876 | J1GHE8 | E8BI66 | X7NZ16 | A0A0J5MIB1 | A0A025G7T3 |
| F3VD13 | UPI000472C058 | S4IB83 | S0YT63 | UPI0002CC9136 | K4VZX0 |
| K3KG98 | UPI0005F8A7CD | E7XYR0 | H4JUM1 | UPI000269547E | K4XMA4 |
| G0F7H1 | UPI0005ED3E27 | V7WD74 | A0A073H2N3 | UPI00034730CE | A0A0H3XBG3 |
| E6B0S3 | S1I248 | A0A0J6D7Q1 | A0A017I312 | UPI0003910F49 | H9UZ11 |
| E0J3Y2 | UPI000512EA8D | V1U5Z5 | A0A080ECD1 | UPI00057C0D33 | C8UJJ5 |
| A0A037Y8I6 | UPI0002CB816A | E8EQ65 | L5GW49 | A0A0G3PID9 | A0A0A8UGD6 |
| A0A0E2U8R4 | UPI0006815C5F | E8GKX8 | S1P4I2 | A0A0J4WXG0 | UPI0005B345AD |
| E8Y8R2 | A0A0H7LQT5 | E7Y7G4 | V2T0S1 | V3D6C7 | I6FW96 |
| A0A0E0U5P0 | UPI0002CA127F | E7WDV6 | A0A073UI66 | A0A060UYE6 | UPI0004713F51 |
| B7L973 | UPI0003BB4FC5 | E8H1P2 | V6FB56 | M7P8V6 | UPI0002CC83F4 |
| E3PP00 | UPI0002C92D2D | S4M012 | J7RN24 | W8XG71 | A0A0F5SGW9 |
| A0A0E0Y7I2 | A0A0F0YW97 | E8CHG5 | S0XLH4 | V3KJ79 | UPI0069BE650 |
| A0A0E3H4E0 | A0A0F6K2Y9 | S4JDI0 | A0A064T2Q3 | W8XNG3 | A0A069X2G5 |
| C8TYP3 | UPI0002515E81 | V2N400 | M9F528 | A0A098GXV9 | A0A080FIP4 |
| A0A0E1M3W0 | UPI000699EF6E | S4LF58 | S1D3C3 | UPI0004D54D12 | A0A073T7U4 |
| A0A090L9E8 | V3IA60 | E8DQ33 | H4KPG7 | UPI0005EDDA48 | A0A0F1AYX8 |
| A0A0A0F8P2 | A0A0I2HXR0 | V2P0K5 | V8KDE4 | UPI0005F08B1C | A0A0J1YCS9 |
| UPI0005E69EA7 | UPI000579D3C9 | A0A0H5PMN6 | A0A070P4C7 | UPI0002CC5FF6 | A0A0J0HLB6 |
| W1G679 | A0A0J9AH48 | V2ISV7 | U9Y365 | R0D8R6 | A0A0F0RX59 |
| C0VZH1 | T9ARP5 | V1SA88 | V0YN02 | UPI0002CB96B1 | UPI0005CAF560 |
| UPI0006978729 | U9ZZ52 | T2PQM4 | V4B7K3 | A0A0H0HV04 | A0A0D7LBX3 |
| UPI0003EE8CC5 | B7NFB5 | E8AAS2 | E9YLR4 | S3IGV1 | H4JFN3 |
| W1WHJ6 | UPI000445D59E | E8CTA8 | M8LCT6 | UPI00068E1050 | A0A0J1M123 |
| D8ASL4 | UPI0003EF87D0 | E7WWF9 | M9GJI0 | A0A0J4LFX4 | X7HIN0 |
| UPI0006695A36 | A0A0F4BA88 | E8FMH0 | L3Q9J9 | A0A0H0CH29 | A0A064CY91 |
| UPI0002C95A23 | V5KL37 | E7WRB0 | S0X3S7 | A0A0J0K9Y5 | S0TTK4 |
| W1XFI9 | V2MBS7 | E7X696 | V0Y7G3 | W7NZ36 | UPI0006520C97 |
| UPI00050ADC02 | A0A0H3T6D2 | E8GBI9 | A0A070PK74 | B5EZS8 | UPI0002CC3250 |

TABLE 7-continued

List of *E. coli* PcrA homologs that have 50% identity to and 80% overlap. 1029 members of Uniref 50% identity cluster is shown (citable UniProtKB and UniParc accession numbers are shown).

| | | | | | |
|---|---|---|---|---|---|
| W1WI72 | X5GT01 | V1K5C8 | H4L599 | H7EDN3 | UPI0002CB3E81 |
| UPI0005097CC3 | UPI00056EBE4B | X0NNF5 | S1EDJ9 | UPI0002E3BEE2 | UPI0004DA7107 |
| Q8KI59 | J1QP03 | V2AKC0 | T9IU72 | UPI0004E2422C | Q05311 |
| UPI00044FBFBE | A0A0J2C8A9 | E7VT49 | A0A079Y2R2 | A0A0J5MX43 | A0A0D6IPI8 |
| UPI0005CCFA15 | E1ITF3 | A0A0J6JML4 | A0A0G3J263 | A0A085HQF9 | A0A0E8MI42 |
| Q9R2U0 | A0A0D1CQK0 | V1I8L5 | H3KWA8 | A0A078LAH7 | A0A021WR03 |
| UPI00050A604C | V6FP78 | E8E0U7 | H4LJP0 | A0A0H0R1B4 | S5IH33 |
| V0V674 | V2ASN4 | S4JVA6 | T6GSY1 | UPI0005575061 | V2KFI5 |
| A0A0A7A0U6 | UPI0000627EB24 | E7ZFI6 | T6LNG9 | UPI0004D8B75C | A0A0H3SHZ2 |
| E2X518 | UPI000237C903 | V2H9R2 | H4IZK5 | UPI000452C3C5 | E8XJD9 |
| Q329Y9 | A0A0J5L635 | E8BMX2 | T5NEX8 | R8WLR8 | A0A0H3NUG9 |
| A0A0J1JGH9 | A0A085GMJ6 | G5NKF6 | N3MX37 | S0XDX3 | V7QPA0 |
| W1FYY2 | UPI0005E94CC5 | V2A9V9 | A0A029P4R5 | A0A0A1B385 | V1H945 |
| A0A0A1R5N6 | U1VBA4 | A0A0G2MMZ1 | A0A027YRP2 | UPI00016C8460 | A0A0F6B9B3 |
| A0A073VBC0 | UPI00066656EE | V1MAM1 | L3PWK5 | UPI000675DF85 | A0A0F7JES7 |
| I6FY95 | A0A0H3FP62 | B3YFM1 | S1GVU2 | A0A0E1LGB9 | UPI0005F937F6 |
| A0A0D7LIV8 | UPI0005014921 | A0A0H2WUN6 | M9K6A8 | D2ZMD4 | L0MA89 |
| X7I032 | UPI0005063C446F | V1XNT7 | T9TBM0 | UPI00003ED146B | UPI0004B98CEC |
| D4BE43 | UPI0002CAC6D5 | A0A0H3S2Q8 | D7ZK11 | A0A0E2A5Z6 | E1I441 |
| UPI0001C3403D | UPI0002694D6 | X2KCL1 | L3NT10 | A0A0I2G829 | D8ADU8 |
| G5P1B6 | UPI0002B60DFC | A0A0H3IIW8 | H4K9Z1 | UPI0002C8DC1E | UPI0001FB4B2C |
| G5LGM2 | I6FIC1 | C0Q3C2 | S0VUG2 | UPI00066659C9 | D7XDB2 |
| A0A0H2VE91 | A0A073VVJ1 | V2NKZ3 | M2P544 | UPI0003EF3546 | UPI00050B0CB8 |
| Q1R4C1 | UPI0003F93F50 | A0A0H4VNJ1 | E3XW04 | UPI000370A2F0 | A0A0I0YDW9 |
| W8ZQE8 | L4IV51 | V7UEH9 | S0V315 | A0A0J0PQF7 | UPI0003FF3A54 |
| A0A024KJK2 | A0A0J8YSU2 | M4LQ08 | N2JTA5 | E6WHH6 | UPI00067E3DB0 |
| UPI00050B495A | UPI0002CAC228 | Q57HQ6 | H4IIM4 | UPI00057BE5A7 | UPI00050ABBE7 |
| A0A090ND62 | A0A0F0R0L1 | A0A089GCQ8 | A0A026RVL8 | UPI0003BF7FA1 | UPI00050BC0F6 |
| A0A024L7U7 | U2MK71 | S5HQI6 | E9XUJ2 | T8XXA5 | UPI0001FB4D65 |
| I0VX51 | UPI0005575034C | A0A0H3BQS9 | A0A017JGC0 | A0A0H0BBN2 | A0A0I2EFX3 |
| C9XT80 | UPI0000282E630 | V1SQB1 | D6JHC8 | A0A0F3XJB2 | V6E727 |
| UPI0003027365 | UPI0005307602 | A0A0H3RDJ9 | T5ZU25 | A0A085PA08 | V0VKJ6 |
| K8BR96 | UPI0006A629C6 | V0GAX0 | Q8X8P5 | D6IG48 | UPI000589632A |
| W0AUM0 | UPI0006A6039B | A0A0F0IT73 | B1LLY4 | L4UZM9 | UPI0002A4D3B7 |
| UPI0002B9DE03 | UPI0002CC68E2 | A0A0D5WNL4 | R6TVJ8 | L3C1J2 | UPI000628182D |
| K8A0N1 | UPI0002CCA014 | A0A0F2ZMT8 | A0A0G3JMG2 | UPI0004D7F7DF | UPI00062757E2 |
| UPI0005196C1F | A0A0D5WY30 | A0A0G2NZ21 | D3QXA5 | UPI0006800C6C | UPI0005A6F37 |
| E3G3X3 | A0A0K0HFZ6 | V5ZRD0 | D3H4V1 | UPI0002CCBDA0 | UPI0005CEF8A7 |
| A0A0B5INH2 | UPI00056ED442 | V7IJT2 | A0A023Z641 | UPI0002CB0C5E | A0A0H7L7Z4 |
| UPI0006969E0D | UPI0002CA6A43 | V2D935 | C6EG01 | A0A0J1LKQ0 | A0A0I1QVM4 |
| A0A0J8ZBK9 | F1ZPQ8 | B5Q5I2 | B7UND0 | A0A0G2NT28 | UPI0004643C70 |
| UPI0002EE2722 | E9Z1A2 | V1RGT6 | L9HYA4 | V2PRV4 | A0A0I2RPB4 |
| A0A0J1RJH0 | I2REU8 | X4BR52 | UPI0003H3PUC7 | UPI0002CBC0D7 | UPI000281D683 |
| A0A066P4B2 | UPI0005EA4E43 | UPI0004A8DEFA | A0A0F6GUU7 | B3HAV2 | A0A0I0V6U1 |
| F5S3C5 | UPI0003BCDF55 | G5P176 | Q3YVF3 | UPI00050A9E00 | W1WLH4 |
| A0A0E2M6M6 | UPI0002C935D9 | G9WCL2 | A0A0F6FES0 | UPI0004D4FB82 | UPI00069A9A9D |
| A0A0J0P9D3 | A0A090V7I4 | G5MAR0 | A0A0G3KBA3 | M8PMP0 | A0A0H7RCS5 |
| A0A0J0VSA8 | A0A089Q428 | UPI00067C89D7 | A0A0F6CBC7 | UPI000483DDB5 | UPI00050B3740 |
| A0A0J0QVP3 | UPI00039807B5 | UPI00067AC747 | J2YWY3 | A0A0D7ESI8 | W1ASV1 |
| A0A0J0LCW8 | UPI0004DA8D8C | UPI00069F6BC0 | B7LU43 | A0A0J0DP92 | W1DW14 |
| A0A0A6EFN1 | UPI00004635F02 | UPI0002A6DF22 | A0A025C616 | UPI000352C78C | J2X0N7 |
| A0A0F1A8N0 | UPI000463708C | UPI00067D0E8D | A0A0H4S4M4 | G4C8R9 | G5LGM3 |
| A0A0F1HGJ1 | R9VNE2 | UPI00028DE27E | A0A0H2Z4N7 | UPI0005AA8C72 | UPI0002B9DB1F |
| A0A074TPI3 | UPI0002CC3EDA | UPI0005F857AB | F0JWA1 | UPI0002CC9A6F | X3YLW0 |
| A0A0J9AGF8 | UPI00002695288 | UPI0005797D3A | UPI0005EAF698 | UPI0005C674E6 | UPI0004381BCD |
| UPI000668E496 | UPI00034D611A | J5W6W9 | D7ZU66 | UPI0006658EEE | UPI0002AEB5B0 |
| A0A0J1SRM4 | M7RF80 | A0A0F1L5B3 | UPI000696EBE1 | A0A0J4TS24 | G5QS93 |
| A0A0H0ABS0 | K8AAR4 | UPI0006675A7B | UPI0006995D61 | A0A0C7L099 | G5MAU7 |
| A0A0J2H3P7 | A0A0I2D6J9 | E1J5X4 | UPI0053B46E6 | Z5CP12 | X3UNX0 |
| A0A0E2R9B6 | M8KEA1 | E6BNN4 | UPI0000681EBB3 | D3RH84 | B3PGX1 |
| UPI0004B58C5B | UPI000574FBCF | D7XMB5 | UPI0002C925C5 | B5XYK3 | UPI0002DB7E81 |
| A0A0J2FBS7 | UPI0002A1343F | A0A079F6E9 | B1ERG0 | UPI0005CC1957 | UPI0003B61D19 |
| A0A0J9AI33 | UPI000537C7CA | A0A071AVK4 | UPI0002CB7FF2 | UPI000666ABBF | UPI00037AE6F5 |
| A0A0J8Z8W7 | UPI000472771C | A0A079FJR3 | A0A029K3W3 | R5WI88 | UPI00040A8AC5 |
| H3MDK3 | UPI0002B580C6 | UPI0005AB1B13 | A0A029LTL0 | A0A089PHR7 | A1SQW8 |
| A0A0G3PTS1 | E8DEL4 | UPI0002CBB03B | UPI000390DC2A | A0A0H3CV27 | G5QNH0 |
| A0A0I1EU55 | E7XIB6 | UPI00069C71E8 | S5N2R7 | A0A0H0C242 | G5S3E4 |
| UPI000669A104 | UPI0003915F4D | X5MS66 | G2S5G8 | A0A0F0TB45 | G5SJ34 |
| W0BDW4 | UPI00038FA10B | UPI000614634C | A0A0F2AUK2 | A0A071M1C1 | X3XE62 |
| G8LKV0 | A0A0F6TXR6 | UPI0005ED8E6D | A0A0J0JZA2 | UPI00035E9F50 | UPI000689139D |
| A0A0J0TK85 | UPI000037F6D42 | V1GX81 | UPI0006769073 | F4W269 | G5R9I0 |
| A0A0J0GZG0 | UPI0006145584 | A0A0G3QEA8 | A0A090U681 | UPI00038FA53E | G5P3F2 |
| A0A0G4BNQ9 | UPI0004DAE8E7 | UPI000666A5AA | A0A023V4X1 | A0A0B7GI73 | UPI0003D2FA70 |
| A0A0I0T9Z3 | UPI000315529E | A9MJ02 | A0A0I2BUS0 | A0A0G2MHY8 | A0A084CN62 |
| R4Y7F0 | A0A0J8XHN7 | S1HNI3 | R8WJE0 | A0A0H0DHS6 | UPI00068E1512 |
| C8T0H7 | UPI0003BECD47 | UPI0003BB87D8 | A0A0J0IRI6 | A0A0J0SSF2 | UPI0005D093A3 |
| F4VLD8 | H3N5H9 | | A0A0F3YGX7 | A0A0J0B472 | A0A0H4R3L7 |

TABLE 7-continued

List of *E. coli* PcrA homologs that have 50% identity to and 80% overlap. 1029 members of Uniref 50% identity cluster is shown (citable UniProtKB and UniParc accession numbers are shown).

| | | | | | |
|---|---|---|---|---|---|
| F4SRL8 | K6KT52 | UPI000353E7DB | UPI0002CB932D | A0A0J0ENJ8 | A0A0B8UZ32 |
| F4NQE6 | A0A0H3ENI0 | A0A0F5B4P9 | S0UJP4 | A0A0H0DM28 | A0A0B8V3X1 |
| K8B2N0 | UPI0004D4C5A1 | UPI000250C01F | M8X9A7 | A0A0J0PB20 | U4TEK6 |
| UPI0003A800E6 | UPI000598DBB2 | N4NWV1 | | | |

TABLE 8

*D. radiodurans* UvrD and its Orthologs in Thermophilic Species

| Accession # | Entry name | Protein names | Organism | Gene name |
|---|---|---|---|---|
| Q9RTI9 | Q9RTI9_DEIRA | DNA helicase | *Deinococcus radiodurans* (strain ATCC 13939/DSM 20539/JCM 16871/LMG 4051/NBRC 15346/NCIMB 9279/R1/VKM B-1422) | DR_1775 |
| F0RMJ1 | F0RMJ1_DEIPM | DNA helicase | *Deinococcus proteolyticus* (strain ATCC 35074/DSM 20540/JCM 6276/NBRC 101906/NCIMB 13154/VKM Ac-1939/CCM 2703/MRP) | Deipr_0885 |
| H8GTP8 | H8GTP8_DEIGI | DNA helicase | *Deinococcus gobiensis* (strain DSM 21396/JCM 16679/CGMCC 1.7299/I-0) | uvrD2, DGo_CA1449 |
| C1CVA3 | C1CVA3_DEIDV | DNA helicase | *Deinococcus deserti* (strain VCD115/DSM 17065/LMG 22923) | uvrD, Deide_12100 |
| A0A016QL30 | A0A016QL30_9DEIO | DNA helicase | *Deinococcus phoenicis* | DEIPH_ctg079orf0093 |
| Q1J014 | Q1J014_DEIGD | DNA helicase | *Deinococcus geothermalis* (strain DSM 11300) | Dgeo_0868 |
| D3PR99 | D3PR99_MEIRD | DNA helicase | *Meiothermus ruber* (strain ATCC 35948/DSM 1279/VKM B-1258/21) (*Thermus ruber*) | K649_05745 |
| A0A0D0N7B7 | A0A0D0N7B7_MEIRU | DNA helicase | *Meiothermus ruber* | SY28_04645 |
| E8U932 | E8U932_DEIML | DNA helicase | *Deinococcus maricopensis* (strain DSM 21211/LMG 22137/NRRL B-23946/LB-34) | Deima_1926 |
| D7BGJ6 | D7BGJ6_MEISD | DNA helicase | *Meiothermus silvanus* (strain ATCC 700542/DSM 9946/VI-R2) (*Thermus silvanus*) | Mesil_1937 |
| A0A0A7KLI4 | A0A0A7KLI4_9DEIO | DNA helicase | *Deinococcus swuensis* | QR90_10300 |
| F2NK78 | F2NK78_MARHT | DNA helicase | *Marinithermus hydrothermalis* (strain DSM 14884/JCM 11576/T1) | Marky_1312 |
| A0A0F7JIM6 | A0A0F7JIM6_9DEIO | DNA helicase | '*Deinococcus soli*' Cha et al. 2014 | SY84_01165 |
| E4U8J8 | E4U8J8_OCEP5 | DNA helicase | *Oceanithermus profundus* (strain DSM 14977/NBRC 100410/VKM B-2274/506) | Ocepr_1221 |
| L0A7L7 | L0A7L7_DEIPD | DNA helicase | *Deinococcus peraridilitoris* (strain DSM 19664/LMG 22246/CIP 109416/KR-200) | Deipe_3622 |

TABLE 9

36 seed sequences of UvrD-like helicase group PF00580

| | | | | | |
|---|---|---|---|---|---|
| ADDA_BACSU | EX5B_MYCTU | O53348_MYCTU | PCRA_GEOSE | Q9ZJE1_HELPJ | UVRD_ECOLI |
| ADDA_LACLM | HMI1_YEAST | O66983_AQUAE | PCRA_MYCTU | REP_BUCAP | UVRD_HAEIN |
| EX5B_BORBU | O24736_THETH | O83140_TREPA | PCRA_STAA8 | REP_ECOLI | UVRD_MYCGE |
| EX5B_CHLTR | O25569_HELPY | O83991_TREPA | Q46538_DICNO | REP_HAEIN | UVRD_MYCPN |
| EX5B_ECOLI | O26611_METTH | O84614_CHLTR | Q9Z7D4_CHLPN | SRS2_SCHPO | UVRD_RICPR |
| EX5B_HAEIN | O51319_BORBU | P73465_SYNY3 | Q9ZCJ7_RICPR | SRS2_YEAST | Y340_MYCPN |

TABLE 10

Selected Low-Cysteine or No-Cysteine Wild-Type PcrA Helicases

PcrA with no cysteine from *L. citreum* MK20

| | |
|---|---|
| /gene = "pcrA"<br>/locus_tag = "LCK_00476"<br>/EC_number = "3.6.1.-"<br>/note = "COG0210L;<br>TIGR01073"<br>/codon_start = 1<br>/transl_table = 11<br>/product = "ATP-dependent<br>DNA helicase PcrA"<br>/protein_id = "ACA82309.1"<br>/db_xref = "GI:169803691"<br>(SEQ ID NO: 53) | MSVETLTNGMNNKQAEAVQTTEGPLLIMAGAGSGKTR<br>VLTHRIAHLVQDLNVFPWRILAITFTNKAAREMRERIAA<br>LLSEDVARDIWVSTFHALAVRILRRDGEAIGLAKNFTIED<br>TSAQRTLMKRVINDLNLDTNQYDPRTILGMISNAKNDM<br>LRPRDYAKAADNAFQETVAEVYTAYQAELKRSQSVDF<br>DDLIMLTIDLFQSAPEVLARYQQQFEYLHVDEYQDIND<br>AQYTIVNLLAQRSKNLAVVGDADQSIYGWRGANMMNI<br>LNFEKDYPNAHTVMLEQNYRSTQNILDAANAVINHNNE<br>RVPKKLWTENGKGDQITYYRAQTEHDEANFILSNIQQLR<br>ETKHMAYSDFAVLYRTNAQSRNIEESLVKANMPYSMV<br>GGHKFYERKEILDIMAYMSLITNPDDNAAFERVVNEPKR<br>GLGATSLTRLRELANRLNVSYMKAIESIELAPSITTKAAS<br>KFLTFAEMMTINLRQQSEFLNVTELTELVMTQSGYRQM<br>LAEKNDPDSQARLENLEEFLSVTKEFDDKYQPEDPESIDP<br>VTDFLGTTALMSDLDDFEEGDGAVTLMTLHAAKGLEFP<br>VVFLIGLEEGIFPLSRAMMDEDLLEEERRLAYVGITRAM<br>KKLFLTNAFSRLLYGRTQANEPSRFIAEISPELLETAYSGL<br>SRDKTQKKTLPFDRKMQRATATTYQATPVTKITNGVTG<br>GDQTSWSTGDKVSFIKKWGVGTVISVSGRADDQELKVA<br>FPSEGVKQLLAAFAPIQKVD |

Selected Low Cysteine count thermophilic PcrA helicases

| | |
|---|---|
| >tr\|B5Y6N2\|B5Y6N2_COPPD<br>DNA helicase<br>OS = *Coprothermobacter<br>proteolyticus* (strain ATCC 35245/<br>DSM 5265/BT) GN = pcrA<br>PE = 4 SV = 1 (SEQ ID NO: 54) | MALPQENLIPPSPSHNHLTLSLRSHIGGFFIYNEDVDSVDL<br>SKLNEAQKQAVTAPPKPLAIIAGPGSGKTRVLTYRALFA<br>VKEWHLPPERILAITFTNKAADELKERLGRLIPEGDRIFA<br>ATMHSFAARMLRYFAPYAGISQNFVIYDDDDSKGLIEDI<br>LKQMNMDTKRFRPNDVLNHISAAKARMFDCNTFPEFIR<br>QRYGSWGYYFDTVHQVFMTYERLKEQSQALDFDDLIM<br>VLAQRMEDRPELREMIAGLFDLVMVDEFQDTNFAQYQ<br>MLLYMTNPHYSGMNNVTIVGDPDQSIYGFRAAEYYNIK<br>RFIDDYNPEVVFLDLNYRSNRTIVDSASALINDSPSALFE<br>RKLESIKGAGNKLILRRPFDDADAAITAAFEVQRLFIKMG<br>IPYEEIAVLMRTRALTARVEREFATRNIQYHIIGGVPFFAR<br>REIKDILAYLRLSRNAMDRVSLKRILTMKKRGFGTASLE<br>KLFNFAEENKLTLLEAMKAAVESLLFKKLSMNDYLESL<br>YTLIQTIQE1AEPSQAIYLVMEQENLLDHFRSISKSEEEYIE<br>RTENVKQLISIAEESADMDDFLQRSALGTRENNGGVEGV<br>AISTVHGVKGLEFQAVILYYVTDGFFPHSLSVTTAEKEEE<br>RRLLYVAMTRAKEHLIFYVPYKQPWGNGFEQMARPSPF<br>LRSIPKELWDGKPNEIESLYAPYSPQQKWSE |
| >tr\|E8MZN5\|E8MZN5_ANATU<br>DNA helicase OS = *Anaerolinea<br>thermophila* (strain DSM 14523/<br>JCM 11388/NBRC 100420/<br>UNI-1) GN = pcrA PE = 4 SV = 1<br>(SEQ ID NO: 55) | MDSLEHLNPQQRAAVTASAGPVLVLAGPGSGKTRVLTF<br>RIGYLLSQLGVAPHHILAVTFTNKAAREMQSRVEKLLGH<br>SLQGMWLGTFHAICARILRREQQYLPLDANFVIFDEDDQ<br>QALIKRALRLDKLYRPTSVHAAISNAKNNLILPED<br>YPTATYRDEVVARVYKRYQELLVSSNAVDFDDLLLYA<br>WKLLNEFSTVREQYARRFEHILVDEFQDTNLAQYELVK<br>LLASYHRNLFVVGDEDQSIYRWRGADYRNVLRFEEDFP<br>DRQKILLEQNYRSTQRVLDAAQAVINRNRNRTPKRLKST<br>PEHGEGEKLVLYEAVDDYGEAAFVVDTIQQLVAGGKA<br>RPGDFAIMYRTNAQSRLLEEAFLRAGVPYRLVGAMRFY<br>GRREVKDMIAYLRLVQNPADEASLGRVINVPPRGIGDKS<br>QLALQMEAQRTGRSAGLILMELGREGKDSPHWQALGR<br>NASLLADFGSLLGEWHRLKDEISLPSLFQRILNDLAYREY<br>IDDNTEEGQSRWENVQELLRIAYEYEEKGLTAFLENLAL<br>VSDQDTLPENVEAPTLLTLHAAKGLEFPIVFITGLDDGLIP<br>HNRSLDDPEAMAEERRLFYVGLTRAKKRVYLVRAAQR<br>STYGSFQDSIPSRFLKDIPADLIQQDGRGRRMGRSWQSES<br>RRSWDDNYAGTWGSRPERAKPSHAPILQPRFKPGMRVK<br>HPSWGEGLVVDSRIQDEDETVDIFFDSVGFKRVIASIANL<br>EILS |
| >tr\|E8PM35\|E8PM35_THESS<br>DNA helicase OS = *Thermus<br>scotoductus* (strain ATCC 700910/<br>SA-01) GN = pcrA1 PE = 4 SV = 1<br>(SEQ ID NO: 56) | MQGPQSSHPGDELLRSLNEAQRQAVLHFEGPALVVAGA<br>GSGKTRTVVHRVAYLIAKRGVFPSEILAVTFTNKAAEEM<br>RERLKRMVKGGGELWVSTFHSAALRILRVYGERVGLKP<br>GFVVYDEDDQTALIKEVLKELGLAARPGPLKALLDRAK<br>NRGEAPESLLSELPDYYAGLSRGRLLDVLKRYEEALKA<br>QGALDFGDILLYALRLLEEDPEVLKRVRRRARFIHVDEY<br>QDTNPVQYRFTKLLAGEEANLMAVGDPDQGIYSFRAAD<br>IKNILEFTRDFPGAKVYRLEENYRSTEAILRFANALIVNN<br>ALRLEKTLRPVKPGGEPVRLYRARDARDEARFVAEEILR<br>LGPPFDRVAVLYRTNAQSRLLEQTLASRGVPARVVGGV<br>GFFERAEVKDLLAYARLSLNPLDGVSLKRVLNTPPRGIG<br>PATVEKVEALAREKGLPLFEALRVAAEVLPRPAPLRHFL<br>ALMEELQELAFGPAEGFFRHLLEATDYPAYLREAYPED |

TABLE 10-continued

Selected Low-Cysteine or No-Cysteine Wild-Type PcrA Helicases

| | |
|---|---|
| | YEDRLENVEELLRAAKEAEGLMEFLDKVALTARAEEPG<br>EPAGKVALMTLHNAKGLEFPVVFVVGVEEGLLPHRSSL<br>STLEGLEEERRLFYVGVTRAQERLYLSYAEEREVYGRTE<br>ATRPSRFLEEVEGGLYEEYDPYRASAKVSPSPAPGEARA<br>SKPGAYRGGEKVIHPRFGQGTVVAAMGDEVTVHFEGV<br>GLKRLSLKYADLRPVG |
| >tr\|E8PL08\|E8PL08_THESS<br>DNA helicase OS = Thermus<br>scotoductus (strain ATCC 700910/<br>SA-01) GN = pcrA2 PE = 4 SV = 1<br>(SEQ ID NO: 57) | MLNPEQEAVANHFTGPALVIAGPGSGKTRTVVHRIARLI<br>RKGVDPETVTAVTFTKKAAGEMRERLVHLVGEETATK<br>VFTATFHSLAYHVLKDTGTVRVLPAEQARKLIGEILEDL<br>QAPKKLTAKVAQGAFSRVKNSGGGRRELIALYTDFSPYI<br>ERAWDAYEAYKEEKRLLDPDDLLHQAVHELSTDIDLQA<br>RWQHRARFLIVDEYQDTNLVQFNLLRLLLTPEENLMAV<br>GDPNQAIYAWRGADFRLILEFKKHFPNATVYKLHTNYR<br>SHNGIVTAAKKVITHNTQREDLDLKALRNGDLPTLVQA<br>QSREDEALAVAEVVKRHLDQGTPPEEIAILLRSLAYSRPI<br>EATLRRYRIPYTIVGGLSFWNRKEVQLYLHLLQAASGNP<br>ESTVEVLASLVPGMGPKKARKALETGKYPKEAEEALQL<br>LQDLRAYTGERGEHLASAVQNTLHRHRKTLWPYLLELA<br>DGIEEAAWDRWANLEEAVSTLFAFAHHTPEGDLDTYLA<br>DILLQEEDPEDSGDGVKIMTLHASKGLEFAVVLLPFLVE<br>GAFPSWRSAQNPATLEEERRLFYVGLTRAKEHAYLSYH<br>LVGERGATSPSRFARETPANLIHYNPTIGYQGKETDTLSK<br>LAELF |

Example 10. Cysteine Reactive Crosslinkers and Alternative Crosslinkers

Bis-maleimide crosslinkers with contour length varying from 6 to 25 Angstrom were used as exemplary crosslinkers (Table 2): BMPEG2, BMOE, BMH, DTME, (1,2-Phenylene-bis-maleimide), and (Succinyl Bis[(phenylimino)-2,1-ethanediyl]bis(3-maleimidopropanamide)). Alternatively bis-maleimide crosslinkers such as BMPEG3, BMB, BMDB, (1,4-Phenylene-bis-maleimide), (Bis-maleimidomethyl), and (N,N-[Dithiobis[(carbonylphenylimino)-2,1-ethanediyl]]bis(3-maleimidopropanamide)) or homobifunctional vinylsulfone crosslinker such as HBVS can be used. An alternative crosslinker can be of any crosslinker of desired length that fits the criteria set forth in Example 8 with suitable functional end groups. For crosslinking two cysteines, suitable end groups can be any of the maleimide, haloacetyl, iodoacetyl, pyridyl disulfide, vinylsulfone and other suitable moieties. Table 11 shows examples of bis-maleimide linkers with corresponding lengths.

TABLE 11

Selected Bismaleimide Crosslinkers

| Crosslinker | Spacer Arm Length (Å) | Spacer Arm Composition (between maleimide groups) |
|---|---|---|
| BMOE | 8.0 | Alkane |
| BMDB | 10.2 | Cis-diol (periodate cleavable) |
| BMB | 10.9 | Alkane |
| BMH | 13.0 | Alkane |
| DTME | 13.3 | Disulfide (reducing agent cleavable) |
| BM(PEG)2 | 14.7 | Polyethylene glycol (PEG) |
| BM(PEG)3 | 17.8 | Polyethylene glycol (PEG) |

Example 11. Alternative Crosslinking Methods to Cysteine Crosslinking

As an alternative to cysteine crosslinking chemistry, one can introduce a pair of unnatural amino acids for crosslinking with linkers using different chemistries as defined herein. This may be advantageous over cysteine engineering, because it may eliminate the extra steps of site directed mutagenesis of potentially interfering native cysteines and potentially detrimental effects of such mutations in other related helicases. For example, it was shown herein that in the PcrA helicase, there are two native cysteines that are highly conserved across diverse species (FIGS. 4A and 4B). The mutating out of these two cysteines in PcrA from Bacillus stearothermophilus reduced the ATPase activity by more than 80%. However replacing all five native cysteines in Rep from E. coli had a very minimal effect.

Alternatively, a target residue pair can be introduced, one of which is an unnatural amino acid and the other is a cysteine. Alternatively, one can introduce two or more pairs of target residues, preferably each pair can be specifically targeted with specific crosslinkers that employ orthogonal chemistries so that unwanted inter-pair crosslinking is avoided (for example, one pair of cysteines and one pair of unnatural amino acid residues) for enhanced conformational stability and activity.

Example 12. Unnatural Amino Acids as an Alternative to Cysteine Crosslinking There are nearly one hundred unnatural amino acids (Uaa) that have been genetically incorporated into recombinant or endogenous proteins. These Uaa provide a wide spectrum of side chains that can be covalently crosslinked using a homo or hetero bi-functional linker with suitable end groups. Additionally a multi-branched multi- or homo-functional crosslinkers can be used for secondary conjugation other chemicals, biomolecules such as a DNA polymerase enzyme, in addition to the main crosslinking reaction. Uaa can incorporate specific reactive groups to the specific sites on the proteins, such as aryl iodides, boronic acids, alkynes, azides, or others, or they can be post-transcriptionally or chemically modified to prepare for desired crosslinking chemistry. Examples of Uaa include, but are not limited to, homopropargylglycine, homoallylglycine, azido-phenylalanine, azidohomoalanine and others. Uaa modification and crosslinking reactions include, but are not limited to, azides and cyclooctynes in copper-free click chemistry, nitrones and cyclooctynes, oxime/hydrazone formation from aldehydes and ketones, tetrazine ligation, isonitrile based click reaction, quaricyclane ligations, copper-catalyzed azide-alkyne 1,3-dipolar cycloaddition, copper acetylide to activate terminal alkynes toward reaction with azides, Staudinger ligation, cyclooctyne reactions, and Huisgen cycloaddition. Suitable end groups of these crosslinkers would include, but are not limited to, azide, alkyne, succinimide, phosphine, etc.

Example 13. Selected Super-Family 1B (SF1B) and Super-Family 2 (SF2) Helicases

Figure 12:
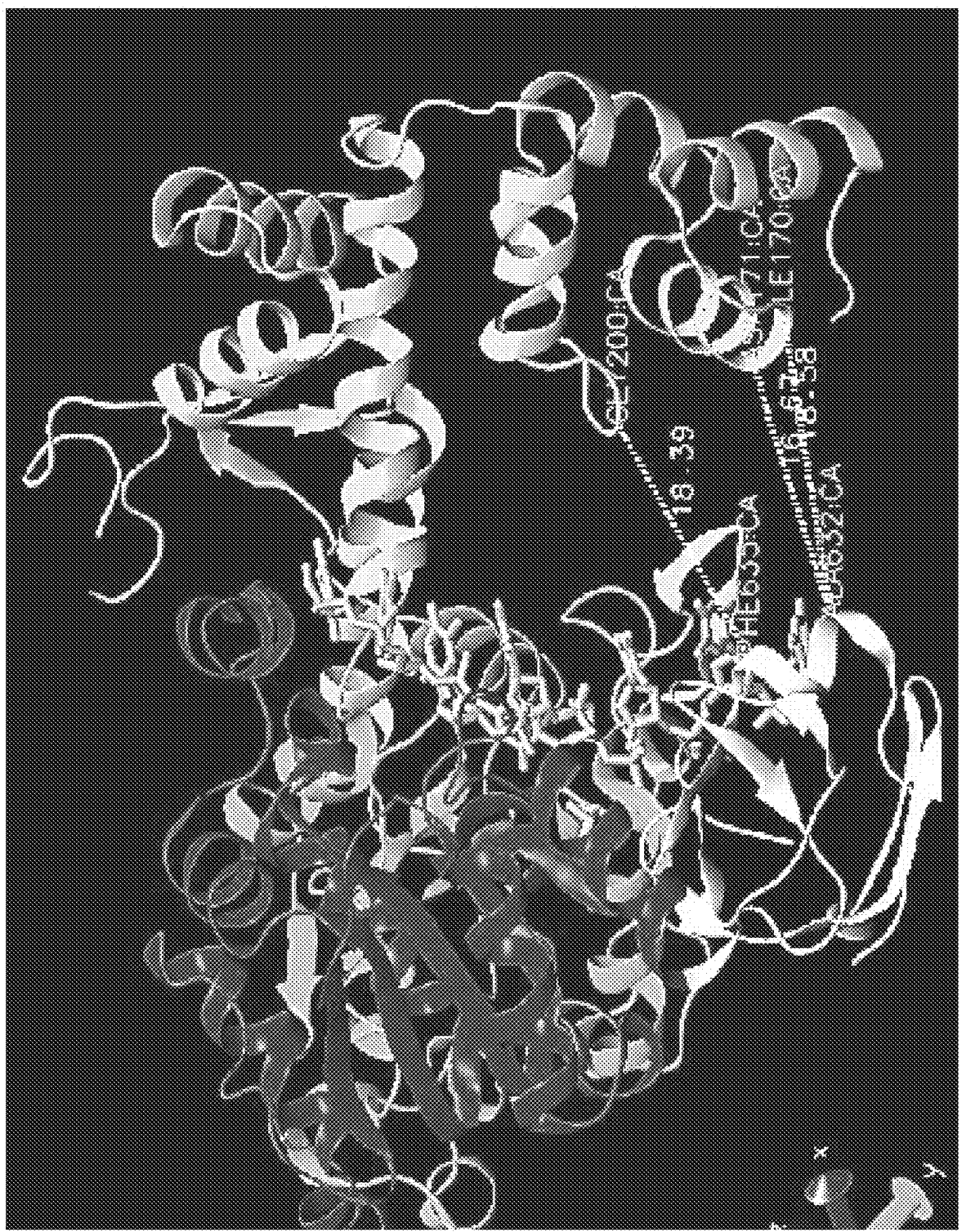
FIG. 12 shows selected target residue pairs for crosslinking, and the specific distances between the pairs, in a ribbon diagram of a structure of RecD2.

Selected SF1B and SF2 helicases are described herein. In an embodiment, the helicase is RecD2. In an embodiment, the RecD2 helicase is from *D. radiodurans*. Selected target residue pairs for crosslinking, and the specific distances between the pairs, in RecD2 are shown in FIG. 12 and Table 12.

TABLE 12

Selected Crosslinking Pairs for 5' to 3' SF1B Superhelicase RecD2

| RecD2 | | Backbone C—C distance in Å |
|---|---|---|
| ALA632 | ILE170 | 18.0 |
| ALA632 | ASN171 | 17.0 |
| PHE635 | GLY200 | 18.0 |

| 1B domain amino acid (RecD2; *D. radiodurans*) | 2B domain amino acid (RecD2; *D. radiodurans*) | Backbone C—C distance in Å |
|---|---|---|
| ARG 410 (B-sheet) | ASN 596 (loop) | 12.91 |
| PRO 413 (B-sheet) | PHE 603 (loop) | 13.04 |
| GLN 414 (B-sheet) | ASN 596 (loop) | 11.13 |
| GLY 415 (loop) | GLU 601 (loop) | 8.38 |
| PHE 416 (loop) | ARG 417 (loop) | 6.36 |
| ARG 417 (loop) | ASN 599 (loop) | 12.43 |
| GLY 418 | TYR 598 (loop) | 11.00 |
| LEU 411 (B-sheet) | PHE 603 (loop) | 13.62 |
| ARG 417 (loop) | ARG 417 (loop) | 10.14 |

Figure 13:
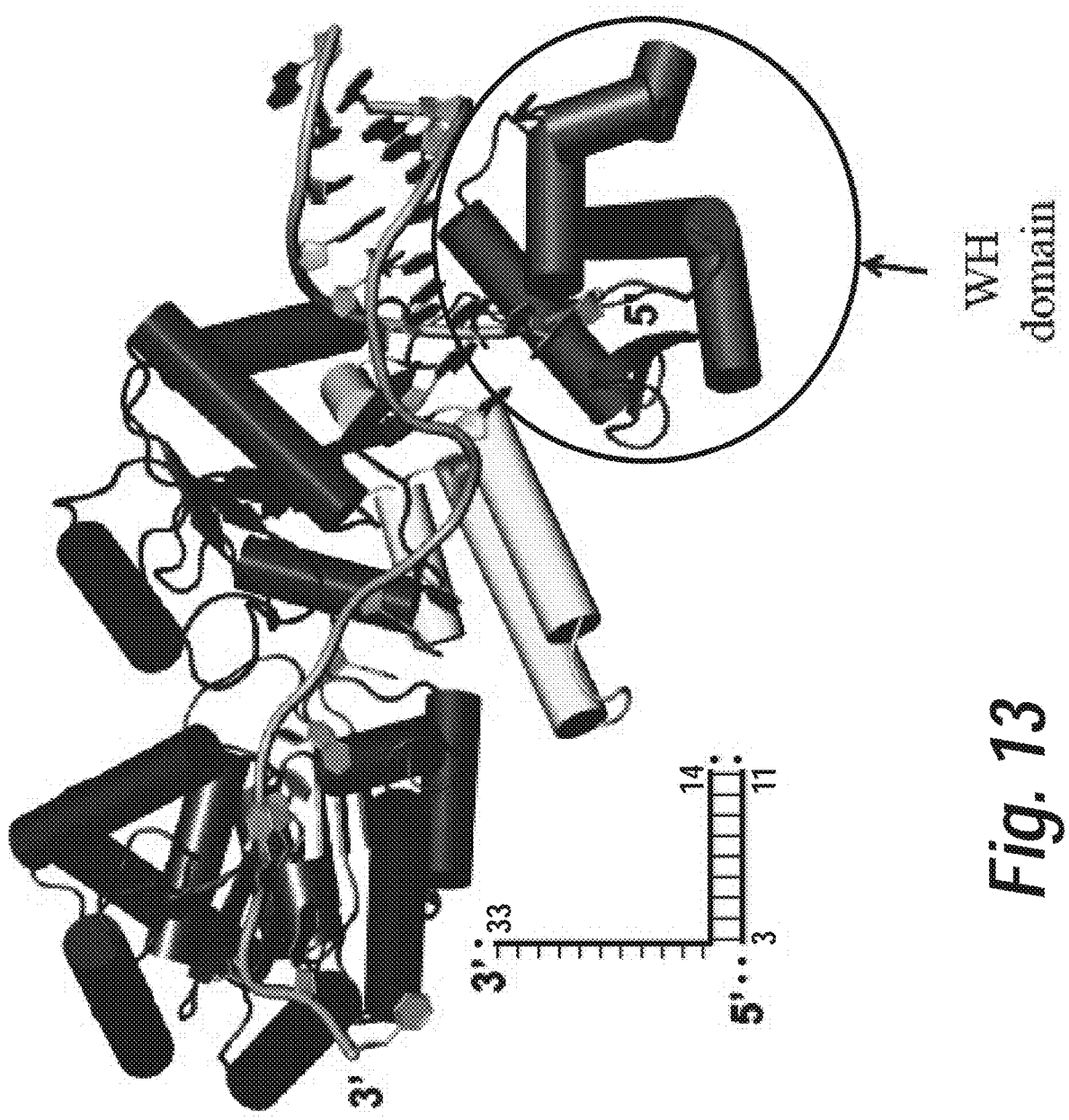
FIG. 13 is a ribbon diagram of a CsRecQ/DNA crystal structure.
Figure 14:
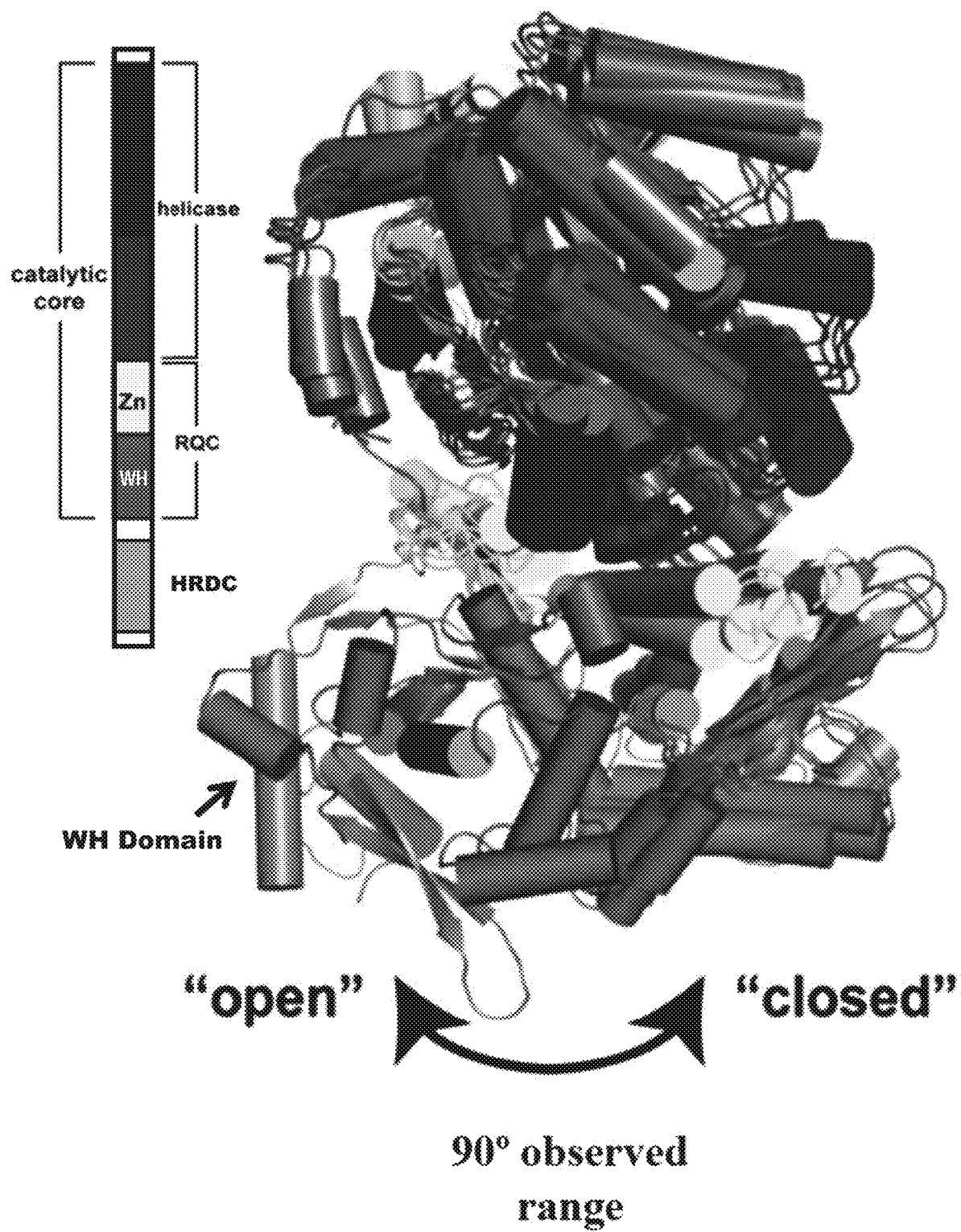
FIG. 14 shows a schematic diagram of RecQ DNA helicase, and an overlay of RecQ structures which highlight the mobility of the WH domain.

RecQ helicase has a winged helix domain (denoted by WH, shown in green in FIG. 13 and FIG. 14) that rotates 90 degrees and makes contact with the duplex in the unwinding conformation (Mathei et al., "Structural mechanisms of DNA binding and unwinding in bacterial RecQ helicases" Proc Natl Acad Sci USA. 2015 Apr. 7; 112(14):4292-7). In an embodiment, stabilization of the WH domain of RecQ leads to superhelicase activation. Stabilization of the closed form of the WH domain can be achieved by crosslinking it to the catalytic core using the residue pairs shown in Table 13.

TABLE 13

Selected Crosslinking Pairs for Superhelicase RecQ

| Catalytic domain | WH domain | Backbone C—C distance in Å |
|---|---|---|
| PHE221 | VAL470 | 7.91 |
| GLU219 | ARG514 | 5.61 |
| LYS212 | GLU467 | 8.90 |
| PHE221 | GLU467 | 6.52 |

Figure 15:
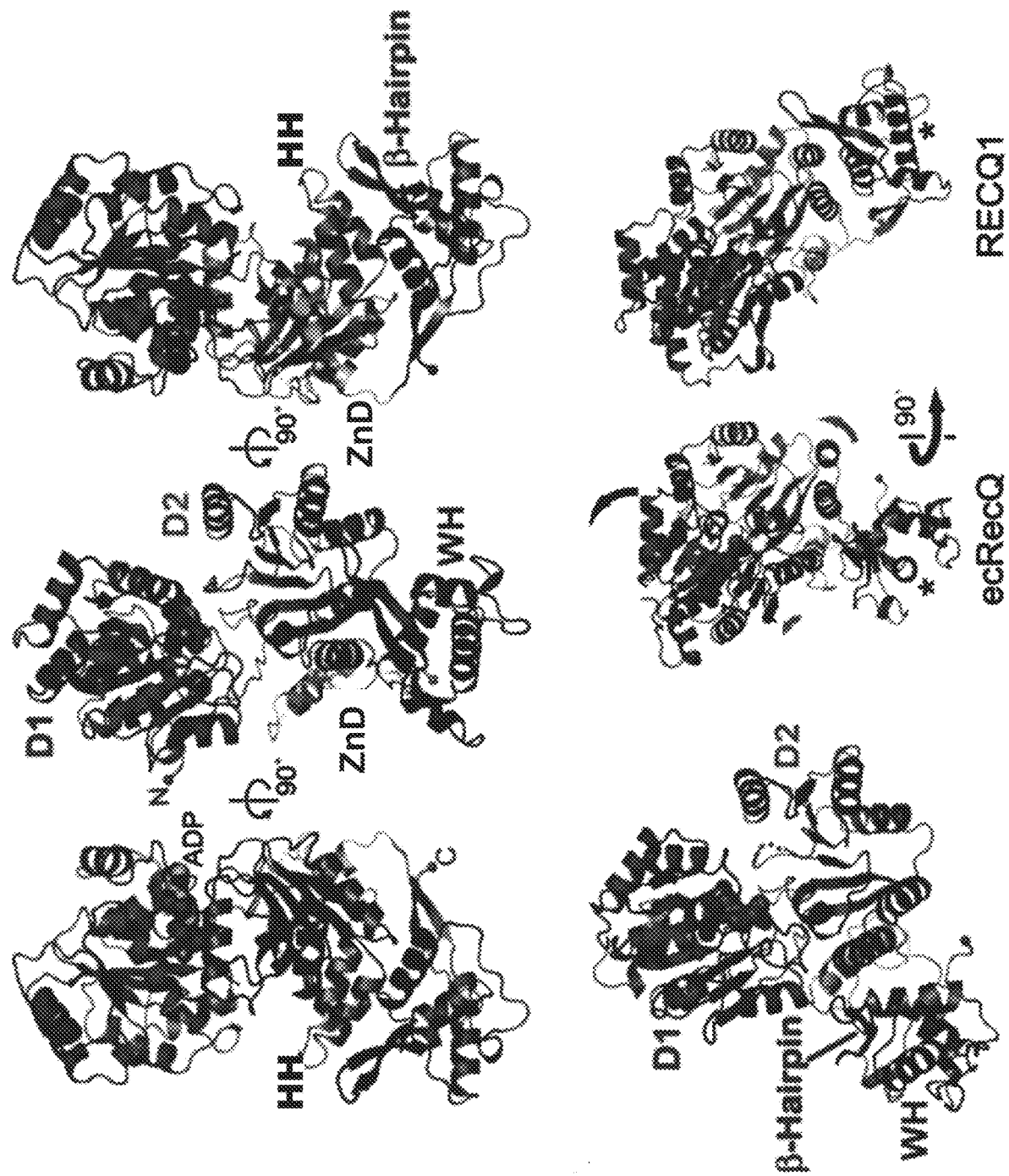
FIG. 15 shows alternate ribbon diagrams of a RecQ1 crystal structure.

RecQ1 helicase also has a winged helix domain (denoted by WH, shown in green in FIG. 15) that rotates 90 degrees and makes contact with the duplex in the unwinding conformation. In an embodiment, stabilization of the WH domain of RecQ1 leads to superhelicase activation. Stabilization of the closed form of the WH domain can be achieved by crosslinking it to the catalytic core using the residue pairs shown in Table 14.

TABLE 14

Selected Crosslinking Pairs for Superhelicase RecQ1

| Zinc finger alpha helix domain amino acid | WH beta hairpin domain amino acid | Backbone C—C distance in Å |
|---|---|---|
| MET429 | TYR564 | 12.17 |
| VAL431 | THR566 | 8.31 |
| MET429 | ALA565 | 8.77 |
| MET429 | THR566 | 7.10 |

5'-3' SF1 superhelicase T4 Dda (FIG. 16) is known to unwind dsDNA as a monomer, and has sequence similarity to *E. coli* recD (exonuclease V). In an embodiment, stabilization of the tower/hook and pin domains leads to superhelicase activation. Stabilization of the closed form of the tower/hook and pin domains can be achieved by crosslinking them using the residue pairs shown in Table 15. Wild-type T4 Dda has 439 amino acids, a 5'-3' unwinding polarity, and 5 cysteines. It is a DNA helicase that stimulates DNA replication and recombination reactions in vitro, and has been suggested to play a role in the initiation of T4 DNA replication in vivo. It acts by dissociating and associating with the DNA molecule being unwound, interacting with UvsX and binding tightly to the gene 32 protein. Selected crosslinking pairs that parallel SF1A helicases are located in the tower/hook and the pin domains based on the crystal structure (FIG. 16) and are listed in Table 15.

TABLE 15

Selected Crosslinking Pairs for Superhelicase T4 Dda

| 1B domain (pin) amino acid | 2B domain (tower/hook) amino acid | Backbone C—C distance in Å |
|---|---|---|
| THR 91 (B-sheet) | TRP 374 (Alpha helix) | 9.77 |
| TYR 92 (B-sheet) | TYR 363 (Alpha helix) | 11.78 |
| TYR 92 (B-sheet) | TYR 363 (Alpha helix) | 11.73 |
| TYR 92 (B-sheet) | LYS 364 (Alpha helix) | 10.42 |
| GLU 93 (loop) | LYS 364 (Alpha helix) | 6.83 |
| GLU 93 (loop) | ALA 372 (loop) | 9.25 |
| GLU 93 (loop) | PRO 373 (loop) | 10.45 |
| GLU 93 (loop) | SER 375 (Alpha helix) | 10.38 |
| GLU 94 (loop) | TRP 374 (Alpha helix) | 8.25 |
| GLU 94 (loop) | ALA 372 (Alpha helix) | 8.25 |
| GLU 94 (loop) | SER 375 (Alpha helix) | 10.73 |
| GLU 94 (loop) | TRP 378 (Alpha helix) | 8.58 |
| VAL 96 (B-sheet) | LYS 381 (Alpha helix) | 12.55 |
| VAL 96 (B-sheet) | TRP 374 (Alpha helix) | 12.36 |
| VAL 96 (B-sheet) | TRP 378 (Alpha helix) | 10.56 |

Structural data have been obtained for the SF1B RNA helicase Upf1 (5'-3' SF1B RNA/DNA helicase) in complexes with phosphate, ADP and the non-hydrolysable ATP analogue, ADPNP (Cheng et al, 2006), although a structure with bound RNA remains lacking. These structures reveal a conformational change that accompanies binding of ATP and which is very similar to that which occurs during catalysis in SF1A helicases such as PcrA.

Example 14. Identifying Suitable Crosslinking Sites for Immobilizing 2B Domain at a Particular Rotational Conformation Between the Open and Closed Form It has been shown herein that the closed and open forms captured in the crystal structures are the active and the inactive states of the Rep helicase, respectively, which can be interconverted by a 133 degree rotation of the 2B domain around an axis. Therefore, the active conformation can be defined through definition of the range of a rotational angle, θ (theta), relative to the closed form with θ=0 (FIG. 17). For example, in an embodiment, Rep-X becomes a superhelicase if θ<40 degrees. In addition, arresting the helicase in an intermediate conformation, such as, e.g. θ=40 degrees, may allow a new function. While immobilizing the 2B domain at an angle θ=40 degrees, it was found that residue pairs distances increase more than 10 Å when θ changes from 40 degrees to 0 degrees (to closed form), and increase more than 20 Å when θ changes from 40 degrees to 130 degrees (to open form). Positions of residues at the desired θ, can be interpolated from open and closed form crystal structures via rigid body rotation of the 2B domain around an axis. Having performed this calculation for θ=40 degrees of Rep helicase, it was found that 2B residues that satisfy this criteria are residues 515 and 518-525, and the residues on the rest of the protein structure satisfying the criteria are residues 543-547. For example, crosslinking residues 521 to residue 547 on with a crosslinker with a length of about 10 Å, restricts the 2B domain to a conformation of θ=40 degrees. Similar to restricting the 2B conformation to θ=0 degrees (closed form), corresponding residues to restrict in helicases with unknown structures can be determined via sequence alignment.

Rigid body rotation of the 2B domain around a chosen axis can convert the closed form to the open form or vice versa. In the case of *E. coli* Rep, the chosen axis intersects the alpha carbons of residue ILE371 and residue SER280 or residue ALA603. In an embodiment, the chosen axis intersects the alpha carbons of residue ILE371 and residue SER280. Theta is the angle of rotation around this chosen axis from the closed form toward the open form. According to this definition, theta is 0 degrees for the closed form. In the case of *E. coli* Rep, theta increases to 133 degrees when it is rotated around the chosen axis to obtain the open form. Theta for the open form may vary between different helicases.

Thus, in an embodiment of a modified helicase described herein, the first amino acid and second amino acid, together with an axis vector defined by an alpha carbon of ILE371, from which the vector originates, and an alpha carbon of SER280 or an alpha carbon of ALA603 of *E. coli* Rep helicase, define an angle, theta, wherein theta is about 355 degrees to about 25 degrees in an active conformation. In an embodiment, theta is about 355 degrees, about 0 degrees, about 5 degrees, about 10 degrees, about 15 degrees, about 20 degrees or about 25 degrees, or any increment or point between about 355 degrees to about 25 degrees. In another embodiment, theta is about 0 degrees in an active conformation. In an embodiment, theta is about 60 degrees to about 155 degrees in an inactive conformation. In an embodiment, theta is about 60 degrees, about 65 degrees, about 70 degrees, about 75 degrees, about 80 degrees, about 85 degrees, about 90 degrees, about 95 degrees, about 100 degrees, about 105 degrees, about 110 degrees, about 115 degrees, about 120 degrees, about 125 degrees, about 130 degrees, about 133 degrees, about 135 degrees, about 140 degrees, about 145 degrees, about 150 degrees, or about 155 degrees, or any increment or point between about 60 degrees to about 155 degrees. In another embodiment, theta is about 133 degrees in an inactive conformation. In an embodiment, the axis vector is defined by an alpha carbon of ILE371 and an alpha carbon of SER280 of *E. coli* Rep helicase. In another embodiment, the axis vector is defined by an alpha carbon of ILE 371 and an alpha carbon of SER280 of *E. coli* Rep helicase.

Example 15. Examples of Thermophilic Orthologs/Homologs of UvrD, Rep and PcrA

Based on the crosslinking target site selection criteria established in Example 8, and analogous to identification of suitable crosslinking sites in hologous helicases as described in Example 9, by sequence alignment and structural homology modeling, the corresponding crosslinking target residues are identified in helicases with unknown structures. Subsequently these helicases can be converted to superhelicase forms. Thus, in an embodiment, Rep-like thermophilic helicases featuring low or no cysteine content, and homologs or orthologs thereof, are also suitable candidates for cross-linking to form a thermophilic superhelicase. Selected examples of thermophilic orthologs or homologs of UvrD, Rep and PcrA are shown in Tables 16-18. In certain exemplary embodiments, a suitable UvrD, Rep or PcrA helicase is selected from the following species: *Thermococcus* sp. EXT9, *Thermococcus sp.* IRI48, *Thermococcus sp.* IRI33, *Thermococcus sp.* AMT7, *Thermococcus nautili, Thermococcus onnurineus* (strain NA1), *Thermococcus kodakarensis* (strain ATCC BAA-918/JCM 12380/KOD1) (*Pyrococcus kodakaraensis* (strain KOD1)), *Thermococcus sibiricus* (strain MM 739/DSM 12597), *Thermococcus paralvinellae, Thermus aquaticus* Y51MC23, *Thermus aquaticus* Y51MC23, *Thermus aquaticus* Y51MC23, *Thermus sp.* RL, *Thermus sp.* RL, *Thermus sp. 2.9, Salinisphaera hydrothermalis* C41B8, *Thermus filiformis, Meiothermus ruber, Thermus sp.* NMX2.A1, *Thermus thermophilus* JL-18, *Thermus scotoductus* (strain ATCC 700910/SA-01), *Thermus scotoductus* (strain ATCC 700910/SA-01), *Oceanithermus profundus* (strain DSM 14977/NBRC 100410/VKM B-2274/506), *Oceanithermus profundus* (strain DSM 14977/NBRC 100410/VKM B-2274/506), *Oceanithermus profundus* (strain DSM 14977/NBRC 100410/VKM B-2274/506), *Oceanithermus profundus* (strain DSM 14977/NBRC 100410/VKM B-2274/506), *Oceanithermus profundus* (strain DSM 14977/NBRC 100410/VKM B-2274/506), *Thermus oshimai* JL-2, *Thermus oshimai* JL-2, *Thermus oshimai* JL-2, *Thermomonospora curvata* (strain ATCC 19995/DSM 43183/JCM 3096/NCIMB 10081), *Thermodesulfatator indicus* (strain DSM 15286/JCM 11887/CIR29812), *Geobacillus stearothermophilus* (*Bacillus stearothermophilus*), *Coprothermobacter proteolyticus* (strain ATCC 35245/DSM 5265/BT), *Meiothermus silvanus* (strain ATCC 700542/DSM 9946/VI-R2) (*Thermus silvanus*), *Anaerolinea thermophila* (strain DSM 14523/JCM 11388/NBRC 100420/UNI-1), *Thermoanaerobacterium thermosaccharolyticum* M0795, *Meiothermus ruber* (strain ATCC 35948/DSM 1279/VKM B-1258/21) (*Thermus ruber*), *Meiothermus ruber* (strain ATCC 35948/DSM 1279/VKM B-1258/21) (*Thermus ruber*), *Deinococcus radiodurans* (strain ATCC 13939/DSM 20539/JCM 16871/LMG 4051/NBRC 15346/NCIMB 9279/R1/VKM B-1422), *Thermodesulfobium narugense* DSM 14796, *Thermus thermophilus* (strain HB8/ATCC 27634/DSM 579), *Dictyoglomus thermophilum* (strain ATCC 35947/DSM 3960/H-6-12), *Thermus thermophilus* (strain SG0.5JP17-16), *Thermus thermophilus* (strain SG0.5JP17-16), *Thermus thermophilus* (strain SG0.5JP17-16), *Thermus sp.* CCB_US3_UF1, *Deinococcus geothermalis* (strain DSM 11300), *Thermus thermophilus* (strain HB27/ATCC BAA-163/DSM 7039), *Thermus thermophilus* (strain HB27/ATCC BAA-163/DSM 7039), *Marinithermus hydrothermalis* (strain DSM 14884/JCM 11576/T1).

TABLE 16

| Entry (3D) | Entry name | Protein names | Organism | Length | Gene names (primary)/Gene encoded by |
|---|---|---|---|---|---|
| L0B9N8 | L0B9N8_9EURY | UvrD Rep helicase SFI | *Thermococcus* sp. EXT9 | 591 | Plasmid pEXT9a |
| L0B9J0 | L0B9J0_9EURY | UvrD Rep helicase SFI | *Thermococcus* sp. IRI48 | 547 | Plasmid pIRI48 |
| L0BAD9 | L0BAD9_9EURY | UvrD Rep helicase SFI | *Thermococcus* sp. IRI33 | 591 | Plasmid pIRI33 |
| L0BAT5 | L0BAT5_9EURY | UvrD Rep helicase | *Thermococcus* sp. AMT7 | 591 | Plasmid pAMT7 |
| W8NUG2 | W8NUG2_9EURY | Superfamily I DNA and RNA helicase and helicase subunits | *Thermococcus nautili* | 665 | |
| B6YXQ7 | B6YXQ7_THEON | UvrD/REP helicase | *Thermococcus onnurineus* (strain NA1) | 533 | |
| Q5JFK3 | Q5JFK3_THEKO | DNA helicase, UvrD/REP family | *Thermococcus kodakarensis* (strain ATCC BAA-918/JCM 12380/ KOD1) (*Pyrococcus kodakaraensis* (strain KOD1)) | 661 | |
| C6A0T5 | C6A0T5_THESM | DNA helicase, UvrD/REP family | *Thermococcus sibiricus* (strain MM 739/DSM 12597) | 716 | |
| W0I5I1 | W0I5I1_9EURY | DNA helicase, UvrD/REP family protein | *Thermococcus paralvinellae* | 659 | |
| B7AA42 | B7AA42_THEAQ | DNA helicase (EC 3.6.4.12) | *Thermus aquaticus* Y51MC23 | 701 | |
| B7A5I6 | B7A5I6_THEAQ | DNA helicase (EC 3.6.4.12) | *Thermus aquaticus* Y51MC23 | 868 | |
| B7A954 | B7A954_THEAQ | DNA helicase (EC 3.6.4.12) | *Thermus aquaticus* Y51MC23 | 542 | |
| H7GEQ7 | H7GEQ7_9DEIN | DNA helicase (EC 3.6.4.12) | *Thermus* sp. RL | 1030 | |
| H7GH69 | H7GH69_9DEIN | DNA helicase (EC 3.6.4.12) | *Thermus* sp. RL | 693 | |
| A0A0B0SAG4 | A0A0B0SAG4_9DEIN | DNA helicase (EC 3.6.4.12) | *Thermus* sp. 2.9 | 692 | |
| A0A084IL47 | A0A084IL47_9GAMM | ATP-dependent DNA helicase Rep (EC 3.6.4.12) | *Salinisphaera hydrothermalis* C41B8 | 670 | rep |
| A0A0A2WMV1 | A0A0A2WMV1_THEFI | DNA helicase (EC 3.6.4.12) | *Thermus filiformis* | 665 | |
| A0A0D0N7B7 | A0A0D0N7B7_MEIRU | DNA helicase (EC 3.6.4.12) | *Meiothermus ruber* | 706 | |
| W2U4X3 | W2U4X3_9DEIN | DNA helicase (EC 3.6.4.12) | *Thermus* sp. NMX2.A1 | 710 | |
| H9ZQB5 | H9ZQB5_THETH | DNA helicase (EC 3.6.4.12) | *Thermus thermophilus* JL-18 | 693 | |
| E8PM35 | E8PM35_THESS | DNA helicase (EC 3.6.4.12) | *Thermus scotoductus* (strain ATCC 700910/SA-01) | 708 | pcrA1 |
| E8PL08 | E8PL08_THESS | DNA helicase (EC 3.6.4.12) | *Thermus scotoductus* (strain ATCC 700910/SA-01 | 621 | pcrA2 |
| E4U8J8 | E4U8J8_OCEP5 | DNA helicase (EC 3.6.4.12) | *Oceanithermus profundus* (strain DSM 14977/ NBRC 100410/ VKM B-2274/ 506) | 719 | |

TABLE 16-continued

| Entry (3D) | Entry name | Protein names | Organism | Length | Gene names (primary)/Gene encoded by |
|---|---|---|---|---|---|
| E4U4N5 | E4U4N5_OCEP5 | DNA helicase (EC 3.6.4.12) | *Oceanithermus profundus* (strain DSM 14977/ NBRC 100410/ VKM B-2274/ 506) | 917 | |
| E4UAI1 | E4UAI1_OCEP5 | DNA helicase (EC 3.6.4.12) | *Oceanithermus profundus* (strain DSM 14977/ NBRC 100410/ VKM B-2274/ 506) | 889 | Plasmid pOCEPR01 |
| E4UAI8 | E4UAI8_OCEP5 | DNA helicase (EC 3.6.4.12) | *Oceanithermus profundus* (strain DSM 14977/ NBRC 100410/ VKM B-2274/ 506) | 638 | Plasmid pOCEPR01 |
| E4UAI4 | E4UAI4_OCEP5 | AAA ATPase | *Oceanithermus profundus* (strain DSM 14977/ NBRC 100410/ VKM B-2274/ 506) | 606 | Plasmid pOCEPR01 |
| K7QW32 | K7QW32_THEOS | DNA helicase (EC 3.6.4.12) | *Thermus oshimai* JL-2 | 693 | |
| K7QWX5 | K7QWX5_THEOS | DNA helicase (EC 3.6.4.12) | *Thermus oshimai* JL-2 | 694 | Plasmid pTHEOS01 |
| K7QTS9 | K7QTS9_THEOS | DNA helicase (EC 3.6.4.12) | *Thermus oshimai* JL-2 | 854 | |
| D1AF88 | D1AF88_THECD | DNA helicase (EC 3.6.4.12) | *Thermomonospora curvata* (strain ATCC 19995/ DSM 43183/ JCM 3096/ NCIMB 10081) | 799 | |
| F8A884 | F8A884_THEID | DNA helicase (EC 3.6.4.12) | *Thermodesulfatator indicus* (strain DSM 15286/ JCM 11887/ CIR29812) | 503 | |
| A0A087LEB0 | A0A087LEB0_GEOSE | Uncharacterized protein | *Geobacillus stearothermophilus* (*Bacillus stearothermophilus*) | 807 | |
| B5Y6N2 | B5Y6N2_COPPD | DNA helicase (EC 3.6.4.12) | *Coprothermobacter proteolyticus* (strain ATCC 35245/DSM 5265/BT) | 696 | pcrA |
| D7BJL0 | D7BJL0_MEISD | DNA helicase (EC 3.6.4.12) | *Meiothermus silvanus* (strain ATCC 700542/ DSM 9946/VI-R2) (*Thermus silvanus*) | 646 | Plasmid pMESIL02 |
| E8MZN5 | E8MZN5_ANATU | DNA helicase (EC 3.6.4.12) | *Anaerolinea thermophila* (strain DSM 14523/JCM 11388/NBRC 100420/UNI-1) | 737 | pcrA |
| L0INW7 | L0INW7_THETR | ATP-dependent exoDNAse (Exonuclease V), alpha subunit/ helicase superfamily I member | *Thermoanaerobacterium thermosaccharolyticum* M0795 | 769 | Plasmid pTHETHE01 |

TABLE 16-continued

| Entry (3D) | Entry name | Protein names | Organism | Length | Gene names (primary)/Gene encoded by |
|---|---|---|---|---|---|
| D3PR99 | D3PR99_MEIRD | DNA helicase (EC 3.6.4.12) | Meiothermus ruber (strain ATCC 35948/ DSM 1279/VKM B-1258/21) (Thermus ruber) | 706 | |
| D3PLL2 | D3PLL2_MEIRD | DNA helicase (EC 3.6.4.12) | Meiothermus ruber (strain ATCC 35948/ DSM 1279/VKM B-1258/21) (Thermus ruber) | 920 | |
| Q9RTI9 (X-ray crystallography (3)) | Q9RTI9_DEIRA | DNA helicase (EC 3.6.4.12) | Deinococcus radiodurans (strain ATCC 13939/DSM 20539/JCM 16871/LMG 4051/NBRC 15346/NCIMB 9279/R1/VKM B-1422) | 745 | |
| M1E5C5 | M1E5C5_9FIRM | DNA helicase (EC 3.6.4.12) | Thermodesulfobium narugense DSM 14796 | 610 | |
| Q5SIE7 | Q5SIE7_THET8 | DNA helicase (EC 3.6.4.12) | Thermus thermophilus (strain HB8/ ATCC 27634/ DSM 579) | 692 | |
| B5YD55 | B5YD55_DICT6 | DNA helicase (EC 3.6.4.12) | Dictyoglomus thermophilum (strain ATCC 35947/DSM 3960/H-6-12) | 656 | |
| F6DJA4 | F6DJA4_THETG | DNA helicase (EC 3.6.4.12) | Thermus thermophilus (strain SG0.5JP17-16) | 722 | Plasmid pTHTHE1601 |
| F6DIL2 | F6DIL2_THETG | DNA helicase (EC 3.6.4.12) | Thermus thermophilus (strain SG0.5JP17-16) | 692 | |
| F6DJ67 | F6DJ67_THETG | DNA helicase (EC 3.6.4.12) | Thermus thermophilus (strain SG0.5JP17-16) | 1014 | Plasmid pTHTHE1601 |
| G8N9P8 | G8N9P8_9DEIN | DNA helicase (EC 3.6.4.12) | Thermus sp. CCB_US3_UF1 | 704 | |
| Q1J014 | Q1J014_DEIGD | DNA helicase (EC 3.6.4.12) | Deinococcus geothermalis (strain DSM 11300) | 741 | |
| Q745W4 | Q745W4_THET2 | DNA helicase (EC 3.6.4.12) | Thermus thermophilus (strain HB27/ ATCC BAA-163/ DSM 7039) | 551 | Plasmid pTT27 |
| Q72IS0 | Q72IS0_THET2 | DNA helicase (EC 3.6.4.12) | Thermus thermophilus (strain HB27/ ATCC BAA-163/ DSM 7039) | 692 | uvrD |
| F2NK78 | F2NK78_MARHT | DNA helicase (EC 3.6.4.12) | Marinithermus hydrothermalis (strain DSM 14884/JCM 11576/T1) | 716 | |

TABLE 17

| Entry | Sequence | SEQ ID NO: |
|---|---|---|
| L0B9N8 | MSEALPVTSFEFSLPEESVIKIYGPPGIGKITTLVRIIEHLIGFHDHTEFLESYGLSLLFGQYGAEDV IFMTFQTSALKEFEARTGIKVKDRQNKPGRYYSTVHGIAFRLLIDSGAIDGVITQNFGSLSPEDW FRLFCRQNGLRFESSEMGYSNVFNDGNRLWNALTWAYNVYYPTKGPIKARHEALKRLAPKL WKYPPLWEEYKTEKGILDYNDMLVKAYEGLKSGEIDPRNLPGHKYSPKVLIVDEFQDLSPLQFE IFRLLANYMDLVIIAGDDDQTIFSYQGADPRLMNYVPGREIVLKRSYRLPIVVQAKAMTVISKTR HRKEKTVAPRIDLGDFKYLFWFPDFLNDLVREAQEGHSIFILVRTNRQVLKLGKELILAGVHF RHLKVDYRSIWEAGSKEWGTFRDLVQALLKARRGEELEIADLVTILYYSELIDWHLGEKLPEKER YKKIAEQMEKTIEAIEKGLMPFDILKVKDDPFSVLDLEKIESLSPRHGKVAVELIREIMKEKSQW SVPRDAEIYLDTLHASKGREADWFLINDLPRKWSSILKTREELDAERRVWYVGLTRARKKVYLL NGKHPFPVL | 58 |
| L0B9J0 | MRVKIYGPPGIGKITTLQRTIDYTLGNSSEPPIPLPESFPIDLEPKNLAFVSFINTAIDVIGKRTGI TTRSKEAPYMRTIHGLILSVLAEHFDPVAVDNLGKLADIQAEFSMRMGYYYSKDPFEFAEGN MKFNVITRALELYLPKTGDVEEALKLIDNREDRKFALAWYRYKRQQKIMDFDDILVIGYEHLEDF YVPVEVAFIDEGQDNGPLDYILLEKGFEGAKFVFLAGDPLQSIYGFKGADPRLFVRWKADKEIIL PRSYRLPKKVWLLSQSWALSLGIKGAWRYAPSEKLGRVSRMKFIEALSYAVEQAKRGSVLIL ARTNSLVKFVGNILSIEFGVAYGHLKRASYWESHLLKFIEGLQMLKLWDGVTPIKVQDTKPITGL IRKLKDKHAREVLRRWRDSRQWSLEVQAVLQRIKKNPSEYFYITDFDRQALKAYFSKARLDLTE ELIIDTIHAAKGEEADWIFLDFIPTRSEERINPEELQEKLVAYVGFTRAREELIIVPIPAIKYHPMR DFMGVRQILGWNFHKHLLIKELVGGL | 59 |
| L0BAD9 | MSEALPVTSFEFSLPRERIIKLYGAPGIGKITTLVKIIEHLIGFQDHTEFLENYGINLPFGQYEPGE VIFMTFQTSALKEFEARTGIKVKDRQNKPGRYYSTVHGIAFRLLIDSGAVDGLITQNFGSLSPED WFRNFCRQNGLRFESSEMGYSNVFNEGNQLWNALTWAYNVYYPTKGPKARYEALKRLAPK LWKFPPLWEEYKKGRGILDYNDMLVRAYEGLRSGEIDPRNLPGHKYSPKVLIVDEFQDLSPLQ FEIFRLLANHMDLVIIAGDDDQTIFSYQGADPRLMNYVPGLEWLRKSHRLPIWQAKALTVISK TRHRKEKTVAPRIDLGDFKYKLFWFPDFLNDLVREAQEGHSIFILVRTNRQVLKLGKELILAGV HFEHLKVDYRSIWEAGSKEWGTFRDLVQALLKAKRGEELEVADLVTILYYSELIDWHLGEGISE KERYKKIAEQMEKTIEAIEKGLMPFDVLRVKENPFSVLDLEKIESLSPRHGKVAVELIKELMKEKS QWSIPKDARIYLDTLHASKGREADWFLINDLPRKWSSILKTREELDAERRVWYVGLTRARKK VYLLNGKHPFPVL | 60 |
| L0BAT5 | MSEALSITSFDFTLPRERIIKIYGPPGIGKITTLVRIIEHLIGFQDHTEFLENYGLSLPFGQYGAEDV IFMTFQTSALKEFEARTGIKVKDRQNKPGRYYSTVHGIAFRLLIDSGAVDGLITQNFGSLSPED WFRHFCRQNGLRFESSEMGYSNIFNEGNQLWNALTWAYNVYYPTKGPKARYEALKRLAPK LWKFPPLWEEYKKEKGILDYNDMLIRAYEGLKSGEIDPRNLPGHKYSPKVLIVDEFQDLSPLQFEI FRLLANHMDLVIIAGDDDQTIFSYQGADPRLMNYVPGREIVLSKSYRLPIWQAKALTVISKTRH RKEKTVAPRIDLGDFKYKLFWFPDFLNDLVREAQEGHSIFILVRTNRQVLKLGKELILAGVHFEH LKVDYRSIWEAGSKEWGTFRDLVQALLKAKKGERISLEVADLVTILYYSELIDWHLGERISEKERYK KIAEQMEKTIEAIEKGLMPFDILKVKENPFSVLDLEKIESLSPRHGKVAVELIKELMKEKSQWSIP KDAKIYLDTLHASKGREADWFLINDLPRKWSNILKTREELDAERRVWYVGLTRARKKVYLLNG KHPFPIL | 61 |
| W8NUG2 | MNEKLSKFIAKLKVLIEMERKAEIEAMRAEMRRLSGREREKVGRAVLGLNGKVIGEELGYFL VRYGREREIKTEISVGDLWISKRDPLKSDLVGTVVEKGKRFITVALETVPEWALKSVRIDLYAND ITFKRWLENLENLRESGRRALELYLGLREPEGGEEVEFTPFDKSLNASQRRAIAKALGSPDFFLIH GPFGTGKTRTLVELIRQEVARGNRVLATAESNVAVDNLVERLVDSGLKVVRVGHPSRVSRGLH ETTLAYLMTQHELYGELRELRVIGENLKEKRDTFTKPAPKYRRGLTDRQILRLAEKGIGTRGVPA RLIREMAQWLKINEQVQKTFDDARKLEERIAREIIREADWLTTNSSAGLEWDYGSYDVAIIDE ATQATIPSVLIPINRAGRFVLAGDHKQLPPTILSEKAKELSKTLFEGLIERYPGKSEMLTVQYRMN ERLMEFPSREFYDGRIEADESIRRITLADLGVKSPEDGDAWAELVKPENVLVFIDTARREDRFER QRYGSESRENPLEARLVKEAVEGLLRLGVKAEWIGVITPYDDQRDLISSLLPEEIEVKTVDGYQG REKEVIVLSFVRSNRKGELGFLKDLRRLNVSLTRAKRKLILIGDSSTLSSHPTYRRLVEFVRERETV VDAKRLIGKVKIK | 62 |
| B6YXQ7 | MTAPIPTFYSILGVAGAGKITQLIDLLNYLNFENSRNEKIWERHFEPVELNRIAFISFSNTAIQEIA NRIGIEKARKKSAPGRYFRTVTGLAEVLLYENNLMTFEEVRSVSKLEGFRIKWAREHGMYYKP RDNDISYSGNEFFAEYSRLVNTYYHVKSLSEIIEMHSKSHLLLDYIREKEKLGIVDYEDILMRAYDY RNDIWDLEYMIIDEAQDNSLLDYATLLPIAKNNATELVLAGDDAQUYDFRGANYKLFHKLIER SEIILNLTETRRFGSEIANLATAIIDDMNYIQKREVLSAATHSTKVAHIDLFQMMSILQNMATTD LTVYILARTNAVLNYVAKVLDEYKIQYKKNERITDFDRFLLSLNRLMRNEYTNDDIYTIYNYLRNK VAREEELKERLFQHKLHVVTEKDVLGILLLLAYEQTTAKRILTTAKNTNFKIKLSTIHSAKGSEADW FLINSVPHKTKMKILENYEGEKRVLYVAVTRARKFLFIVDQPVARRYEQLYYIRSYESRAQGSLV NRVAVPVA | 63 |
| Q5JFK3 | MNEKEVLLSKFIAHLKELVEMERRAEIEAMRLEMRRLSGREREKVGRAVLGLNGKVIGEELGYF LVRYGRDREIKTEISVGDLWISKRDPLKSDLVGTVVEKGKRFLTVAIETVPEWALKGVRIDLYAN DITFKRWMENLDNLRESGRKALELYLGLREPEESEPVEFQPFDKSLNASQRGAIAKALGSGDFF LVHGPFGTGKTRTLVELIRQEVARGHKVLATAESNVAVDNIVERLADSGLKVVRIGHPSRVSKA LHETTLAYLITQHDLYAELRELRVIGENLKEKRDTFTKPAPKYRRGLSDREILRLAEKGIGTRGVPA RLIREMAEWIRINQQVQKTFDDARKLEERIAREIIQEADWLTTNASAGLEWDYGEYDVAVID EATQATIPSVLIPINRAKRFVLAGDHKQLPPTILSEKAKELSKTLFEGLIERYPEKSEMLTVQYRM NERLMEFPSREFYDGKIAHESVKNITLADLGVSEPEFGNFWDEALKPENVLVFIDTSKREDRF ERQRRGSDSRENPLEAKLVTETVEKLLEMGVKPDWIGVITPYDDQRDLISSMVGEDIEVKTVD GYQGREKEIIVLSFVRSNRRGELGFLTDLRRLNVSLTRAKRKLIAVGDSSTLSNHPTYRRFIEFVRE RGTFIEIDGKKH | 64 |

TABLE 17-continued

| Entry | Sequence | SEQ ID NO: |
|---|---|---|
| C6A075 | MTRVQIPAGAPKYGPVAQPGQSARLISGRSGVRSPAGPPKALLKERFRELFIHKNPVITMHVK<br>NYIAKLVDLVELEREAEIEAMREEMRRLKGYEREKVGRAILNLNGKIIGEEFGFKLVKYGRKEAF<br>KTEIGVGDLVVISKGNPLASDLVGTVVEKGSRFIVVALETVPSWAFRNVRIDLYANDITFRRQLE<br>NLKKLSESGIRALKLILGKETPLKSSPEEFTPFDRNLNQSQKEAVSYALGSEDFFLIHGPFGTKTR<br>TLVELIVQEVKRGNKILATAESNVAVDNLVERLWGKVKLVRLGHPSRVSVHLKESTLAFQVESH<br>ERYRKVRELRNKAERLAVMRDQYKKPTPQMRRGLTNNQILKLAYRGRGSRGVPAKDIKQMA<br>QWITLNEQIQKLYKFAEKIESEIIQEIIEDVDVVLSTNSSAALEFIKDAEFDVAIIDEASQATIPSVLIP<br>IAKARRFVLAGDHKQLPPTILSEEARALSETLFEKLIELYPFKAKMLEIQYRMNQLLMEFPSREFY<br>NGKIKADGSVKDITLADLKVREPFFGEPWDSILKREEPLIFVDTSNRTDKWERQRKGSTSRENP<br>LEALLVREIVERLLRMGIKKEWIGIITPYDDQVDSIRSIIQDDEIEIHTVDGYQGREKEIIILSLVRSN<br>KKGELGFLMDLRRLNVSITRAKRKLVVIGDSETLVNHETYKRLIHFVKKYGRYIELGDTGIN | 65 |
| W0I5I1 | MNLIRYINHLKELVELEREAEIEAMREEMRKLTGYEREKVGRAVLGLNGKIIGEEFGYKLVKYGR<br>KQEIKTEISVGDLVVISKGNPLASDLIGTVTEKGKRFLVVALETVPSWALRNVRIDLYANDITFKR<br>QIENLDKLSESGKRALRFILGLEKPKESIDIEFKPFDEQLNESQKKAVGLALGSEDFFLIHGPFGTG<br>KTRTVAEVILQEVKRGKKVLATAESNVAVDNLVERLWGKVKLVRLGHPSRVSKHLKESTLAYQ<br>VEIHEKYKRVREFRNKAERLAMLRDQYTKPTPQWRRGLTDRQILRLAEKGIGARGIPARVIKS<br>MAQWITFNEKVQRLYNEAKKIEEEIVKEIIRQADVVLSTNSSAALEFIKDIKFDVAVIDEASQATI<br>PSVLIPIAKANKFILAGDHKQLPPTILSEEAKELSETLFEKLIELYPSKAKMLEIQYRMNERLMEFPS<br>KEFYNGKIKAYDGVKNITLLDLGVRVFSFGEPWDSILNLKEPLVFVDTSKHPEKWERQRKGSLS<br>RENLLEAELVKEIVQKLLRMGIKPESIGVITPYDDQRDLISLLLENDEIEVKIVDGYQGREKEVIILS<br>FVRSNKKGELGFLTDLRRLNVSLTRAKRKLIAIGDSETLSAHPTYKRFVEFVKEKGIFVQLNQYVS<br>QTS | 66 |
| B7AA42 | MGEAHPSEEALLSSLNEAQRQAVLHFEGPALVVAGAGSGKTRIVVHRVAYLIARRGVFPSEIL<br>AVTFTNKAAEEMKARLKAMVRGAGELWVSTFHAAALRILRVYGERVGLKPGFVVYDEDDQT<br>ALLKEVLKELGLAAKPGPIKSLLDRAKNQGVPPEHLLLELPEFYAGLSRGRLQDVLHRYQEALRA<br>QGALDFGDILLYALKLLEEDGEVLKRVRKRARFIHVDEYQDTNPVQYRFTRLLAGEEANLMAV<br>GDPDQGIYSFRAADIRNILDFTQDYPKARVYRLEDNYRSTEAILRFANAVIVKNALRLEKTLRPV<br>KKGGEPVRLFRAESARDEARFVAEEIARLGPPFDRVAVLYRTNAQSRLLEQALASRGIPARVVG<br>GVGFFERAEVKDLLAYARLSLNPLDAVSLKRVLNIPPRGIGPATVEKVQAIARERGLPLFEALKV<br>AALTLPRPEPLRAFLALMEELMDLAFGPAEAFFRHLLLATDYPAYLKEAYPEDAEDRLENVEELL<br>RAAKEAESLMDFLDKVALTARAEEPAEAEGRVALMTLHNAKGLEFPVVFLVGVEEGLLPHRSS<br>LSTQEGLEEERRLFYVGVTRAQERLYLSYAQEREIYGRLEPVRPSRFLEEVDEGLYEVYDPYRQSS<br>RKPIPPPHRALPGAFRGGEKVVHPRFGPGTVVAAAGDEVTVHFEGVGLKRLSLKYADLRPA | 67 |
| B7A5I6 | MRVYLASAGTGKTHALVEELKGLIQSGVPLRRIAALTFTRKAAEELRGRAKRAVLALSAEDPRLK<br>EAEREVHGALFTTIHGFMAEALRHTAPLLSLDPDFALLDTFLAEALFLEEARSLLYRKGLDGGLA<br>RALLHLYRKRTLAETLHPLPGAEGVFALYLEALEGYRRRLPAFLSPSDLEALALRILENPEALRRVV<br>ERFPHILLDEYQDTGPLQGRFFQGLKEAGARLVVVGDPKQSIYLFRNARVEVFREALKQAEEVR<br>YLSTTYRHAQAVAEFLNRFTALFGEEGVRVRPHRQEVGRVEVHWVVGEGGLEEKRRAEAHLL<br>LDRLMALREEGYAFSQMAVLVRSRSSLPPLEAAFRARGVPYALGRGRSFFARPEVRDLYHALR<br>LSLLEGPPGPEERLALLAFLRGPWVGLDLSEVEEEALKAQDPIPLLPEAVRAKLRALRALAGLPPLE<br>ALKRLSRDEAFLRRLSPRARVNLDALLLLAAMERFPPDLEALLEWLRLRAEDPEAAELPEGEEGV<br>QVLTVHGAKGLEWPVVALFDLSRGENPKEEDLLVGLGGEVALRGTPAYKEVRKALRKAQAEE<br>ARRLLYVALSRARDVLIVTGSASGRPGPWVEALERLGLGPESQDPLVRRHPFKALPPLGDRPQ<br>TPPPPPLPAPYAHLAFPERPLPFVYSPSAFTKAKEPVPLAEALEKEALPEFYRALGTLVHYAIARH<br>LDPEDEGAMAGLLLQEVAFPPAEGEKRRLLEEVRDLLRRYRGMLGPSLPPLEAREEDHAELPLV<br>LPLGGTVWYGILDRLYRVGGRWYLEDYKTDREVRPEAYRFQLAIYRRALLEAWGVEAEARLVY<br>LRHGLVHPLDPEELERALKEGFPGMGPGEGGEKA | 68 |
| B7A954 | MKGLTGSSRLRVYGPPGTGKTTWLKNEVERLLRSGVPGEEIAVCAFSRAAFREFASRLAGQVP<br>EENLGTIHSLAYRAIGRPPLALTKDALSDWNRRVPDTWRVTPRVDGRGADLLDVMDPYEDE<br>DSRPPGDKLYDRVAYLRNTLAPMAAWSEEERAFFQAWKSWMNAKGLVDFPGMLEAAALAK<br>PGGLGARFLLVDEAQDLTPLQLLLVEKWAQGARLALVGDDDQAIYGFMGADGASFLGVPVE<br>DELVLGQSYRVPARVQRVAEAVIRRVQNRAPKRYAPRGDEGEVRLLWVPPEDPYHAVVDAL<br>ERVNRGESVLFLATAKYLLEELKRELLRVGEPYANPYAPHRHSFNLFPQGARSAWEKARSFLFP<br>NRIAADVKAVVTKHVSSKVFAVKGEEARRYIESFPDEEKVGDDHPIWNVFRPEHRPHAVGRD<br>VSWLLDHLLGNAPKTMRQSLMVALKSPEAVLQGRARVWIGTIHSVKGGEADWVYVWPGY<br>TRKAAREHPDQLHRLFYVAATRARKGLVLMDQGKAPHGYVWPRVDEFWGEVWV | 69 |
| H7GEQ7 | MEANLYVAGAGTGKTYTLAERYLGFLEEGLSPLQVVAVTFTERAALELRHRVRQMVGERSLG<br>KERVLAELEAAPIGTLHALAARVCREFPEEAGVPADFQVMEDLEAALLLEAWLEEALLEALQ<br>DPRYAPLVEAVGYEGLLDTLREVAKDPLAARELLEKGLGEVAKALRLEAWRXLRRRMEELFHG<br>ERPEERYPGFPKGWRXEEPEVVPDLLAWAGEVKFNKKPWLEYKXDPALXRLLKLLGGVKEGFS<br>PGPADERLEEVWPLLRELAEGVLARLEERRFRARRLGYADLEVHALRALEXEEVRAYYRGRFRR<br>LLVDEFQDTNPVQVRLLQALFPDLRAWTVVGDPNQSIYSFRRADPKVMERFQXEAAKEGLRV<br>RRLEKSHRYHQGLADFHNRFPPPLLPGYGAVSAERKPEGEGPWVFHFQGDLEAQARFIAQEV<br>GRLLSEGFQVYDLGEKAYRPMSLRDVAVLGRTVVRDLARVEAALRRLEVPAVEAGGGNLLETR<br>AFKDAYLALRFLGDPXDEEALVGLLRSPFFALTDGEVRRLAEARGEGETLWEVLEREGDLSAEA | 70 |

TABLE 17-continued

| Entry | Sequence | SEQ ID NO: |
|---|---|---|
| | ERARETLRGLLRRKALEAPSRLLQRLDGATGYTGVAARLPQGRRRVKDWEGTLDLVRKLEVGS<br>EDPFLVARHLRLIIRSGLSVERPPLEAGEAVILLTVHGAKGLEWPWFVLNVGGWNRLGSWK<br>NNKTKPLFRPGLALVPPVLDEXGNPSALFHLAKRRVEEEEKQEENRLLYVAATRASERLYLLLSP<br>DLSPDKGDLDPQTLIGAGSLEKGLEATEPERPWSGEEGEVEVLEERIQGLPLEALPVSLLPLAAR<br>DPEAARRRLLGEPEXEGGEAWXPXXPQETEEEVPGGAGVGRMTHALLERFEAXEDLEREGRA<br>FLEESFPGAEGEEVEEALRLARTFLTAEVFAPYRGNAVAKEVPVALELLGVRLEGRADRVGED<br>VVVLDYKTDRGVDAXAYLLQVGVYALALGKPRALVADLREGKLYEGASQQVEEKAEEVLRRLM<br>GGEGQGRQPYPLAATDPGHGAPG | |
| H7GH69 | MSDALLAPLNEAQRQAVLHFEGPALWAGAGSGKTRTVVHRVAYLVARRGVFPSEILAVTFT<br>NKAAEEMRERLRGLVPGAGEVWVSTFHAAALRILRVYGERVGLRPGFVVYDEDDQTALLKEV<br>LKELALSARPGPIKALLDRAKNRGVGLKALLGELPEYYAGLSRGRLGDVLVRYQEALKAQGALD<br>FGDILLYALRLLEEDEEVLRLVRKRARFIHVDEYQDTSPVQYRFTRLLAGEEANLMAVGDPDQG<br>IYSFRAADIKNILDFIRDYPEARVYRLEENYRSTEAILRXANAVIVKNALRLEKALRPVKRGGEPV<br>RLYRAEDAREEARFVAEEIARLGPPWDRYAVLYRTNAQSRLLEQALAGRGIPARWGGVGFFE<br>RAEVKDLLAYARLALNPLDAVSLKRVLNIPPRGIGPATVVARVQLLAQEKGLPPWEALKEAART<br>FXRAEPLRHFVALVEELQDLVFGPAEAFFRHLLEATDYPTYLREAYPEDAEDRLENVEELLRAAK<br>EAEDLQDFLDRVALTAKAEEPAEAEGKVALMTLHNAKGLEFPWFLVGVEEGLLPHRNSLSTLE<br>GLEEERRLFYVGITRAQERLYLSHAEERERVYGRREPARPSRFLEEVEEGLYEVYDPYRXPKPXPPP<br>HRPRPGAFRGGERWHPRFGPGTVVAAQGDEVTVHFEGXGLKRLSLKYAELXPA | 71 |
| A0A0B0SAG4 | MDEALLSSLNEAQRQAVLHFQGPALWAGAGSGKTRTVVHRVAYLIAHRGVYPTEILAVTFTN<br>KAAEEMRERLKGMVRGAGEVWVSTFHAAALRILRVYGERVGLKPGFVVYDEDDQTALLKEV<br>LKELGLSAKPGPIKALLDRAKNRGEPPEALLAELPEYYAGLSRRRLLDVFFRYQEALKAQGALDF<br>GDILLYALRLLEEDQEVLARVRKRARFIHVDEYQDTNPVQYRFTKLLAGEEANLMAVGDPDQG<br>IYSFRAADIKNILQFTADFPGAKVYRLEENYRSTEAILRFANAVIVKNALRLEKTLRPVKRGGEPV<br>RLFRAKDAREEARFVAEEILRLGPPFDRIAVLYRTNAQSRLLEQALAGRGVGARWGGVGFFER<br>AEVKDLLAYARLALNPLDSVSLKRILNTPPRGIGPATVEKVARLAQEKGLPLFEALKRAELLPRPE<br>PVRHFVALMEELMDLAFGPAEAFFRHLLQATDYPAYLREAYPEDHEDRLENVEELLRAAKEAE<br>SLLDFLDKVALTARAEEPAGAEGKVFLMTLHNAKGLEFPVVFLVGVEEGLLPHRNSLNTLEALE<br>EERRLFYVGVTRAQERLYLSYAEEREVYGRLEATRPSRFLEEVEEGLYQEYDPYRSPRPVPPSHR<br>PKPGAFKGGEKVVHPRFGPGTVVAASGDEVTVHFEGVGLKRLSLKYADLRPA | 72 |
| A0A084IL47 | MALPKLNPQQDAAMRYLDGPLLVLAGAGSGKTGVITRKIAHLIARGYDARRVVAVTFTNKM<br>REMKQRASKLISADDARGLTVSTFHSLGLQMIREEHAALGYKPRFSIFDSEDADKVLADLVGR<br>DGDHRKATKAAISNWKSALIDPETATAQATGSDIPLARAYGEYQRRLKAYNAVDFDDLLALPV<br>HLLSTDHEARERWQSRFRYLLVDEYQDTNAAQYEMMRLLAGARAAFTVVGDDDQSIYAWR<br>GARPGNIADLSRDFPHLKVIKLEQNYRSVGNVLSAANQLIGASNQRAYEKTLWSAMGPGDRV<br>RVIAAPDEAGEAERIASEISSHKLRLGTAYGDYAILYRGNFQGSRAFEKALRERDIPYRVSGGRSFF<br>ERSEIRDLVTYLKLMVNPDDDAAFLRIVNLPRREIGPATLEALGRYAGSRHISLFDAARGIGLAG<br>GVGERSGRRLADFVDWLRNLTQDSEGMTPRELVSQLIVDIDYRNWLRDTSANTKAARKRIEN<br>LDDFIGWLDRLDNAEDGKPVTLEDVVRRLSLMDFANQSEKDVENQVHLLTLHAAKGLEFDH<br>VFLAGLEEGMLPHHACLEDDKIEEERRLLYVGITRARKTLALTYARKRRRGEESDSVPSRFLEEL<br>PADELDWPSATGIRSKAANAEQGRDQVAALRAMLGASADS | 73 |
| A0A0A2WMV1 | MPQVGFTDHFFKGLEALSREEQNRVREAVFAFMQDPKHPSFKLHRLEDIKTDRFWSARVSK<br>DLRLILYHHPEMGWIFAYVGHHDDAYRWAETHQAEVHPKLGLLQIFRVVEEVRVEPRKIKPLL<br>PDYPDDYLLDLGVPPSYLKPLRLVETEDQLLGLIEGLPQDVQERLLDLAAGRPVTLPPKLAPSEE<br>WFKHPLSRQHIHFIQNLDELRQALSYPWERWMVFLHPAQREAVERVFQGPARVTGPAGTG<br>KTVVALHRAAALARRYPEEPLLLTTFNRFLASRLRSGLQRLLGEVPPNLIVENLHSLARRLHEQH<br>VGPVKLVKEEDYGPWLLEAAQGLEYGKNFLLSEFAFADAWGLYTWEAYRGFPRTGRVGPLTA<br>RERLKLFGAFQKVWGRMENEGALTFNGLHRLRQRAEEGALPRFRAVVVDEAQDLGPAELLL<br>VRALAQEAPDSLFFALDPAQRIYKSPLSWQALGLEVRGRSIRLKVNYRTTREIAKRAEAVLPKEV<br>EGEMREVLSLLQGPEPEIRGFPTQEACQAELVRWLRWLLEQGVRPEEVAVLARVRKLAEGLA<br>EGLRRAGIPVVLLSDQEDPGEGVRLGTVHSAKGLEFRAVALFGANRGLFPLESLLREAPSEADR<br>EALLAQERNLLYVAMSRARERLWVGYWDEGSPFLTP | 74 |
| A0A0D0N7B7 | MSDLLSSLNPSQREAVLHFEGPALVVAGAGSGKTRTVVHRIAYLLRERRVYPAEILAVTFTNKA<br>AGEMKERLEKMVGRSARDLWVTTFHAAAVRILRTYGEYVGLKPGFVIYDEDDQNTLLKEVLK<br>ELELEAKPGPFRSMIDRIKNRGAGLAEYMREAPDFIGGVPRDVAAEVRRYQNSLRMQGALD<br>FNDLLLLTIELFEQHPEVLHKVQQRARFIHVDEYQDTNPVQYRLTRLLAGERPNLMVVGDPDQ<br>SIYGFRNADINNILDFTKDYPGARVIRLEENYRSSSSILRVANAVIEKNALRLEKVLRPTKPGGEPV<br>RLYRAPNAREEAAFVAREIVKLGGYQQVAVLYRTNAQSRLLEEHLRRANVPVRLVGAVGFFER<br>REIKDLLAYGRVAVNPDDSINLRRIVNTPPRGIGATTVARLVEHAQKTGITVFEAFRAAEQVISR<br>PQQVQAFVRLLDELMEAAFESGPTAFFQRVLEQTGFREALKQEPDGEDRLQNVEELLRAAQD<br>WEEEEGGSLADFLDSVALTAKAEEPQGDAPVEAVFLMTLHNAKGLEFPTVFLVGLEENLLPHR<br>NSLHRLEDLEEEERRLFYVGITRAQERLYLSYAEERETYGKREYTRPSRFLQDIPQDLLKEVGAFGD<br>GETRVLSQARPEPKPRTQPAEFKGGEKVHPKFGSGTVVAAMGGEVTVMFPGVGLKRLAVK<br>FAGLERLE | 75 |
| W2U4X3 | MQGPQSSHPGDELLRSLNEAQRQAVLHFEGPALVVAGAGSGKTRTVVHRVAYLIAKRGVFPS<br>EILAVTFTNKAALEMRERLKRMVKGAGELWVSTFHSAALRILRVYGERVGLRPGFVVYDEDD<br>QTALIKEVLKELGLAARPGPLKALLDRAKNRGEAPESLLSELPDYYAGLSRGRLLDVLKRYEEALK<br>AQGALDFGDILLYALRLLEEDPEVLKRVRRRARFIHVDEYQDTNPVQYRFTKLLAGEEANLMA<br>VGDPDQGIYSFRAADIKNILEFTRDFPGAKVYRLEENYRSTEAILRFANALIVNNALREKTLRPV<br>KPGGEPVRLYRARDARDEARFVAEEILRLGPPFDRVAVLYRTNAQSRLLEQALASRGVPARVV<br>GGVGFFERAEVKDLLAYARLSLNPLDGVSLKRVLNTPPRGIGPATVEKVEALAREKGLPLFEALR | 76 |

TABLE 17-continued

| Entry | Sequence | SEQ ID NO: |
|---|---|---|
| | VAAEVLPRPAPLRHFLALMEELQELAFGPAEGFFRHLLEATDYPAYLREAYPEDHEDRLENVEE<br>LLRAAKEAEGLMEFLDKVALTARAEEPGEPAGKVALMTLHNAKGLEFPVVFVVGVEEGLLPHR<br>SSLSTLEGLEEERRLFYVGVTRAQERLYLSYAEEREVYGRTEATRPSRFLEEVEGGLYEEYDPYRA<br>SAKVSPSPAPSEARASKPKPGAYRGGEKVIHPRFGQGTVVAAMGDEVTVHFEGVGLKRLSLK<br>YADLRPVG | |
| H9ZQB5 | MSDALLAPLNEAQRQAVLHFEGPALVVAGAGSGKTRTVVHRVAYLVARRGVFPSEILAVTFT<br>NKAAEEMRERLRGLVPGAGEVWVSTFHAAALRILRVYGERVGLRPGFVVYDEDDQTALLKEV<br>LKELALSARPGPIKALLDRAKNRGVGLEALLGELPEYYAGLSRGRLADVLVRYQEALKAQGALD<br>FGDILLYALRLLKEDEEVLRLVRKRARFIHVDEYQDTSPVQYRFTRLLAGEEANLMAVGDPDQG<br>IYSFRAADIKNILDFIRDYPEARVYRLEENYRSTEAILRLANAVIVKNALRLEKALRPVKRGGEPV<br>RLYRAEDAREEEARFVAEEIARLGPPWDRYAVLYRTNAQSRLLEQALAGRGIPARVVGGVGFFE<br>RAEVKDLLAYARLALNPLDAVSLKRVLNIPPRGIGPATWARVQLLAQEKGLPPWEALKEAART<br>SSRVEPLRHFVALVEELQDLVFGPAEAFFRHLLEATDYPTYLREAYPEDAEDRLENVEELLRAAK<br>EAEDLQDFLDKVALTAKAEEPAEAEGKVALMTLHNAKGLEFPVVFLVGVEEGLLPHRNSLSTLE<br>GLEEERRLFYVGITRAQERLYLSHAEEREVYGRREPARPSRFLEEVEEGLYEVYDPYRVPKPAPPP<br>HRPRPGAFRGGERVVHPRFGPGTVVAAQGDEVTVHFEGFGLKRLSLKYAELRPA | 77 |
| E8PM35 | MQGPQSSHPGDELLRSLNEAQRQAVLHFEGPALVVAGAGSGKTRTVVHRVAYLIAKRGVFPS<br>EILAVTFTNKAAEEMRERLKRMVKGGGELWVSTFHSAALRILRVYGERVGLKPGFVVYDEDD<br>QTALIKEVLKELGLAARPGPLKALLDRAKNRGEAPESLLSELPDYYAGLSRGRLLDVLKRYEEALK<br>AQGALDFGDILLYALRLLEEDPEVLKRVRRRARFIHVDEYQDTNPVQYRFTKLLAGEEANLMA<br>VGDPDQGIYSFRAADIKNILEFTRDFPGAKVYRLEENYRSTEAILRFANALIVNNALRLEKTLRPV<br>KPGGEPVRLYRARDARDEARFVAEEILRLGPPFDRVAVLYRTNAQSRLLEQTLASRGVPARVV<br>GGVGFFERAEVKDLLAYARLSLNPLDGVSLKRVLNTPPRGIGPATVEKVEALAREKGLPLFEALR<br>VAAEVLPRPAPLRHFLALMEELQELAFGPAEGFFRHLLEATDYPAYLREAYPEDYEDRLENVEE<br>LLRAAKEAEGLMEFLDKVALTARAEEPGEPAGKVALMTLHNAKGLEFPVVFVVGVEEGLLPHR<br>SSLSTLEGLEEERRLFYVGVTRAQERLYLSYAEEREVYGRTEATRPSRFLEEVEGGLYEEYDPYRA<br>SAKVSPSPAPGEARASKPGAYRGGEKVIHPRFGQGTVVAAMGDEVTVHFEGVGLKRLSLKYA<br>DLRPVG | 78 |
| E8PL08 | MLNPEQEAVANHFTGPALVIAGPGSGKTRTVVHRIARLIRKGVDPETVTAVTFTKKAAGEMR<br>ERLVHLVGEETATKVFTATFHSLAYHVLKDIGTVRVLPAEQARKLIGEILEDLQAPKKLTAKVAQ<br>GAFSRVKNSGGGRRELIALYTDFSPYIERAWDAYEAYKEEKRLLDFDDLLHQAVHELSTDIDLQ<br>ARWQHRARFLIVDEYQDTNLVQFNLLRLLLTPEENLMAVGDPNQAIYAWRGADFRLILEFKK<br>HFPNATVYKLHTNYRSHNGIVTAAKKVITHNTQREDLDLKALRNGDLPTLVQAQSREDEALAV<br>AEVVKRHLDQGTPPEEIAILLRSLAYSRPIEATLRRYRIPYTIVGGLSFWNRKEVQLYLHLLQAAS<br>GNPESTVEVLASLVPGMGPKKARKALETGKYPKEAEEALQLLQDLRAYTGERGEHLASAVQN<br>TLHRHRKTLWPYLLELADGIEEEAAWDRWANLEEAVSTLFAFAHHTPEGDLDTYLADILLQEED<br>PEDSGDGVKIMTLHASKGLEFAVVLLPFLVEGAFPSWRSAQNPATLEEEERRLFYVGLTRAKEH<br>AYLSYHLVGERGATSPSRFARETPANLIHYNPTIGYQGKETDTLSKLAELF | 79 |
| E4U8J8 | MSARDLLSSLNEQQQAAVQHFLGPALVIAGAGSGKTRTVVHRVAYLLAEREVYPAEVLAVTFT<br>NKAAGEMRERLSRMVGRAAGELWVSTFHSASLRILRRYGERIGLKPGFVVYDDDDQRVLLKE<br>VLGSLGLEARPTYVRAVLDRIKNRMWSVDEFLAHADDWVGGLTKQQMAEVYARYQQRLAE<br>NNAVDFNDLLLRTIELFERHPEALEAVRQRARFIHVDEYQDTNPAQYRLTKLLAGDEANLMVV<br>GDPDQSIYGFRNADIQNILGFERDYRGAVVYRLEANYRSTAAILRVANALIERNQQRLEKTLRP<br>VKPAGEPVRLYRAPDHREEEAAFVAREVARLAGERALDDFAVLYRTNAQSRVLEEAFRRLNLPA<br>RIVGGVGFYEREVKDVLAYARLAVNPADDVALRRVINVPARGVGAASVGKLAAWAQAQG<br>VSLLEAAHRAGELLAARQAAAVAKFTDLLTTLREAAEGTGPEAFLRLVLAETGYSEMLRREGDS<br>EPRLENLEELLRAAAEWEEEHGGSVAEFLDEIALTARAEEPNAAPEKSVTLMTLHNAKGLEFPV<br>VFVVGVEEGLLPHRSSLGSDAEIEEERRLLYVGITRAQERLYLTLSEERETWGQRERVRPSRFLEE<br>IPEDFLKPVGPFGDAHEPAPAPLSSAPVNRAAKGSASGFRGGEKVRHPRYGEGTVVATSGEG<br>ARQEVTVHFAEAGLKRLLVKYAGLERIE | 80 |
| E4U4N5 | MKVRIASAGTGKTYALTSRFTAALAEHPPYRLAAVTFTRSAAAELKARLRERLLAIAAGRFQPSG<br>AEDVPPEAVVRRAGALATEVLGATVTTIHGFFAELLRQNALALGLEPDFLRIDASESQQ1FAEEA<br>RAYVYLNEEDDALAEVLGRLFAKRSLAAELRPQGEAAEALWAHFRAVLERYARRLGGEALGPA<br>DIELHAWRLLERAGREEALAARIRSRLARVFVDEYQDTSPLQGRVFAALEALGVEVEVVGDPK<br>QSIYAFRNADVEVFREAMRRGEPLPPLVTSWRHDRALVRFLNRYDWVAEERPEAFARAEA<br>PPVEARPDAGPGRVRLQLVQGEARQDALRPYEADQLARWLQERHAEHAWRDMAVLVRSH<br>SSVPLLVRALAAHGLPHVVVGGRGFYDLIEVRDLVHAARVALDPRGRFSLAAFLRGPFAGLDL<br>GRVERVLAAEDPLAELERAAPEVAERVDRLVRWVQTLRPLDFFERMVRTPFLEGASYLERLEP<br>PARANVDQLLFKLASRRYGRLEFLLRDLEDLRGSDEAGVPGFDAVRIYTMHGSKGLEWPV<br>VAVFDLNRGQPDGAEPFYVRPGSGEFAAEGDPDYPRFAAEWKERERQEAYRLLYVALSRPRS<br>RLLLSLSVQLKPDGEGLRPKFWRRTLGRTLIEEMNLAAWDALEVERLDAARLPAPKAAAAAPR<br>RAADVDERLRAPVEPLARPPVYSPSALKAERPAPPELDDEGDVAVELEEPGVDPGLVARTGIL<br>VHYAIGQDWGPERLQDLWNQEAVQRLTEPERTRVKTEVAQRLETYWRLLGTELPALDERDE<br>DYAEFPLLLPTRTARLDTVWEGVIDRLYRVGDVWVLEDYKTDRELHPERYHFQLALYRRAVAA<br>AWGIEPEARLVYLRFGEVVPLEAQLLEEAFERGTREAEEV | 81 |
| E4UAI1 | MKVIVASAGTGKTTRLTQRYLEHLEQHPPQRVAAVTFTNKAAAELRERIFEALGRGSFYDFTPS<br>PALAERLADYQVRVLEAPIGTIHSFFGYLLRLTAPMLGLDPHFEVIDPATARAWFLEEVRNLAIIE<br>GAEVDETVTTALVELFKRRSISEAFEGTGDASRSLVAGFKKVYARWLTRLGGRYLDPSEIERRAL<br>ALIRHPEALERVRSRLGVVLVDEYQDTAPIQARVFEALEEAGVPIEVVGDPKQSIYAFRDADVE<br>GFREAHRRARENGNVETLTVSYRHPPALADFLNAFTSAEAALGKAFTAEEEAPEVKPGREGDAR<br>VELITVTPGDGKATLDALRNGEARLLARELRRLHDEEGYDYGQMLVLFRRRHQLPPLLRALRG | 82 |

TABLE 17-continued

| Entry | Sequence | SEQ ID NO: |
|---|---|---|
| | AGLPFAVVGLRGLYEEPEVRELYHALRLATGEAPRDSLAVFLSGPFGGLTLGQVREVLAQDAPE SYLTLHHPEAAERLLRLRADAEKMRPAEALTRLIEAPTAKGPPFLDLLELEMADTVLYVLGRIEH TRTYPEAVATLESFRSGGEEEASLARLGGDAVRVMSAHAAKGLQAPVVVIFDADRTFNGNSD ELVIEPRTGRVALNGEDAYESIAQALKARKEGEDHRLIYVALSRSSERLIVSAAVKEPRKGSWLH HLTEVLNLGSKFEHRNVTLAEIALEEPIEQEAATLPVDPELATLPPAPPAVSSPTALKAERELEV PDPEEAWPADPEARLLGRIVGILVHEGIQRDWDPDDPEVLLALEGEQVLEEVPADRRPAVIEE VATLLRVYRTLLGSAIPSLEEREVDLAELPLVYPLGATAWEGVIDRLYRVGDVWYLEDYKTDREV HPERYHSQLALYREAVRKHWGIEPEVRLVYLRTGQVVPLDAAALKEGLASYTGG | |
| E4UAI8 | MNEHERVIAHEVGPAAVVAGAGSGKTRAATLRAARLARTGERVGLVTFTASAAEEMRQRVL AEDVPAKHVWAGTFHSLAFQILRQFPEAGGYEGFPEVLTPNDELRLFRRLWAELLDQDLDAEL RRKLVKALGFFRKARAEEEALEGWAARAGESLELDAEMLEALMISFQLRKREAGLASFDDLIEG ASRALGDKDVRKWADRRFPFLIVDEYQDTSRAQETFLAALMPGEAPNLMVIGDPNQAIYGW RGAGSRTFERFQARYPQAVLYPLRKNYRSTRAVLRLAERAIARLYRSGQEAYYRLEGVKEEGEP PVLLTPPNAAAEATDVAREVARAVASGVPPEEIAVLARSSMQLAGVEDRLARLGVATRLLGGI RLSERREVKILVQLLKAAWSLHERALVDFIEEAVPGLGERTLTRVEHAARPYNLVDRIMNDGA FVRGFSTRVQQGLFMTRTLLQLARATFEGVTGEAFAERFREFAQDLYGELLPGYLARIGKQGP NEEARRRHLERFVATVEAFAREEAEGGLDDLLARLAFLEQQDGPAVTLGTVHAVKGLEFEWF WGMVEGAFPILADDSDPEEERRLFYVAATRAKRRLYLSAPTYGPRGKILQPSRYLEEALDEGLV RLQKVRPAA | 83 |
| E4UAI4 | MVSEGRWKIERVVYLKDGFAWAVRNEAGERHTAVGEMPTPVEGTWVRMETEHTVHPRY GPRLRWRFLGLAPPPSKELAKIEGYLKLGFSEEAASWLAARFGSRPERAFDKPQELLVPGVPRE VLRRVFPRLERLLGGLIDLLGEGHTAAPLFLLAERSGLGKEEIQELAREARKQRLIVEEQGRYGLV QPYRTERSIADGLLFRLKPGRGLRLIPPAGHGLSDEQARIFKLVRENRVVVLTGGPGSGKTTTIA ILLAAPELHRMRFGIAAPTGKAARRIAEVARLPAETIHRLLGLGEARRPLYHARNPLPYDLLVID ETSMLDAEIAAFLVDALAPSTSVIFVGDPDQLPPVGPGQFLRDLMTRVATLRLTQIFRQAQDS PIVNGAYALREGRMPLADGERLRLLPFEEEAAQTTLRILLDELQRLEQIVGERPQVLVPGNRGP LGVRRLSPFLQQQLNPGGKPLGPIGWGMEAREGDPAVWIHNDYELGIMNGEVGVLRGGGS LGLTFETPTDRFAIPGNKRSLVLAYAMTVHRSQGSEWPAVITILPKAHMALLSRELVYTALTRS KQYHTLLFHPEALYRARAVQASRRYTVVLDVLLRG | 84 |
| K7QW32 | MTAPGHPDALLAPLNPAQQEAVLHFQGPALWAGAGSGKTRTVVHRVAYLMAHRGVYPGE ILAVTFTNKAAEEMKGRLKALVPGAGELWVATFHSAALRILRVYGEAIGLKPGFVVYDEADQE ALLKEVLKELGLSAKPGPLKALLDRAKNRGEAWEALEIPDYYAGLPKGKVLDVLRRYGEALRAQ GALDFGDILVYALRLLEENPEVLAKVRKRARFIHVDEYQDTSPVQYRFARLLAGEEANLMAVG DPDQGIYSFRAADIRNILDFIRDFPGARVYRLEENYRSTEAILRFANAVIQKNRLRLEKTLRPVKP GGEPVRVYAAPEAREEEARFVAEEIFRLGPPYERFAVLYRTNAQSRLLEQALAAKGLPYRWGGV GFFERAEVKDLLAYARLSLNPEDGVSLKRVLNTPPRGIGPATLARLEALAQAEGVPLLGAIRLGA ERFPKPEPLRAFLALLDELADLAFGPPEAFFRHLLSATDYLQYLKEHHPEDAEDRLENVEELLRA AKEAQDLQEFLDRVALTARADQDGGRGVALMTLHNAKGLEFPWFLGVVEEGLLPHQSSLST LEGLEEEERRLFYVGVTRAQDRLYLSYAREREVYGRREPRRMSRFLEEVPEGLYLPHDPYRQGA QPKPAPRAQGAFRGGEKWHPRFGPGTVVAASGDEVTVHFEGVGLKRLSLKYADLRPA | 85 |
| K7QWX5 | MASSLSKAELVPIPEQEKALHLYRSRQDFKLVAVAGSGKITTLRLMAESFPRRHIAYLAFNRA MKEEARRKFPPNTRVFTLHALAYRRTVPGTPYEAKFRLGNGQVRPVHVRERLQVDPLLAYVV RSGLERFIRSGDPEPLPRHLPRDWRKTVEARGPSGFAEVERAVKGVALLWKAMRDPKDPFPL SHDGYVRIWREEGAGGDPPAGVILVDEAQDLDPNFLTVLSGWRGKAQQVFVGDPRQQIYG WRGAVNAMGEIDLPESPLTWSFRFGEPLASFVQAVTARQTQGLVPLVGRAGWATEVHVNL FPIPPPFTILTRSNLGLVTALLEGAQLFSLQKEEAHWGGVEELWVLLTDLQAIKEGGERPRPHPE LLGISKWEEVESLAEYSIVLNRLLRLAKEYDLEALAHKIAQLHGPEEGAKLVLSTAHKAKGREWD RVLLWEDFYWVAAYRWFFPNTAPPPSEPSPEFLEEENIFYVAMTRARLGLHISLPEALAEEEAK RILDRLSQGVPSGEDRGEDERGETLPAPFTGPTPVSPKEATFPLPSLYDRLLSEALNGGRDPLLH LLRDDLARLSALSPTPLPPEVAQALWERARPEEALGAIREGLGAMWREDPYELLRAINALALLG GRNPRKLAKILGDRFPGGEEAEDLLFVARARKRELMGRSLAEFWRGLGASVRHPLLKAYARAR S | 86 |
| K7QTS9 | MRLYVASAGTGKTETLMGELKALLEGGVPLRRVAAVSFTRKSAEELRLRVRRLLEAHREAFWA REALREVHGALFTTLHGFMAEALRHTAPFLGLDPDFRVMDGFLAQALFLEEARSLLFLEGHPE APELLELLEALYEKRSLAEAFTPLPGAEGLLALYERVLARYRARTQEVLGPGDLEAKALLLLRHPE ALGRVAERFSHLLVDEFQDVNPLQGRFLRALEEAGVRWAVGDPKQSIYLFRNARVEVFLRAR AAAEEVRALSRTHRHAKQWELLNRFTTRFFRAEEGNRVEVGVREAEGRVEVHWVLGKLEEAR RAEEARLLAQRLLALRAEGIPFGEMAVLVRARTSLPPLEKALRAAGVPFVRGRGQSFFARPEVR DLYHALRLALAERPYALEDRLSLLAFLRSPFLGLDLSELEEEALRADLPWPLLPKGVQEALEGLRAL ALLPPLEALRRLARDEGFLRRISRRARANLDTLLLLAAGARFPTLEDLLLWLALRAKDPESVELPE GGGGVILLTVHGAKGLEWPWALYDVSRGPSERPPPLLVDEEGRVALKGTEAYRALLKEAERA EREEALRLLYVALSRARDLLLITGSTSQRPGPWAEALQALGLGPDAQDPWVETHPLEAIPPLPPI PQAPQDPRPAPYTPWRGEPRARPPVYSPSAHLKAEAEPLEVLGEGPLEWARAVETLVHY AIARHLDPEDEGAMGGLLRQEVALAFGEGEREALLEEVRLLRAYRSLLSGALPPLEARAEDHA ELPLLLPHKGTVWYGVLDRLYRVGDRWYLDDYKTDQKVRPEAYRFQLALYRKAVLEAWGVE AEARLVYLRHRQWPLSPAELEAAALEGL | 87 |
| D1AF88 | MSSSQVTGRPTFVKDAEIAVEQRRVDQAHARLEEMRAEAQAMIEEGYRQALAGTKGSLVDR DAMVYQAALRVQALNVADDGLVFGRLDLADGQTRYIGRIGVRTRDHEPMVIDWRAPAAEA FYRATPEDPQGWRRRVLHTRGRTVVDLEDDLLDPSAADSLTIVGDGAFIASLARTREGTMRD IVATIQREQDEVIRAPADGTVLVRGAPGTGKTAVALHRVAYLLFRHRRRFGSRGVLWGPNRR FTAYIERVLPSLGEGSATLRSLGDLVEGVSATVHDPPELAALKGSAAMAPVLRRAVTDHPPGA | 88 |

| Entry | Sequence | SEQ ID NO: |
|---|---|---|
| | PDKLRVVHGGVVVELGRPQLDKLRTSLHRRSTGSVNASRRRVAEALLDALWERYVHTGGTEP<br>EPDEPVQGELALWEGILAEGGLAPLDEQDRPSSPADRTSREAFVKNVREQRAFTDFLTAWW<br>PIRRPLDVLRSLGDAARLRRAAGRDLDRAQVELLAASWRRALAGDPPTLSYQDIALLDEIDALL<br>GPPPQPSRATAREEDPYVVDGIDILTGEVVADEDWEPGLQELTTTIERLERARRVDDEVADVR<br>PEYAHIVVDEAQDLSPMQWRMLGRRGRQATINTIVEDPAQSAWEDLEEEARKAMEAALDGP<br>AARRGRSRRPRRRPRHEYELTTNYRNTTEIAAVSARVLRLALPEARPARAVRSSGHRPVIDLVP<br>EEELQAAARRAVRTLLEQVEGTIGVIVPLPGDAWGESDRRALSAGFPERVQVLDVLEAKGLEF<br>DAAVICAPETIAAQSPRGLRVLYVAVSRATQRLTVLTADPVWRRRLAGGESAR | |
| F8A884 | MTSISLDQYQEQAVKAKGNTLVVAGPGAGKTRVLLAKAIHLLEQGIDPEKVLILTFTIKTTQELK<br>ERLASIGIKGVKVDTFHALAYDLLKAKGIKPRLATEEELKALARDLSKRKGLSLKDFRKALDKGEN<br>HYRSLWEEALKLHGLYDFSLLLKEATGHYLQQEKVYLLIDEFQDLNPELTSFLKTFTKAEFFLVGD<br>PAQAIYGFRGACPQVIKEFVDYLAPQIYFLKKSYRVPEKVLNFAETLRETQGFPLEPLEAVQKGG<br>NRLGLSFNKPFNEAKGVAKLVSELLGGLQMEASQRGLAPPEIAILSRVRILLNPIKEAFIKFGIPF<br>QVPSENLKEEISAIESLSDIAKSIKSLKELEAYLAEGPSSVKEAWLESQSLEGFLFRLEMLKTFASISI<br>RKDGVPLLTIHEAKGLEFKVVILVGAEDGLLPFTLLEDYDLAEEKRVAYVAVTRAQESFYFTQVK<br>TGRFLYGHKLSGKVSPFFETLPIKEKSSKTKPKARQKKLFG | 89 |
| A0A087LEB0 | MTISVIDELLEKNKQNMNKTAKDAVEAQLIAYKKEVKKLQEIRPHPYFGRLDFEDEFGRETIYI<br>GKKGLEKDGELIVVDWRTDLGRLYNAYQGVQKTFQIGKENRPVTIHGKRGIVIKNGKVIKVTDI<br>GKSEIIENDNGEKVKYMDDYLKEILTNTEEAHRLRDIIASIQAEQDEIIRLPLKDTIIVQGAAGSGK<br>STIALHRISYLLYQYHEQVKPKDILILAPNEIFLSYIKDIVPEIEIEIGIEQRTFYDWASTYFTDVHDIPD<br>LHEQYVHIYGSTEKEDLIKIAKYKGSLRFKKLLDDFVEYIGNIMIPHGDVVIESGVILSKEEIHQFY<br>HAKEHLPLNVRMKEVKEFIINWRNEQINIRKQQIEDEFEEAYRKWVVTLPEGEERKAVYEALEK<br>AKQLRMKIFQEKMQHEISLIVKKMENIPALLMYKSVFQKKVFEKFHPDIDEELLSLLLKNGRQIK<br>QERFMYEDIAPLIYLDAKINGKKLQYEHIVIDEAQDYSPFQLAIMKDYAKSMTILGDIAQGIFSYV<br>GLDRWEEIESYVFKEKEFKRLHLQTSYRSTKQIMDLANRVLLNSNYDFPLVIPVNRPGDVPTIKK<br>VESIGELYDEIVNSIRIFEEKGYKKIAILTASKQGAIDTYDQLMRRQITQMEVITEGHQALKEKIVII<br>PSYLVKGLEFDAVIIEDVSDETFKDETQHAKMLYMSITRAHHDLHLFYRGNISPLLEERDPSAPP<br>KPRKSFADWLITDINDPYVEPQVEAVKRVKKEDMIRLFDDEEEEFVEEAFEDDRERYYDFHAW<br>LKVWRRWAEMRKQLDEKS | 90 |
| B5Y6N2 | MALPQENLIPPSPSHNHLTLSLRSHIGGFFIYNEDVDSVDLSKLNEAQKQAVTAPPKPLAIIAGP<br>GSGKTRVLTYRALFAVKEWHLPPERILAITFTNKAADELKERLGRLIPEGDRIFAATMHSFAAR<br>MLRYFAPYAGISQNFVIYDDDDSKGLIEDILKQMNMDTKRFRPNDVLNHISAAKARMFDCNT<br>FPEFIRQRYGSWGYYFDTVHQVFMTYERLKEQSQALDFDDLIMVLAQRMEDRPELREMIAGL<br>FDLVMVDEFQDTNFAQYQMLLYMTNPHYSGMNNVTIVGDPDQSIYGFRAAEYYNIKRFIDD<br>YNPEWFLDLNYRSNRTIVDSASALINDSPSALFERKLESIKGAGNKLILRRPFDDADAAITAAFE<br>VQRLHKMGIPYEEIAVLMRTRALTARVEREFATRNIQYHIIGGVPFFARREIKDILAYLRLSRNA<br>MDRVSLKRILTMKKRGFGTASLEKLFNFAEENKLTLLEAMKAAVESLLFKKLSMNDYLESLYTLI<br>QTIQEIAEPSQAIYLVMEQENLLDHFRSISKSEEEYIERTENVKQLISIAEESADMDDFLQRSALG<br>TRENNGGVEGVAISTVHGVKGLEFQAVILYYVTDGFFPHSLSVTTAEKEEEERRLLYVAMTRAKE<br>HLIFYVPYKQPWGNGFEQMARPSPFLRSIPKELWDGKPNEIESLYAPYSPQQKWSE | 91 |
| D7BJL0 | MNDPIRHKEGPALVFAGAGAGKTRTLTQRVKWLVEEGEDPYSITLVTFTNKAAGEMKERIAR<br>LVEAPLAEAVWVGTFHRFCLQSLQVYGREIGLEKVAVLDSAAQRKLAERIIAGLFPAKPPRGFT<br>PMAALGAVSRAANSGWDDIQLATMYADLTEKIVNFRWAYEANKKGLALDYDDLLLRGVRL<br>LKLSEGAARMVRRRAAYLMVDEFQDTNGVQLELVRAIAPGTSPNLMWGDPDRSIYGWRG<br>ANYRTILEFRQHYPGAAVYGLYTNYRSQAGWEVANRIIAQNATRKPEMQEAHLPQSEEPFL<br>VAKNRWEEAHFVAQAVEFYRGQGIALEEMAVLMRANFLSRDLEQALRLRGIPYQFTGGRSFF<br>ERREIQLGMAVLKVLANPKDSLAVAALVEEMVEGAGPLGIQKVLEAAKAANLSPLEAFRNPA<br>MVKGLRGKEVQAEAMRLAEVLQDQVARLAAEAPEYHALLKETLDRLGFEAWLDRLGEESEQ<br>VYSRKANLDRLLQGMQEWQEVNPGAPLQDLVGILLLEAGDTPAEEGQGVHLMTVHASKG<br>MEFRWFVIGLNEGLFPLSKASSSFEGLEEERRLMYVAVTRAKEVLHLSYAADGWSRFAQEAR<br>VPVEEYDPRLGWSGRQNQQALKALLEIA | 92 |
| E8MZN5 | MDSLEHLNPQQRAAVTASAGPVLVLAGPGSGKTRVLTFRIGYLLSQLGVAPHHILAVTFTNKA<br>AREMQSRVEKLLGHSLQGMWLGTFHAICARILRREQQYLPLDANFVIFDEDDQQALIKRALR<br>DLNLDEKLYRPTSVHAAISNAKNNLILPEDYPTATYRDEWARVYKRYQELLVSSNAVDFDDLLL<br>YAWKLLNEFSTVREQYARRFEHILVDEFQDTNLAQYELVKLLASYHRNLFVVGDEDQSIYRWR<br>GADYRNVLRFEEDFPDRQKILLEQNYRSTQRVLDAAQAVINRNRNRTPKRLKSTPEHGEGEKL<br>VLYEAVDDYGEAAFVVDTIQQLVAGGKARPGDFAIMYRTNAQSRLLEEAFLRAGVPYRLVGA<br>MRFYGRREVKDMIAYLRLVQNPADEASLGRVINVPPRGIGDKSQLALQMEAQRTGRSAGLIL<br>MELGREGKDSPHWQALGRNASLLADFGSLLGEWHRLKDEISLPSLFQRILNDLAYREYIDDNT<br>EEGQSRWENVQELLRIAYEYEEKGLTAFLENLALVSDQDTLPENVEAPTLLTLHAAKGLEFPIVF1<br>TGLDDGLIPHNRSLDDPEAMAEERRLFYVGLTRAKKRVYLVRAAQRSTYGSFQDSIPSRFLKDI<br>PADLIQQDGRGRRMGRSWQSESRRSWDDNYAGTVVGSRPERAKPSHAPILQPRFKPGMRV<br>KHPSWGEGLVVDSRIQDEDETVDIFFDSVGFKRVIASIANLEILS | 93 |
| L0INW7 | MDINGQIIKLNRNKTQGTLKLTNGQKIKFKINSDSVKPIFLYEYYKFKGNMIEDTLIIDDIYGIAND<br>ININDFTELFPSVAHDKINNICNRFNVLHVGNLIDLINDENFITVVNDTIGEEKATIFLSNLQKIKD<br>RQEYIDVWDIIKKTNPTFDINVPIKIVNALKYRASMNNITVSGLKIKESPWIIEQLDIFDSITERKKIA<br>ENIATHYGLSNDSNKAVISYAIAMTNNYIQQGHSYIPYYTLVSRVSNSLKLDFNKVNDTLKFLPN<br>DNKSGYLIRDNKYKDEINEYNSDKKIGYSVYLPKIFHMEKYIADIISSILKKKSTINKIELQKNLKLY<br>RSENKLIFSKEQEEAIFSISDNKITVITGGAGIGKITVIKAIIDLVNKMGYTPVVLAPTGIASQRVA<br>PNVGSTIHKYARIFDTYDPVFDEIEEENKENNSGKVIIVDEMSMITVPVFAKLLSVTLDADSFIFVG<br>DPNQLPPIGAGGVFEALIELGNKNINNINTVVLNQSFRSKNSIVKNAQNILEDKPIYEDDNLNIIE | 94 |

TABLE 17-continued

| Entry | Sequence | SEQ ID NO: |
|---|---|---|
| | AKSWNKIADEVVNLIRKLLDNGVQYSDIMVLSSKRGEGKNGVSLLNERIRKEIFNNKGKYAVG DIVITTRNDYDNKSSYFRSKELKKYINSIRHEERPTIFNGTVGVIKDISDNEVIIEYNTPMPVEAKY NMEELDWYIEYGFAITVHKAQGGQAKYIIFASDEPRNISREMLYTAITRCKNGKVFLIGGENED WKIKKEHSFVLSKLKYRILDNIHQQEKESKINSKIVLINQ | |
| D3PR99 | MSDLLSSLNPSQQEAVLHFEGPALVVAGAGSGKTRTVVHRIAYLLRERRVYPAEILAVTFTNKA AGEMKERLEKMVGRPARDLWVSTFHAAAVRILRTYGEYVGLRPGFVIYDEDDQNTLLKEVLK ELELEAKPGPFRAMIDRIKNRGAGLAEYMREAPDFIGGVPKDAAAEVRYKQSGLRMQGALD FNDLLLLTIELFEQHPEVLHKVQQRARFIHVDEYQDTNPVQYKLTRLLAGERPNLMVVGDPDQ SIYGFRSADINNILDFTKDYPGARVIRLEENYRSSSSILRVANAVIEKNALRLEKVLRPTRPGGEPV RLYRAPNAREEAAFVAREIVKLGNFQQIAVLYRTNAQSRLLEEHLRRANVPVRLVGAVGFFER REIKDLLAYGRVAVNPADSINLRRIVNIPPRGIGATTVSRLVEHAQKTGTFVFEAFRVAEQVISR PQQVQAFVRLLDELIEAAFESGPTAFFQRVLEQTGFREALKQEPDGEDRLQNVEELLRAAQD WEEEEGGSLSDFLDSVALTAKAEEPQGDAPAEAVTLMTLHNAKGLEFPTVFLVGLEENLLPHR NSLHRLEDLEEERRLFYVGITRAQERLYLSYAEERETYGKREYTRPSRFLEDIPQDLLKEVGAFGD SEVRVLPQARPEPKPRTQLAEFKGGEKVRHPKFGSGTVVAAMGGEVTVMFPGVGLKRLAVK FAGLERLE | 95 |
| D3PLL2 | MKVRVASAGTGKTASLVLRYLELIAKGTPLRRIAGVTFTRKAADELRVRVAAAIEEVLQTGRHLS FVASGGSRAAFQEAAREIAGATLSTIHGFMAQCLRLAAPLLHLDPDFSMLGDWEAQAIFEEE WQTLRYLAQDAHHPLFGLVSDELTEPLLHLFSRRSQAEVFEPAAGEANQHLLQVYQTVYAAY EARLGANLLSPSELERKALELARNDRAMKRVLERVRVLLVDEYQDVNPVQGAFFAALEQARLP IEIVGDPKQSIYAFRNADVSVFRKALREGKSEPPLTHSYRHSRVLVRFLNGLIGYLAKEGLGFGLE EAPPVEGVRPEQGRLEVHWVVGELPEELRKQEARVLAGRLAALRGPIEYSQMAVLVRSYGS VRFLEEALAEAQIPYVLLQGRGYYEREVRDLYHALRAALDPRGLSLAVFLRSPFGQHTEAGPL KPLELPQIEGVLRADDPLGRLAQHWPSVYERLRQIQAQVRLMAPLEVLKFLIRAPLMDGRPYH DFLEPRARENVDALLFYFAPRPPQNLEGLLERLELLSRQADAGDVPQSGEGVQILTVHQAKGL EWPLVAVFDLGRMNVHRPQPLYLGQGPNGGDGGRLRRWVALPETPQFEAFRQQVKLQEE EESYRLLYVAASRARDILLLTASASHGQPEGWGKVLEAMNLGPASKPYHRPDFHLQTWPYQ PAPPVVRVLSQPAPLQPSPWVDARFEPEPFPPLFSPSALKRLEAEPLPLPDPEEGEAVPGRARAI GTLVHYAIGQNWRPDNPQHLANLEAQEVMFPFGPDERRGIMAEVQALLEHYQELLGRALP WPRDEDYPEFAVALPLGSTVWQGVIDRLYRVGQQWYLEDYKTDQEMRPERYLVQLGIYLAA IRQAWQIEPEVRLVYLRFGWVERLDKAILEAALGEIMPKGEGLRR | 96 |
| Q9RTI9 | MTSSAGPDLLQALNPTQAQAADHFTGPALVIAGAGSGKTRTLIYRIAHLIGHYGVHPGEILAVT FINKAAAEMRERAGHLVPGAGDLWMSTFHSAGVRILRTYGEHIGLRRGFVIYDDDDQLDIIK EVMGSIPGIGAETQPRVIRGIIDRAKSNLWTPDDLDRSREPFISGLPRDAAAEAYRRYEVRKKG QNAIDFGDLITETVRLFKEVPGVLDKVQNKAKFIHVDEYQDTNRAQYELTRLLASRDRNLLVVG DPDQSIYKFRGADIQNILDFQKDYPDAKVYMLEHNYRSSARVLEAANKLIENNTERLDKTLKPV KEAGQPVTFHRATDHRAEGDYVADWLTRLHGEGRAWSEMAILYRTNAQSRVIEESLRRVQI PARIVGGVGFYDRREIRDILAYARLALNPADDVALRRIIGRPRRGIGDTALQKLMEWARTHHTS VLTACANAAEQNILDRGAHKATEFAGLMEAMSEAADNYEPAAFLRFVMETSGYLDLLRQEG QEGQVRLENLEELVSAAEEWSQDEANVGGSIADFLDDAALLSSVDDMRTKAENKGAPEDAV TLMTLHNAKGLEFPVVFIVGVEQGLLPSKGAIAEGPSGIEEERRLFYVGITRAMERLLMTAAQN RMQFGKTNAAEDSAFLEDIEGLFDTVDPYGQPIEYRAKTWKQYRPTVPAATTAVKNTSPLTAE LAYRGGEQVKHPKFGEGQVLAVAGVGERQEVIVHFASAGTKKLMVKFANLTKL | 97 |
| M1E5C5 | MDLNLNEDQKRAVYSDSRALLIVAGAGTGKTRVLTTRAARLIKENPDARYLLLTFTKKAAREM TTRVRELIEEDTKNRLYSGTFHSFCSNIIRRSERVGLINDFVIIDESDSLDLMKKVFSRIYSKEKID SLIFKPKDILSLYSYARNNNQDFIEIVQRKYKYVNFEDIKKIISLYELNKKERNYLDFDDLLMYGLLA IKTLEKSPFDEVLVDEFQDTNQIQAEMLYYFYDLGSRISAVGDDAQSIYSFRGAYYENMFNFIKR LDAEKIILSSNYRSTQQILDIANSIIQQSSYSSIKKELVANVRLKENVKPKLVIVSDDWEEARYVARE MQKFGEKGLKVAALYRAAYIGRNLESQLNSMGIKYSFYGGQKLTESAHAKDFMSFLRVFVNP KDEIALIRILKMFPGIGEKKAEKIKDAVISGDNLKKALSKEKNLEELNIFFDKLFKITDWHDLLELVF DFYKDIMNRLYPENYEEREEDLIKFMDMSSNYDNLVEYLEAFTLDPVEKSEFDNNNVILSTIHS AKGLEFDVVFLLSVIESVYPHFRAQSTDEIEEEERRLFYVAITRAKQRLIFTFPRHSKKSRGYFAKNTI SPFLREKDNYLEVFIAR | 98 |
| Q5SIE7 | MSDALLAPLNEAQRQAVLHFEGPALWAGAGSGKTRTVVHRVAYLVARRGVFPSEILAVTFT NKAAEEMRERLRGLVPGAGEVVVSTFHAAALRILRVYGERVGLRPGFVVYDEDDQTALLKEV LKELALSARPGPIKALLDRAKNRGVGLKALLGELPEYYAGLSRGRLGDVLVRYQEALKAQGALD FGDILLYALRLLEEDEEVLRLVRKRARFIHVDEYQDTSPVQYRFTRLLAGEEANLMAVGDPDQG IYSFRAADIKNILDFIRDYPEARVYRLEENYRSTEAILRFANAVIVKNALRLEKALRPVKRGGEPV RLYRAEDAREEARFVAEEIARLGPPWDRYAVLYRTNAQSRLLEQALAGRGIPARWGGVGFFE RAEVKDLLAYARLALNPLDAVSLKRVLNIPPRGIGPATVVARVQLLAQEKGLPPWEALKEAART FSRPEPLRHFVALVEELQDLVFGPAEAFFRHLLEATDYPAYLREAYPEDAEDRLENVEELLRAAK EAEDLQDFLDRVALTAKAEEPAEAEGRVALMTLHNAKGLEFPWFLVGVEEGLLPHRNSVSTL EGLEEEERRLFYVGITRAQERLYLSHAEEREVYGRREPARPSRFLEEVEEGLYEVYDPYRRPPSPPP HRPRPGAFRGGERWHPRFGPGTVVAAQGDEVTVHFEGFGLKRLSLKYAELKPA | 99 |
| B5YD55 | MNNQFDSEKKIFIIPSRKKKEFLERIEKDLNEEQRKVVLEADGPSLVIAGPGSGKTRTIVYRVGYL VALGYSPKNIMLLTFTNQAARHMINRTQALIRESIEEIWGGTFHHVGNVRILRVYGKIIGINEQY NILDREDSLDLIDECLEELFPEENLGKGILGELFSYKVNTGKNWDEVLKIKAPQIIDKIEIVQKVFER YEKRRELNVLDYDDLLFFWYRLLLESEKTRKILNDRFLYILVDEYQDTNWLQGEIIRLTREENKN ILWGDDAQSIYSFRGATIENILSFPEIFPGTRIFYLVFNYRSTPEIINLANEIIKRNTRQYFKEIKPVL KSGSKPKLVWVRDDEEEAQFVEVIKELHKEGVKYKDIGVLFRSNYHSMAVQMELTLQGIPYE VRGGLRFFEQAHIKDMISLLKILFNPQDEISAQRFFKLFPGIGRAYAKKLSQVLKESKDFDKIFQ | 100 |

TABLE 17-continued

| Entry | Sequence | SEQ ID NO: |
|---|---|---|
| | MQFSGRTLEGLRILKNIWDKIKVIPVQNFSEILRVFFNEYYKDYLERNYPDFKDREKDVDQLILLS ERYDDLEKFLSELTLYTYAGEKLLEEEEEKDFVVLSTIHQAKGLEWHAVFILRLVQGDFPSYKS | |
| F6DJA4 | MDNIEEERRLFYVAVTRAKRELYVITYLTRKVKDMNVFTKPSIFLEELPYKELFEEWIVQREI MLSPFGGEEETKAIPLEEEILLAWRVFSAALPPNFLAPVSASLHTLVREAEGKEGAELEAYAWER LEELARTSWKDAIQSFLEVAAEKPEVLRAGLLWFRTWNRLSPEEREALYRKAERFKPTAELASK ASFLQGPPPPPKPLSPSVQAARSSPPRFTPTPEQEEAVRAFLSREDMKLVAVAGSGKTTTLRL MAQSAPKERLLYVAFNRSVRDEAERTFPGNVEVLTLHGLAHRHWRGSGAYQRKLAARNGR VTPGDVLEALELPRERYALAYVIRSTLEAFLRSASEVPTPAHIPPEYREVLQRRDKDPFSERYVLK AVRLIWKLMQDPDDSFPLSFDGFVKIWAQAGAKIRGYDAVLVDEAQDLSPVFLQVLEAHRGE LRRVYVGDPRQQIYGWRGAVNAMDKLDAPERKLTWSFRFGEDLARGVRRFLAHVGSPIELH GKAPWDTEVSLARPEPPYTALCRTNAGAVEAVTSFLLEEGREGARVFVVGGVDEIAWLLRDA HLLKVGGEREKPHPELALVENWEELEELAKEVNHPQARMLVRLARRYDLLELARLLKHAQADE EGKADLWSTLHKAKGREWDRWLWGDFIPVWDEKVREFYRKQGALDELKEEENVVYVALT RARRFLGLDQLPDLHERFFQGEGLVKPPSVSPLSVGGAGVSADLLRELEVRVLAKLEDRLKEVA EVLAALLVEEASKAVAEAMREMGLLGEEG | 101 |
| F6DIL2 | MSDALLAPLNEAQRQAVLHFEGPALWAGAGSGKTRTVVHRVAYLVARRGVFPSEILAVTFT NKAAEEMRERLRGLVPGAGEVWVSTFHAAALRILRVYGERVGLRPGFVVYDEDDQTALLKEV LKELALSARPGPIKALLDRAKNRGVGLKALLGELPEYYAGLSRGRLGDVLVRYQEALKAQGALD FGDILLYALRLLEEDEEVLRLVRKRARFIHVDEYQDTSPVQYRFTRLLAGEEANLMAVGDPDQG IYSFRAADIKNILDFIRDYPEARVYRLEENYRSTEAILRFANAVIVKNALRLEKALRPVKRGGEPV RLRYRAEDAREEARFVAEEIARLGPPWDRYAVLYRTNAQSRLLEQALAGRGIPARWGGVGFFE RAEVKDLLAYARLALNPLDAVSLKRVLNIPPRGIGPATVVARVQLLAQEKGLPPWEALKEAART FPRAEPLRHFVALVEELQDLVFGPAEAFFRHLLEATDYPTYLREAYPEDAEDRLENVEELLRAAK EAEDLQDFLDRVALTAKAEEPAEAEGKVALMTLHNAKGLEFPWFLVGVEEGLLPHRNSLSTLE GLEEEERRLFYVGITRAQERLYLSHAEEREVYGRREPARPSRFLEEVEEGLYEVYDPYRRPPSPPPH RPRPGAFRGGERWHPRFGPGTVVAAQGDEVTVHFEGVGLKRLSLKYAELKPA | 102 |
| F6DJ67 | MEANLYVAGAGTGKTYTLAERYLGFLEEGLSPLQWAVTFTERAALELRHRVRQMVGERSLG HKERVLAELEEAAPIGTLHALAARVCREFPEEAGVPADFQVMEDLEAALLLEAWLEEALLEALQ DPRYAPLVEAVGYEGLLDTLREVAKDPLAARELLEKGLGEVAKALRLEAWRALRRRMEELFHG ERPEERYPGFPKGWRTEEPEWPDLLAWAGEVKFNKKPWLEYKGDPALERLLKLLGGVKEGF SPGPADERLEEVWPLLRELAEGVLARLEERRFRARRLGYADLEVHALRALEREEVRAYYRGRFR RLLVDEFQDTNPVQVRLLQALFPDLRAWTVVGDPNQSIYSFRRADPKVMERFQAEAAKEGL RVRRLEKSHRYHQGLADFHNRFFPPPLLPGYGAVSAERKPEGEGPWVFHFQGDLEAQARFIAQ EVGRLLSEGFQVYDLGEKAYRPMSLRDVAVLGRTWRDLARVAEALRRLEVPAVEAGGGNLLE TRAFKDAYLALRFLGDPKDEEALVGLLRSPFFALTDGEVRRLAEARGEGETLWEVLEREGDLSA EAERARETLRGURRKALEAPSRLLQRLDGATGYTGVAARLPQGRRRVKDWEGILDLVRKLEV GSEDPFLVARHLRLIIRSGLSVERPPLEAGEAVTLLTVHGAKGLEWPWFVLNVGGWNRLGS WKNNKTKPLFRPGLALVPPVLDEEGNPSALFHLAKRRVEEEEKQEENRLLYVAATRASERLYLL LSPDLSPDKGDLDPQTLIGAGSLEKGLEATEPERPWSGEEGEVEVLEERIQGLPLEALPVSLLPLA ARDPEAARRRLLGEPEPEGGEAWEPDGPQETEEEVPGGAGVGRMTHALLERFEAPEDLERE GRAFLEESFPGAEGEEVEEALRLARTFLTAEVFAPYRGNAVAKEVPVALELLGVRLEGRADRVG EDWVLDYKTDRGVDAKAYLLQVGVYALALGKPRALVADLREGKLYEGASQQVEEKAEEVLRR LMGGDRPEA | 103 |
| G8N9P8 | MDAFPSGKPLDEAWLSSLNEAQRQAVLHFEGPALWAGAGSGKTRTVVHRVAYLMARRGV YPSEILAVTFTNKAAEEMRERLKAMVKGAGELWVSTFHAAALRILRFYGERVGLKPGFVVYDE DDQTALLKEVLKELGVSAKPGPIKALLDRAKNRGEPPERLLADLPEYYAGLSRGRLLDVLHRYQ QALWAQGALDFGDILLLALKLLEEDPEVRKRVRKRARFIHVDEYQDTSPVQYRLTKLLAGEEAN LMAVGDPDQGIYSFRAADIKNILQFTEDFPGAKVYRLEENYRSTERILRFANAVIVKNALRLEKT LRPVKSGGEPVRLFRARDAREEARFVAEEVLRLGPPYDRVAVLYRTNAQSRLLEQALASRGIGA RVVGGVGFFERAEVKDLLAYARLALNPLDAVSLKRVLNTPPRGIGPATVEKVQAIAQEKGLPLY EALVAAQVLPRPEPLRHFLALMEELMDLAFGPAEAFFRHLLEATDYPAYLKEAYPEDLERLE NVEELLRAAREAEGLMDFLDKVALTARAEEPGEAAGGKVALMTLHNAKGLEFPVVFLVGVEEG LLPHRSSVSTLEGLEEERRLFYVGVTRAQERLYLSYAEEREVYGRPEASRPSRFLEEVEEGLYEEY DPYRLPPPKVPPPHRAKPGAFRGGEKVVHPRFGLGTVVAASGDEVTVHFDGVGLKRLSLKY ADLRPA | 104 |
| Q1J014 | MPDLPASSLLAQLNPNQAQAANHYTGPALVIAGAGSGKTRTLVYRIAHLIGHYGVDPGEILAV TFINKAAAEMRERARHLVEGADRLWMSTFHSAGVRILRAYGEHIGLKRGFVIYDDDDQLDIL KEIMGSIPGIGAETHPRVLRGILDRAKSNLLTPADLARHPEPFISGLPREVAAEAYRRYEARKG QNAIDFGDLITETVRLFQEVPAVLERVQDRARFIHVDEYQDTNKAQYELTRLLASRDRNLLVVG DPDQSIYRFRGADIQNILDFQKDYLDAKVYMLEQNYRSSARVLTIANKLIENNAERLEKTLRPVK EDGHPVLFHRATDQRAEGDFVAEWLTRLHAEGMRFSDMAVLYRTNAQSRVIEESLRRVQIP AKIVGGVGFYDRREIKDVLAYARLAINPDDDVALRRIIGRPKRGIGDTALERLMEWARVNGTSI LTACAHAQELNILERGAQKAVEFAGLMHAMSEAADNDEPGPFLRYVIETSGYLDLLRQEGE GQVRLENLEELVSAAEEWSRENEGTIGDFLDDAALLSSVDDMRTKQENKDVPEDAVTLMTL HNAKGLEFPVVFIVGTEEGLLPSKNALLEPGGIEEERRLFYVGITRAMERLFLTAAQNRMQYGK TLATEDSRFLEEIKGGFDTVDAYGQVIDDRPKSWKEYRPTESARPGAVKNTSPLTEGMAYRGG EKVRHPKFGEGQVLAVAGLGDRQEVTVHFPSAGTKKLLVKFANLIRA | 105 |
| Q745W4 | MALRPTEEQLKAVEAYRSGQDLKVVAVAGSGKTTTLRLMAEATPGKRGLYLAFNRSVQQEA ARKFPRNVRPYTLHALAFRMAVARDEGYRAKFQAGKGHLPAQAVAEALGLRNPLLLHAVLGT LEAFLRSEAASPDPGMIPLAYRTLRAGTKTWPEEEAFVLRGVEALWRRMTDPKDPFPLPHGA YVKLWALSEPDLSFAEALLVDEAQDLDPIFLKVLEAHRGRVQRVYVGDPRQQIYGWRGAINA | 106 |

TABLE 17-continued

| Entry | Sequence | SEQ ID NO: |
|---|---|---|
| | MDRLEAPEARLTWSFRFAETLARFVRNLTALQDRPVEVRGKAPWATRVDAALPRPPFTVLCR<br>TNAGVVGAVVVTHEVHRGRVHVVGGVEELVHLLRDAALLKKGEKRTDPHPDLAMVETVVEE<br>LEALAEAGYAPAYGVLRLAQEHPDLEALAAYLERAVVTPVEVAAGVVVSTAHKAKGREWDRV<br>VLWDDFYPWWEEGAAARVNWGSDPAHLEEENLLYVAATRARKHLSLAQIRDLLEAVDRMG<br>VYRVAEEATRAYLLLSAEVLRGVATDPRVPAEHRVRALKALGYLERGEEALDSPGKPGGQG | |
| Q72IS0 | MSDALLAPLNEAQRQAVLHFEGPALWAGAGSGKTRTVVHRVAYLVARRGVFPSEILAVTFT<br>NKAAEEMRERLRGLVPGAGEVWVSTFHAAALRILRVYGERVGLRPGFVVYDEDDQTALLKEV<br>LKELALSARPGPIKALLDRAKNRGVYGLKALLGELPEYYAGLSRGRLGDVLVRYQEALKAQGALD<br>FGDILLYALRLLEEDEEVLRLVRKRARFIHVDEYQDTSPVQYRFTRLLAGEEANLMAVGDPDQG<br>IYSFRAADIKNILDFIRDYPEARVYRLEENYRSTEAILRFANAVIVKNALRLEKALRPVKRGGEPV<br>RLYRAEDAREEARFVAEEIARLGPPWDRYAVLYRTNAQSRLLEQALAGRGIPARWGGVGFFE<br>RAEVKDLLAYARLALNPLDAVSLKRVLNIPPRGIGPATVVARVQLLAQEKGLPPWEALKEAART<br>FPRPEPLRHFVALVEELQDLVFGPAEAFFRHLLEATDYPAYLREAYPEDAEDRLENVEELLRAAK<br>EAEDLQDFLDRVALTAKAEEPAEAEGRVALMTLHNAKGLEFPWFLVGVEEGLLPHRNSVSTL<br>EGLEEEERRLFYVGITRAQERLYLSHAEEREVYGRREPARPSRFLEEVEEGLYEVYDPYRRPPSPPP<br>HRPRPGAFRGGERWHPRFGPGTVVAAQGDEVTVHFEGFGLKRLSLKYAELKPA | 107 |
| F2NK78 | MDLLRDLNPAQREAVQHYTGPALWAGAGSGKTRTVVHRIAYLIRHRGVYPTEILAVTFTNKA<br>AGEMKERLARMVGPAARELWVSTFHSAALRILRVYGEYIGLKPGFVVYDEDDQLALLKEVLG<br>GLGLETRPQYARGVIDRIKNRMWSVDAFLREAEDWVGGLPKEQMAAVYQAYEARMRALG<br>AVDFNDLLLKVIGLFEAHPEVLHRVQQRARFIHVDEYQDTNPAQYRLTRLLAGAERNLMWG<br>DPDQSIYGFRNADIHNILNFEKDYPDARVYRLEENYRSTEAILRVANAVIEKNALRLEKTLRPVRS<br>GGDPVFLYRAPDHREEAAFVAREVQRLKGRGRRLDEIAVLYRTNAQSRVLEEAFRRQNLGVRI<br>VGGVGFYERREVKDVLAYARAAVNPADDLAVKRVLNVPARGIGQTSLAKLSQLAETARVSFFE<br>ALRRAGEVLARPQAQAVQRFVALIEGLANAAYDTGPDAFLRLVLAETGYADMLRREPDGEAR<br>LENLEELLRAAREWEEQHAGTIADFLDEVALTARAEEPEGEVPAEAVTLMTLHNAKGLEFPW<br>FIVGVEEGLLPHRSSTARVEDLEEEERRLFYVGITRAQERLYLTLSEERETYGRREAVRASRFLEDIP<br>EAFLQPLSPFGEPLGAGREPVAVRPTRRSSAAGGFRGGEKVRHPRFGQGLWAASGEGDRQE<br>VTVHFAGVGLKKLLVKYAGLERIE | 108 |

TABLE 18

```
>tr|L0B9N8|L0B9N8_9EURY UvrD Rep helicase SFI OS = Thermococcus
sp. EXT9 GN = e9a-1 PE = 4 SV = 1 (SEQ ID NO: 58)
MSEALPVTSFEFSLPEESVIKIYGPPGTGKTTTLVRIIEHLIGFHDHTEFLESYGLSLLF
GQYGAEDVIFMTFQTSALKEFEARTGIKVKDRQNKPGRYYSTVHGIAFRLLIDSGAIDGV
ITQNFGSLSPEDWFRLFCRQNGLRFESSEMGYSNVFNDGNRLWNALTWAYNVYYPTKGPK
ARHEALKRLAPKLWKYPPLWEEYKTEKGILDYNDMLVKAYEGLKSGEIDPRNLPGHKYSP
KVLIVDEFQDLSPLQFEIFRLLANYMDLVIIAGDDDQTIFSYQGADPRLMNYVPGREIVL
KRSYRLPIVVQAKAMTVISKTRHRKEKTVAPRTDLGDFKYKLFWFPDFLNDLVREAQEGH
SIFILVRTNRQVLKLGKELILAGVHFRHLKVDYRSIWEAGSKEWGTFRDLVQALLKARRG
EELEIADLVTILYYSELIDWHLGEKLPEKERYKKIAEQMEKTIEAIEKGLMPFDILKVKD
DPFSVLDLEKIESLSPRHGKVAVELIREIMKEKSQVVSVPRDAEIYLDTLHASKGREADV
VFLINDLPRKWSSILKTREELDAERRVWYVGLTRARKKVYLLNGKHPFPVL >tr|L0B9J0|L0B9J0_9EURY UvrD Rep helicase SFI OS = Thermococcus
sp. IRI48 GN = i48-1 PE = 4 SV = 1 (SEQ ID NO: 59)
MRVKIYGPPGTGKTTTLQRTIDYTLGNSSEPPIPLPESFPTDLEPKNLAFVSFTNTAIDV
IGKRTGITTRSKEAPYMRTIHGLILSVLAEHFDPVAVDNLGKLADIQAEFSMRMGYYYSK
DPFEFAEGNMKFNVITRALELYLPKTGDVEEALKLIDNREDRKFALAWYRYKRQKKIMDF
DDDILVIGYEHLEDFYVPVEVAFIDEGQDNGPLDYILLEKGFEGAKFVFLAGDPLQSIYGF
KGADPRLFVRWKADKEIILPRSYRLPKKVWLLSQSWALSLGIKGAVVRYAPSEKLGRVSR
MKFIEALSYAVEQAKRGRSVLILARTNSLVKFVGNILSIEFGVAYGHLKRASYWESHLLK
FIEGLQMLKLWDGVTPIKVQDTKPITGLIRKLKDKHAREVLRRWRDSRQWSLEVQAVLQR
IKKNPSEYFYITDFDRQALKAYFSKARLDLTEELIIDTIHAAKGEEADVVIFLDFIPTRS
EERINPEELQEKLVAYGFTRAREELIIVPTPAIKYHPMRDFMGVRQILGVVNFHKHLLI
KELVGGL >tr|L0BAD9|L0BAD9_9EURY UvrD Rep helicase SFI OS = Thermococcus
sp. IRI33 GN = i33-1 PE = 4 SV = 1 (SEQ ID NO: 60)
MSEALPVTSFEFSLPRERIIKLYGAPGTGKTTTLVKIIEHLIGFQDHTEFLENYGINLPF
GQYEPGEVIFMTFQTSALKEFEARTGIKVKDRQNKPGRYYSTVHGIAFRLLIDSGAVDGL
ITQNFGSLSPEDWFRNFCRQNGLRFESSEMGYSNVFNEGNQLWNALTWAYNVYYPTKGPK
ARYEALKRLAPKLWKFPPLWEEYKKGRGILDYNDMLVRAYEGLRSGEIDPRNLPGHKYSP
KVLIVDEFQDLSPLQFEIFRLLANHMDLVIIAGDDDQTIFSYQGADPRLMNYVPGLEVVL
RKSHRLPIVVQAKALTVISKTRHRKEKTVAPRTDLGDFKYKLFWFPDFLNDLVREAQEGH
SIFILVRTNRQVLKLGKELILAGVHFEHLKVDYRSIWEAGSKEWGTFRDLVQALLKAKRG
EELEVADLVTILYYSELIDWHLGEGISEKERYKKIAEQMEKTIEAIEKGLMPFDVLRVKE
NPFSVLDLEKIESLSPRHGKVAVELIKELMKEKSQVVSIPKDARIYLDTLHASKGREADV
VFLINDLPRKWSSILKTREELDAERRVWYVGLTRARKKVYLLNGKHPFPVL
```

TABLE 18-continued

>tr|L0BAT5|L0BAT5_9EURY UvrD Rep helicase OS = Thermococcus sp.
AMT7 GN = a7-1 PE = 4 SV = 1 (SEQ ID NO: 61)
MSEALSITSFDFTLPRERIIKIYGPPGTGKTTTLVRIIEHLIGFQDHTEFLENYGLSLPF
GQYGAEDVIFMTFQTSALKEFEARTGIKVKDRQNKPGRYYSTVHGIAFRLLIDSGAVDGL
ITQNFGSLSPEDWFRHFCRQNGLRFESSEMGYSNIFNEGNQLWNALTWAYNVYYPTKGPK
ARYEALKRLAPKLWKFPPLWEEYKKEKGILDYNDMLIRAYEGLKSGEIDPRNLPGHKYSP
KVLIVDEFQDLSPLQFEIFRLLANHMDLVIIAGDDDQTIFSYQGADPRLMNYVPGREIVL
SKSYRLPIVVQAKALTVISKTRHRKEKTVAPRTDLGDFKYKLFWFPDFLNDLVREAQEGH
SIFILVRTNRQVLKLGKELILAGVHFEHLKVDYRSIWEAGSKEWGTFRDLVQALLKAKKG
EELEVADLVTILYYSELIDWHLGERISEKERYKKIAEQMEKTIEAIEKGLMPFDILKVKE
NPFSVLDLEKIESLSPRHGKVAVELIKELMKEKSQVVSIPKDAKIYLDTLHASKGREADV
VFLINDLPRKWSNILKTREELDAERRVWYVGLTRARKKVYLLNGKHPFPIL >tr|W8NUG2|W8NUG2_9EURY Superfamily I DNA and RNA helicase and
helicase subunits OS = Thermococcus nautili GN = BD01_1302 PE = 4
SV = 1 (SEQ ID NO: 62)
MNENEKLSKFIAKLKVLIEMERKAEIEAMRAEMRRLSGREREKVGRAVLGLNGKVIGEEL
GYFLVRYGREREIKTEISVGDLVVISKRDPLKSDLVGTVVEKGKRFITVALETVPEWALK
SVRIDLYANDITFKRWLENLENLRESGRRALELYLGLREPEGGEEVEFTPFDKSLNASQR
RAIAKALGSPDFFLIHGPFGTGKTRTLVELIRQEVARGNRVLATAESNVAVDNLVERLVD
SGLKVVRVGHPSRVSRGLHETTLAYLMTQHELYGELRELRVIGENLKEKRDTFTKPAPKY
RRGLTDRQILRLAEKGIGTRGVPARLIREMAQWLKINEQVQKTFDDARKLEERIAREIIR
EADVVLTTNSSAGLEVVDYGSYDVAIIDEATQATIPSVLIPINRAGRFVLAGDHKQLPPT
ILSEKAKELSKTLFEGLIERYPGKSEMLTVQYRMNERLMEFPSREFYDGRIEADESIRRI
TLADLGVKSPEDGDAWAEVLKPENVLVFIDTARREDRFERQRYGSESRENPLEARLVKEA
VEGLLRLGVKAEWIGVITPYDDQRDLISSLLPEEIEVKTVDGYQGREKEVIVLSFVRSNR
KGELGFLKDLRRLNVSLTRAKRKLILIGDSSTLSSHPTYRRLVEFVRERETVVDAKRLIG
KVKIK >tr|B6YXQ7|B6YXQ7_THEON UvrD/REP helicase OS = Thermococcus
onnurineus (strain NA1) GN = TON_1380 PE = 4 SV = 1 (SEQ ID NO: 63)
MTAPIPTTYSILGVAGAGKTTQLIDLLNYLNFENSRNEKIWERHFEPVELNRIAFISFSN
TAIQEIANRTGIEIKARKKSAPGRYFRTVTGLAEVLLYENNLMTFEEVRSVSKLEGFRIK
WAREHGMYYKPRDNDISYSGNEFFAEYSRLVNTYYHVKSLSEIIEMHSKSHLLLDYIREK
EKLGIVDYEDILMRAYDYRNDIVVDLEYMIIDEAQDNSLLDYATLLPIAKNNATELVLAG
DDAQLIYDFRGANYKLFHKLIERSEIILNLTETRRFGSEIANLATAIIDDMNYIQKREVL
SAATHSTKVAHIDLFQMMSILQNMATTDLTVYILARTNAVLNYVAKVLDEYKIQYKKNER
ITDFDRFLLSLNRLMRNEYTNDDIYTIYNYLRNKVAREEELKERLFQHKLHWTEKDVLGI
LLLAYEQTTAKRILTTAKNTNFKIKLSTIHSAKGSEADVVFLINSVPHKTKMKILENYEG
EKRVLYVAVTRARKFLFIVDQPVARRYEQLYYIRSYESRAQGSLVNRVAVPVA >tr|Q5JFK3|Q5JFK3_THEKO DNA helicase, UvrD/REP family
OS = Thermococcus kodakarensis (strain ATCC BAA-918/JCM 12380/
KOD1) GN = TK0178 PE = 4 SV = 1 (SEQ ID NO: 64)
MNEKEVLLSKFIAHLKELVEMERRAEIEAMRLEMMRRLSGREREKVGRAVLGLNGKVIGEE
LGYFLVRYGRDREIKTEISVGDLVVISKRDPLKSDLVGTVVEKGKRFLTVAIETVPEWAL
KGVRIDLYANDITFKRWMENLDNLRESGRKALELYLGLREPEESEPVEFQPFDKSLNASQ
RGAIAKALGSGDFFLVHGPFGTGKTRTLVELIRQEVARGHKVLATAESNVAVDNIVERLA
DSGLKVVRIGHPSRVSKALHETTLAYLITQHDLYAELRELRVIGENLKEKRDTFTKPAPK
YRRGLSDREILRLAEKGIGTRGVPARLIREMAEWIRINQQVQKTFDDARKLEERIAREII
QEADVVLTTNASAGLEVVDYGEYDVAVIDEATQATIPSVLIPINRAKRFVLAGDHKQLPP
TILSEKAKELSKTLFEGLIERYPEKSEMLTVQYRMNERLMEFPSREFYDGKIKAHESVKN
ITLADLGVSEPEFGNFWDEALKPENVLVFIDTSKREDRFERQRRGSDSRENPLEAKLVTE
TVEKLLEMGVKPDWIGVITPYDDQRDLISSMVGEDIEVKTVDGYQGREKEIIVLSFVRSN
RRGELGFLTDLRRLNVSLTRAKRKLIAVGDSSTLSNHPTYRRFIEFVRERGTFIEIDGKK
H >tr|C6A075|C6A075_THESM DNA helicase, UvrD/REP family
OS = Thermococcus sibiricus (strain MM 739/DSM 12597)
GN = TSIB_2009 PE = 4 SV = 1 (SEQ ID NO: 65)
MTRVQIPAGAPKYGPVAQPGQSARLISGRSGVRSPAGPPKALLKERFRELFIHKNPVITM
HVKNYIAKLVDLVELEREAEIEAMREEMRRLKGYEREKVGRAILNLNGKIIGEEFGFKLV
KYGRKEAFKTEIGVGDLVVISKGNPLASDLVGTVVEKGSRFIVVALETVPSWAFRNVRID
LYANDITFRRQLENLKKLSESGIRALKLILGKETPLKSSPEEFTPFDRNLNQSQKEAVSY
ALGSEDFFLIHGPFGTGKTRTLVELIVQEVKRGNKILATAESNVAVDNLVERLWGKVKLV
RLGHPSRVSVHLKESTLAFQVESHERYRKVRELRNKAERLAVMRDQYKKPTPQMRRGLIN
NQILKLAYRGRGSRGVPAKDIKQMAQWITLNEQIQKLYKFAEKIESEIIQEIIEDVDVVL
STNSSAALEFIKDAEFDVAIIDEASQATIPSVLIPIAKARRFVLAGDHKQLPPTILSEEA
RALSETLFEKLIELYPFKAKMLEIQYRMNQLLMEFPSREFYNGKIKADGSVKDITLADLK
VREPFFGEPWDSILKREEPLIFVDTSNRTDKWERQRKGSTSRENPLEALLVREIVERLIR
MGIKKEWIGIITPYDDQVDSIRSIIQDDEIEIHTVDGYQGREKEIIILSLVRSNKKGELG
FLMDLRRLNVSITRAKRKLVVIGDSETLVNHETYKRLIHFVKKYGRYIELGDTGIN >tr|W0I5I1|W0I5I1_9EURY DNA helicase, UvrD/REP family protein
OS = Thermococcus paralvinellae GN = TES1_2001 PE = 4 SV = 1 (SEQ ID
NO: 66)
MNLIRYINHLKELVELEREAEIEAMREEMRKLTGYEREKVGRAVLGLNGKIIGEEFGYKL
VKYGRKQEIKTEISVGDLVVISKGNPLASDLIGTVTEKGKRFLVVALETVPSWALRNVRI
DLYANDITFKRQIENLDKLSESGKRALRFILGLEKPKESIDIEFKPFDEQLNESQKKAVG TABLE 18-continued

```
LALGSEDFFLIHGPFGTGKTRTVAEVILQEVKRGKKVLATAESNVAVDNLVERLWGKVKL
VRLGHPSRVSKHLKESTLAYQVEIHEKYKRVREFRNKAERLAMLRDQYTKPTPQWRRGLT
DRQILRLAEKGIGARGIPARVIKSMAQWITFNEKVQRLYNEAKKIEEEIVKEIIRQADVV
LSTNSSAALEFIKDIKFDVAVIDEASQATIPSVLIPIAKANKFILAGDHKQLPPTILSEE
AKELSETLFEKLIELYPSKAKMLEIQYRMNERLMEFPSKEFYNGKIKAYDGVKNITLLDL
GVRVFSFGEPWDSILNLKEPLVFVDTSKHPEKWERQRKGSLSRENLLEAELVKEIVQKLL
RMGIKPESIGVITPYDDQRDLISLLLENDEIEVKTVDGYQGREKEVIILSFVRSNKKGEL
GFLTDLRRLNVSLTRAKRKLIAIGDSETLSAHPTYKRFVEFVKEKGIFVQLNQYVSQTS

>tr|B7AA42|B7AA42_THEAQ DNA helicase OS = Thermus aquaticus
Y51MC23 GN = TaqDRAFT_3809 PE = 4 SV = 1 (SEQ ID NO: 67)
MGEAHPSEEALLSSLNEAQRQAVLHFEGPALVVAGAGSGKTRTVVHRVAYLIARRGVFPS
EILAVTFTNKAAEEMKARLKAMVRGAGELWVSTFHAAALRILRVYGERVGLKPGFVVYDE
DDQTALLKEVLKELGLAAKPGPIKSLLDRAKNQGVPPEHLLLELPEFYAGLSRGRLQDVL
HRYQEALRAQGALDFGDILLYALKLLEEDGEVLKRVRKRARFIHVDEYQDTNPVQYRFTR
LLAGEEANLMAVGDPDQGIYSFRAADIRNILDFTQDYPKARVYRLEDNYRSTEAILRFAN
AVIVKNALRLEKTLRPVKKGGEPVRLFRAESARDEARFVAEEIARLGPPFDRVAVLYRTN
AQSRLLEQALASRGIPARVVGGVGFFERAEVKDLLAYARLSLNPLDAVSLKRVLNTPPRG
IGPATVEKVQAIARERGLPLFEALKVAALTLPRPEPLRAFLALMEELMDLAFGPAEAFFR
HLLLATDYPAYLKEAYPEDAEDRLENVEELLRAAKEAESLMDFLDKVALTARAEEPAEAE
GRVALMTLHNAKGLEPPVVFLVGVEEGLLPHRSSLSTQEGLEEERRLFYVGVTRAQERLY
LSYAQEREIYGRLEPVRPSRFLEEVDEGLYEVYDPYRQSSRKPTPPPHRALPGAFRGGEK
VVHPRFGPGTVVAAAGDEVTVHFEGVGLKRLSLKYADLRPA >tr|B7A5I6|B7A5I6_THEAQ DNA helicase OS = Thermus aquaticus
Y51MC23 GN = TaqDRAFT_5093 PE = 4 SV = 1 (SEQ ID NO: 68)
MRVYLASAGTGKTHALVEELKGLIQSGVPLRRIAALTFTRKAAEELRGRAKRAVLALSAE
DPRLKEAEREVHGALFTTIHGFMAEALRHTAPLLSLDPDFALLDTFLAEALFLEEARSLL
YRKGLDGGLARALLHLYRKRTLAETLHPLPGAEGVFALYLEALEGYRRRLPAFLSPSDLE
ALALRILENPEALRRVVERFPHILLDEYQDTGPLQGRFFQGLKEAGARLVVVGDPKQSIY
LFRNARVEVFREALKQAEEVRYLSTTYRHAQAVAEFLNRFTALFGEEGVRVRPHRQEVGR
VEVHWVVGEGGLEEKRRAEAHLLLDRLMALREEGYAFSQMAVLVRSRSSLPPLEAAFRAR
GVPYALGRGRSFFARPEVRDLYHALRLSLLEGPPGPEERLALLAFLRGPWVGLDLSEVEE
ALKAQDPIPLLPEAVRAKLRALRALAGLPPLEALKRLSRDEAFLRRLSPRARVNLDALLL
LAAMERFPDLEALLEWLRLRAEDPEAAELPEGEEGVQVLTVHGAKGLEWPVVALFDLSRG
ENPKEEDLLVGLGGEVALRGTPAYKEVRKALRKAQAEEEARRLLYVALSRARDVLIVTGSA
SGRPGPWVEALERLGLGPESQDPLVRRHPFKALPPLGDRPQTPPPPPLPAPYAHLAFPER
PLPFVYSPSAFTKAKEPVPLAEALEKEALPEFYRALGTLVHLAPLEAAREEDHAELPLVLPLGGTVWY
GILDRLYRVGGRWYLEDYKTDREVRPEAYRFQLAIYRRALLEAWGVEAEARLVYLRHGLV
HPLDPEELERALKEGFPGMGPGEGGEKA >tr|B7A954|B7A954_THEAQ DNA helicase OS = Thermus aquaticus
Y51MC23 GN = TaqDRAFT_4764 PE = 4 SV = 1 (SEQ ID NO: 69)
MKGLTGSSRLRVYGPPGTGKTTWLKNEVERLLRSGVPGEEIAVCAFSRAAFREFASRLAG
QVPEENLGTIHSLAYRAIGRPPLALTKDALSDWNRRVPDTWRVTPRVDGRGADLLDVMDP
YEDEDSRPPGDKLYDRVAYLRNTLAPMAAWSEEERAFFQAWKSWMNAKGLVDFPGMLEAA
LAKPGGLGARFLLVDRVEAQDLTPLQLLLVEKWAQGARLALVGDDDQAIYGFMGADGASFLG
VPVEDELVLGQSYRVPARVQRVAEAVIRRVQNRAPKRYAPRGDEGEVRLLWVPPEDPYHA
VVDALERVNRGESVLFLATAKYLLEELKRELLRVGEPYANPYAPHRHSFNLFPQGARSAW
EKARSFLFPNRIAADVKAWTKHVSSKVFAVKGEEARRYIESFPDEEKVGDDHPIWNVFRP
EHRPHAVGRDVSWLLDHLLGNAPKTMRQSLMVALKSPEAVLQGRARVWIGTIHSVKGGEA
DWVYVWPGYTRKAAREHPDQLHRLFYVAATRARKGLVLMDQGKAPHGYVWPRVDEFWGEV
WV >tr|H7GEQ7|H7GEQ7_9DEIN DNA helicase OS = Thermus sp. RL
GN = RLTM_02916 PE = 4 SV = 1 (SEQ ID NO: 70)
MEANLYVAGAGTGKTYTLAERYLGFLEEGLSPLQVVAVTFTERAALELRHRVRQMVGERS
LGHKERVLAELEAAPIGTLHALAARVCREFPEEAGVPADFQVMEDLEAALLLEAWLEEAL
LEALQDPRYAPLVEAVGYEGLLDTLREVAKDPLAARELLEKGLGEVAKALRLEAWRXLRR
RMEELFHGERPEERYPGFPKGWRXEEPEVVPDLLAWAGEVKFNKKPWLEYKXDPALXRLL
KLLGGVKEGFSPGPADERLEEVWPLLRELAEGVLARLEERRFRARRLGYADLEVHALRAL
EXEEVRAYYRGRFRRLLVDEFQDTNPVQVRLLQALFPDLRAWTVVGDPNQSIYSFRRADP
KVMERFQXEAAKEGLRVRRLEKSHRYHQGLADFHNRFFPPLLPGYGAVSAERKPEGEGPW
VPHFQGDLEAQARFIAQEVGRLLSEGFQVYDLGEKAYRPMSLRDVAVLGRTWRDLARVAE
ALRRLEVPAVEAGGGNLLETRAFKDAYLALRFLGDPXDEEALVGLLRSPFFALTDGEVRR
LAEARGEGETLWEVLEREGDLSAEAERARETLRGLLRRKALEAPSRLLQRLDGATGYTGV
AARLPQGRRRVKDWEGTLDLVRKLEVGSEDPFLVARHLRLLLRSGLSVERPPLEAGEAVT
LLTVHGAKGLEWPVVFVLNVGGWNRLGSWKNNKTKPLFRPGLALVPPVLDEXGNPSALFH
LAKRRVEEEEKQEENRLLYVAATRASERLYLLLSPDLSPDKGDLDPQTLIGAGSLEKGLE
ATEPERPWSGEEGEVEVLEERIQGLPLEALPVSLLPLAARDPEAARRRLLGEPEXEGEAS
WXPXXPQETEEEVPGGAGVGRMTHALLERFEAXEDLEREGRAFLEESFPGAEGEEVEEAL
RLARTFLTAEVFAPYRGNAVAKEVPVALELLGVRLEGRADRVGEDWLDYKTDRGVDAXA
YLLQVGVYALALGKPRALVADLREGKLYEGASQQVEEKAEEVLRRLMGGEGQGRQPYPLA
ATDPGHGAPG >tr|H7GH69|H7GH69_9DEIN DNA helicase OS = Thermus sp. RL
GN = RLTM_07977 PE = 4 SV = 1 (SEQ ID NO: 71)
MSDALLAPLNEAQRQAVLHFEGPALVVAGAGSGKTRTVVHRVAYLVARRGVFPSEILAVT
FTNKAAEEMRERLRGLVPGAGEVWVSTFHAAALRILRVYGERVGLRPGFVVYDEDDQTAL
```

TABLE 18-continued

```
LKEVLKELALSARPGPIKALLDRAKNRGVGLKALLGELPEYYAGLSRGRLGDVLVRYQEA
LKAQGALDFGDILLYALRLLEEDEEVLRLVRKRARFIHVDEYQDTSPVQYRFTRLLAGEE
ANLMAVGDPDQGIYSFRAADIKNILDFTRDYPEARVYRLEENYRSTEAILRXANAVIVKN
ALRLEKALRPVKRGGEPVRLYRAEDAREEEARFVAEEIARLGPPWDRYAVLYRTNAQSRLL
EQALAGRGIPARVVGGVGFFERAEVKDLLAYARLALNPLDAVSLKRVLNTPPRGIGPATW
ARVQLLAQEKGLPPWEALKEAARTFXRAEPLRHFVALVEELQDLVFGPAEAFFRHLLEAT
DYPTYLREAYPEDAEDRLENVEELLRAAKEAEDLQDFLDRVALTAKAEEPAEAEGKVALM
TLHNAKGLEFPVVFLVGVEEGLLPHRNSLSTLEGLEEERRLFYVGITRAQERLYLSHAEE
REVYGRREPARPSRFLEEVEEGLYEVYDPYRXPKPXPPPHRPRPGAFRGGERVVHPRFGP
GTVVAAQGDEVTVHFEGXGLKRLSLKYAELXPA

>tr|A0A0B0SAG4|A0A0B0SAG4_9DEIN DNA helicase OS = Thermus sp.
2.9 GN = QT17_08170 PE = 4 SV = 1 (SEQ ID NO: 72)
MDEALLSSLNEAQRQAVLHFQGPALVVAGAGSGKTRTVVHRVAYLIAHRGVYPTEILAVT
FTNKAAEEMRERLKGMVRGAGEVWVSTFHAAALRILRVYGERVGLKPGFVVYDEDDQTAL
LKEVLKELGLSAKPGPIKALLDRAKNRGEPPEALLAELPEYYAGLSRRRLLDVFFRYQEA
LKAQGALDFGDILLYALRLLEEDQEVLARVRKRARFIHVDEYQDTNPVQYRFTKLLAGEE
ANLMAVGDPDQGIYSFRAADIKNILQFTADFPGAKVYRLEENYRSTEAILRFANAVIVKN
ALRLEKTLRPVKRGGEPVRLFRAKDAREEEARFVAEEILRLGPPFDRIAVLYRTNAQSRLL
EQALAGRGVGARVVGGVGFFERAEVKDLLAYARLALNPLDSVSLKRILNTPPRGIGPATV
EKVARLAQEKGLPLFEALKRAELLPRPEPVRHFVALMEELMDLAFGPAEAFFRHLLQATD
YPAYLREAYPEDHEDRLENVEELLRAAKEAESLLDFLDKVALTARAEEPAGAEGKVFLMT
LHNAKGLEFPVVFLVGVEEGLLPHRNSLNTLEALEEERRLFYVGTRAQERLYLSYAEER
EVYGRLEATRPSRFLEEVEEGLYQEYDPYRSPRPVPPSHRPKPGAFKGGEKVVHPRFGPG
TVVAASGDEVTVHFEGVGLKRLSLKYADLRPA >tr|A0A084IL47|A0A084IL47_9GAMM ATP-dependent DNA helicase Rep
OS = Salinisphaera hydrothermalis C41B8 GN = rep PE = 3 SV = 1
(SEQ ID NO: 73)
MALPKLNPQQDAAMRYLDGPLLVLAGAGSGKTGVITRKIAHLIARGYDARRVVAVTFTNK
AAREMKQRASKLISADDARGLTVSTFHSLGLQMIREEHAALGYKPRFSIFDSEDADKVLA
DLVGRDGDHRKATKAAISNWKSALIDPETATAQATGSDIPLARAYGEYQRRLKAYNAVDF
DDLLALPVHLLSTDHEARERWQSRFRYLLVDEYQDTNAAQYEMMRLLAGARAAFTVVGDD
DQSIYAWRGARPGNIADLSRDFPHLKVIKLEQNYRSVGNVLSAANQLIGASNQRAYEKTL
WSAMGPGDRVRVIAAPDEAGEAERIASEISSHKLRLGTAYGDYAILYRGNFQSRAFEKAL
RERDIPYRVSGGRSFFERSEIRDLVTYLKLMVNPDDDAAFLRIVNLPRREIGPATLEALG
RYAGSRHISLFDAARGIGLAGGVGERSGRRLADFVDWLRNLTQDSEGMTPRELVSQLIVD
IDYRNWLRDTSANTKAARKRIENLDDFIGWLDRLDNAEDGKPVTLEDVVRRLSLMDFANQ
SEKDVENQVHLLTLHAAKGLEFDHVFLAGLEEGMLPHHACLEDDKIEEERRLLYVGITRA
RKTLALTYARKRRRGGEESDSVPSRFLEELPADELDWPSATGTRSKAANAEQGRDQVAAL
RAMLGASADS >tr|A0A0A2WMV1|A0A0A2WMV1_THEFI DNA helicase OS = Thermus
filiformis GN = THFILI_00990 PE = 4 SV = 1 (SEQ ID NO: 74)
MPQVGFTDHFFKGLEALSREEQNRVREAVFAFMQDPKHPSFKLHRLEDIKTDRFWSARVS
KDLRLILYHHPEMGWIFAYVGHHDDAYRWAETHQAEVHPKLGLLQIFRVVEEVRVEPRKI
KPLLPDYPDDYLLDLGVPPSYLKPLRLVETEDQLLGLIEGLPQDVQERLLDLAAGRPVTL
PPKLAPSEEWFKHPLSRQHIHFIQNLDELRQALSYPWERWMVFLHPAQREAVERVFQGPA
RVTGPAGTGKTVVALHRAAALRRYPEEPLLLTTFNRFLASRLRSGLQRLLGEVPPNLTV
ENLHSLARRLHEQHVGPVKLVKEEDYGPWLLEAAQGLEYGKNFLLSEFAFADAWGLYTWE
AYRGFPRTGRGVPLTARERLKLFGAFQKVWGRMENEGALTFNGLLHRLRQRAEEGALPRF
RAVVVDEAQDLGPAELLLVRALAQEAPDSLFFALDPAQRIYKSPLSWQALGLEVRGRSIR
LKVNYRTTREIAKRAEAVLPKEVEGEMREVLSLLQGPEPEIRGFPTQEACQAELVRWLRW
LLEQGVRPEEVAVLARVRKLAEGLAEGLRRAGIPVVLLSDQEDPGEGVRLGTVHSAKGLE
FRAVALFGANRGLFPLESLLREAPSEADREALLAQERNLLYVAMSRARERLWVGYWDEGS
PFLTP >tr|A0A0D0N7B7|A0A0D0N7B7_MEIRU DNA helicase OS = Meiothermus
ruber GN = SY28_04645 PE = 4 SV = 1 (SEQ ID NO: 75)
MSDLLSSLNPSQREAVLHFEGPALVVAGAGSGKTRTVVHRIAYLLRERRVYPAEILAVTF
TNKAAGEMKERLEKMVGRSARDLWVTTFHAAAVRILRTYGEYVGLKPGFVIYDEDDQNTL
LKEVLKELELEAKPGPFRSMIDRIKNRGAGLAEYMREAPDFIGGVPRDVAAEVYRRYQNS
LRMQGALDFNDLLLLTIELFEQHPEVLHKVQQRARFIHVDEYQDTNPVQYRLTRLLAGER
PNLMVVGDPDQSIYGFRNADINNILDFTKDYPGARVIRLEENYRSSSSILRVANAVIEKN
ALRLEKVLRPTKPGGEPVRLYRAPNAREEAAFVAREIVKLGGYQQVAVLYRTNAQSRLLE
EHLRRANVPVRLVGAVGFFERREIKDLLAYGRVAVNPDDSINLRRIVNTPPRGIGATTVA
RLVEHAQKTGITVFEAFRAAEQVISRPQQVQAFVRLLDELMEAAFESGPTAFFQRVLEQT
GFREALKQEPDGEDRLQNVEELLRAAQDWEEEEGGSLADFLDSVALTAKAEEPQGDAPVE
AVTLMTLHNAKGLEFPTVFLVGLEENLLPHRNSLHRLEDLEEERRLFYVGITRAQERLYL
SYAEERETYGKREYTRPSRFLQDIPQDLLKEVGAFGDGETRVLSQARPEPKPRTQPAEFK
GGEKVKHPKFGSGTVVAAMGGEVTVMFPGVGLKRLAVKFAGLERLE >tr|W2U4X3|W2U4X3_9DEIN DNA helicase OS = Thermus sp. NMX2.A1
GN = TNMX_07060 PE = 4 SV = 1 (SEQ ID NO: 76)
MQGPQSSHPGDELLRSLNEAQRQAVLHFEGPALVVAGAGSGKTRTVVHRVAYLIAKRGVF
PSEIAVTFTNKAALEMRERLKRMVKGAGELWVSTFHSAALRILRVYGERVGLKPGFVVY
DEDDQTALIKEVLKELGLAARPGPLKALLDRAKNRGEAPESLLSELPDYYAGLSRGRLLD
VLKRYEEALKAQGALDFGDILLYALRLLEEDPEVLKRVRRRARFIHVDEYQDTNPVQYRF
TKLLAGEEANLMAVGDPDQGIYSFRAADIKNILEFTRDFPGAKVYRLEENYRSTEAILRF
ANALIVNNALRLEKTLRPVKPGGEPVRLYRARDAREARFVAEEILRLGPPFDRVAVLYR
```

TABLE 18-continued

TNAQSRLLEQALASRGVPARVVGGVGFFERAEVKDLLAYARLSLNPLDGVSLKRVLNTPP
RGIGPATVEKVEALAREKGLPLFEALRVAAEVLPRPAPLRHFLALMEELQELAFGPAEGF
FRHLLEATDYPAYLREAYPEDHEDRLENVEELLRAAKEAEGLMEFLDKVALTARAEEPGE
PAGKVALMTLHNAKGLEFPVVFVVGVEEGLLPHRSSLSTLEGLEEERRLFYVGVTRAQER
LYLSYAEEREVYGRTEATRPSRFLEEVEGGLYEEYDPYRASAKVSPSPAPSEARASKPKP
GAYRGGEKVIHPRFGQGTVVAAMGDEVTVHFEGVGLKRLSLKYADLRPVG

>tr|H9ZQB5|H9ZQB5_THETH DNA helicase OS = Thermus thermophilus
JL-18 GN = TtJL18_0620 PE = 4 SV = 1 (SEQ ID NO: 77)
MSDALLAPLNEAQRQAVLHFEGPALVVAGAGSGKTRTVVHRVAYLVARRGVFPSEILAVT
FTNKAAEEMRERLRGLVPGAGEVWVSTFHAAALRILRVYGERVGLRPGFVVYDEDDQTAL
LKEVLKELALSARPGPIKALLDRAKNRGVGLEALLGELPEYYAGLSRGRLADVLVRYQEA
LKAQGALDFGDILLYALRLLKEDEEVLRLVRKRARFIHVDEYQDTSPVQYRFTRLLAGEE
ANLMAVGDPDQGIYSFRAADIKNILDFTRDYPEARVYRLEENYRSTEAILRLANAVIVKN
ALRLEKALRPVKRGGEPVRLYRAEDAREEARFVAEEIARLGPPWDRYAVLYRTNAQSRLL
EQALAGRGIPARVVGGVGFFERAEVKDLLAYARLALNPLDAVSLKRVLNTPPRGIGPATW
ARVQLLAQEKGLPPWEALKEAARTSSRVEPLRHFVALVEELQDLVFGPAEAFFRHLLEAT
DYPTYLREAYPEDAEDRLENVEELLRAAKEAEDLQDFLDKVALTAKAEEPAEAEGKVALM
TLHNAKGLEFPVVFLVGVEEGLLPHRNSLSTLEGLEEERRLFYVGITRAQERLYLSHAEE
REVYGRREPARPSRFLEEVEEGLYEVYDPYRVPKPAPPPHRPRPGAFRGGERVVHPRFGP
GTVVAAQGDEVTVHFEGFGLKRLSLKYAELRPA >tr|E8PM35|E8PM35_THESS DNA helicase OS = Thermus scotoductus
(strain ATCC 700910/SA-01) GN = pcrA1 PE = 4 SV = 1 (SEQ ID NO:
78)
MQGPQSSHPGDELLRSLNEAQRQAVLHFEGPALVVAGAGSGKTRTVVHRVAYLIAKRGVF
PSEILAVTFTNKAAEEMRERLKRMVKGGGELWVSTFHSAALRILRVYGERVGLKPGFVVY
DEDDQTALIKEVLKELGLAARPGPLKALLDRAKNRGEAPESLLSELPDYYAGLSRGRLLD
VLKRYEEALKAQGALDFGDILLYALRLLEEDPEVLKRVRRRARFIHVDEYQDTNPVQYRF
TKLLAGEEEANLMAVGDPDQGIYSFRAADIKNILEFTRDFPGAKVYRLEENYRSTEAILRF
ANALIVNNALRLEKTLRPVKPGGEPVRLYRARDARDEARFVAEEILRLGPPFDRVAVLYR
TNAQSRLLEQTLASRGVPARVVGGVGFFERAEVKDLLAYARLSLNPLDGVSLKRVLNTPP
RGIGPATVEKVEALAREKGLPLFEALRVAAEVLPRPAPLRHFLALMEELQELAFGPAEGF
FRHLLEATDYPAYLREAYPEDYEDRLENVEELLRAAKEAEGLMEFLDKVALTARAEEPGE
PAGKVALMTLHNAKGLEFPVVFVVGVEEGLLPHRSSLSTLEGLEEERRLFYVGVTRAQER
LYLSYAEEREVYGRTEATRPSRFLEEVEGGLYEEYDPYRASAKVSPSPAPGEARASKPGA
YRGGEKVIHPRFGQGTVVAAMGDEVTVHFEGVGLKRLSLKYADLRPVG >tr|E8PL08|E8PL08_THESS DNA helicase OS = Thermus scotoductus
(strain ATCC 700910/SA-01) GN = pcrA2 PE = 4 SV = 1 (SEQ ID NO:
79)
MLNPEQEAVANHFTGPALVIAGPGSGKTRTVVHRIARLIRKGVDPETVTAVTFTKKAAGE
MRERLVHLVGEETATKVFTATFHSLAYHVLKDTGTVRVLPAEQARKLIGEILEDLQAPKK
LTAKVAQGAFSRVKNSGGGRRELIALYTDFSPYIERAWDAYEAYKEEKRLLDFDDLLHQA
VHELSTDIDLQARWQHRARFLIVDEYQDTNLVQFNLLRLLLTPEENLMAVGDPNQAIYAW
RGADFRLILEFKKHFPNATVYKLHTNYRSHNGIVTAAKKVITHNTQREDLDLKALRNGDL
PTLVQAQSREDEALAVAEVVKRHLDQGTPPEEIAILLRSLAYSRPIEATLRRYRIPYTIV
GGLSFWNRKEVQLYLHLLQAASGNPESTVEVLASLVPGMGPKKARKALETGKYPKEAEEA
LQLLQDLRAYTGERGEHLASAVQNTLRHRKTLWPYLLELADGIEEAAWDRWANLEEAVS
TLFAFAHHTPEGDLDTYLADILLQEEDPEDSGDGVKIMTLHASKGLEFAVVLLPFLVEGA
FPSWRSAQNPATLEEERRLFYVGLTRAKEHAYLSYHLVGERGATSPSRFARETPANLIHY
NPTIGYQGKETDTLSKLAELF >tr|E4U8J8|E4U8J8_OCEP5 DNA helicase OS = Oceanithermus
profundus (strain DSM 14977/NBRC 100410/VKM B-2274/506)
GN = Ocepr_1221 PE = 4 SV = 1 (SEQ ID NO: 80)
MSARDLLSSLNEQQQAAVQHFLGPALVIAGAGSGKTRTVVHRVAYLLAEREVYPAEVLAV
TFTNKAAGEMRERLSRMVGRAAGELWVSTFHSASLRILRRYGERIGLKPGFVVYDDDDQR
VLLKEVLGSLGLEARPTYVRAVLDRIKNRMWSVDEFLAHADDWVGGLTKQQMAEVYARYQ
QRLAENNAVDFNDLLLRTIELFERHPEALEAVRQRARFIHVDEYQDTNPAQYRLTKLLAG
DEANLMVVGDPDQSIYGFRNADIQNILGFERDYRGAVVYRLEANYRSTAAILRVANALIE
RNQQRLEKTLRPVKPAGEPVRLYRAPDHREEAAFVAREVARLAGERALDDFAVLYRTNAQ
SRVLEEAFRRLNLPARIVGGVGFYERREVKDVLAYARLAVNPADDVALRRVINVPARGVG
AASVGKLAAWAQAQGVSLLEAAHRAGELLAARQAAAVAKFTDLLTTLREAAEGTGPEAFL
RLVLAETGYSEMLRREGDSEPRLENLEELLRAAAEWEEEHGGSVAEFLDEIALTARAEEP
NAAPEKSVILMTLHNAKGLEFPVVFVVGVEEGLLPHRSSLGSDAEIEEERRLLYVGITRA
QERLYLTLSEERETWGQRERVRPSRFLEEIPEDFLKPVGPFGDAHEPAPAPLSSAPVNRA
AKGSASGFRGGEKVRHPRYGEGTVVATSGEGARQEVTVHFAEAGLKRLLVKYAGLERIE >tr|E4U4N5|E4U4N5_OCEP5 DNA helicase OS = Oceanithermus
profundus (strain DSM 14977/NBRC 100410/VKM B-2274/506)
GN = Ocepr_1575 PE = 4 SV = 1 (SEQ ID NO: 81)
MKVRIASAGTGKTYALTSRFTAALAEHPPYRLAAVTFTRSAAAELKARLRERLLAIAAGR
FQPSGAEDVPPEAVVRRAGALATEVLGATVTTIHGFFAELLRQNALALGLEPDFLRIDAS
ESQQIFAEEARAYVYLNEEDDALAEVLGRLFAKRSLAAELRPQGEAAEALWAHFRAVLER
YARRLGGEALGPADIELHAWRLLERAGREEALAARIRSRLARVFVDEYQDTSPLQGRVFA
ALEALGVEVEVVGDPKQSIYAFRNADVEVFREAMRRGEPLPPLVTSWRHDRALVRFLNRY
VDWVAEERPEAFARAEAPPVEARPDAGPGRVRLQLVQGEARQDALRPYEADQLARWLQER
HAEHAWRDMAVLVRSHSSVPLLVRALAAHGLPHVVVGGRGFYDLIEVRDLVHAARVALDP
RGRFSLAAFLRGPFAGLDLGRVERVLAAEDPLAELERAAPEVAERVDRLVRWVQTLRPLD TABLE 18-continued FFERMVRTPFLEGASYLERLEPPARANVDQLLFKLASRRYGRLEFLLRDLEDLRGSDEAG
VPEGGFDAVRIYTMHGSKGLEWPVVAVFDLNRGQPDGAEPFYVRPGSGEFAAEGDPDYPR
FAAEWKERERQEAYRLLYVALSRPRSRLLLSLSVQLKPDGEGLRPKFWRRTLGRTLIEEM
NLAAWDALEVERLDAARLPAPKAAAAAPRRAADVDERLRAPVEPLARPPVYSPSALKAER
PAPPELDDEGDVAVELEEPGVDPGLVARTVGILVHYAIGQDWGPERLQDLWNQEAVQRLT
EPERTRVKTEVAQRLETYWRLLGTELPALDERDEDYAEFPLLLPTRTARLDTVWEGVIDR
LYRVGDVWVLEDYKTDRELHPERYHFQLALYRRAVAAAWGIEPEARLVYLRFGEVVPLEA
QLLEEAFERGTREAEEV >tr|E4UAI1|E4UAI1_OCEP5 DNA helicase OS = Oceanithermus
profundus (strain DSM 14977/NBRC 100410/VKM B-2274/506)
GN = Ocepr_2312 PE = 4 SV = 1 (SEQ ID NO: 82)
MKVIVASAGTGKTTRLTQRYLEHLEQHPPQRVAAVTFTNKAAAELRERIFEALGRGSFYD
FTPSPALAERLADYQVRVLEAPIGTIHSFFGYLLRLTAPMLGLDPHFEVIDPATARAWFL
EEVRNLAIIEGAEVDETVTTALVELFKRRSISEAFEGTGDASRSLVAGFKKVYARWLTRL
GGRYLDPSEIERRALALIRHPEALERVRSLGVVLVDEYQDTAPIQARVFEALEEAGVPI
EVVGDPKQSIYAFRDADVEGFREAHRRARENGNVETLTVSYRHPPALADFLNAFTSAEAA
LGKAFTAEEAPEVKPGREGDARVELITVTPGDGKATLDALRNGEARLLARELRRLHDEEG
YDYGQMLVLFRRRHQLPPLLRALRGAGLPFAVVGLRGLYEEPEVRELYHALRLATGEAPR
DSLAVFLSGPFGGLTLGQVREVLAQDAPESYLTLHHPEAAERLLRLRADAEKMRPAEALT
RLIEAPTAKGPPFLDLLELEMADTVLYVLGRIEHTRTYPEAVATLESFRSGGEEEASLAR
LGGDAVRVMSAHAAKGLQAPVVVIFDADRTFNGNSDELVIEPRTGRVALNGEDAYESIAQ
ALKARKEGEDHRLIYVALSRSSERLIVSAAVKEPRKGSWLHHLTEVLNLGSKFEHRNVTL
AEIALEEPIEQEAATLPVDPELATPLPPAPPAVSSPTALKAERELEVPDPEEAWPADPEA
RLLGRIVGILVHEGIQRDWDPDDPEVLLALEGEQVLEEVPADRRPAVIEEVATLLRVYRT
LLGSAIPSLEEREVDLAELPLVYPLGATAWEGVIDRLYRVGDVWYLEDYKTDREVHPERY
HSQLALYREAVRKHWGIEPEVRLVYLRTGQVVPLDAAALKEGLASYTGG >tr|E4UAI8|E4UAI8_OCEP5 DNA helicase OS = Oceanithermus
profundus (strain DSM 14977/NBRC 100410/VKM B-2274/506)
GN = Ocepr_2319 PE = 4 SV = 1 (SEQ ID NO: 83)
MNEHERVIAHEVGPAAVVAGAGSGKTRAATLRAARLARTGERVGLVTFTASAAEEMRQRV
LAEDVPAKHVWAGTFHSLAFQILRQFPEAGGYEGFPEVLTPNDELRLFRRLWAELLDQDL
DAELRRKLVKALGFFRKARAEEEALEGWAARAGESLELDAEMLEALMISFQLRKREAGLAS
FDDLIEGASRALGDKDVRKWADRRFPFLIVDEYQDTSRAQETFLAALMPGEAPNLMVIGD
PNQAIYGWRGAGSRTFERFQARYPQAVLYPLRKNYRSTRAVLRLAERAIARLYRSGQEAY
YRLEGVKEEGEPPVLLTPPNAAAEATDVAREVARAVASGVPPEEIAVLARSSMQLAGVED
RLARLGVATRLLGGIRLSERREVKTLVQLLKAAWSLHERALVDFIEEAVPGLGERTLTRV
EHAARPYNLVDRIMNDGAFVRGFSTRVQQGLFMTRILLQLARATFEGVTGEAFAERFREF
AQDLYGELLPGYLARIGKQGPNEEARRRHLERFVATVEAFAREEAEGGLDDLLARLAFLE
QQDGPAVTLGTVHAVKGLEFEVVFVVGMVEGAFPILADDSDPEEERRLFYVAATRAKRRL
YLSAPTYGPRGKILQPSRYLEEALDEGLVRLQKVRPAA >tr|E4UAI4|E4UAI4_OCEP5 AAA ATPase OS = Oceanithermus profundus
(strain DSM 14977/NBRC 100410/VKM B-2274/506)
GN = Ocepr_2315 PE = 4 SV = 1 (SEQ ID NO: 84)
MVSEGRWKIERVVYLKDGFAVVAVRNEAGERHTAVGEMPTPVEGTWVRMETEHTVHPRYG
PRLRVVRFLGLAPPPSKELAKIEGYLKLGFSEEAASWLAARFGSRPERAFDKPQELLVPG
VPREVLRRVFPRLERLLGGLIDLLGEGHTAAPLFLLAERSGLGKEEIQELAREARKQRLI
VEEQGRYGLVQPYRTERSIADGLLFRLKPGRGLRLTPPAGHGLSDEQARIFKLVRENRVV
VLTGGPGSGKTTTIATLLAAPELHRMRFGIAAPTGKAARRIAEVARLPAETIHRLLGLGE
ARRPLYHARNPLPYDLLVIDETSMLDAEIAAFLVDALAPSTSVIFVGDPDQLPPVGPGQF
LRDLMTRVATLRLTQIFRQAQDSPIVNGAYALREGRMPLADGERLRLLPFEEEAAQTTLR
TLLDELQRLEQIVGERPQVLVPGNRGPLGVRRLSPFLQQQLNPGGKPLGPIGWGMEAREG
DPAVWIHNDYELGIMNGEVGVLRGGGSLGLTFETPTDRFAIPGNKRSRLVLAYAMTVHRS
QGSEWPAVITILPKAHMALLSRELVYTALTRSKQYHTLLFHPEALYRARAVQASRRYTWL
DVLLRG >tr|K7QW32|K7QW32_THEOS DNA helicase OS = Thermus oshimai JL-2
GN = Theos_1787 PE = 4 SV = 1 (SEQ ID NO: 85)
MTAPGHPDALLAPLNPAQQEAVLHFQGPALVVAGAGSGKTRTVVHRVAYLMAHRGVYPGE
ILAVTFTNKAAEEMKGRLKALVPGAGELWVATFHSAALRILRVYGEAIGLKPGFVVYDEA
DQEALLKEVLKELGLSAKPGPLKALLDRAKNRGEAWEALEIPDYYAGLPKGKVLDVLRRY
QEALRAQGALDFGDILVYALRLLEENPEVLAKVRKRARFIHVDEYQDTSPVQYRFARLLA
GEEEANLMAVGDPDQGIYSFRAADIRNILDFTRDFPGARVYRLEENYRSTEAILRFANAVI
QKNRLRLEKTLRPVKPGGEPVRVYAAPEAREEARFVAEEIFRLGPPYERFAVLYRTNAQS
RLLEQALAAKGLPYRVVGGVGFFERAEVKDLLAYARLSLNPEDGVSLKRVLNTPPRGIGP
ATLARLEALAQAEGVPLLGAIRLGAERFPKPEPLRAFLALLDELADLAFGPPEAFFRHLL
SATDYLQYLKEHHPEDAEDRLENVEELLRAAKEAQDLQEFLDRVALTARADQDGGRGVAL
MTLHNAKGLEFPVVFLVGVEEGLLPHQSSLSTLEGLEEERRLFYVGVTRAQDRLYLSYAR
EREVYGRREPRRMSRFLEEVPEGLYLPHDPYRQGAQPKPAPRAQGAFRGGEKVVHPRFGP
GTVVAASGDEVTVHFEGVGLKRLSLKYADLRPA >tr|K7QWX5|K7QWX5_THEOS DNA helicase OS = Thermus oshimai JL-2
GN = Theos_2419 PE = 4 SV = 1 (SEQ ID NO: 86)
MASSLSKAELVPTPEQEKALHLYRSRQDFKLVAVAGSGKTTTLRLMAESFPRRHIAYLAF
NRAMKEEARRKFPPNTRVFTLHALAYRRTVPGTPYEAKFRLGNGQVRPVHVRERLQVDPL
LAYVVRSGLERFIRSGDPEPLPRHLPRDWRKTVEARGPSGFAEVERAVKGVALLWKAMRD
PKDPFPLSHDGYVRIWREEGAGGDPPAGVILVDEAQDLDPNFLTVLSGWRGKAQQVFVGD
PRQQIYGWRGAVNAMGEIDLPESPLTWSFRFGEPLASFVQAVTARQTQGLVPLVGRAGWA TABLE 18-continued

```
TEVHVNLFPTPPPFTILTRSNLGLVTALLEGAQLFSLQKEEAHVVGGVEELVWLLTDLQAI
KEGGERPRPHPELLGISKWEEVESLAEYSIVLNRLLRLAKEYDLEALAHKIAQLHGPEEG
AKLVLSTAHKAKGREWDRVLLWEDFYWVAAYRWFFPNTAPPPSEPSPEFLEEENIFYVAM
TRARLGLHISLPEALAEEEAKRILDRLSQGVPSGEDRGEDERGETLPAPFTGPTPVSPKE
ATFPLPSLYDRLLSEALNGGRDPLLHLLRDDLARLSALSPTPLPPEVAQALWERARPEEA
LGAIREGLGAMWREDPYELLRAINALALLGGRNPRKLAKILGDRFPGGEEAEDLLFVARA
RKRELMGRSLAEFWRGLGASVRHPLLKAYARARS

>tr|K7QTS9|K7QTS9_THEOS DNA helicase OS = Thermus oshimai JL-2
GN = Theos_0356 PE = 4 SV = 1 (SEQ ID NO: 87)
MRLYVASAGTGKTETLMGELKALLEGGVPLRRVAAVSFTRKSAEELRLRVRRLLEAHREA
FWAREALREVHGALFTTLHGFMAEALRHTAPFLGLDPDFRVMDGFLAQALFLEEARSLLF
LEGHPEAPELLELLEALYEKRSLAEAFTPLPGAEGLLALYERVLARYRARTQEVLGPGDL
EAKALLLLRHPEALGRVAERFSHLLVDEFQDVNPLQGRFLRALEEAGVRVVAVGDPKQSI
YLFRNARVEVFLRARAAAEEVRALSRTHRHAKQVVELLNRFTTRFFRAEEGNRVEGVREA
EGRVEVHWVLGKLEEARRAEARLLAQRLLALRAEGIPFGEMAVLVRARTSLPPLEKALRA
AGVPFVRGRGQSFFARPEVRDLYHALRLALAERPYALEDRLSLLAFLRSPFLGLDLSELE
EALRAEDPWPLLPKGVQEALEGLRALALLPPLEALRRLARDEGFLRRISRRARANLDTLL
LLAAGARFPTLEDLLLWLALRAKDPESVELPEGGGGVTLLTVHGAKGLEWPVVALYDVSR
GPSERPPPLLVDEEGRVALKGTEAYRALLKEAERAEREEALRLLYVALSRARDLLLITGS
TSQRPGPWAEALQALGLGPDAQDPWVETHPLEAIPPLPPIPQAPQDPRPAPYTPWRGEPR
ARPPVYSPSAHLKAEAEPLEVLGEGEALPEWARAVGTLVHYAIARHLDPEDEGAMGGLLR
QEVALAFGEGEREALLEEVRALLRAYRSLLSGALPPLEARAEDHAELPLLLPHKGTVWYG
VLDRLYRVGDRWYLDDYKTDQKVRPEAYRFQLALYRKAVLEAWGVEAEARLVYLRHRQVV
PLSPAELEAALEGL >tr|D1AF88|D1AF88_THECD DNA helicase OS = Thermomonospora
curvata (strain ATCC 19995/DSM 43183/JCM 3096/NCIMB
10081) GN = Tcur_4104 PE = 4 SV = 1 (SEQ ID NO: 88)
MSSSQVTGRPTTVKDAEIAVEQRRVDQAHARLEEMRAEAQAMIEEGYRQALAGTKGSLVD
RDAMVYQAALRVQALNVADDGLVFGRLDLADGQTRYIGRIGVRTRDHEPMVIDWRAPAAE
AFYRATPEDPQGVVRRRVLHTRGRTVVDLEDDLLDPSAADSLTIVGDGAFIASLARTREG
TMRDIVATIQREQDEVIRAPADGTVLVRGAPGTGKTAVALHRVAYLLFRHRRRFGSRGVL
VVGPNRRFTAYIERVLPSLGEGSATLRSLGDLVEGVSATVHDPPELAALKGSAAMAPVLR
RAVTDHPPGAPDKLRVVHGGVVVELGRPQLDKLRTSLHRRSTGSVNASRRRVAEALLDAL
WERYVHTGGTEPEPDEPVQGELALWEGILAEGGLAPLDEQDRPSSPADRTSREAFVKNVR
EQRAFTDFLTAWWPIRRPLDVLRSLGDAARLRRAAGRDLDRAQVELLAASWRRALAGDPP
TLSYQDIALLDEIDALLGPPPQPSRATAREEDPYVVDGIDILTGEVVADEDWEPGLQELT
TTIERLERARRVDDEVADVRPEYAHIVVDEAQDLSPMQWRMLGRRGRQATWTIVEDPAQS
AWEDLEEARKAMEAALDGPAARRGRSRRPRRRPRHEYELTTNYRNTTEIAAVSARVLRLA
LPEARPARAVRSSGHRPVIDLVPEEELQAAARRAVRTLLEQVEGTIGVIVPLPGDAWGES
DRRALSAGFPERVQVLDVLEAKGLEFDAAVICAPETIAAQSPRGLRVLYVAVSRATQRLT
VLTADPVWRRRLAGGESAR >tr|F8A884|F8A884_THEID DNA helicase OS = Thermodesulfatator
indicus (strain DSM 15286/JCM 11887/CIR29812)
GN = Thein_0607 PE = 4 SV = 1 (SEQ ID NO: 89)
MTSISLDQYQEQAVKAKGNTLVVAGPGAGKTRVLLAKAIHLLEQGIDPEKVLILTFTIKT
TQELKERLASIGIKGVKVDTFHALAYDLLKAKGIKPRLATEEELKALARDLSKRKGLSLK
DFRKALDKGENHYRSLWEEALKLHGLYDFSLLLKEATGHYLQQEKVYLLIDEFQDLNPEL
TSFLKTFTKAEFFLVGDPAQAIYGFRGACPQVIKEFVDYLAPQIYFLKKSYRVPEKVLNF
AETLRETQGFPLEPLEAVQKGGNRLGLSFNKPFNEAKGVAKLVSELLGGLQMEASQRGLA
PPEIAILSRVRTLLNPIKEAFIKFGIPFQVPSENLKEEISAIESLSDIAKSIKSLKELEA
YLAEGPSSVKEAWLESQSLEGFLFRLEMLKTFASISIRKDGVPLLTIHEAKGLEFKVVIL
VGAEDGLLPFTLLEDYDLAEEKRVAYVAVTRAQESFYFTQVKTGRFLYGHKLSGKVSPFF
ETLPIKEKSSKTKPKARQKKLFG >tr|A0A087LEB0|A0A087LEB0_GEOSE Uncharacterized protein
OS = Geobacillus stearothermophilus GN = GT94_17890 PE = 4 SV = 1
(SEQ ID NO: 90)
MTISVIDELLEKNKQNMNKTAKDAVEAQLIAYAKKEVKKLQEIRPHPYFGRLDFEDEFGR
ETIYIGKKGLEKDGELIVVDWRTDLGRLYNAYQGVQKTFQIGKENRPVTIHGKRGIVIKN
GKVIKVTDIGKSEIIENDNGEKVKYMDDYLKEILTNTEEAHRLRDIIASIQAEQDEIIRL
PLKDTIIVQGAAGSGKSTIALHRISYLLYQYHEQVKPKDILILAPNEIFLSYIKDIVPEI
EIEGIEQRTFYDWASTYFTDVHDIPDLHEQYVHIYGSTEKEDLIKIAKYKGSLRFKKLLD
DFVEYIGNTMIPHGDVVIESGVILSKEEIHQFYHAKEHLPLNVRMKEVKEFIINWRNEQI
NIRKQQIEDEFEEAYRKWVVTLPEGEERKAVYEALEKAKQLRMKIFQEKMQHEISLIVKK
MENIPALLMYKSVFQKKVFEKFHPDIDEELLSLLLKNGRQIKQERFMYEDIAPLIYLDAK
INGKKLQYEHIVIDEAQDYSPFQLAIMKDYAKSMTILGDIAQGIFSFYGLDRWEEIESYV
FKEKEFKRLHLQTSYRSTKQIMDLANRVLLNSNYDFPLVIPVNRPGDVPTIKKVESIGEL
YDEIVNSIRIFEEKGYKKIAILTASKQGAIDTYDQLMRRQITQMEVITEGHQALKEKIVI
IPSYLVKGLEFDAVIIEDVSDETFKDETQHAKMLYMSITRAHHDLHLFYRGNISPLLEER
DPSAPPKPRKSFADWLITDINDPYVEPQVEAVKRVKKEDMIRLFDDEEEEFVEEAFEDDR
ERYYDFHAWLKVWRRWAEMRKQLDEKS >tr|B5Y6N2|B5Y6N2_COPPD DNA helicase OS = Coprothermobacter
proteolyticus (strain ATCC 35245/DSM 5265/BT) GN = pcrA PE = 4
SV = 1 (SEQ ID NO: 91)
MALPQENLIPPSPSHNHLTLSLRSHIGGFFIYNEDVDSVDLSKLNEAQKQAVTAPPKPLA
IIAGPGSGKTRVLTYRALFAVKEWHLPPERILAITFTNKAADELKERLGRLIPEGDRIFA
```

TABLE 18-continued

```
ATMHSFAARMLRYFAPYAGISQNFVIYDDDDSKGLIEDILKQMNMDTKRFRPNDVLNHIS
AAKARMFDCNTFPEFIRQRYGSWGYYFDTVHQVFMTYERLKEQSQALDFDDLIMVLAQRM
EDRPELREMIAGLFDLVMVDEFQDTNFAQYQMLLYMTNPHYSGMNNVTIVGDPDQSIYGF
RAAEYYNIKRFIDDYNPEVVFLDLNYRSNRTIVDSASALINDSPSALFERKLESIKGAGN
KLILRRPFDDADAAITAAFEVQRLHKMGIPYEEIAVLMRTRALTARVEREFATRNIQYHI
IGGVPFFARREIKDILAYLRLSRNAMDRVSLKRILTMKKRGFGTASLEKLFNFAEENKLT
LLEAMKAAVESLLFKKLSMNDYLESLYTLIQTIQEIAEPSQAIYLVMEQENLLDHFRSIS
KSEEEYIERTENVKQLISIAEESADMDDFLQRSALGTRENNGGVEGVAISTVHGVKGLEF
QAVILYYVTDGFFPHSLSVTTAEKEEERRLLYVAMTRAKEHLIFYVPYKQPWGNGFEQMA
RPSPFLRSIPKELWDGKPNEIESLYAPYSPQQKWSE

>tr|D7BJL0|D7BJL0_MEISD DNA helicase OS = Meiothermus silvanus
(strain ATCC 700542/DSM 9946/VI-R2) GN = Mesil_3574 PE = 4
SV = 1 (SEQ ID NO: 92)
MNDPIRHKEGPALVFAGAGAGKTRTLTQRVKWLVEEGEDPYSITLVTFTNKAAGEMKERI
ARLVEAPLAEAVWVGTFHRFCLQSLQVYGREIGLEKVAVLDSAAQRKLAERIIAGLFPAK
PPRGFTPMAALGAVSRAANSGWDDIQLATMYADLTEKIVNFRWAYEEAKKGLGALDYDDL
LLRGVRLLKLSEGAARMVRRRAAYLMVDEFQDTNGVQLELVRAIAPGTSPNLMVVGDPDR
SIYGWRGANYRTILEFRQHYPGAAVYGLYTNYRSQAGVVEVANRIIAQNATRKPEMQEAH
LPQSEEPFLLVAKNRWEEAHFVAQAVEFYRGQGIALEEMAVLMRANFLSRDLEQALRLRG
IPYQFTGGRSFFERREIQLGMAVLKVLANPKDSLAVAALVEEMVEGAGPLGIQKVLEAAK
AANLSPLEAFRNPAMVKGLRGKEVQAEAMRLAEVLQDQVARLAAEAPEYHALLKETLDRL
GFEAWLDRLGEESEQVYSRKANLDRLLQGMQEWQEVNPGAPLQDLVGILLLEAGDTPAEE
GQGVHLMTVHASKGMEFRVVFVIGLNEGLFPLSKASSSFEGLEEERRLMYVAVTRAKEVL
HLSYAADGVVSRFAQEARVPVEEYDPRLGWSGRQNQQALKALLEIA >tr|E8MZN5|E8MZN5_ANATU DNA helicase OS = Anaerolinea
thermophila (strain DSM 14523/JCM 11388/NBRC 100420/UNI-1)
GN = pcrA PE = 4 SV = 1 (SEQ ID NO: 93)
MDSLEHLNPQQRAAVTASAGPVLVLAGPGSGKTRVLTFRIGYLLSQLGVAPHHILAVTFT
NKAAREMQSRVEKLLGHSLQGMWLGTFHAICARILRREQQYLPLDANFVIFDEDDQQALI
KRALRDLNLDEKLYRPTSVHAAISNAKNNLILPEDYPTATYRDEVVARVYKRYQELLVSS
NAVDFDDLLLYAWKLLNEFSTVREQYARRFEHILVDEFQDTNLAQYELVKLLASYHRNLF
VVGDEDQSIYRWRGADYRNVLRFEEDPPDRQKILLEQNYRSTQRVLDAAQAVINRNRNRT
PKRLKSTPEHGEGEKLVLYEAVDDYGEAAFVVDTIQQLVAGGKARPGDFAIMYRTNAQSR
LLEEAFLRAGVPYRLVGAMRFYGRREVKDMIAYLRLVQNPADEASLGRVINVPPRGIGDK
SQLALQMEAQRTGRSAGLILMELGREGKDSPHWQALGRNASLLADFGSLLGEWHRLKDEI
SLPSLFQRILNDLAYREYIDDNTEEGQSRWENVQELLRIAYEYEEKGLTAFLENLALVSD
QDTLPENVEAPILLTLHAAKGLEFPIVFITGLDDGLIPHNRSLDDPEAMAEERRLFYVGL
TRAKKRVYLVRAAQRSTYGSFQDSIPSRFLKDIPADLIQQDGRGRRMGRSWQSESRRSWD
DNYAGTWGSRPERAKPSHAPILQPRFKPGMRVKHPSWGEGLVVDSRIQDEDETVDIFFDS
VGFKRVIASIANLEILS >tr|L0INW7|L0INW7_THEIR ATP-dependent exoDNAse (Exonuclease
V), alpha subunit/helicase superfamily I member
OS = Thermoanaerobacterium thermosaccharolyticum M0795
GN = Thethe_02902 PE = 4 SV = 1 (SEQ ID NO: 94)
MDINGQIIKLNRNKTQGILKLINGQKIKFKINSDSVKPIFLYEYYKFKGNMIEDTLIIDD
IYGIANDININDFTELFPSVAHDKINNICNRFNVLHVGNLIDLINDENFITVVNDTIGEE
KATIFLSNLQKIKDRQEYIDVWDIIKKINPTFDINVPIKIVNALKYRASMNNITVSQLIK
ESPWIIEQLDIFDSITERKKIAENIATHYGLSNDSNKAVISYAIAMTNNYIQQGHSYIPY
YILVSRVSNSLKLDFNKVNDILKFLPNDNKSGYLIRDNKYKDEIENEYNSDKKIGYSVYL
PKIFHMEKYIADIISSILKKKSTINKIELQKNLKLYRSENKLIFSKEQEEAIFSISDNKI
TVITGGAGIGKTIVIKAIIDLVNKMGYTPVVLAPTGIASQRVAPNVGSTIHKYARIFDTY
DPVFDEIEENKENNSGKVIIVDEMSMITVPVFAKLLSVILDADSFIFVGDPNQLPPIGAG
GVFEALIELGNKNINNINTVVLNQSFRSKNSIVKNAQNILEDKPIYEDDNLNIIEAKSWN
KIADEVVNLIRKLLDNGVQYSDIMVLSSKRGEGKNGVSLLNERIRKEIFNNKGKYAVGDI
VITTRNDYDNKSSYFRSKELKKYINSIRHEERPTIFNGTVGVIKDISDNEVIIEYNTPMP
VEAKYNMEELDWYIEYGFAITVHKAQGGQAKYIIFASDEPRNISREMLYTAITRCKNGKV
FLIGGENEDWKIKKEHSFVLSKLKYRILDNIHQQEKESKINSKIVLINQ >tr|D3PR99|D3PR99_MEIRD DNA helicase OS = Meiothermus ruber
(strain ATCC 35948/DSM 1279/VKM B-1258/21) GN = K649_05745
PE = 4 SV = 1 (SEQ ID NO: 95)
MSDLLSSLNPSQQEAVLHFEGPALVVAGAGSGKTRIVVHRIAYLLRERRVYPAEILAVIF
INKAAGEMKERLEKMVGRPARDLWVSTFHAAAVRILRTYGEYVGLRPGFVIYDEDDQNTL
LKEVLKELELEAKPGPFRAMIDRIKNRGAGLAEYMREAPDFIGGVPKDAAAEVYRKYQSG
LRMQGALDFNDLLLLTIELFEQHPEVLHKVQQRARFIHVDEYQDINPVQYKLIRLLAGER
PNLMVVGDPDQSIYGFRSADINNILDFIKDYPGARVIRLEENYRSSSSILRVANAVIEKN
ALRLEKVLRPTRPGGEPVRLYRAPNAREEEAAFVAREIVKLGNFQQIAVLYRTNAQSRLL
EEHLRRANVPVRLVGAVGFFERREIKDLLAYGRVAVNPADSINLRRIVNIPPRGIGATIVS
RLVEHAQKTGITVFEAFRVAEQVISRPQQVQAFVRLLDELIEAAFESGPTAFFQRVLEQT
GFREALKQEPDGEDRLQNVEELLRAAQDWEEEEGGSLSDFLDSVALTAKAEEPQGDAPAE
AVILMILHNAKGLEFPTVFLVGLEENLLPHRNSLHRLEDLEEERRLFYVGITRAQERLYL
SYAEERETYGKREYTRPSRFLEDIPQDLLKEVGAFGDSEVRVLPQAREPEPKPRTQLAEFK
GGEKVRHPKFGSGTVVAAMGGEVIVMFPGVGLKRLAVKFAGLERLE
```

TABLE 18-continued

>tr|D3PLL2|D3PLL2_MEIRD DNA helicase OS = *Meiothermus ruber*
(strain ATCC 35948/DSM 1279/VKM B-1258/21) GN = K649_10770
PE = 4 SV = 1 (SEQ ID NO: 96)
MKVRVASAGIGKTASLVLRYLELIAKGTPLRRIAGVIFTRKAADELRVRVAAAIEEVLQT
GRHLSFVASGGSRAAFQEAAREIAGAILSTIHGFMAQCLRLAAPLLHLDPDPFSMLGDWEA
QAIFEEEWQTLRYLAQDAHHPLFGLVSDELTEPLLHLFSRRSQAEVFEPAAGEANQHLLQ
VYQTVYAAYEARLGANLLSPSELERKALELARNDRAMKRVLERVRVLLVDEYQDVNPVQG
AFFAALEQARLPIEIVGDPKQSIYAFRNADVSVFRKALREGKSEPPLTHSYRHSRVLVRF
LNGLTGYLAKEGLGFGLEEAPPVEGVRPEQGRLEVHWVVGELPLEELRKQEARVLAGRLA
ALRGPIEYSQMAVLVRSYGSVRFLEEALAEAQIPYVLLQGRGYYERQEVRDLYHALRAAL
DPRGLSLAVFLRSPFGQHTEAGPLKPLELPQIEGVLRADDPLGRLAQHWPSVYERLRQIQ
AQVRLMAPLEVLKFLIRAPLMDGRPYHDFLEPRARENVDALLFYFAPRPPQNLEGLLERL
ELLSRQADAGDVPQSGEGVQILTVHQAKGLEWPLVAVFDLGRMNVHRPQPLYLGQGPNGG
DGGRLRRWVALPETPQFEAFRQQVKLQEEEESYRLLYVAASRARDTLLLTASASHGQPEG
WGKVLEAMNLGPASKPYHRPDFHLQTWPYQPAPPVRVLSQPAPLQPSPWVDARFEPEPFP
PLFSPSALKRLEAEPLPLPDPEEGEAVPGRARAIGTLVHYAIGQNWRPDNPQHLANLEAQ
EVMFPFGPDERRGIMAEVQALLEHYQELLGRALPWPRDEDYPEFAVALPLGSTVWQGVID
RLYRVGQQWYLEDYKTDQEMRPERYLVQLGIYLAAIRQAWQIEPEVRLVYLRFGWVERLD
KAILEAALGEIMPKGEGLRR >tr|Q9RTI9|Q9RTI9_DEIRA DNA helicase OS = *Deinococcus
radiodurans* (strain ATCC 13939/DSM 20539/JCM 1687/ LMG
4051/NBRC 15346/NCIMB 9279/R1/VKM B-1422) GN = DR_1775
PE = 1 SV = 1 (SEQ ID NO: 97)
MTSSAGPDLLQALNPTQAQAADHFTGPALVIAGAGSGKTRTLIYRIAHLIGHYGVHPGEI
LAVTFTNKAAAEMRERAGHLVPGAGDLWMSTFHSAGVRILRTYGEHIGLRRGFVIYDDDD
QLDIIKEVMGSIPGIGAETQPRVIRGIIDRAKSNLWTPDDLDRSREPFISGLPRDAAAEA
YRRYEVRKKGQNAIDFGDLITETVRLFKEVPGVLDKVQNKAKFIHVDEYQDTNRAQYELT
RLLASRDRNLLVVGDPDQSIYKFRGADIQNILDFQKDYPDAKVYMLEHNYRSSARVLEAA
NKLIENNTERLDKTLKPVKEAGQPVTFHRATDHRAEGDYVADWLTRLHGEGRAWSEMAIL
YRTNAQSRVIEESLRRVQIPARIVGGVGFYDRREIRDILAYARLALNPADDVALRRIIGR
PRRGIGDTALQKLMEWARTHHTSVLTACANAAEQNILDRGAHKATEFAGLMEAMSEAADN
YEPAAFLRFVMETSGYLDLLRQEGQGEQVRLENLEELVSAAEEWSQDEANVGGSIADFLD
DAALLSSVDDMRTKAENKGAPEDAVTLMTLHNAKGLEFPVVFIVGVEQGLLPSKGAIAEG
PSGIEEERRLFYVGITRAMERLLMTAAQNRMQFGKTNAAEDSAFLEDIEGLFDTVDPYGQ
PIEYRAKTWKQYRPTVPAATTAVKNTSPLTAELAYRGGEQVKHPKFGEGQVLAVAGVGER
QEVTVHFASAGTKKLMVKFANLTKL >tr|M1E5C5|M1E5C5_9FIRM DNA helicase OS = *Thermodesulfobium
narugense* DSM 14796 GN = Thena_1375 PE = 4 SV = 1 (SEQ ID NO: 98)
MDLNLNEDQKRAVYSDSRALLIVAGAGTGKTRVLTTRAARLIKENPDARYLLLTFTKKAA
REMTTRVRELIEEDTKNRLYSGTFHSFCSNIIRRRSERVGLTNDFVIIDESDSLDLMKKV
FSRIYSKEKIDSLIFKPKDILSLYSYARNNNQDFIEIVQRKYKYVNFEDIKKIISLYELN
KKERNYLDFDDLLMYGLLAIKTLEKSPFDEVLVDEFQDTNQIQAEMLYYFYDLGSRISAV
GDDAQSIYSFRGAYYENMFNFIKRLDAEKIILSSNYRSTQQILDIANSIIQSSYYSSIKKE
LVANVRLKENVKPKLVIVSDDWEEARYVAREMQKFGEKGLKVAALYRAAYIGRNLESQLN
SMGIKYSFYGGQKLTESAHAKDFMSFLRVFVNPKDEIALIRILKMFPGIGEKKAEKIKDA
VISGDNLKKALSKEKNLEELNIFFDKLFKITDWHDLLELVFDFYKDIMNRLYPENYEERE
EDLIKFMDMSSNYDNLVEYLEAFTLDPVEKSEFDNNNVILSTIHSAKGLEFDVVFLLSVI
ESVYPHFRAQSTDEIEEERRLFYVAITRAKQRLIFTFPPRHSKKSRGYFAKNTISPFLREK
DNYLEVFIAR >tr|Q5SIE7|Q5SIE7_THET8 DNA helicase OS = *Thermus thermophilus*
(strain HB8/ATCC 27634/DSM 579) GN = TTHA1427 PE = 4 SV = 1 (SEQ
ID NO: 99)
MSDALLAPLNEAQRQAVLHFEGPALVVAGAGSGKTRTVVHRVAYLVARRGVFPSEILAVT
FTNKAAEEMRERLRGLVPGAGEVWVSTFHAAALRILRVYGERVGLRPGFVVDEDDQTAL
LKEVLKELALSARPGPIKALLDRAKNRGVGLKALLGELPEYYAGLSRGRLGDVLVRYQEA
LKAQGALDFGDILLYALRLLEEDEEVLRLVRKRARFIHVDEYQDTSPVQYRFTRLLAGEE
ANLMAVGDPDQGIYSFRAADIKNILDFTRDYPEARVYRLEENYRSTEAILRFANAVIVKN
ALRLEKALRPVKRGGEPVRLYRAEDAREEARFVAEEIARLGPPWDRYAVLYRTNAQSRLL
EQALAGRGIPARVVGGVGFFERAEVKDLLAYARLALNPLDAVSLKRVLNTPPRGIGPATW
ARVQLLAQEKGLPPWEALKEAARTFSRPEPLRHFVALVEELQDLVFGPAEAFFRHLLEAT
DYPAYLREAYPEDAEDRLENVEELLRAAKEADLQDFLDRVALTAKAEEPAEAEGRVALM
TLHNAKGLEFPVVFLVGVEEGLLPHRNSVSTLEGLEEERRLFYVGITRAQERLYLSHAEE
REVYGRREPARPSRFLEEVEEGLYEVYDPYRRPPSPPPHRPRPGAFRGGERVVHPRFGPG
TVVAAQGDEVTVHFEGFGLKRLSLKYAELKPA >tr|B5YD55|B5YD55_DICT6 DNA helicase OS = *Dictyoglomus
thermophilum* (strain ATCC 35947DSM 3960/H-6-12)
GN = DICTH_0581 PE = 4 SV = 1 (SEQ ID NO: 100)
MNNQFDSEKKIFIIPSRKKKEFLERIEKDLNEEQRKVVLEADGPSLVIAGPGSGKTRTIV
YRVGYLVALGYSPKNIMLLTFTNQAARHMINRTQALIRESIEEIWGGTFHHVGNRILRVY
GKIIGINEQYNILDREDSLDLIDECLEELFPEENLGKGILGELFSYKVNTGKNWDEVLKI
KAPQIIDKIEIVQKVFERYEKRKRELNVLDYDDLLFFWYRLLLESEKTRKILNDRFLYIL
VDEYQDTNWLQGEIIRLTREENKNILVVGDDAQSIYSFRGATIENILSFPEIFPGTRIFY
LVFNYRSTPEIINLANEIIKRNTRQYFKEIKPVLKSGSKPKLVWVRDDEEEAQFVVEVIK
ELHKEGVKYKDIGVLFRSNYHSMAVQMELTLQGIPYEVRGGLRFFEQAHIKDMISLLKIL
FNPQDEISAQRFFKLFPGIGRAYAKKLSQVLKESKDFDKIFQMQFSGRTLEGLRILKNIW TABLE 18-continued DKIKVIPVQNFSEILRVFFNEYYKDYLERNYPDFKDREKDVDQLILLSERYDDLEKFLSE
LTLYTYAGEKLLEEEEEKDFVVLSTIHQAKGLEWHAVFILRLVQGDFPSYKSMDNIEEE
RRLFYVAVTRAKRELYVITYLTRKVKDMNVFTKPSIFLEELPYKELFEEWIVQREI >tr|F6DJA4|F6DJA4_THETG DNA helicase OS = Thermus thermophilus
(strain SG0.5JP17-16) GN = Ththe16_2124 PE = 4 SV = 1 (SEQ ID NO:
101)
MLSPFGGEEETKAIPLEEEILLAWRVFSAALPPNFLAPVSASLHTLVREAEGKEGAELEA
YAWERLEELARTSVVKDAIQSFLEVAAEKPEVLRAGLLWFRTWNRLSPEEREALYRKAER
FKPTAELASKASFLQGPPPPPKPLSPSVQAARSSPPRFTPTPEQEEAVRAFLSREDMKLV
AVAGSGKTTTLRLMAQSAPKERLLYVAFNRSVRDEAERTFPGNVEVLTLHGLAHRHVVRG
SGAYQRKLAARNGRVTPGDVLEALELPRERYALAYVIRSTLEAFLRSASEVPTPAHIPPE
YREVLQRRDKDPFSERYVLKAVRLIWKLMQDPDDSFPLSFDGFVKIWAQAGAKIRGYDAV
LVDEAQDLSPVFLQVLEAHRGELRRVYVGDPRQQIYGWRGAVNAMDKLDAPERKLTWSFR
FGEDLARGVRRFLAHVGSPIELHGKAPWDTEVSLARPEPPYTALCRTNAGAVEAVTSFLL
EEGREGARVFVVGGVDEIAWLLRDAHLLKVGGEREKPHPELALVENWEELEELAKEVNHP
QARMLVRLARRYDLLELARLLKHAQADEEGKADLVVSTLHKAKGREWDRVVLWGDFIPVW
DEKVREFYRKQGALDELKEEENVVYVALTRARRFLGLDQLPDLHERFFQGEGLVKPPSVS
PLSVGGAGVSADLLRELEVRVLAKLEDRLKEVAEVLAALLVEEASKAVAEAMREMGLLGE
EG >tr|F6DIL2|F6DIL2_THETG DNA helicase OS = Thermus thermophilus
(strain SG0.5JP17-16) GN = Ththe16_1438 PE = 4 SV = 1 (SEQ ID NO:
102)
MSDALLAPLNEAQRQAVLHFEGPALVVAGAGSGKTRTVVHRVAYLVARRGVFPSEILAVT
FTNKAAEEMRERLRGLVPGAGEVWVSTFHAAALRILRVYGERVGLRPGFVVYDEDDQTAL
LKEVLKELALSARPGPIKALLDRAKNRGVGLKALLGELPEYYAGLSRGRLGDVLVRYQEA
LKAQGALDFGDILLYALRLLEEDEEVLRLVRKRARFIHVDEYQDTSPVQYRFTRLLAGEE
ANLMAVGDPDQGIYSFRAADIKNILDFTRDYPEARVYRLEENYRSTEAILRFANAVIVKN
ALRLEKALRPVKRGGEPVRLYRAEDAREEARFVAEEIARLGPPWDRYAVLYRTNAQSRLL
EQALAGRGIPARVVGGVGFFERAEVKDLLAYARLALNPLDAVSLKRVLNTPPRGIGPATW
ARVQLLAQEKGLPPWEALKEAARTFPRAEPLRHFVALVEELQDLVFGPAEAFFRHLLEAT
DYPTYLREAYPEDAEDRLENVEELLRAAKEAEDLQDFLDRVALTAKAEEPAEAEGKVALM
TLHNAKGLEFPVVFLVGVEEGLLPHRNSLSTLEGLEEERRLFYVGITRAQERLYLSHAEE
REVYGRREPARPSRFLEEVEEGLYEVYDPYRRPPSPPPHRPRPGAFRGGERVVHPRFGPG
TVVAAQGDEVTVHFEGVGLKRLSLKYAELKPA >tr|F6DJ67|F6DJ67_THETG DNA helicase OS = Thermus thermophilus
(strain SG0.5JP17-16) GN = Ththe16_2078 PE = 4 SV = 1 (SEQ ID NO:
103)
MEANLYVAGAGTGKTYTLAERYLGFLEEGLSPLQVVAVTFTERAALELRHRVRQMVGERS
LGHKERVLAELEAAPIGTLHALAARVCREFPEEAGVPADFQVMEDLEAALLLEAWLEEAL
LEALQDPRYAPLVEAVGYEGLLDTLREVAKDPLAARELLEKGLGEVAKALRLEAWRALRR
RMEELFHGERPEERYPGFPKGWRTEEPEVVPDLLAWAGEVKFNKKPWLEYKGDPALERLL
KLLGGVKEGFSPGPADERLEEVWPLLRELAEGVLARLEERRFRARRLGYADLEVHALRAL
EREEVRAYYRGRFRRLLVDEFQDTNPVQVRLLQALFPDLRAWTVVGDPNQSIYSFRRADP
KVMERFQAEAAKEGLRVRRLEKSHRYHQGLADFHNRFFPPLLPGYGAVSAERKPEGEGPW
VPHFQGDLEAQARFIAQEVGRLLSEGFQVYDLGEKAYRPMSLRDVAVLGRTWRDLARVAE
ALRRLEVPAVEAGGGNLLETRAFKDAYLALRFLGDPKDEEALVGLLRSPFFALTDGEVRR
LAEARGEGETLWEVLEREGDLSAEAERARETLRGLLRRKALEAPSRLLQRLDGATGYTGV
AARLPQGRRRVKDWEGTLDLVRKLEVGSEDPFLVARHLRLLLRSGLSVERPPLEAGEAVT
LLTVHGAKGLEWPVVFVLNVGGWNRLGSWKNNKTKPLFRPGLALVPPVLDEEGNPSALFH
LAKRRVEEEEKQEENRLLYVAATRASERLYLLLSPDLSPDKGDLDPQTLIGAGSLEKGLE
ATEPERPWSGEEGEVEVLEERIQGLPLEALPVSLLPLAARDPEAARRRLLGEPEPEGGEA
WEPDGPQETEEEVPGGAGVGRMTHALLERFEAPEDLEREGRAFLEESFPGAEGEEVEEAL
RLARTFLTAEVFAPYRGNAVAKEVPVALELLGVRLEGRADRVGEDWVLDYKTDRGVDAKA
YLLQVGVYALALGKPRALVADLREGKLYEGASQQVEEKAEEVLRRLMGGDRPEA >tr|G8N9P8|G8N9P8_9DEIN DNA helicase OS = Thermus sp.
CCB_US3_UF1 GN = TCCBUS3UF1_17030 PE = 4 SV = 1 (SEQ ID NO: 104)
MDAFPSGKPLDEAWLSSLNEAQRQAVLHFEGPALVVAGAGSGKTRTVVHRVAYLMARRGV
YPSEILAVTFTNKAAEEMRERLKAMVKGAGELWVSTFHAAALRILRFYGERVGLKPGFVV
YDEDDQTALLKEVLKELGVSAKPGPIKALLDRAKNRGEPPERLLADLPEYYAGLSRGRLL
DVLHRYQQALWAQGALDFGDILLLALKLLEEDPEVRKRVRKRARFIHVDEYQDTSPVQYR
LTKLLAGEEANLMAVGDPDQGIYSFRAADIKNILQFTEDFPGAKVYRLEENYRSTERILR
FANAVIVKNALRLEKTLRPVKSGGEPVRLFRARDAREEARFVAEEVLRLGPPYDRVAVLY
RTNAQSRLLEQALASRGIGARVVGGVGFFERAEVKDLLAYARLALNPLDAVSLKRVLNTP
PRGIGPATVEKVQAIAQEKGLPLYEALKVAAQVLRPREPLRHFLALMEELMDLAFGPAEA
FFRHLLEATDYPAYLKEAYPEDLEDRLENVEELLRAAREAEGLMDFLDKVALTARAEEPG
EAGGKVALMTLHNAKGLEFPVVFLVGVEEGLLPHRSSVSTLEGLEEERRLFYVGVTRAQE
RLYLSYAEEREVYGRPEASRPSRFLEEVEEGLYEEYDPYRLPPPKPVPPPHRAKPGAFRG
GEKVVHPRFGLGTVVAASGDEVTVHFDGVGLKRLSLKYADLRPA >tr|Q1J014|Q1J014_DEIGD DNA helicase OS = Deinococcus
geothermalis (strain DSM 11300) GN = Dgeo_0868 PE = 4 SV = 1 (SEQ ID
NO: 105)
MPDLPASSLLAQLNPNQAQAANHYTGPALVIAGAGSGKTRTLVYRIAHLIGHYGVDPGEI
LAVTFTNKAAAEMRERARHLVEGADRLWMSTFHSAGVRILRAYGEHIGLKRGFVIYDDDD
QLDILKEIMGSIPGIGAETHPRVLRGILDRAKSNLLTPADLARHPEPFISGLPREVAAEA
YRRYEARKKGQNAIDFGDLITETVRLFQEVPAVLERVQDRARFIHVDEYQDTNKAQYELT TABLE 18-continued

```
RLLASRDRNLLVVGDPDQSIYRFRGADIQNILDFQKDYLDAKVYMLEQNYRSSARVLTIA
NKLIENNAERLEKTLRPVKEDGHPVLFHRATDQRAEGDFVAEWLTRLHAEGMRFSDMAVL
YRTNAQSRVIEESLRRVQIPAKIVGGVGFYDRREIKDVLAYARLAINPDDDVALRRIIGR
PKRGIGDTALERLMEWARVNGTSILTACAHAQELNILERGAQKAVEFAGLMHAMSEAADN
DEPGPFLRYVIETSGYLDLLRQEGQEGQVRLENLEELVSAAEEWSRENEGTIGDFLDDAA
LLSSVDDMRTKQENKDVPEDAVTLMTLHNAKGLEFPVVFIVGTEEGLLPSKNALLEPGGI
EEERRLFYVGITRAMERLFLTAAQNRMQYGKTLATEDSRFLEEIKGGFDTVDAYGQVIDD
RPKSWKEYRPTESARPGAVKNTSPLTEGMAYRGGEKVRHPKFGEGQVLAVAGLGDRQEVT
VHFPSAGTKKLLVKFANLTRA

>tr|Q745W4|Q745W4_THET2 DNA helicase OS = Thermus thermophilus
(strain HB27/ATCC BAA-163/DSM 7039) GN = TT_P0191 PE = 4 SV = 1
(SEQ ID NO: 106)
MALRPTEEQLKAVEAYRSGQDLKVVAVAGSGKTTTLRLMAEATPGKRGLYLAFNRSVQQE
AARKFPRNVRPYTLHALAFRMAVARDEGYRAKFQAGKGHLPAQAVAEALGLRNPLLLHAV
LGTLEAFLRSEAASPDPGMIPLAYRTLRAGTKTWPEEEAFVLRGVEALWRRMTDPKDPFP
LPHGAYVKLWALSEPDLSFAEALLVDEAQDLDPIFLKVLEAHRGRVQRVYVGDPRQQIYG
WRGAINAMDRLEAPEARLTWSFRFAETLARFVRNLTALQDRPVEVRGKAPWATRVDAALP
RPPFTVLCRTNAGVVGAVVVTHEVHRGRVHVVGGVEELVHLLRDAALLKKGEKRTDPHPD
LAMVETWEELEALAEAGYAPAYGVLRLAQEHPDLEALAAYLERAWTPVEVAAGVVVSTAH
KAKGREWDRVVLWDDFYPWWEEGAAARVNWGSDPAHLEEENLLYVAATRARKHLSLAQIR
DLLEAVDRMGVYRVAEEATRAYLLLSAEVLRGVATDPRVPAEHRVRALKALGYLERGEEA
LDSPGKPGGQG >tr|Q72IS0|Q72IS0_THET2 DNA helicase OS = Thermus thermophilus
(strain HB27/ATCC BAA-163/DSM 7039) GN = uvrD PE = 4 SV = 1 (SEQ
ID NO: 107)
MSDALLAPLNEAQRQAVLHFEGPALVVAGAGSGKTRTVVHRVAYLVARRGVFPSEILAVT
FTNKAAEEMRERLRGLVPGAGEVWVSTFHAAALRILRVYGERVGLRPGFVVYDEDDQTAL
LKEVLKELALSARPGPIKALLDRAKNRGVGLKALLGELPEYYAGLSRGRLGDVLVRYQEA
LKAQGALDFGDILLYALRLLEEDEEVLRLVRKRARFIHVDEYQDTSPVQYRFTRLLAGEE
ANLMAVGDPDQGIYSFRAADIKNILDFTRDYPEARVYRLEENYRSTEAILRFANAVIVKN
ALRLEKALRPVKRGGEPVRLYRAEDAREEARFVAEEIARLGPPWDRYAVLYRTNAQSRLL
EQALAGRGIPARVVGGVGFFERAEVKDLLAYARLALNPLDAVSLKRVLNTPPRGIGPATW
ARVQLLAQEKGLPPWEALKEAARTFPRPEPLRHFVALVEELQDLVFGPAEAFFRHLLEAT
DYPAYLREAYPEDAEDRLENVEELLRAAKEAEDLQDFLDRVALTAKAEEPAEAEGRVALM
TLHNAKGLEFPVVFLVGVEEGLLPHRNSVSTLEGLEEERRLFYVGITRAQERLYLSHAEE
REVYGRREPARPSRFLEEVEEGLYEVYDPYRRPPSPPPHRPRPGAFRGGERVVHPRFGPG
TVVAAQGDEVTVHFEGFGLKRLSLKYAELKPA >tr|F2NK78|F2NK78_MARHT DNA helicase OS = Marinithermus
hydrothermalis (strain DSM 14884/JCM 11576/T1)
GN = Marky_1312 PE = 4 SV = 1 (SEQ ID NO: 108)
MDLLRDLNPAQREAVQHYTGPALVVAGAGSGKTRTVVHRIAYLIRHRGVYPTEILAVTFT
NKAAGEMKERLARMVGPAARELWVSTFHSAALRILRVYGEYIGLKPGFVVYDEDDQLALL
KEVLGGLGLETRPQYARGVIDRIKNRMWSVDAFLREAEDWVGGLPKEQMAAVYQAYEARM
RALGAVDFNDLLLKVIGLFEAHPEVLHRVQQRARFIHVDEYQDTNPAQYRLTRLLAGAER
NLMVVGDPDQSIYGFRNADIHNILNFEKDYPDARVYRLEENYRSTEAILRVANAVIEKNA
LRLEKTLRPVRSGGDPVFLYRAPDHREEAAFVAREVQRLKGRGRRLDEIAVLYRTNAQSR
VLEEAFRRQNLGVRIVGGVGFYERREVKDVLAYARAAVNPADDLAVKRVLNVPARGIGQT
SLAKLSQLAETARVSFFEALRRAGEVLARPQAQAVQRFVALIEGLANAAYDTGPDAFLRL
VLAETGYADMLRREPDGEARLENLEELLRAAREWEEQHAGTIADFLDEVALTARAEEPEG
EVPAEAVTLMTLHNAKGLEFPVVFIVGVEEGLLPHRSSTARVEDLEEERRLFYVGITRAQ
ERLYLTLSEERETYGRREAVRASRFLEDIPEAFLQPLSPFGEPLGAGREPVAVRPTRRSS
AAGGFRGGEKVRHPRFGQGLVVAASGEGDRQEVTVHFAGVGLKKLLVKYAGLERIE
```

REFERENCES

1. B. Choi, G. Zocchi, Y. Wu, S. Chan, L. Jeanne Perry, Allosteric control through mechanical tension. *Phys Rev Lett* 95, 078102 (2005).
2. M. Volgraf et al., Allosteric control of an ionotropic glutamate receptor with an optical switch. *Nat Chem Biol* 2, 47-52 (2006).
3. M. Tomishige, R. D. Vale, Controlling kinesin by reversible disulfide cross-linking. Identifying the motility-producing conformational change. *J Cell Biol* 151, 1081-1092 (2000).
4. B. Schierling et al., Controlling the enzymatic activity of a restriction enzyme by light. *Proceedings of the National Academy of Sciences of the United States of America* 107, 1361-1366 (2010).
5. D. M. Veine, K. Ohnishi, C. H. Williams, Jr., Thioredoxin reductase from *Escherichia coli*: evidence of restriction to a single conformation upon formation of a crosslink between engineered cysteines. *Protein science: a publication of the Protein Society* 7, 369-375 (1998).
6. T. M. Lohman, E. J. Tomko, C. G. Wu, Non-hexameric DNA helicases and translocases: mechanisms and regulation. *Nat Rev Mol Cell Biol* 9, 391-401 (2008).
7. A. Niedziela-Majka, M. A. Chesnik, E. J. Tomko, T. M. Lohman, *Bacillus stearothermophilus* PcrA monomer is a single-stranded DNA translocase but not a processive helicase in vitro. *The Journal of biological chemistry* 282, 27076-27085 (2007).
8. T. Ha et al., Initiation and re-initiation of DNA unwinding by the *Escherichia coli* Rep helicase. *Nature* 419, 638-641 (2002).
9. B. Sun et al., Impediment of *E. coli* UvrD by DNA-destabilizing force reveals a strained-inchworm mechanism of DNA unwinding. *The EMBO journal*, (2008).

10. W. Cheng, J. Hsieh, K. M. Brendza, T. M. Lohman, E. coli Rep oligomers are required to initiate DNA unwinding in vitro. *Journal of molecular biology* 310, 327-350 (2001).

11. N. K. Maluf, C. J. Fischer, T. M. Lohman, A Dimer of Escherichia coli UvrD is the active form of the helicase in vitro. *Journal of molecular biology* 325, 913-935 (2003).

12. M. S. Dillingham, Superfamily I helicases as modular components of DNA-processing machines. *Biochemical Society transactions* 39, 413-423 (2011).

13. M. Yamaguchi, V. Dao, P. Modrich, MutS and MutL activate DNA helicase II in a mismatch-dependent manner. *The Journal of biological chemistry* 273, 9197-9201 (1998).

14. L. E. Mechanic, B. A. Frankel, S. W. Matson, Escherichia coli MutL loads DNA helicase II onto DNA. *The Journal of biological chemistry* 275, 38337-38346 (2000).

15. P. Soultanas et al., Plasmid replication initiator protein RepD increases the processivity of PcrA DNA helicase. *Nucleic acids research* 27, 1421-1428 (1999).

16. A. F. Slatter, C. D. Thomas, M. R. Webb, PcrA helicase tightly couples ATP hydrolysis to unwinding double-stranded DNA, modulated by the initiator protein for plasmid replication, RepD. *Biochemistry* 48, 6326-6334 (2009).

17. P. Soultanas, M. S. Dillingham, D. B. Wigley, Escherichia coli ribosomal protein L3 stimulates the helicase activity of the Bacillus stearothermophilus PcrA helicase. *Nucleic acids research* 26, 2374-2379 (1998).

18. J. E. Yancey, S. W. Matson, The DNA unwinding reaction catalyzed by Rep protein is facilitated by an RHSP-DNA interaction. *Nucleic acids research* 19, 3943-3951 (1991).

19. S. Barranco-Medina, R. Galletto, DNA binding induces dimerization of Saccharomyces cerevisiae Pif1. *Biochemistry* 49, 8445-8454 (2010).

20. H. S. Subramanya, L. E. Bird, J. A. Brannigan, D. B. Wigley, Crystal structure of a DExx box DNA helicase. *Nature* 384, 379-383 (1996).

21. S. Korolev, J. Hsieh, G. H. Gauss, T. M. Lohman, G. Waksman, Major domain swiveling revealed by the crystal structures of complexes of E. coli Rep helicase bound to single-stranded DNA and ADP. *Cell* 90, 635-647 (1997).

22. J. Y. Lee, W. Yang, UvrD helicase unwinds DNA one base pair at a time by a two-part power stroke. *Cell* 127, 1349-1360 (2006).

23. H. Jia et al., Rotations of the 2B sub-domain of E. coli UvrD helicase/translocase coupled to nucleotide and DNA binding. *Journal of molecular biology* 411, 633-648 (2011).

24. K. M. Brendza et al., Autoinhibition of Escherichia coli Rep monomer helicase activity by its 2B subdomain. *Proceedings of the National Academy of Sciences of the United States of America* 102, 10076-10081 (2005).

25. W. Cheng et al., The 2B domain of the Escherichia coli Rep protein is not required for DNA helicase activity. *Proceedings of the National Academy of Sciences of the United States of America* 99, 16006-16011 (2002).

26. S. Myong, I. Rasnik, C. Joo, T. M. Lohman, T. Ha, Repetitive shuttling of a motor protein on DNA. *Nature* 437, 1321-1325 (2005).

27. G. Lee, M. A. Bratkowski, F. Ding, A. Ke, T. Ha, Elastic Coupling Between RNA Degradation and Unwinding by an Exoribonuclease. *Science* (New York, N.Y 336, 1726-1729 (2012).

28. M. C. Murphy, I. Rasnik, W. Cheng, T. M. Lohman, T. Ha, Probing single-stranded DNA conformational flexibility using fluorescence spectroscopy. *Biophysical journal* 86, 2530-2537 (2004).

29. J. A. Ali, T. M. Lohman, Kinetic measurement of the step size of DNA unwinding by Escherichia coli UvrD helicase. *Science* (New York, N.Y 275, 377-380 (1997).

30. J. R. Moffitt et al., Intersubunit coordination in a homomeric ring ATPase. *Nature* 457, 446-450 (2009).

31. L. R. Brewer, P. R. Bianco, Laminar flow cells for single-molecule studies of DNA-protein interactions. *Nature methods* 5, 517-525 (2008).

32. T. T. Perkins, H. W. Li, R. V. Dalal, J. Gelles, S. M. Block, Forward and reverse motion of single RecBCD molecules on DNA. *Biophysical journal* 86, 1640-1648 (2004).

33. J. G. Yodh, M. Schlierf, T. Ha, Insight into helicase mechanism and function revealed through single-molecule approaches. *Quarterly reviews of biophysics* 43, 185-217 (2010).

34. W. Zhang et al., Directional loading and stimulation of PcrA helicase by the replication initiator protein RepD. *Journal of molecular biology* 371, 336-348 (2007).

35. C. Machon et al., RepD-mediated recruitment of PcrA helicase at the Staphylococcus aureus pC221 plasmid replication origin, oriD. *Nucleic acids research* 38, 1874-1888 (2010).

36. J. Park et al., PcrA helicase dismantles RecA filaments by reeling in DNA in uniform steps. *Cell* 142, 544-555 (2010).

37. M. J. Comstock, H. Jia, T. M. Lohman, T. Ha, Y. R. Chemla. (2014).

38. M. N. Dessinges, T. Lionnet, X. G. Xi, D. Bensimon, V. Croquette, Single-molecule assay reveals strand switching and enhanced processivity of UvrD. *Proceedings of the National Academy of Sciences of the United States of America* 101, 6439-6444 (2004).

39. J. G. Yodh, B. C. Stevens, R. Kanagaraj, P. Janscak, T. Ha, BLM helicase measures DNA unwound before switching strands and hRPA promotes unwinding reinitiation. *The EMBO journal* 28, 405-416 (2009).

40. B. X. Huang, H. Y. Kim, Interdomain conformational changes in Akt activation revealed by chemical cross-linking and tandem mass spectrometry. *Mol Cell Proteomics* 5, 1045-1053 (2006).

41. D. Branton et al., The potential and challenges of nanopore sequencing. *Nature biotechnology* 26, 1146-1153 (2008).

42. A. H. Laszlo et al., Decoding long nanopore sequencing reads of natural DNA. *Nature biotechnology*, (2014).

43. M. Vincent, Y. Xu, H. Kong, Helicase-dependent isothermal DNA amplification. *EMBO reports* 5, 795-800 (2004).

44. I. L. Urbatsch et al., Cysteines 431 and 1074 are responsible for inhibitory disulfide cross-linking between the two nucleotide-binding sites in human P-glycoprotein. *The Journal of biological chemistry* 276, 26980-26987 (2001).

45. I. Rasnik, S. Myong, W. Cheng, T. M. Lohman, T. Ha, DNA-binding orientation and domain conformation of the E. coli rep helicase monomer bound to a partial duplex junction: single-molecule studies of fluorescently labeled enzymes. *Journal of molecular biology* 336, 395-408 (2004).
46. R. Roy, S. Hohng, T. Ha, A practical guide to single-molecule FRET. *Nat Methods* 5, 507-516 (2008).
47. C. Joo, T. Ha, in *Cold Spring Harb Protoc.* (2012), vol. 2012.
48. Y. Harada, K. Sakurada, T. Aoki, D. D. Thomas, T. Yanagida, Mechanochemical coupling in actomyosin energy transduction studied by in vitro movement assay. *Journal of molecular biology* 216, 49-68 (1990).
49. T. Yanagida, M. Nakase, K. Nishiyama, F. Oosawa, Direct observation of motion of single F-actin filaments in the presence of myosin. *Nature* 307, 58-60 (1984).
50. I. Rasnik, S. A. McKinney, T. Ha, Nonblinking and long-lasting single-molecule fluorescence imaging. *Nat Methods* 3, 891-893 (2006).
51. C. J. CLOPPER, E. S. PEARSON, THE USE OF CONFIDENCE OR FIDUCIAL LIMITS ILLUSTRATED IN THE CASE OF THE BINOMIAL. *Biometrika* 26, 404-413 (1934).
52. J. Gal, R. Schnell, S. Szekeres, M. Kalman, Directional cloning of native PCR products with preformed sticky ends (autosticky PCR). *Molecular & general genetics: MGG* 260, 569-573 (1999).
53. Z. Qi, R. A. Pugh, M. Spies, Y. R. Chemla, Sequence-dependent base pair stepping dynamics in XPD helicase unwinding. *Elife* (Cambridge) 2, e00334 (2013).
54. M. P. Landry, P. M. McCall, Z. Qi, Y. R. Chemla, Characterization of photoactivated singlet oxygen damage in single-molecule optical trap experiments. *Biophysical journal* 97, 2128-2136 (2009).
55. C. Bustamante, Y. R. Chemla, J. R. Moffitt, *High-resolution dual-trap optical tweezers with differential detection*. Single-molecule techniques: a laboratory manual (Cold Spring Harbor Laboratory Press, Cold Spring Harbor, NY, 2008).
56. K. Berg-Srensen, H. Flyvbjerg, Power spectrum analysis for optical tweezers. *Review of Scientific Instruments* 75, 594-612 (2004).

All patents, patent applications, patent application publications and other publications that are cited herein are hereby incorporated by reference as if set forth in their entirety.

It should be understood that the methods, procedures, operations, composition, and systems illustrated in figures may be modified without departing from the spirit of the present disclosure. For example, these methods, procedures, operations, devices and systems may comprise more or fewer steps or components than appear herein, and these steps or components may be combined with one another, in part or in whole.

Furthermore, the present disclosure is not to be limited in terms of the particular embodiments described in this application, which are intended as illustrations of various embodiments. Many modifications and variations can be made without departing from its scope and spirit. Functionally equivalent methods and apparatuses within the scope of the disclosure, in addition to those enumerated herein, will be apparent to those skilled in the art based on the foregoing descriptions.

SEQUENCE LISTING

The patent contains a lengthy sequence listing. A copy of the sequence listing is available in electronic form from the USPTO web site (https://seqdata.uspto.gov/?pageRequest=docDetail&DocID=US12173334B2). An electronic copy of the sequence listing will also be available from the USPTO upon request and payment of the fee set forth in 37 CFR 1.19(b)(3).

What is claimed is:

1. A method of catalyzing an unwinding reaction of a double-stranded DNA, comprising contacting the double-stranded DNA with a conformationally-constrained helicase
    wherein the conformationally-constrained helicase is selected from the group consisting of a Rep helicase from *E. coli*, a UvrD helicase from *E. coli*, a PcrA helicase from *B. stearothermophilus*, or a homolog thereof;
    wherein the conformationally-constrained helicase comprises a first subdomain comprising a 1A or a 1B subdomain having a first amino acid and a second subdomain comprising a 2B subdomain having a second amino acid,
    wherein the first amino acid corresponds to any one of positions 84-116 or 178-196 of the helicase amino acid sequence, relative to SEQ ID NO:32;
    wherein the second amino acid corresponds to any one of positions 388-411, 422-444, and 518-540 of the helicase amino acid sequence, relative to SEQ ID NO:32;
    wherein a side chain of the first amino acid is covalently crosslinked to a side chain of the second amino acid with a linker to form an active, conformationally-constrained helicase;
    wherein said first amino acid is less than about 20 Å from said second amino acid when the helicase is in an active conformation, and
    wherein the conformationally-constrained helicase comprises at least one degree of freedom less than a helicase that is not constrained as such.

2. The method of claim 1, wherein the conformationally-constrained helicase is chemically crosslinked.

3. The method of claim 1, wherein the conformationally-constrained helicase comprises SEQ ID NO:4 or SEQ ID NO:12.

4. The method of claim 1, wherein the linker comprises an alkyl having a length in the range from C7 to C23.

5. The method of claim 1, wherein the first amino acid is covalently crosslinked to the second amino acid by a disulfide bond or a chemical crosslinker.

6. The method of claim 5, wherein the chemical crosslinker is a bis-maleimide crosslinker.

7. The method of claim 5, wherein the chemical cross-linker has a length of from about 6 Å to about 25 Å.

8. The method of claim 1, wherein the chemical cross-linker is selected from the group consisting of

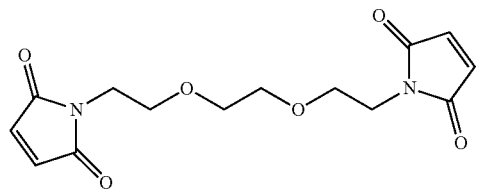

1-[2-[2-[2-(2,5-dioxopyrrol-1-yl)ethoxy]ethoxy]ethyl]pyrrole-2,5-dione,

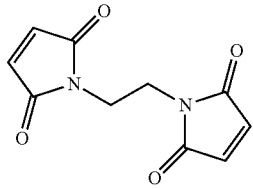

1-[2-(2,5-dioxopyrrol-1-yl)ethyl]pyrrole-2,5-dione,

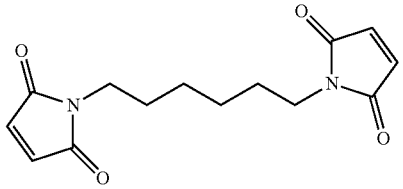

1-[6-(2,5-dioxopyrrol-1-yl)hexyl]pyrrole-2,5-dione,

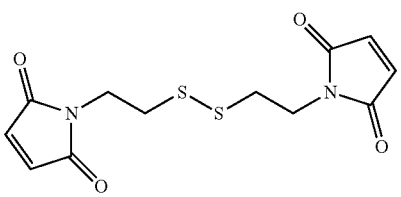

1-[2-[2-(2,5-dioxopyrrol-1-yl)ethyldisulfanyl]ethyl]pyrrole-2,5-dione,

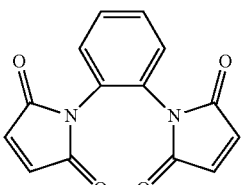

1-[2-(2,5-dioxopyrrol-1-yl)phenyl]pyrrole-2,5-dione, and

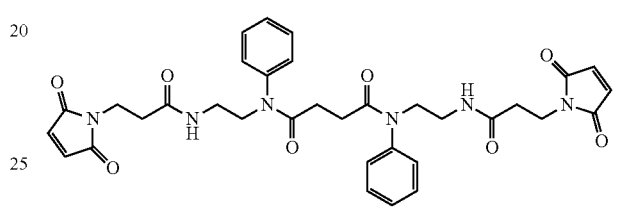

N,N'-bis[2-[3-(2,5-dioxopyrrol-1-yl)propanoylamino]ethyl]-N,N'-diphenylbutanediamide.

* * * * *